US009241994B2

(12) United States Patent
Igawa

(10) Patent No.: US 9,241,994 B2
(45) Date of Patent: Jan. 26, 2016

(54) PHARMACEUTICAL COMPOSITIONS CONTAINING SC(FV)2

(75) Inventor: Tomoyuki Igawa, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 510 days.

(21) Appl. No.: 11/916,979

(22) PCT Filed: Jun. 9, 2006

(86) PCT No.: PCT/JP2006/311600
§ 371 (c)(1),
(2), (4) Date: Aug. 7, 2008

(87) PCT Pub. No.: WO2006/132352
PCT Pub. Date: Dec. 14, 2006

(65) Prior Publication Data
US 2009/0214535 A1    Aug. 27, 2009

(51) Int. Cl.
C07K 16/00     (2006.01)
C12P 21/08     (2006.01)
A61K 39/395    (2006.01)
A61K 9/00      (2006.01)
A61K 47/02     (2006.01)
A61K 47/18     (2006.01)
A61K 47/26     (2006.01)
C07K 16/28     (2006.01)
A61K 39/00     (2006.01)

(52) U.S. Cl.
CPC ......... A61K 39/39591 (2013.01); A61K 9/0019 (2013.01); A61K 47/02 (2013.01); A61K 47/183 (2013.01); A61K 47/26 (2013.01); C07K 16/2866 (2013.01); A61K 2039/505 (2013.01); C07K 2317/24 (2013.01); C07K 2317/622 (2013.01); C07K 2317/626 (2013.01); C07K 2317/75 (2013.01); C07K 2317/76 (2013.01)

(58) Field of Classification Search
CPC .............. C07K 2317/622; C07K 2317/31; C07K 2317/626; C07K 2317/94
See application file for complete search history.

(56) References Cited

U.S. PATENT DOCUMENTS

| | | | |
|---|---|---|---|
| 4,946,778 A | 8/1990 | Ladner et al. | |
| 5,077,216 A | 12/1991 | Morganelli et al. | |
| 5,223,241 A | 6/1993 | Isobe et al. | |
| 5,516,672 A * | 5/1996 | Yamasaki et al. | 435/184 |
| 5,618,920 A | 4/1997 | Robinson et al. | |
| 5,747,654 A | 5/1998 | Pastan et al. | |
| 5,780,021 A | 7/1998 | Sobel | |
| 5,789,554 A | 8/1998 | Leung et al. | |
| 5,837,242 A | 11/1998 | Holliger et al. | |
| 5,837,821 A | 11/1998 | Wu | |
| 5,840,344 A | 11/1998 | Fukushima | |
| 5,877,291 A | 3/1999 | Mezes et al. | |
| 5,885,574 A | 3/1999 | Elliott | |
| 5,892,020 A * | 4/1999 | Mezes et al. | 536/23.53 |
| 5,908,925 A * | 6/1999 | Cohen et al. | 536/23.53 |
| 5,977,322 A | 11/1999 | Marks et al. | |
| 6,013,067 A | 1/2000 | Fibbe et al. | |
| 6,042,829 A | 3/2000 | Uckun et al. | |
| 6,126,980 A | 10/2000 | Smith et al. | |
| 6,132,992 A | 10/2000 | Ledbetter et al. | |
| 6,171,586 B1 * | 1/2001 | Lam et al. | 424/130.1 |
| 6,183,744 B1 | 2/2001 | Goldenberg | |
| 6,319,499 B1 | 11/2001 | Elliott | |
| 6,323,000 B2 | 11/2001 | Briggs et al. | |
| 6,342,220 B1 | 1/2002 | Adams et al. | |
| 6,361,769 B1 | 3/2002 | Tovey | |
| 6,368,596 B1 | 4/2002 | Ghetie et al. | |
| 6,579,692 B1 | 6/2003 | Fukushima | |
| 6,683,157 B2 | 1/2004 | Briggs et al. | |
| 6,699,686 B1 | 3/2004 | Brocard et al. | |
| 6,719,972 B1 | 4/2004 | Gribben et al. | |
| 6,759,043 B2 | 7/2004 | Fukushima | |
| 6,903,194 B1 | 6/2005 | Sato et al. | |
| 7,115,373 B2 | 10/2006 | Hashida et al. | |
| 7,262,278 B2 | 8/2007 | Tawara et al. | |
| 7,456,260 B2 | 11/2008 | Rybak et al. | |
| 7,550,140 B2 * | 6/2009 | Bakker et al. | 424/130.1 |
| 7,691,588 B2 * | 4/2010 | Tsuchiya et al. | 435/7.2 |
| 7,749,501 B2 * | 7/2010 | Gelfand | 424/133.1 |

(Continued)

FOREIGN PATENT DOCUMENTS

AU    755822       3/1999
AU    2004297111   6/2005

(Continued)

OTHER PUBLICATIONS

Lower, Chemical Equilibrium, A Chem1 Reference Text, 2001, pp. 1-28.*
Ausubel et al., Short Protocols in Molecular Biology, 3rd Edition, 1985, p. A1-44.*
The Protein Protocols Handbook, second edition, edited by Walker, Springer-Verlag New York, LLC, 2002, pp. 1035-1046.*
Goel et al., J. Biochem., 2000, 127:829-836.*
Short Protocols in Molecular Biology, 3rd Edition, Edited by Ausubel et al., 1995, p. 11-27.*

(Continued)

Primary Examiner — Hong Sang
(74) Attorney, Agent, or Firm — Fish & Richardson P.C.

(57) ABSTRACT

The present inventor discovered stabilizing agents/stabilizing conditions for suppressing isomerization reactions of sc(Fv)2. It was also discovered that the above-mentioned isomerization reactions can be suppressed through use of freeze-dried formulations. As disclosed herein, by applying the discovered stabilizing agents/stabilizing conditions or the freeze-dried formulation, the isomerization reaction of an sc(Fv)2-type molecule from the bivalent scFv type to the single chain diabody type, and/or the isomerization reaction from a single chain diabody type to a bivalent scFv type can be suppressed in both directions or one direction.

11 Claims, 44 Drawing Sheets

(56) References Cited

U.S. PATENT DOCUMENTS

| | | | |
|---|---|---|---|
| 7,993,642 | B2 | 8/2011 | Tsunoda et al. |
| 8,008,073 | B2 | 8/2011 | Tsunoda et al. |
| 8,158,385 | B2 | 4/2012 | Ozaki et al. |
| 8,945,543 | B2 | 2/2015 | Igawa et al. |
| 2001/0006796 | A1 | 7/2001 | Briggs et al. |
| 2002/0028178 | A1 | 3/2002 | Hanna et al. |
| 2002/0155537 | A1 | 10/2002 | Carter et al. |
| 2002/0193571 | A1* | 12/2002 | Carter et al. ............... 530/387.3 |
| 2002/0197706 | A1 | 12/2002 | Nadkarni et al. |
| 2003/0073161 | A1 | 4/2003 | Briggs et al. |
| 2003/0082612 | A1 | 5/2003 | Snodgrass et al. |
| 2003/0103979 | A1 | 6/2003 | Leung et al. |
| 2003/0147894 | A1 | 8/2003 | Fukushima et al. |
| 2003/0148409 | A1 | 8/2003 | Rossi et al. |
| 2003/0157100 | A1 | 8/2003 | Fukushima et al. |
| 2003/0157577 | A1 | 8/2003 | Fukushima et al. |
| 2003/0190316 | A1* | 10/2003 | Kakuta et al. ............. 424/132.1 |
| 2003/0202975 | A1 | 10/2003 | Tedder |
| 2003/0211108 | A1 | 11/2003 | Fukushima et al. |
| 2004/0001828 | A1 | 1/2004 | Tuscano et al. |
| 2004/0033228 | A1* | 2/2004 | Krause et al. ............. 424/145.1 |
| 2004/0058393 | A1 | 3/2004 | Fukishima et al. |
| 2004/0073013 | A1 | 4/2004 | Fukushima et al. |
| 2004/0091475 | A1 | 5/2004 | Tsuchiya et al. |
| 2004/0219643 | A1 | 11/2004 | Winter et al. |
| 2004/0242847 | A1 | 12/2004 | Fukushima et al. |
| 2005/0130224 | A1 | 6/2005 | Saito et al. |
| 2005/0214278 | A1 | 9/2005 | Kakuta et al. |
| 2005/0220787 | A1 | 10/2005 | Lobo |
| 2005/0267222 | A1 | 12/2005 | Iwata et al. |
| 2006/0058511 | A1 | 3/2006 | Tanikawa et al. |
| 2006/0159673 | A1 | 7/2006 | Kojima |
| 2006/0189794 | A1 | 8/2006 | Tsuchiya et al. |
| 2006/0222643 | A1 | 10/2006 | Tsunoda et al. |
| 2006/0269989 | A1 | 11/2006 | Miyazaki et al. |
| 2006/0275301 | A1 | 12/2006 | Ozaki et al. |
| 2007/0003556 | A1 | 1/2007 | Tsuchiya et al. |
| 2007/0087381 | A1* | 4/2007 | Kojima .......................... 435/7.1 |
| 2007/0280951 | A1 | 12/2007 | Kimura et al. |
| 2007/0281327 | A1 | 12/2007 | Nakano et al. |
| 2008/0009038 | A1 | 1/2008 | Ohtomo et al. |
| 2008/0107654 | A1* | 5/2008 | Kikuchi et al. ............ 424/139.1 |
| 2008/0206229 | A1 | 8/2008 | Ono et al. |
| 2008/0248037 | A1 | 10/2008 | Li et al. |
| 2008/0274110 | A1 | 11/2008 | Ozaki et al. |
| 2008/0286280 | A1 | 11/2008 | Kallmeyer et al. |
| 2009/0022687 | A1 | 1/2009 | Matsumoto et al. |
| 2009/0028854 | A1 | 1/2009 | Igawa et al. |
| 2009/0062184 | A1 | 3/2009 | Maeda et al. |
| 2009/0117097 | A1 | 5/2009 | Igawa et al. |
| 2009/0162352 | A1 | 6/2009 | Adler et al. |
| 2009/0297501 | A1 | 12/2009 | Igawa et al. |
| 2009/0311718 | A1 | 12/2009 | Fukushima et al. |
| 2010/0015133 | A1 | 1/2010 | Igawa et al. |
| 2010/0040600 | A1 | 2/2010 | Yoshikubo et al. |
| 2010/0092457 | A1 | 4/2010 | Aburatani et al. |
| 2010/0092461 | A1 | 4/2010 | Matsumoto et al. |
| 2010/0150927 | A1 | 6/2010 | Kimura et al. |
| 2011/0059488 | A1 | 3/2011 | Tsunoda et al. |
| 2012/0244142 | A1 | 9/2012 | Kimura et al. |

FOREIGN PATENT DOCUMENTS

| | | |
|---|---|---|
| AU | 2002210917 | 5/2006 |
| CA | 2272245 | 5/1998 |
| CA | 2 331 641 | 11/1999 |
| CN | 1244805 | 2/2000 |
| DE | 198 19 846 | 11/1999 |
| EP | 437622 | 7/1991 |
| EP | 562125 | 9/1993 |
| EP | 721015 | 7/1996 |
| EP | 0 774 511 | 5/1997 |
| EP | 0 811 691 | 12/1997 |
| EP | 1035132 | 9/2000 |
| EP | 1 178 826 | 2/2002 |
| EP | 1 310 252 | 5/2003 |
| EP | 1 327 681 | 7/2003 |
| EP | 1327680 | 7/2003 |
| EP | 1369431 | 12/2003 |
| EP | 1396500 | 3/2004 |
| EP | 1 475 100 | 11/2004 |
| EP | 1 475 101 | 11/2004 |
| EP | 1 500 665 | 1/2005 |
| EP | 0 969 866 | 6/2005 |
| EP | 1561759 | 8/2005 |
| EP | 1712565 | 10/2006 |
| EP | 1757686 | 2/2007 |
| EP | 1870458 | 12/2007 |
| EP | 1 925 319 | 5/2008 |
| EP | 1262548 | 8/2008 |
| EP | 2 048 230 | 4/2009 |
| JP | 3-41033 | 2/1991 |
| JP | 5-097703 | 4/1993 |
| JP | 7-503622 | 4/1995 |
| JP | 7-236475 | 9/1995 |
| JP | 8-500979 | 2/1996 |
| JP | 9289892 | 11/1997 |
| JP | 10-505231 | 5/1998 |
| JP | 10-508868 | 9/1998 |
| JP | 10-510842 | 10/1998 |
| JP | 11-500916 | 1/1999 |
| JP | 11-092500 | 4/1999 |
| JP | 2000-95800 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-543822 | 12/2002 |
| JP | 2002-544173 | 12/2002 |
| JP | 2003-515323 | 5/2003 |
| JP | 2004-086682 | 3/2004 |
| JP | 2004-086862 | 3/2004 |
| JP | 2004-292455 | 10/2004 |
| JP | 2005-529616 | 10/2005 |
| KR | 10-2004-0085185 | 10/2004 |
| MX | 9905856 | 7/2000 |
| WO | WO9100739 | 1/1991 |
| WO | WO9116928 | 11/1991 |
| WO | WO9219759 | 11/1992 |
| WO | WO 93/05799 | 4/1993 |
| WO | WO9306862 | 4/1993 |
| WO | WO 94/05690 | 3/1994 |
| WO | WO9413806 | 6/1994 |
| WO | WO9604925 | 2/1996 |
| WO | WO 96/24370 | 8/1996 |
| WO | WO 96/27011 | 9/1996 |
| WO | WO9626648 | 9/1996 |
| WO | WO 96/34892 | 11/1996 |
| WO | WO9636360 | 11/1996 |
| WO | WO9640218 | 12/1996 |
| WO | WO9701633 | 1/1997 |
| WO | WO 97/10354 | 3/1997 |
| WO | WO9731108 | 8/1997 |
| WO | WO9732601 | 9/1997 |
| WO | WO9734632 | 9/1997 |
| WO | WO9822136 | 5/1998 |
| WO | WO9828331 | 7/1998 |
| WO | WO9844001 | 8/1998 |
| WO | WO9841641 | 9/1998 |
| WO | WO9842378 | 10/1998 |
| WO | WO 98/50431 | 11/1998 |
| WO | WO9902567 | 1/1999 |
| WO | WO9903495 | 1/1999 |
| WO | WO9910494 | 3/1999 |
| WO | WO9912973 | 3/1999 |
| WO | WO9917364 | 4/1999 |
| WO | WO0023593 | 4/2000 |
| WO | WO 00/44788 | 8/2000 |
| WO | WO0053634 | 9/2000 |
| WO | WO 00/69462 | 11/2000 |
| WO | WO0067795 | 11/2000 |
| WO | WO0075191 | 12/2000 |
| WO | WO 01/36486 | 5/2001 |

(56) References Cited

FOREIGN PATENT DOCUMENTS

| WO | WO 01/44282 | 6/2001 |
|---|---|---|
| WO | WO 01/70775 | 9/2001 |
| WO | WO0164713 | 9/2001 |
| WO | WO0166737 | 9/2001 |
| WO | WO 01/79494 | 10/2001 |
| WO | WO0174388 | 10/2001 |
| WO | WO0177342 | 10/2001 |
| WO | WO0187337 | 11/2001 |
| WO | WO0197858 | 12/2001 |
| WO | WO0204021 | 1/2002 |
| WO | WO0222212 | 3/2002 |
| WO | WO 02/33072 | 4/2002 |
| WO | WO 02/33073 | 4/2002 |
| WO | WO0228894 | 4/2002 |
| WO | WO02078612 | 10/2002 |
| WO | WO02094880 | 11/2002 |
| WO | WO02096457 | 12/2002 |
| WO | WO02097033 | 12/2002 |
| WO | WO03002607 | 1/2003 |
| WO | WO03033538 | 4/2003 |
| WO | WO03033654 | 4/2003 |
| WO | WO 03/057168 | 7/2003 |
| WO | WO 03/068260 | 8/2003 |
| WO | WO 03/087163 | 10/2003 |
| WO | WO03086324 | 10/2003 |
| WO | WO 03/097105 | 11/2003 |
| WO | WO 03/103723 | 12/2003 |
| WO | WO 03/106974 | 12/2003 |
| WO | WO03104425 | 12/2003 |
| WO | WO03107218 | 12/2003 |
| WO | WO2004003019 | 1/2004 |
| WO | WO 2004/019966 | 3/2004 |
| WO | WO2004003499 | 4/2004 |
| WO | WO2004026332 | 4/2004 |
| WO | WO2004037293 | 5/2004 |
| WO | WO2004081048 | 9/2004 |
| WO | WO2004087763 | 10/2004 |
| WO | WO 2004/111233 | 12/2004 |
| WO | WO2005004912 | 1/2005 |
| WO | WO 2005/044857 | 5/2005 |
| WO | WO 2005/056604 | 6/2005 |
| WO | WO2005056602 | 6/2005 |
| WO | WO2005056603 | 6/2005 |
| WO | WO2005056604 | 6/2005 |
| WO | WO2005056605 | 6/2005 |
| WO | WO2005056798 | 6/2005 |
| WO | WO2005100560 | 10/2005 |
| WO | WO 2005/107784 | 11/2005 |
| WO | WO 2006/101173 | 9/2006 |
| WO | WO2006123724 | 11/2006 |
| WO | WO2008007755 | 1/2008 |
| WO | WO2008071394 | 6/2008 |

OTHER PUBLICATIONS

Moore et al., "Kinetics and thermodynamics of dimer formation and dissociation for a recombinant humanized monoclonal antibody to vascular endothelial growth factor," Biochemistry, 38:13960-13967 (1999).
USPTO Notice of Allowance in U.S. Appl. No. 10/551,504, mailed Jan. 7, 2010, 13 pages.
Fish & Richardson P.C., Amendment in Reply to Office Action dated Aug. 13, 2009 in U.S. Appl. No. 10/560,098, filed Feb. 16, 2010, 14 pages.
European Search Report for App. Ser. No. EP 06 76 6512, dated Nov. 30, 2009, 6 pages.
Cochlovius et al., "Treatment of human B cell lymphoma xenografts with a CD3×CD19 diabody and T cells", The Journal of Immunology 165:888-895, 2000.
De Jonge et al., "In vivo retargeting of T cell effector function by recombinant bispecific single chain Fv (anti-CD3×anti-idiotype) induces long-term survival in the murine BCL1 lymphoma model", The Journal of Immunology 161:1454-1461, 1998.
Desplancq et al., "Multimerization behaviour of single chain Fv variants for the tumour-binding antibody B72.3", Protein Engineering 7(8):1027-1033, 1994.
Gruber et al., "Efficient tumor cell lysis mediated by a bispecific single chain antibody expressed in *Escherichia coli*", Journal of Immunology 152:5368-5374, 1994.
Jäger et al., "Folding and assembly of an antibody Fv fragment, a heterodimer stabilized by antigen", Journal of Molecular Biology 285:2005-2019, 1999.
Kipriyanov et al., "Bispecific CD3×CD19 diabody for T cell-mediated lysis of malignant human B cells", In. J. Cancer 77:763-772, 1998.
Kipriyanov et al., "Bispecific tandem diabody for tumor therapy with imprived antigen binding and pharmacokinetics", Journal of Molecular Biology 293:41-56, 1999.
Kipriyanov et al., "Effect of domain order on the activity of bacterially produced bispecific single-chain Fv antibodies", Journal of Molecular Biology 330:99-111, 2003.
Korn et al., "Recombinant bispecific antibodies for the targeting of adenoviruses to CEA-expressing tumour cells: a comparative analysis of bacterially expressed single-chain diabody and tandem scFv", The Journal of Gene Medicine 6:642-651, 2004.
Kriangkum et al., "Bispecific and bifunctional single chain recombinant antibodies", Biomolecular Engineering 18:31-40, 2001.
Kurucz et al., "Retargeting of CTL by an efficiently refolded bispecific single-chain Fv dimer produced in bacteria", The Journal of Immunology 154:4576-4582, 1995.
Le Gall et al., "Effect of linker sequences between the antibody variable domains on the formation, stability and biological activity of a bispecific tandem diabody", Protein Engineering, Design & Selection 17(4):357-366, 2004.
Mack et al., "A small bispecific antibody construct expressed as a functional single-chain molecule with high tumor cell cytotoxicity", Proc. Natl. Acad. Sci. USA 92:7021-7025, 1995.
Mallender et al., "Construction, expression, and activity of a bivalent bispecific single-chain antibody", The Journal of Biological Chemistry 269(1):199-206, 1994.
Meng et al., "The evaluation of recombinant, chimeric, tetravalent antihuman CD22 antibodies", Clinical Cancer Research 10:1274-1281, 2004.
Orita et al., "A novel therapeutic approach for thrombocytopenia by minibody agonist of the thrombopoietin receptor", Blood 105(2):562-566, 2005.
Völkel et al., "Optimized linker sequences for the expression of monomeric and dimeric bispecific single-chain diabodies", Protein Engineering 14(10):815-823, 2001.
Whitlow et al., "An improved linker for single-chain Fv with reduced aggregation and enhanced proteolytic stability", Protein Engineering 6(8):989-995, 1993.
USPTO Restriction Requirement in U.S. Appl. No. 11/910,117, mailed May 3, 2010, 9 pages.
U.S. Appl. No. 11/910,117, filed Aug. 28, 2007, Igawa et al.
U.S. Appl. No. 11/910,128, filed Sep. 28, 2007, Igawa et al.
Abe et al., "Surrogate thrombopoietin," Immunology Letters, 61:73-78 (1998).
Andris-Widhopf et al., "Methods for the generation of chicken monoclonal antibody fragments by phage display," Journal of Immunological Methods, 242:159-181 (2000).
Arndt et al., "Generation of a highly stable, internalizing anti-DC22 single-chain Fv fragment for targeting non-Hodgkin's lymphoma," Int. J. Cancer, 107(5):822-829 (2003).
Bowie et al., "Deciphering the Message in Protein Sequences: Tolerance to Amino Acid Substitutions," Science, 247:1306-1310 (1990).
Carter, "Bispecific human IgG by design," J. Immunol. Methods, 248:7-15 (2001).
Casset et al., "A peptide mimetic of an anti-CD4 monoclonal antibody by rational design," Biochemical and Biophysical Research Communications, 307:198-205 (2003).
Cekaite et al., "Protein Arrays: A versatile toolbox for target identification and monitoring of patient immune responses," Methods Mol. Biol., 360:335-348 (2007).

(56) References Cited

OTHER PUBLICATIONS

Chen et al., "Selection and analysis of an optimized anti-VEGF antibody: crystal structure of an affinity-matured Fab in complex with antigen," *Journal of Molecular Biology*, 293:865-881 (1999).
Clackson et al., "Making antibody fragments using phage display libraries," *Nature*, 352:624-628 (1991).
Creighton, T., "Protein folding," *Biochem. J.*, 270(1):1-16 (1990).
Deng et al., "An Agonist Murine Monoclonal Antibody to the Human c-Mpl Receptor Stimulates Megakaryocytopoiesis," *Blood*, 92:1981-1988 (1998).
Eijsink et al., "Rational engineering of enzyme stability," *Journal of Biotechnology*, 113:105-120 (2004).
Elliott et al., "Activation of the Erythropoietin (EPO) Receptor by Bivalent Anti-EPO Receptor Antibodies," *J. Biol. Chem.*, 271:24691-24697 (1996).
Ewert et al., "Biophysical properties of human antibody variable domains," *J. Mol. Biol.*, 325:531-553 (2003).
Ewert et al., "Stability improvement of antibodies for extracellular and intracellular applications: CDR grafting to stable frameworks and structure-based framework engineering," *Methods*, 34:184-199 (2004).
Ewert et al., "Structure-based improvement of the biophysical properties of immunoglobulin $V_H$ domains with a generalizable approach," *Biochemistry*, 42:1517-1528 (2003).
Goding, "Monoclonal Antibodies: Principles and Practice," *Academic Press*, second Ed., 125:129 (1986).
Goldstein et al., "Cytolytic and Cytostatic Properties of an Anti-Human FcγRI (CD64) x Epidermal Growth Factor Bispecific Fusion Protein," *J. Immunol.*, 158:872-879 (1997).
Hoogenboom et al., "Multi-subunit proteins on the surface of filamentous phage: methodologies for displaying antibody (Fab) heavy and light chains," *Nucleic Acids Res.*, 19:4133-4137 (1991).
Hozumi and Tonegawa, "Evidence for somatic rearrangement of immunoglobulin genes coding for variable and constant regions," *Proc. Natl. Acad. Sci. USA*, 73(10):3628-3632 (1976).
Kipriyanov and Little, "Generation of Recombinant Antibodies," *Molecular Biotechnology*, 12:173-201 (1999).
Kontermann, R., "Recombinant bispecific antibodies for cancer therapy," *Acta Pharmacol. Sin.*, 26(1):1-9 (2005).
Krebber et al., "Reliable cloning of functional antibody variable domains from hybridomas and spleen cell repertoires employing a reengineered phage display system," *J. Immunol. Methods*, 201:35-55 (1997).
Kumar et al., "Molecular cloning and expression of the fabs of human autoantibodies in *Escherichia coli*," *The Journal of Biological Chemistry*, 275(41):35129-35136 (2000).
Kumar et al., "The second PDZ domain of INAD is a type I domain involved in binding to eye protein kinase C. Mutational analysis and naturally occuring variants," *J. Biol. Chem.*, 276(27):24971-24977 (2001).
Little et al., "Of mice and men: hybridoma and recombinant antibodies," *Immunol. Today*, 21:364-370 (2000).
Liu et al., "Functional interactions between arginine-133 and aspartate-88 in the human reduced folate carrier: evidence for a charge-pair association," *Biochem. J.*, 358:511-516 (2001).
Maity et al., "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).
McGuinness et al., "Phage diabody repertoires for selection of large number of bispecific antibody fragments," *Nature Biotechnology*, 14(9):1149-1154 (1996).
Merchant et al., "An efficient route to human bispecific IgG," *Nature Biotechnology*, 16:677-681 (1996).
Ngo et al., "Computational Complexity, Protein Structure Prediction, and the Levinthal Paradox ," *The Protein Folding Problem and Tertiary Structure Prediction*, Merz, Jr. et al. Editors, Birkhauser Boston, 433-506 (1994).
Nieba et al., "Disrupting the hydrophobic patches at the antibody variable/constant domain interface: improved in vivo folding and physical characterization of an engineered scFv fragment," *Protein Engineering*, 10(4):435-444 (1997).
Nishii, "CD22 antibody therapy," *Current Therapy*, 20:47-50 (2001) (English translation included).
Nohaile et al., "Altering dimerization specificity by changes in surface electrostatics," *PNAS* 98(6):3109-3114 (2001).
Palacios et al., "IL-3-dependent mouse clones that express B-220 surface antigen, contain Ig genes in germ-line configuration, and generate B lymphocutes in vivo," *Cell*, 41:727-734 (1985).
Peipp et al., "Bispecific antibodies targeting cancer cells," *Biochem. Soc. Trans.*, 30:507-511 (2002).
Rajagopal et al., "A form of anti-Tac (Fv) which is both single-chain and disulfide stabilized: comparison with its single-chain and disulfide-stabilized homologs," *Protein Engineering*, 10(12):1453-1459 (1997).
Ridgway et al., "'Knobs-into-holes' engineering of antibody $C_H3$ domains for heavy chain heterodimerization," *Protein Eng.*, 9:617-621 (1996).
Rousch et al., "Somatostatin displayed on filamentous phage as a receptor-specific agonist," *Br. Pharmacol.*, 125:5-16 (1998).
Sal-Man et al., "Arginine mutations within a transmembrane domain of Tar, an *Escherichia coli* aspartate receptor, can drive monodimer dissociation and heterodimer association n vivo," *Biochem. J.*, 385(1):29-36 (2005).
Segal et al., "Bispecific antibodies in cancer therapy," *Current Opinion in Immunology*, 11:558-582 (1999).
Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).
Shimba et al., "Comparative thermodynamic analyses of the Fv, Fab* and Fab fragments of anti-dansyl mouse monoclonal antibody," *FEBS Letters*, 360:247-250 (1995).
Shire et al., "Challenges in the development of high protein concentration formulations," *Journal of Pharmaceutical Sciences*, 93(6):1390-1402 (2004).
Skerra, "Use of the tetracycline promoter for the tightly regulated production of a murine antibody fragment in *Escherichia coli*," *Gene*, 151:131-135 (1994).
Smith-Gill et al., "Contributions of immunoglobulin heavy and light chains to antibody specificity for lysozyme and two haptens," *The Journal of Immunology*, 139:4135-4144 (1987).
Song et al., "Light chain of natural antibody plays a dominant role in protein antigen binding," *Biochemical and Biophysical Research Communications*, 268:390-394, (2000).
Souyri, M., "Mpl: from an acute myeloproliferative virus to the isolation of the long sought thrombopoietin," *Seminars in Hematology*, 35(3):222-231 (1998).
Tan et al., "Contributions of a highly conserved $V_H/V_L$ hydrogen bonding interaction to scFv folding stability and refolding efficiency," *Biophysical Journal*, 75:1473-1482 (1998).
Tang et al., "Selection of linkers for a catalytic single-chain antibody using phage display technology", *The Journal of Biological Chemistry*, 271(26):15682-15686 (1996).
Turner et al., "Importance of the linker in expression of single-chain Fv antibody fragments: optimization of peptide sequence using phage display technology," *Journal of Immunological Methods*, 205:43-54 (1997).
Van Den Burg et al., "Selection of mutations for increased protein stability," *Curr. Opin. Biotechnol.*, 13(4):333-337 (2002).
Vieille et al., "Hyperthermophilic enzymes: sources, uses, and molecular mechanisms for thermostability," *Microbiology and Molecular Biology Reviews*, 65(1):1-43 (2001).
Wells, "Perspectives in Biochemistry," *Biochemistry*, 29(37):8509-8517 (1990).
Worn et al., "Stability engineering of antibody single-chain Fv fragments," *J. Mol. Biol.*, 305:989-1010 (2001).
Zhu et al., "Remodeling domain interfaces to enhance heterodimer formation," *Protein Science*, 6:781-788 (1997).
USPTO Restriction Requirement in U.S. Appl. No. 10/551,504, mailed Jun. 27, 2008, 6 pages.

(56) References Cited

OTHER PUBLICATIONS

Fish & Richardson P.C., Response to Restriction Requirement dated Jun. 27, 2008 in U.S. Appl. No. 10/551,504, filed Sep. 29, 2008, 13 pages.
USPTO Restriction Requirement in U.S. Appl. No. 10/551,504, mailed Dec. 16, 2008, 5 pages.
Fish & Richardson P.C., Response to Restriction Requirement dated Dec. 16, 2008 in U.S. Appl. No. 10/551,504, filed Dec. 23, 2008, 14 pages.
USPTO Non-Final Office Action in U.S. Appl. No. 10/551,504, mailed Apr. 15, 2009, 35 pages.
Fish & Richardson P.C., Amendment in Reply to Action dated Apr. 15, 2009 in U.S. Appl. No. 10/551,504, filed Aug. 14, 2009, 19 pages.
Japanese Patent Office, International Search Report for App. Ser. No. PCT/JP2004/018506, mailed Mar. 22, 2005, 3 pages.
European Search Report for App. Ser. No. EP 04 82 0316, dated Jul. 17, 2008, 3 pages.
USPTO Restriction Requirement in U.S. Appl. No. 10/560,098, mailed Jul. 13, 2007, 9 pages.
Fish & Richardson P.C., Response to Restriction Requirement dated Jul. 13, 2007 in U.S. Appl. No. 10/560,098, filed Aug. 10, 2007, 6 pages.
USPTO Non-Final Office Action in U.S. Appl. No. 10/560,098, mailed Oct. 23, 2007, 17 pages.
USPTO Final Office Action in U.S. Appl. No. 10/560,098, mailed Sep. 11, 2008, 20 pages.
USPTO Interview Summary for U.S. Appl. No. 10/560,098, mailed Jun. 5, 2009, 8 pages.
Fish & Richardson P.C., Amendment in Reply to Office Action dated Sep. 11, 2008 in U.S. Appl. No. 10/560,098, filed Jun. 10, 2009, 12 pages.
USPTO Office Action in U.S. Appl. No. 10/560,098, mailed Aug. 13, 2009, 21 pages.
Japanese Patent Office, International Search Report for App. Ser. No. PCT/JP2004/008585, mailed Sep. 7, 2004, 4 pages.
Japanese Patent Office, International Preliminary Report on Patentability for App. Ser. No. PCT/JP2004/008585, 10 pages.
Japanese Patent Office, International Search Report for App. Ser. No. PCT/JP2006/306800, mailed May 16, 2006, 4 pages.
International Preliminary Report on Patentability for App. Ser. No. PCT/JP2006/306800, dated Oct. 3, 2007, 6 pages.
European Search Report for App. Ser. No. EP 06 73 0748, dated Apr. 22, 2009, 7 pages.
Japanese Patent Office, International Search Report for App. Ser. No. PCT/US2006/306803, mailed Jul. 11, 2006, 4 pages.
International Preliminary Report on Patentability for App. Ser. No. PCT/US2006/306803, dated Oct. 3, 2007, 6 pages.
Japanese Patent Office, International Search Report for App. Ser. No. PCT/JP2006/311575, mailed Sep. 26, 2006, 3 pages.
International Preliminary Report on Patentability for App. Ser. No. PCT/JP2006/311575, dated Dec. 11, 2007, 5 pages.
Japanese Patent Office, International Search Report for App. Ser. No. PCT/JP2006/311600, mailed Aug. 29, 2006, 2 pages.
International Preliminary Report on Patentability for App. Ser. No. PCT/JP2006/31160, dated Dec. 11, 2007, 8 pages.
Fish & Richardson P.C., Amendment in Reply to Action dated Mar. 3, 2011 in U.S. Appl. No. 11/916,351, filed Aug. 2, 2011, 17 pages.
USPTO Notice of Allowability in U.S. Appl. No. 10/530,696, mailed Aug. 15, 2011, 3 pages.
USPTO Non-Final Office Action in U.S. Appl. No. 10/582,304, mailed Aug. 15, 2011, 10 pages.
USPTO Restriction Requirement in U.S. Appl. No. 10/530,696, mailed Oct. 19, 2006, 8 pages.
Fish & Richardson P.C., Response to Restriction Requirement dated Oct. 19, 2006, in U.S. Appl. No. 10/530,696, filed Nov. 16, 2006, 1 page.
USPTO Non-Final Office Action in U.S. Appl. No. 10/530,696, mailed Dec. 21, 2006, 19 pages.
Fish & Richardson P.C., Amendment in Reply to Office Action dated Dec. 21, 2006 in U.S. Appl. No. 10/530,696, filed Apr. 23, 2007, 16 pages.
USPTO Final Office Action in U.S. Appl. No. 10/530,696, mailed Aug. 8, 2007, 13 pages.
USPTO Interview Summary in U.S. Appl. No. 10/530,696, mailed Nov. 26, 2007, 3 pages.
Fish & Richardson P.C., Amendment in Reply to Office Action dated Aug. 8, 2007 in U.S. Appl. No. 10/530,696, filed Dec. 6, 2007, 12 pages.
USPTO Advisory Action in U.S. Appl. No. 10/530,696, mailed Dec. 14, 2007, 3 pages.
USPTO Non-Final Office Action in U.S. Appl. No. 10/530,696, mailed Feb. 5, 2008, 9 pages.
Fish & Richardson, Amendment in Reply to Action dated Feb. 5, 2008 in U.S. Appl. No. 10/530,696, filed Aug. 5, 2008, 7 pages.
USPTO Non-Final Office Action in U.S. Appl. No. 10/530,696, mailed Nov. 17, 2008, 18 pages.
Fish & Richardson, Amendment in Reply to Action dated Nov. 17, 2008 in U.S. Appl. No. 10/530,696, filed Feb. 17, 2009, 14 pages.
USPTO Final Office Action in U.S. Appl. No. 10/530,696, mailed Jun. 8, 2009, 10 pages.
Fish & Richardson, Amendment in Reply to Action dated Jun. 8, 2009 in U.S. Appl. No. 10/530,696, filed Nov. 30, 2009, 10 pages.
USPTO Non-Final Office Action in U.S. Appl. No. 10/530,696, mailed Apr. 23, 2010, 9 pages.
Fish & Richardson, Amendment in Reply to Action dated Apr. 23, 2010 in U.S. Appl. No. 10/530,696, filed Oct. 22, 2010, 8 pages.
International Search Report for App. Ser. No. PCT/JP2003/013063, mailed Nov. 18, 2003, 2 pages.
International Preliminary Report on Patentability for App. Ser. No. PCT/JP2003/013063, dated Feb. 6, 2004, 4 pages.
European Search Report for App. Ser. No. EP 03 75 1456, dated Apr. 4, 2006, 2 pages.
USPTO Restriction Requirement in U.S. Appl. No. 10/582,304, mailed Nov. 20, 2008, 7 pages.
Fish & Richardson P.C., Response to Restriction Requirement dated Nov. 20, 2008 in U.S. Appl. No. 10/582,304, filed Dec. 16, 2008, 3 pages.
USPTO Non-Final Office Action in U.S. Appl. No. 10/582,304, mailed Apr. 1, 2009, 38 pages.
Fish & Richardson P.C., Amendment in Reply to Action dated Apr. 1, 2009 in U.S. Appl. No. 10/582,304, filed Jun. 30, 2009, 15 pages.
USPTO Non-Final Office Action in U.S. Appl. No. 10/582,304, mailed Sep. 15, 2009, 22 pages.
Fish & Richardson P.C., Amendment in Reply to Action dated Sep. 15, 2009 in U.S. Appl. No. 10/582,304, filed Jan. 13, 2010, 13 pages.
USPTO Non-Final Office Action in U.S. Appl. No. 10/582,304, mailed Mar. 24, 2010, 10 pages.
Fish & Richardson P.C., Amendment in Reply to Action dated Mar. 24, 2010 in U.S. Appl. No. 10/582,304, filed Jul. 26, 2010, 14 pages.
USPTO Non-Final Office Action in U.S. Appl. No. 10/582,304, mailed Oct. 14, 2010, 7 pages.
International Search Report for App. Ser. No. PCT/JP2004/018501, mailed Mar. 29, 2005, 2 pages.
International Preliminary Report on Patentability for App. Ser. No. PCT/JP2004/018501, dated Nov. 4, 2005, 7 pages.
European Search Report for App. Ser. No. EP 04 82 0311, dated Jan. 28, 2009, 4 pages.
International Search Report for App. Ser. No. PCT/JP2004/005152, mailed Jul. 20, 2004, 2 pages.
International Preliminary Report on Patentability for App. Ser. No. PCT/JP2004/005152, dated Feb. 14, 2005, 6 pages.
European Search Report for App. Ser. No. EP 04 72 6750, dated Feb. 4, 2008, 3 pages.
USPTO Non-Final Office Action in U.S. Appl. No. 11/547,747, mailed Jun. 1, 2009, 41 pages.
Fish & Richardson P.C., Amendment in Reply to Action dated Jun. 1, 2009 in U.S. Appl. No. 11/547,747, filed Nov. 30, 2009, 12 pages.
USPTO Final Office Action in U.S. Appl. No. 11/547,747, mailed Feb. 19, 2010, 15 pages.
Fish & Richardson P.C., Amendment in Reply to Action dated Feb. 19, 2010 in U.S. Appl. No. 11/547,747, filed Jun. 18, 2010, 13 pages.

(56) References Cited

OTHER PUBLICATIONS

International Search Report for App. Ser. No. PCT/JP2007/063946, mailed Aug. 14, 2007, 7 pages.
International Preliminary Report on Patentability for App. Ser. No. PCT/JP2007/063946, dated Jan. 20, 2009, 10 pages.
European Search Report for App. Ser. No. EP 07 79 0727, dated Nov. 13, 2009, 5 pages.
USPTO Restriction Requirement in U.S. Appl. No. 10/548,727, mailed Apr. 12, 2007, 6 pages.
Fish & Richardson P.C., Reply to Restriction Requirement dated Apr. 12, 2007 in U.S. Appl. No. 10/548,727, filed May 3, 2007, 1 page.
USPTO Non-Final Office Action in U.S. Appl. No. 10/548,727, mailed Aug. 3, 2007, 21 pages.
Fish & Richardson P.C., Amendment in Reply to Action dated Aug. 3, 2007 in U.S. Appl. No. 10/548,727, filed Jan. 15, 2008, 15 pages.
USPTO Final Office Action in U.S. Appl. No. 10/548,727, mailed Apr. 29, 2008, 23 pages.
USPTO Advisory Action in U.S. Appl. No. 10/548,727, mailed Sep. 24, 2008, 6 pages.
USPTO Non-Final Office Action in U.S. Appl. No. 10/548,727, mailed Jan. 28, 2009, 16 pages.
Fish & Richardson P.C., Amendment in Reply to Action dated Jan. 28, 2009 in U.S. Appl. No. 10/548,727, filed Jun. 26, 2009, 9 pages.
USPTO Notice of Allowance in U.S. Appl. No. 10/548,727, mailed Nov. 25, 2009, 29 pages.
International Search Report for App. Ser. No. PCT/JP2004/003334, mailed Jun. 15, 2004, 3 pages.
International Preliminary Report on Patentability for App. Ser. No. PCT/JP2004/003334, dated May 2, 2005, 6 pages.
USPTO Notice of Allowance in U.S. Appl. No. 10/551,504, mailed May 26, 2010, 7 pages.
USPTO Notice of Allowance in U.S. Appl. No. 10/551,504, mailed Dec. 16, 2010, 5 pages.
USPTO Restriction Requirement in U.S. Appl. No. 12/874,872, mailed Dec. 15, 2010, 6 pages.
International Search Report for App. Ser. No. PCT/JP2008/054443, dated May 27, 2008, 7 pages.
Schwartz et al., "A 50-kDa Integrin-associated Protein Is Required for Integrin-regulated Calcium Entry in endothelial Cells," J. Biol. Chem., 268(27):19931-19934 (1993).
Scott, "The Problem with Potency," Nature Biotechnology, 23(9):1037-1039 (2005).
Sekimoto et al., "Eradication of human myeloma cells by a recombinant HLA class I-specific single chain Fv diabody," 45th Annual Meeting of the American Society of Hematology, San Diego, CA, USA (Dec. 6-9, 2003).
Sekimoto et al., "Eradication of Human Myeloma Cells by a Recombinant HLA Class I-Specific Single Chain Fv Diabody," Blood, 102:932a, XP009106629 (Abstract #3469) (Nov. 2003) [Abstract of the American Society of Hematology 45th Annual Meeting, Dec. 6-9, 2003, San Diego, California].
Sekine et al., Enrichment of Anti-Glomerular Antigen Antibody-Producing Cells in the Kidneys of MRL/MpJ-Fas(lpr) Mice, J. Immunol., 172:3913-3921 (2004).
Sheridan et al., "Control of TRAIL-Induced Apoptosis by a Family of Signaling and Decoy Receptors," Science, 277:818-821 (1997).
Shigeta et al., "Sperm-immobilizing monoclonal antibody to human seminal plasma antigens," Clin. Exp. Immunol., 42:458-462 (1980).
Shulman et al., "A better cell line for making hybridomas secreting specific antibodies," Nature, 276:269-270 (1978).
Skolnick et al., "From genes to protein structure and function: novel applications of computational approaches in the genomic era," Trends in Biotechnology, 18:34-39 (2000).
Smith et al., "Inhibition of T Cell Activation by a Monoclonal Antibody Reactive Against the α3 Domain of Human MHC Class I Molecules," J. Immunol., 153:1054-1067 (1994).
Sonneveld, "Multidrug resistance in haematological malignancies," J. Intern. Med., 247:521-534 (2000).
Souyri et al., "A putative truncated cyotokine receptor gene transduced by the myeloproliferative leukemia virus immortalizes hematopoietic progenitors," Cell, 63:1137-1147 (1990).
Spaargaren et al., "Antibody-induced Dimerization Activates the Epidermal Growth Factor Receptor Tyrosine Kinase," The J. Biol. Chem., 266(3):1733-1739 (1981).
Stancovski et al., "Mechanistic aspects of the opposing effects of monoclonal antibodies to the ERBB2 receptor on tumor growth," Proc. Natl. Acad. Sci. USA, 88:8691-8695 (1991).
Stein et al., "Characterization of humanized IgG4 anti-HLA-DR monoclonal antibody that lacks effector cell functions but retains direct antilymphoma activity and increases the potency of rituximab," Blood, 108(8):2736-2744 (2006).
Suzuki et al., "YM477, a Novel Orally-Active Thrombopoietin Receptor Agonist," Blood (ASH Annual Meeting Abstracts), 106:Abstract 2298 (2005).
Tahtis et al., "Biodistribution Properties of 111Indium-labeled C-Functionalized trans-Cyclohexyl Diethylenetriaminepentaacetic Acid Humanized 3S193 Diabody and F(ab')2 Constructs in a Breast Carcinoma Xenograft Model," Clin. Cancer Res., 7:1061-1072 (2001).
Tedder et al., "CD22, a B Lymphocyte-Specific Adhesion Molecule That Regulates Antigen Receptor Signaling," Annu. Rev. Immunol., 15:481-504 (1997).
Thilenius et al., "Agonist antibody and Fas ligand mediate different sensitivity to death in the signaling pathways of Fas and cytoplasmic mutants," Eur. J. Immunol., 27:1108-1114 (1997).
Trowbridge, I.S., "Interspecies Spleen-Myeloma Hybrid Producing Monoclonal Antibodies Against Mouse Lymphocyte Surface Glycoprotein, T200," J. Exp. Med., 148:313-323 (1978).
Tsukakoshi, New Pharmacology, 3rd revised edition, Nankodo Co., Ltd., 557-568 (1997).
Vajdos et al., "Comprehensive functional maps of the antigen-binding site of an anti-ErbB2 antibody obtained with shotgun scanning mutagenesis," Journal of Molecular Biology, 320:415-428 (2002).
Van Geelen et al., "Differential modulation of the TRAIL receptors and the CD95 receptor in colon carcinoma cell lines," Br. J. Cancer, 89(2):363-373 (2003).
Vargas-Madrazo et al., "An improved model of association for VH-VL immunoglobulin domains: asymmetries between VH and VL in the packing of some interface residues," J. Mol. Recognit., 16(3):113-20 (2003).
Verma et al., "Antibody engineering: Comparison of bacterial, yeast, insect and mammalian expression systems," Journal of Immunological Methods, 216:165-181 (1998).
Vernon-Wilson et al., "CD47 is a ligand for rat macrophage membrane signal regulatory protein SIRP (OX41) and human SIRPalpha 1," Eur. J. Immunol., 30:2130-2137 (2000).
Verstegen et al., "Thrombopoietin is a major limiting factor for selective outgrowth of human umbilical cord blood cells in non-obese diabetic/severe combined immunodeficient recipient mice," Br. J. Haematol., 122(5):837-846 (2003).
Wakalee et al., Ann. Oncol. On-line publication (Jul. 24, 2009).
Walczak et al., "TRAIL-R2: A Novel Apoptosis-Mediating Receptor for TRAIL," EMBO J., 16:5386-5397 (1997).
Ward et al., "Binding activities of a repertoire of single immunoglobulin variable domains secreted from *Escherichia coli*," Nature, 341:544-546 (1989).
Whitlow et al., "Multivalent Fvs: characterization of single-chain Fv oligomers and preparation of a bispecific Fv," Protein Eng., 7(8):1017-1026 (1994).
Wiley et al., "Identification and Characterization of a New Member of the TNF Family that Induces Apoptosis," Immunity, 3:673-682 (1995).
Winkler et al., "Changing the Antigen Binding Specificity by Single Point Mutations of an Anti-p24 (HIV-1) Antibody," J. Imm., 265:4505-4514 (2000).
Woodle et al., "Anti-Human Class I MHC Antibodies Induce Apoptosis by a Pathway That Is Distinct from the Fas Antigen-Mediated Pathway," J. Immunol., 158:2156-2164 (1997).

(56) References Cited

OTHER PUBLICATIONS

Woodle et al., "Anti-Human Class I α3 Domain-Specific Monoclonal Antibody Induces Programmed Cell Death in Murine Cells Expressing Human Class I MHC Transgenes," Transplant Proc., 30:1059-1060 (1998).
Woodle et al., "Class I MHC Mediates Programmed Cell Death in Human Lymphoid Cells," Transplantation, 64:140-146 (1997).
Wu et al., "Humanization of a murine monoclonal antibody by simultaneous optimization of framework and CDR residues," Journal of Molecular Biology, 294:151-162 (1999).
Wu et al., "Multimerization of a chimeric anti-CD20 single-chain Fv-Fc fusion protein is mediated through variable domain exchange," Protein Eng., 14(12):1025-33 (2001).
Wu et al., "Tumor localization of anti-CEA single-chain Fvs: improved targeting by non-covalent dimers," Immunotechnology, 2:21-36 (1996).
Xie et al., "Direct Demonstration of MuSK Involvement in Acetylcholine Receptor Clustering Through Identification of Agonist ScFv," Nature Biotechnology, 15(8):768-771 (1997).
Xiong et al., "Efficient inhibition of human B-cell lymphoma xenografts with an anti-CD20 X anti-CD3 bispecific diabody," Cancer Lett., 177:29-39 (2002).
Xu et al., "Insight into hepatocellular carcinogenesis at transcriptome level by comparing gene expression profiles of hepatocellular carcinoma with those of corresponding noncancerous liver," Proc. Natl. Acad. Sci. USA, 98:15089-15094 (2001).
Yagita et al., "TRAIL and its receptors as targets for cancer therapy," Cancer Sci., 95:777-783 (2004).
Yanabu et al., "Tyrosine phosphorylation and p72syk activation by an anti-glycoprotein lb monoclonal antibody," Blood, 89(5):1590-1598 (1997).
Yarden et al., "Self-phosphorylation of epidermal growth factor receptor: evidence for a model of intermolecular allosteric activisation," Biochemistry, 26(5):1434-1442 (1987).
Yelton et al., "Fusion of Mouse Myeloma and Spleen Cells," Current Topics in Microbiology and Immunology, 81:1-7 (1978).
Zhu et al., "An efficient route to the production of an IgG-like bispecific antibody", Protein Eng., 13:361-367 (2000).
USPTO Non-Final Office Action in U.S. Appl. No. 10/582,304, mailed Dec. 9, 2010, 12 pages.
Fish & Richardson P.C., Amendment and Response to Restriction Requirement dated Sep. 3, 2010 in U.S. Appl. No. 11/916,351, filed Dec. 2, 2010, 9 pages.
USPTO Non-Final Office Action in U.S. Appl. No. 11/916,981, mailed Dec. 3, 2010, 8 pages.
Caron et al., "Engineered Humanized Dimeric Forms of IgG Are More Effective Antibodies," J. Exp. Med., 176:1191-1195 (1992).
Chatellier et al., "Functional mapping of conserved residues located at the VL and VH domain interface of a Fab," J. Mol. Biol., 264(1):1-6 (1996).
Chien et al., "Significant structural and functional change of an antigen-binding site by a distant amino acid substitution: Proposal of a structural mechanism," Proc. Nat. Acad. Sco. USA, 86:5532-5536 (1989).
Chirgwin et al., "Isolation of biologically active ribonucleic acid from sources enriched in ribonuclease," Biochemistry, 18(24):5294-5299 (1979).
Chuntharapai et al. "Isotype-Dependent Inhibition of Tumor Growth in Vivo by Monoclonal Antibodies to Death Receptor 4," J. Immunol., 166:4891-4898 (2001).
Clark, "CD22, a B Cell-Specific Receptor, Mediates Adhesion and Signal Transduction," J. Immunol., 150:4715-4718 (1993).
Co et al., "A Humanized Antibody Specific for the Platelet Integrin gpIIb/IIIa," J. Immunol., 152:2968-2976 (1994).
Cochlovius et al., "Cure of Burkitt's Lymphoma in Severe Combined Immunodeficiency Mice by T Cells, Tetravalent CD3×CD19 Tandem Diabody and CD28 Costimulation," Cancer Res., 60:4336-4341 (2000).

Cooper et al., "Transendothelial migration of neutrophils involves integrin-associated protein (CD47)," Proc. Natl. Acad. Sci. USA, 92:3978-3982 (1995).
Daniel et al., "Induction of Apoptosis in Human Lymphocytes by Human Anti-HLA Class I Antibodies," Transplantation, 75:1380-1386 (2003).
Davies et al., "Antibody VH domains as small recognition units," Biotechnology (N.Y.), 13(5):475-9 (1995).
De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).
De Jonge et al., "Production and Characterization of Bispecific Single-Chain Antibody Fragments," Mol. Immunol., 32:1405-1412 (1995).
De Leon et al., "High resolution human leukocyte antigen (HLA) class I and class II allele typing in Mexican mestizo women with sporadic breast cancer: case-control study," BMC Cancer, 9(48):1-9 (2009).
De Pascalis et al., "Grafting of 'abbreviated' complementary-determining regions containing specificity-determining residues essential for ligand contact to engineer a less immunogenic humanized monoclonal antibody," Journal of Immunology, 169:3076-3084 (2002).
De Sauvage et al., "Stimulation of Megakaryocytopoiesis and Thrombopoiesis by the c-Mpl Ligand," Nature, 369:533-538 (1994).
De St. Groth et al., "Production of Monoclonal Antibodies: Strategy and Tactics," Journal of Immunological Methods, 35:1-21 (1980).
Degli-Esposti et al., "Cloning and Characterization of TRAIL-R3, a Novel Member of the Emerging TRAIL Receptor Family," J. Exp. Med., 186:1165-1170 (1997).
Denardo et al., "Anti-HLA-DR/anti-DOTA Diabody Construction in a Modular Gene Design Platform: Bispecific Antibodies for Pretargeted Radioimmunotherapy," Cancer Biother. Radiopharm., 16:525-535 (2001).
Dillman, "Monoclonal antibodies for treating cancer," Ann. Int. Med., 11(7):592-603 (1989).
Dorai et al., "Mammalian cell expression of single-chain Fv (sFv) antibody proteins and their C-terminal fusions with interleukin-2 and other effector domains," Biotechnology, 12(9):890-897 (1994).
Dufner et al., "Harnessing phage and ribosome display for antibody optimization," Trends Biotechnol., 24(11):523-529 (2006).
Ebert et al., "Expression of Metallothionein II in Intestinal Metaplasia, Dysplasia, and Gastric Cancer," Cancer Res., 60:1995-2001 (2000).
EMBL Accession No. AY081858, dated Jan. 2, 2003, 1 page.
EMBL Accession No. U27005, dated Aug. 31, 1995, 1 page.
Emery et al., "Osteoprotegerin Is a Receptor for the Cytotoxic Ligand TRAIL," J. Biol. Chem., 273:14363-14367 (1998).
Fayen et al., "Negative signaling by anti-HLA class I antibodies is dependent upon two triggering events," Int. Immunol., 10:1347-1358 (1998).
Felgenhauer et al. "Nucleotide Sequences of the cDNAs Encoding the V-Regions of H- and L-Chains of a Human Monoclonal Antibody Specific to HIV-1-gp41," Nucleic Acids Research, 18(16):4927 (1990).
Fisk et al., "Increased sensitivity of Adriamycin-selected Tumor Lines to CTL-mediated Lysis Results in Enhanced Drug Sensitivity," Cancer Res., 58:4790-4793 (1998).
Fox et al., "Thrombopoietin expands hematopoietic stem cells after transplantation," J. Clin. Invest., 110(3):389-394 (2002).
Fujimoto et al., "50-kD integrin-associated protein does not detectably influence several functions of glycoprotein IIb-IIIa complex in human platelets," Blood, 86(6):2174-2182 (1995).
Fukushima et al., "Apoptosis of Bone Marrow Cells Via Integrin Associated Protein by the Novel Monoclonal Antibody," Blood, 94(10):479A (1999).
Fukushima et al., "Enhanced hematopoiesis in vivo and in vitro by splenic stromal cells derived from the mouse with recombinant granulocyte colony-stimulating factor," Blood, 80(8):1914-1922 (1992).
Funaro et al., "Monoclonal antibodies and therapy of human cancers," Biotechnol. Adv., 18:385-401 (2000).

(56) References Cited

OTHER PUBLICATIONS

Galfre et al., "Preparation of monoclonal antibodies: strategies and procedures," Methods in Enymology, 73:3-46 (1981).
Galfre et al., "Rat x rat hybrid myelomas and a monoclonal anti-Fd portion of mouse IgG," Nature, 277:131-133 (1979).
Genestier et al., "Caspase-dependent Ceramide Production in Fas- and HLA Class I-mediated Peripheral T Cell Apoptosis," J. Biol. Chem., 273:5060-5066 (1998).
Genestier et al., "Antibodies to HLA Class 1 α1 Domain Trigger Apoptosis of CD40-Activated Human B Lymphocytes," Blood, 90:726-735 (1997).
Genestier et al., "Fas-Independent Apoptosis of Activated T Cells Induced by Antibodies to the HLA Class I α1 Domain," Blood, 90:3629-3639 (1997).
Genestier et al., "T cell sensitivity to HLA class I-mediated apoptosis is dependent on interleukin-2 and interleukin-4," Eur. J. Immunol., 27:495-499 (1997).
Ghetie et al., "Homodimerization of tumor-reactive monoclonal antibodies markedly increases their ability to induce growth arrest or apoptosis of tumor cells," Proc. Natl. Acad. Sci. USA, 94:7509-7514 (1997).
Giusti et al., "Somatic diversification of S107 from an antiphosphocholine to an anti-DNA autoantibody is due to a single base change in its heavy chain variable region," Proc. Natl. Acad. Sci. USA, 84:2926-2930 (1987).
Goel et al., "99mTc-Labeled Divalent and Tetravalent CC49 Single-Chain Fv's: Novel Imaging Agents for Rapid in Vivo Localization of Human Colon Carcinoma," J. Nucl. Med., 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," Cancer Res., 60:6964-6971 (2000).
Goto et al., "A Novel Membrane Antigen Selectively Expressed on Terminally Differentiated Human B Cells," Blood, 84:1922-1930 (1994).
Granziero et al., "Adoptive immunotherapy prevents prostate cancer in a transgenic animal model," Eur. J. Immunol., 29:1127-1138 (1999).
Greenspan et al., "Defining epitopes: It's not as easy as it seems," Nature Biotechnology, 17:936-937 (1999).
Grell et al., "TR60 and TR80 tumor necrosis factor (TNF)-receptors can independently mediate cytolysis," Lymphokine and Cytokine Research, 12(3):143-148 (1993).
Griffith et al., "Functional Analysis of TRAIL Receptors Using Monoclonal Antibodies," J. Immunol., 162:2597-2605 (1999).
Gossow and Seemann, "Humanization of Monoclonal Antibodies," Methods in Enzymology, 203:99-121 (1991).
Higa et al., "Administration of anti-interleukin 18 antibody fails to inhibit development of dermatitis in atopic dermatitis-model mice NC/Nga," Br. J. Dermatol., 149(1):39-45 (2003).
Holliger el at., "Specific Killing of Lymphoma Cells by Cytotoxic T-Cells Mediated by a Bispecific Diabody," Protein Engineering, 9(3):299-305 (1996).
Holliger et al., "'Diabodies': Small bivalent and bispecific antibody fragments," Proc. Natl. Acad. Sci. USA, 90:6444-6448 (1993).
Holm et al., "Functional mapping and single chain construction of the anti-cytokeratin 8 monoclonal antibody TS1," Molecular Immunology, 44:1075-1084 (2007).
Hopp et al., "A Short Polypeptide Marker Sequence Useful for Recombinant Protein Identification and Purification," Biotechnology, 6:1204-1210 (1988).
Horan et al., "Dimerization of the extracellular domain of granuloycte-colony stimulating factor receptor by ligand binding: a monovalent ligand induces 2:2 complexes," Biochemistry, 35:4886-4896 (1996).
Hu et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res., 56:3055-3061 (1996).
Huston et al., "Protein Engineering of Antibody Binding Sites: Recovery of Specific Activity in an Anti-Digoxin Single-Chain Fv Analogue Produced in Escherichia coli," Proc. Natl. Acad. Sci. USA, 85:5879-5883 (1988).
Ichikawa et al., "Tumoricidal activity of a novel anti-human DR5 monoclonal antibody without hepatocyte cytotoxicity," Nat. Med., 7:954-960 (2001).
Itoh et al., "The Polypeptide Encoded by the cDNA for Human Cell Surface Antigen Fas Can Mediate Apoptosis," Cell, 66:233-243 (1991).
Jalili et al., "Multi-Drug Resistant Leukemic Cells Highly Express HLA Class I Molecules and Single-Chain Fv Diabody Specific to HLA-A Overcomes Drug Resistance in These Cells," Blood (ASH Annual Meeting Abstracts), 118(11):701a-702a (#2376) (2007).
Jiang et al., "A Novel Peptide Isolated from a Phage Display Peptide Library with Trastuzumab Can Mimic Antigen Epitope of HER-2," J. Biol. Chem., 280(6):4656-4662 (2005).
Jones et al., "Rapid PCR-Cloning of Full-Length Mouse Immunoglobulin Variable Regions," Biotechnology, 9:88-89 (1991).
Kaushansky, "Lineage-specific hematopoietic growth factors," N. Engl. J. Med., 354(19):2034-45 (2006).
Kearney, et al., "A New Mouse Myeloma Cell Line That Has Lost immunoglobulin Expression But Permits the Construction of Antibody-Secreting Hybrid Cells Lines," The Journal of Immunology, 123(4):1548-1550 (1979).
Keen et al., "The use of serum-free medium for the production of functionally active humanized monoclonal antibody from NSO mouse myeloma cells engineered using glutamine synthetase as a selectable marker," Cytotechnology, 18(3):207-217 (Abstract) (1994).
Khalifa et al., "Effects on interaction kinetics of mutations at the VH-VL interface of Fabs depend on the structural context," J. Mol. Recognit., 13(3):127-39 (2000).
Kikuchi et al., "A bivalent single-chain Fv fragment against CD47 induces apoptosis for leukemic cells," Biochem. Biophys. Res. Commum, 315:912-918 (2004).
Kimura et al., "2D7 diabody bound to the α2 domain of HLA class I efficiently induces caspase-independent cell death against malignant and activiated lymphoid cells," Biochem. Biophys. Res. Commun., 325:1201-1209 (2004).
Kipriyanov et al., "Bispecific tandem diabody for tumor therapy with improved antigen binding and pharmacokinetics," Journal of Molecular Biology, 293:41-56 (1999).
Kohler, et al., "Derivation of specific antibody-producing tissue culture and tumor lines by cell fusion," Eur. J. Immunol., 6:511-519 (1976).
Kong et al., "A Single Residue, Aspartic Acid 95, in the o Opioid Receptor Specifies Selective High Affinity Agonist Binding," The Journal of Biological Chemistry, 268(31):23056-23058 (1993).
Kortt et al., "Dimeric and trimeric antibodies: high avidity scFvs for cancer targeting," Biomol. Eng., 18:95-108 (2001).
Kortt et al., "Recombinant anti-sialidase single-chain variable fragment antibody: Characterization, formation of dimmer and higher-molecular-mass multimers and the solution of the crystal structure of the single-chain variable fragment/sialidase complex," Eur. J. Biochem., 221:151-157 (1994).
Kortt et al., "Single-chain Fv fragments of anti-neuraminidase antibody NC10 containing five- and ten- residue linkers form dimmers and with zero-residue linker a trimer," Protein Engineering, 10(4):423-433 (1997).
Kozak, M., "At Least Six Nucleotides Preceding the AUG Initiator Codon Enhance Translation in Mammalian Cells," J. Mol. Biol., 196:947-950 (1987).
Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," Clin. Cancer Res., 6:1476-1487 (2000).
Kulkarni et al., "Construction of a Single-Chain Antibody Derived From 5H7, a Monoclonal Antibody Specific for a Death Signaling Domain of Human Class I Major Histocompatibility Complex," Transplant. Proc., 30:1081 (1998).

(56) References Cited

OTHER PUBLICATIONS

Kulkarni et al., "Programmed Cell Death Signaling Via Cell-Surface Expression of a Single-Chain Antibody Transgene," Transplantation, 69:1209-1217 (2000).

Larrick, et al., "Polymerase Chain Reaction Using Mixed Primers: Cloning of Human Monoclonal Antibody Variable Region Genes From Single Hybridoma Cells," Biotechnology, 7:934-938 (1989).

Law et al., "Observations on the Effect of a Folic-Acid Anatagonist on Transplantable Lymphoid Leukemias in Mice," Journal of the National Cancer Institute, 10:179-193 (1949).

Lazar et al., "Transforming growth factor a: mutation of aspartic acid 47 and leucine 48 results in different biological activities," Molecular and Cellular Biology, 8:1247-1252 (1988).

Le Gall et al., "Effect of linker sequences between the antibody variable domains on the formation, stability and biological activity of a bispecific tandem diabody," Protein Engineering Design & Selection, 17(4):357-366 (2004).

Lebrun et al., "Antibodies to the Extracellular Receptor Domain Restore the Hormone-insensitive Kinase and Conformation of the Mutant Insulin Receptor Valine 382," J. Biol. Chem., 268:11272-11277 (1993).

Ledbetter et al., "Agonistic Activity of a CD4O-Specific Single-Chain Fv Constructed from the Variable Regions of mAb G28-5," Critical Reviews in Immunology, 17:427-435 (1997).

Lei et al., "Characterization of the Erwinia Carotovora pelB Gene and Its Product Pectate Lyase," Journal of Bacterioloqy, 169:4379-4383 (1987).

Li et al., "The Epitope Specificity and Tissue Reactivity of Four Murine Monoclonal Anti-CD22 Antibodies," Cell. Immunol., 118:85-99 (1989).

Lindberg et al., "Molecular Cloning of Integrin-Associated Protein: An Immunoglobulin Family Member with Multiple Membrane-Spanning Domains Implicated in αvβ3-Dependent Ligand Binding," The Journal of Cell Biology, 123 (2):485-496, The Rockefeller University Press (1993).

Lindberg et al., "Rh-Related Antigen CD47 is the Signal-Transducer Integrin-Associated Protein," J. Biol. Chem., 269:1567-1570 (1994).

MacCallum et al., "Antibody-antigen independent interactions: contact analysis and binding site topography," Journal of Molecular Biology, 262:732-745 (1996).

Margulies et al., "Somatic Cell Hybridization of Mouse Myeloma Cells," Cell, 8:405-415 (1976).

Mariuzza et al., "The Structural Basis of Antigen-Antibody Recognition," Ann. Rev. Biophys. Biophys. Chem., 16:139-159 (1987).

Marsters et al., "A Novel Receptor for Apo2L/TRAIL Contains a Truncated Death Domain," Curr. Biol., 7:1003-1006 (1997).

Mateo et al., "CD47 ligation induces caspase-independent cell death in chronic lymphocytic leukemia," Nat. Med., 5(11):1277-1284 (1999).

Mateo et at al., "Induction of Apoptosis in B-Cells From Chronic Lymphocytic Leukemia (B-CLLs) by CD47," FASEB Journal, 12(5):A1082 (1998).

Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," J. Exp. Med., 198:497-503 (2003).

Matsuoka et al., "A Novel Type of Cell Death of Lymphocytes Induced by a Monoclonal Antibody without Participation of Complement," J. Exp. Med., 181:2007-2015 (1995).

Mawby et al., "Isolation and characterization of CD47 glycoprotein: a multispanning membrane protein which is the same as integrin-associated protein (IAP) and the ovarian tumor marker OA3," Biochem. J., 304:525-530 (1994).

McInnes and Schett, "Cytokines in the pathogenesis of rheumatoid arthritis," Nature Reviews/Immunology, 7:429-442 (2007).

Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).

Melguizo et al., "Modulation of HLA class I expression in multidrug-resistant human rhabdomyosarcoma cells," Neoplasma, 50(2):91-96 (2003).

Methia et al., "Oligodeoxynucleotides Antisense to the Proto-Oncogene c-Mpl Specifically Inhibit in Vitro Megakaryocytopoiesis," Blood, 82(5):1395-1401 (1993).

Milili et al., "The VDJ Repertoire Expressed in Human preB Cells Reflects the Selection of Bona Fide Heavy Chains," Eur. J. Immunol., 26:63-69 (1996).

Milligan, "G Protein-Coupled Receptor Dimerization: Function and Ligand Pharmacology," Mol. Pharm., 66:1-7 (2004).

Miyazaki et al., "Future Prospects of Thrombopoietin," Jpn. J. Transfusion Medicine, 46(3):311-316 (2000) [English translation included].

Mizushima et al., "pEF-BOS, a Powerful Mammalian Expression Vector," Nucleic Acids Research, 18(17):5322 (1990).

Mori et al., "Human normal hepatocytes are suspectible to apoptosis signal mediated by both TRAIL-R1 and TRAIL-R2," Cell Death and Differentiation, 11:203-207 (2004).

Mulligan et al., "Synthesis of Rabbit β-Globin in Cultured Monkey Kidney Cells Following Infection with a SV40 β-Globin Recombinant Genome," Nature, 277:108-114 (1979).

Nakamura et al., "A novel non-peptidyl human c-Mpl activator stimulates human megakaryopoiesis and thrombopoiesis," Blood, 107(11):4300-4307 (2006). Epub DOI 10.1182/blood-2005-11-4433 (2006).

Nakamura et al., "A Novel Non-Peptidyl Human C-Mpl Agonist, NIP-004, Stimulates Human Megakaryopoiesis and Thrombopoiesis," Blood (ASH Annual Meeting Abstracts), Abstract 3148 (2005).

Nagayama et al., "Transient hematopoietic stem cell rescue using umbilical cord blood for a lethally irradiated nuclear accident victim," Bone Marrow Transplant. 29(3):197-204 (2002).

Nakayama et al., "Thrombocytosis in preterm infants: a possible involvement of thrombopoietin receptor gene expression," Journal of Molecular Medicine, 83:316-320 (2005).

O'Brien et al., "Monoclonal antibodies for the human insulin receptor stimulate intrinsic receptor-kinase activity," Biochim. Soc. Trans., 14(6):1021-1023 (1986).

Ohtomo et al., "Molecular Cloning and Characterization of a Surface Antigen Preferentially Overexpressed on Multiple Myeloma Cells," Biochem. Biophys. Res. Commun., 258:583-591 (1999).

Ohtsuka et al., "Synergistic induction of tumor cell apoptosis by death receptor antibody and chemotherapy agent through JNK/p38 and mitochondrial death pathway," Oncogene, 22:2034-2044 (2003).

Oka, "Development of Novel Immunotoxin Using Recombinant Alpha-Sarcin and Its Application Treatment of Hematopoietic Tumor," Sankyo Seimei Kagaku Kenkyu Shinko Zaidan Kenkyu Hokokushu, 12:46-56 (1998).

Ono et al., "The humanized anti-HM1.24 antibody effectively kills multiple myeloma cells by human effector cell-mediated cyto-toxicity," Mol. Immunol., 36:387-395 (1999).

Ozaki et al., "A recombinant HLA class I-specific single chain Fv diabody induces cell death in human lymphoid malignancies," 45th Annual Meeting of the American Society of Hematology, San Diego, CA, USA (Dec. 6-9, 2003).

Ozaki et al., "A Recombinant HLA Class I-Specific Single Chain Fv Diabody Induces Cell Death in Human Lymphoid Malignancies," Blood, 102:933a, Abstract No. 3474 (2003).

Ozaki et al., "Humanized Anti-HM1.24 Antibody Mediates Myeloma Cell Cytotoxicity That Is Enhanced by Cytokine Stimulation of Effector Cells," Blood, 93:3922-3930 (1999).

Ozaki et al., "Immunotherapy of Multiple Myeloma With a Monoclonal Antibody Directed Against a Plasma Cell-Specific Antigen, HM1.24," Blood, 90:3179-3186 (1997).

Ozaki et al., "Induction of myeloma cell death by a recombinant HLA class I-specific single-chain Fv diabody," Dai 65 Nihon Ketsueki Gakkai, Dai 45 kai Nihon Ketsueki Gakkai Sokai, Osaka (Aug. 28-31, 2003).

Pan et al., "An Antagonist Decoy Receptor and a Death Domain-Containing Receptor for TRAIL," Science, 277:815-818 (1997).

Pan et al., "The Receptor for the Cytotoxic Ligand TRAIL," Science, 276:111-113 (1997).

(56) References Cited

OTHER PUBLICATIONS

Paul, Fundamental Immunology, 3rd Edition, Raven Press, NY, Chapter 8, pp. 292-295 (1993).
Paul, Fundamental Immunology, Raven Press, NY, Chapter 8, p. 242 (1993).
Pettersen et al., "CD47 Signals T Cell Death," J. Immunol., 7031-7040 (1999).
Pettersen et al., "Role of the TCR Binding Region of the HLA Class I alpha2 Domain in Regulation of Cell Adhesion and Proliferation," J. Immunol., 156:1415-1424 (1996).
GenBank: U27005.1, *Mus musculus*, isolate 7183Liv, Vh7183 Ig heavy chain variable region gene, Vh region, partial cds, 1 page (Apr. 1996).
GenBank: AY081858.1, *Mus musculus*, isolate H3-9 anti-GBM immunoglobulin kappa chain variable region mRNA, partial cds, 1 page (Mar. 2004).
Loffler, "A recombinant bispecific single-chain antibody, CD19×CD3, induces rapid and high lymphoma-directed cytotoxicity by unstimulated T lymphocytes," *Blood*, 95(6):2098-2103 (2000).
International Search Report for App. Ser. No. PCT/JP2004/008585, mailed Sep. 7, 2004, 4 pages.
International Preliminary Report on Patentability for App. Ser. No. PCT/JP2004/008585, dated Apr. 15, 2005, 16 pages.
USPTO Non-Final Office Action in U.S. Appl. No. 11/916,351, mailed Mar. 3, 2011, 11 pages.
USPTO Non-Final Office Action in U.S. Appl. No. 10/530,696, mailed Jan. 7, 2011, 10 pages.
Fish & Richardson, Amendment in Reply to Action dated Jan. 7, 2011 in U.S. Appl. No. 10/530,696, filed Jun. 2, 2011, 5 pages.
International Preliminary Report on Patentability for App. Ser. No. PCT/JP2004/018506, dated Sep. 14, 2006, 9 pages.
Fish & Richardson P.C., Reply to Restriction Requirement dated Dec. 15, 2010 in U.S. Appl. No. 12/874,872, filed Jan. 18, 2011, 8 pages.
Fish & Richardson P.C., Amendment in Reply to Action dated Dec. 9, 2010 in U.S. Appl. No. 10/582,304, filed May 27, 2011, 5 pages.
USPTO Notice of Allowance in U.S. Appl. No. 10/551,504, mailed Mar. 21, 2011, 7 pages.
Fish & Richardson P.C., Amendment in Reply to Action dated Dec. 3, 2010 in U.S. Appl. No. 11/916,981, filed Jun. 2, 2011, 18 pages.
USPTO Restriction Requirement in U.S. Appl. No. 10/582,176, mailed Oct. 19, 2009, 6 pages.
Fish & Richardson P.C., Response to Restriction Requirement dated Oct. 19, 2009 in U.S. Appl. No. 10/582,176, filed Nov. 4, 2009, 1 page.
USPTO Non-Final Office Action in U.S. Appl. No. 10/582,176, mailed Jan. 25, 2010, 7 pages.
Fish & Richardson P.C., Amendment in Reply to Action dated Jan. 25, 2010 in U.S. Appl. No. 10/582,176, filed Jul. 23, 2010, 11 pages.
USPTO Final Office Action in U.S. Appl. No. 10/582,176, mailed Oct. 29, 2010, 11 pages.
Fish & Richardson P.C., Amendment in Reply to Action dated Oct. 29, 2010 in U.S. Appl. No. 10/582,176, filed Apr. 28, 2011, 10 pages.
International Search Report for App. Ser. No. PCT/JP2004/018499, mailed Jan. 18, 2005, 2 pages.
International Preliminary Report on Patentability for App. Ser. No. PCT/JP2004/018499, dated Jan. 26, 2006, 5 pages.
USPTO Restriction Requirement in U.S. Appl. No. 10/582,413, mailed Jan. 4, 2008, 8 pages.
Fish & Richardson P.C., Response to Restriction Requirement dated Jan. 4, 2008 in U.S. Appl. No. 10/582,413, filed Feb. 4, 2008, 2 pages.
USPTO Non-Final Office Action in U.S. Appl. No. 10/582,413, mailed Mar. 31, 2008, 17 pages.
Fish & Richardson P.C., Amendment in Reply to Action dated Mar. 31, 2008 in U.S. Appl. No. 10/582,413, filed Jun. 30, 2008, 20 pages.
USPTO Interview Summary in U.S. Appl. No. 10/582,413, mailed Jun. 30, 2008, 2 pages.
USPTO Notice of Informal or Non-Responsive Amendment in U.S. Appl. No. 10/582,413, mailed Oct. 20, 2008, 3 pages.
USPTO Interview Summary in U.S. Appl. No. 10/582,413, mailed Nov. 12, 2008, 4 pages.
Fish & Richardson P.C., Amendment in Reply to Notice of Informal or Non-Responsive Amendment dated Oct. 20, 2008 in U.S. Appl. No. 10/582,413, filed Nov. 17, 2008, 10 pages.
USPTO Interview Summary in U.S. Appl. No. 10/582,413, mailed Nov. 25, 2008, 4 pages.
USPTO Interview Summary in U.S. Appl. No. 10/582,413, mailed Dec. 24, 2008, 4 pages.
USPTO Restriction Requirement in U.S. Appl. No. 10/582,413, mailed Mar. 11, 2009, 8 pages.
Fish & Richardson P.C., Response to Restriction Requirement dated Mar. 11, 2009 in U.S. Appl. No. 10/582,413, filed Apr. 8, 2009, 8 pages.
USPTO Final Office Action in U.S. Appl. No. 10/582,413, mailed Jun. 25, 2009, 28 pages.
USPTO Interview Summary in U.S. Appl. No. 10/582,413, mailed Oct. 27, 2009, 4 pages.
USPTO Interview Summary in U.S. Appl. No. 10/582,413, mailed Dec. 2, 2009, 4 pages.
USPTO Non-Final Office Action in U.S. Appl. No. 10/582,413, mailed Apr. 16, 2010, 27 pages.
Fish & Richardson P.C., Amendment in Reply to Action dated Apr. 16, 2010 in U.S. Appl. No. 10/582,413, filed Oct. 15, 2010, 11 pages.
USPTO Final Office Action in U.S. Appl. No. 10/582,413, mailed Dec. 23, 2010, 12 pages.
International Search Report for App. Ser. No. PCT/JP2004/018493, mailed Mar. 22, 2005, 2 pages.
International Preliminary Report on Patentability for App. Ser. No. PCT/JP2004/018493, dated Dec. 20, 2005, 7 pages.
European Search Report for App. Ser. No. EP 04 82 0305, dated Oct. 6, 2008, 3 pages.
Fish & Richardson P.C., Amendment and Response to Restriction Requirement mailed May 3, 2010 in U.S. Appl. No. 11/910,117, filed Nov. 2, 2010, 11 pages.
USPTO Non-Final Office Action in U.S. Appl. No. 11/910,117, mailed Jan. 24, 2011, 10 pages.
Fish & Richardson P.C., Amendment in Reply to Action dated Jan. 24, 2011 in U.S. Appl. No. 11/910,117, filed Jun. 23, 2011, 20 pages.
Beresford et al., "Binding Characteristics and Tumor Targeting of a Covalently Linked Divalent CC49 Single-Chain Antibody," Int. J. Cancer, 81:911-917 (1999).
Borden et al., "Lymphokines and Cytokines as Cancer Treatment," Cancer, 65:800-814 (1990).
Byers, "What Can Randomized Controlled Trials Tell us About Nutrition and Cancer Prevention?," CA Cancer J. Clin., 49:353-361 (1999).
Carpenter et al., "Rational design of stable lyophilized protein formulations: some practical advice," Pharmaceutical Research, 14(8):969-975 (1997).
Carpenter et al., "Rational design of stable lyophilized protein formulations: theory and practice," Pharma Biotechnol., 13:109-133 (2001).
Chowdhury et al., "Engineering scFvs for improved stability," Methods Mol. Biol., 207:237-54 (2003).
Cleland et al., "A specific molar ratio of stabilizer to protein is required for storage stability of a lyophilized monoclonal antibody," Journal of Pharmaceutical Sciences, 90(3):310-321 (2001).
Daniel et al., "Pathway of apoptosis induced in Jurkat T Lymphoblasts by anti-HLA Class I antibodies," Human Immunology, 65(3):189-199 (2004).
Frokjaer et al., "Protein drug stability: a formulation challenge," Nature Rev Drug Discov. 4:298-306 (2005).
Garcia-Gonzalez et al., "Purification of murine IgG3 and IgM monoclonal antibodies by euglobulin precipitation," Journal of Immunological Methods, 111:17-23 (1988).
Gombotz et al., "The stabilization of a human IgM monoclonal antibody with poly(vinylpyrrolidone)," Pharmaceutical Research, 11(5):624-632 (1994).
Hudson et al., "High avidity scFv multimers; diabodies and triabodies," J. Immunol. Methods, 231:177-189 (1999).

(56) References Cited

OTHER PUBLICATIONS

Jung et al., "The importance of framework residues H6, H7 and H10 in antibody heavy chains: experimental evidence for a new structural subclassification of antibody V(H) domains," J. Mol. Biol., 309(3):701-16 (2001).
Lee et al., "Reversible dimer formation and stability of the anti-tumour single chain Fv antibody MFE-23 by neutron scattering, analytical ultracentrifugation, and NMR and FR-IR spectroscopy," J. Mol. Biol., 320:107-127 (2002).
Lin et al., "Structure-function relationships in glucagon: properties of highly purified des-His-1-, monoiodo-, and (des-Asn-28, Thr-29)(homoserine lactone-27)-glucagon," Biochemistry, 14:1559-1563 (1975).
Martsev et al., "Antiferritin single-chain antibody: a functional protein with incomplete folding?" FEBS Letters, 441:458-462 (1998).
Schwartz et al., "A superactive insulin: [B10-aspartic acid]insulin(human)," Proc. Natl. Acad. Sci. U.S.A., 84:6408-6411 (1987).
Sekimoto et al., "A Single-Chain Fv Diabody Against Human Leukocyte Antigen-A Molecules Specifically Induces Myeloma Cell Death in the Bone Marrow Environment," Cancer Res., 67(3):1184-1192 (2007).
Sharma et al., "Study of IgM aggregation in serum of patients with macroglobulinemia," Clin Chem Lab Med, 38(8):759-764 (2000).
Wang et al., "Instability, stabilization, and formulation of liquid protein pharmaceuticals," International Journal of Pharmaceutics, 185:129-188 (1999).
Wang et al., "Lyophilization and developemtn of solid protein pharmaceuticals," International Journal of Pharmaceutics, 203:1-60 (2000).
Wang et al., "Protein aggregation and its inhibition in biopharmaceutics," International Journal of Pharmaceutics, 289:1-30 (2005).
USPTO Restriction Requirement in U.S. Appl. No. 11/916,351, mailed Sep. 3, 2010, 8 pages.
European Search Report for App. Ser. No. EP 06 75 7198, dated Jun. 11, 2010, 2 pages.
International Search Report for App. Ser. No. PCT/JP2006/311625, mailed Aug. 22, 2006, 2 pages.
International Preliminary Report on Patentability for App. Ser. No. PCT/JP2006/311625, dated Dec. 11, 2007, 4 pages.
USPTO Restriction Requirement in U.S. Appl. No. 11/916,981, mailed Mar. 31, 2010, 5 pages.
Fish & Richardson P.C., Response to Restriction Requirement dated Mar. 31, 2010 and Preliminary Amendment in U.S. Appl. No. 11/916,981, filed Sep. 29, 2010, 6 pages.
Alexander et al., "Studies of the c-Mpl Thrombopoietin Receptor through Gene Disruption and Activation," Stem Cells, 14(suppl 1):124-132 (1996).
Arndt et al., "Factors Influencing the Dimer to Monomer Transition of an Antibody Single-Chain Fv Fragment," Biochemistry, 37:12918-12926 (1998).
Avent et al., "Monoclonal antibodies that recognize different membrane proteins that are deficient in Rhnull human erythrocytes. One group of antibodies reacts with a variety of cells and tissues whereas the other group is erythroid-specific," Biochem. J., 251:499-505 (1988).
Ballmaier et al., "c-mpl mutations are the cause of congenital amegakaryocytic thrombocytopenia," Blood, 97:139-146 (2001).
Bartley et al., "Identification and Cloning of a Megakaryocyte Growth and Development Factor That is a Ligand for the Cytokine Receptor Mpl," Cell, 77:1117-1124 (1994).
Bazil et al., "Apoptosis of human hematopoietic progenitor cells induced by crosslinking of surface CD43, the major sialoglycoprotein of leukocytes," Blood, 86:502-511 (1995).
Bazzoni et al., "Chimeric tumor necrosis factor receptors with constitutive signaling activity," Proc. Natl. Acad. Sci. USA, 92(12):5376-5580 (1995).

Berger et al., "Inhibition of intractable nucleases with ribonucleoside-vanadyl complexes: isolation of messenger ribonucleic acid from resting lymphocytes," Biochemistry, 18(23):5143-5149 (1979).
Bodmer et al., "TRAIL Receptor-2 Signals Apoptosis Through FADD and Caspase-8," Nat. Cell Biol., 2:241-243 (2000).
Boger et al., "Cytokine receptor dimerization and activation: prospects for small molecule agonists," Bioorganic and Medicinal Chemistry, 9(3):557-562 (2001).
Brinkmann et al., "FTY720: targeting G-protein-coupled receptors for sphingosine 1-phosphate in transplantation and autoimmunity," Curr. Opin. Immunol., 14:569-575 (2002).
Brooke et al., "Human lymphocytes interact directly with CD47 through a novel member of the signal regulatory protein (SIRP) family," J. Immunol., 173:2562-2570 (2004).
Brown et al., "Integrin-associated protein (CD47) and its ligands," Trends Cell Biology, 11(3):130-135 (2001).
Brown et al. "Integrin-associated protein: a 50-kD plasma membrane antigen physically and functionally associated with integrins," J. Cell Biology, 111(6 Pt 1):2785-2794 (1990).
Bruenke et al., "A recombinant bispecific single-chain Fv antibody against HLA class II and FcγRIII (CD16) triggers effective lysis of lymphoma cells," Br. J. Haematol., 125:167-179 (2004).
Buchsbaum et al., "Antitumor Efficacy of TRA-8 Anti-DR5 Monoclonal Antibody Alone or in Combination with Chemotherapy and/or Radiation Therapy in a Human Breast Cancer Model," Clin. Cancer Res., 9:3731-3741 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol., 111:2129-2138 (1990).
Burrone et al., "Stimulation of HLA-A,B,C by IFN-alpha. The derivation of Molt 4 variants and the differential expression of HLA-A,B,C subsets," The EMBO Journal, 4(11):2855-2860 (1985).
Burthem et al., "Hairy cell interactions with extracellular matrix: expression of specific integrin receptors and their role in the cell's response to specific adhesive proteins," Blood, 84(3):873-882 (1994).
Caldas et al., "Humanization of the anti-CD18 antibody 6.7: an unexpected effect of a framework residue in binding to antigen," Mol. Immunol., 39:941-952 (2003).
Cangemi et al., "IFN-alpha mediates the up-regulation of HLA class I on melanoma cells without switching proteasome to immunoproteasome," International Immunology, 15(12):1415-1421 (2005).
CAPLUS Accession No. 2005:547624, 2 pages (2008).
Arndt et al., "Antigen binding and stability properties of non-covalently linked anti-CD22 single-chain Fv dimers," *FEBS Lett.*, 578(3):257-261 (2004).
Bork et al., "The immunoglobulin fold. Structural classification, sequence patterns and common core," *J. Mol. Biol.*, 242(4):309-320 (1994).
Colcher et al., "Single-chain antibodies in pancreatic cancer," *Ann N Y Acad. Sci.*, 880:263-280 (1999).
USPTO Final Office Action in U.S. Appl. No. 11/916,981, mailed Feb. 28, 2014, 6 pages.
Fish & Richardson P.C., Amendment in Reply to Action dated Nov. 8, 2012 in U.S. Appl. No. 11/910,117, filed May 7, 2013, 18 pages.
Albrecht et al., "Production of soluble ScFvs with C-terminal-free thiol for site-specific conjugation or stable dimeric ScFvs on demand," *Bioconjug. Chem.*, 15:16-26 (2004).
Columbia Encyclopedia, "Structural Isomers," 3 pages (2013).
USPTO Final Office Action in U.S. Appl. No. 11/910,117, mailed Jul. 2, 2013, 18 pages.
USPTO Non-Final Office Action in U.S. Appl. No. 11/910,117, mailed Nov. 8, 2012, 10 pages.
U.S. Appl. No. 11/916,981, filed Feb. 15, 2008.
U.S. Appl. No. 11/916,351, filed Aug. 7, 2008.
U.S. Appl. No. 10/582,176, filed Apr. 18, 2007.
U.S. Appl. No. 11/547,747, filed Jun. 11, 2007.
U.S. Appl. No. 10/582,304, filed Apr. 20, 2007.
U.S. Appl. No. 12/307,042, filed Jul. 21, 2009.

(56) References Cited

OTHER PUBLICATIONS

U.S. Appl. No. 13/497,545, filed Jun. 1, 2012.
Devito et al., "Epitope fine specificity of human anti-HLA-A2 antibodies. Identification of four epitopes including a haptenlike epitope on HLA-A2 at lysine 127," *Hum. Immunol.*, 37:165-177 (1993).
Heppner et al., "Tumor heterogeneity: biological implications and therapeutic consequences," *Cancer Metastasis Rev.*, 2:5-23 (1983).
Kornbluth et al., "Evidence for the role of class I and class II HLA antigens in the lytic function of a cloned line of human natural killer cells," *J. Immunol.*, 134:728-735 (1985).
Lozano et al., "Identification of the amino acid residues defining an intralocus determinant in the alpha 1 domain of HLA-A molecules," *Immunogenetics*, 30:50-53 (1989).
Spear et al., "Evidence for a shared HLA-A intralocus determinant defined by monoclonal antibody 131," *J. Exp. Med.*, 162:1802-1810 (1985).
Rowe et al., "Handbook of Pharmaceutical Excipients, 4$^{th}$ ed.," 381-382 (2003), Published by the Pharmaceutical Press and the American Pharmaceutical Association.
USPTO Non-Final Office Action in U.S. Appl. No. 11/916,981, mailed Oct. 1, 2013, 7 pages.
Kubo et al., "A human monoclonal antibody that detects HLA-Al, A23 and A24 antigens," *Tissue Antigens*, 41:186-189 (1993).
Mulder et al., "A human monoclonal antibody against HLA-Cwl and a human monoclonal antibody against an HLA-A locus determinant derived from a single uniparous female," *Tissue Antigens*, 52:393-396 (1998).
Scheinberg et al , "Inhibition of cell proliferation with an HLA-A-specific monoclonal antibody," *Tissue Antigens*, 38:213-223 (1991).
Wang et al., "Specificity and functional characteristics of anti-HLA-A mAbs LGIII-147.4.1 and LGIII-220.6.2," *Tissue Antigens*, 62:139-148 (2003).
Fish & Richardson P.C., Amendment in Reply to Action dated Sep. 12, 2011 in U.S. Appl. No. 11/916,981, filed May 8, 2012, 6 pages.
International Search Report for App. Ser. No. PCT/JP2010/066494, mailed Dec. 28, 2010, 6 pages.
International Preliminary Report on Patentability for App. Ser. No. PCT/JP2010/066494, dated Apr. 11, 2012, 8 pages.
Fish & Richardson P.C., Reply to Action dated Jul. 2, 2013 in U.S. Appl. No. 11/910,117, filed Dec. 20, 2013, 22 pages.
Fish & Richardson P.C., Amendment in Reply to Action dated Oct. 1, 2013 in U.S. Appl. No. 11/916,981, filed Dec. 30, 2013, 21 pages.
Armijos et al., "Comparison of the effectiveness of two topical paromomycin treatments versus meglumine antimoniate for New World cutaneous leishmaniasis," *Acta Trop.*, 91(2):153-60 (2004).
Friton et al., "Clinical efficacy of meloxicam (Metacam) and flunixin (Finadyne) as adjuncts to antibacterial treatment of respiratory disease in fattening cattle," *Berl. Munch Tierarztl. Wochenschr.*, 117(7-8):304-9 (2004).
Goyen et al., "Gadobenate dimeglumine (MultiHance) for magnetic resonance angiography: review of the literature," *Eur. Radiol.*, 13 Suppl 3:N19-27 (2003).
Grossman et al., "Multiple sclerosis: gadolinium enhancement in MR imaging," *Radiology*, 161(3):721-5 (1986).
Fish & Richardson P.C., Amendment in Reply to Action dated Oct. 28, 2011 in U.S. Appl. No. 11/916,351, filed Apr. 30, 2012, 28 pages.
Humes et al., "Direct toxic effect of the radiocontrast agent diatrizoate on renal proximal tubule cells," *Am. J. Physiol.*, 252(2):F246-F255 (1987).
Pettersen et al., "The TCR-Binding Region of the HLA Class I $\alpha_2$ Domain Signals Rapid Fas-Independent Cell Death: A Direct Pathway for T Cell-Mediated Killing of Target Cells?" *J. Immunol.*, 160:4343-4352 (1998).
Pettersen, "CD47 and death signaling in the immune system," *Apoptosis*, 5:299-306 (2000).
Piétri-Rouxel et al., "The biochemical effect of the naturally occurring Trp64→Arg mutation on human β3-adrenoceptor activity," *Eur. J. Biochem.*, 247:1174-1179 (1997).

Plückthun et al., "New protein engineering approaches to multivalent and bispecific antibody fragments," *Immunotechnology*, 3:83-105 (1997).
Prados et al., "Induction of drug resistance in embryonal rhabdomyosarcoma treated with conventional chemotherapy is associated with HLA class I increase," *Neoplasma*, 53(3):226-231 (2006).
Reff et al., "A review of modifications to recombinant antibodies: attempt to increase efficacy in oncology applications," *Critical Reviews in Oncology and Hematology*, 40:25-35 (2001).
Reinhold et al., "In vivo expression of alternatively spliced forms of integrin-associated protein (CD47)," *J Cell Science*, 108:3419-3425 (1995).
Reiter et al., "Engineering interchain disulfide bonds into conserved framework regions of Fv fragments: improved biochemical characteristics of recombinant immunotoxins containing disulfide-stabilized Fv," *Protein Engineering*, 7(5):697-704 (1994).
Reiter et al., "Stabilization of the Fv Fragments in Recombinant Immunotoxins by Disulfide Bonds Engineered into Conserved Framework Regions," *Biochemistry*, 33:5451-5459 (1994).
Retter et al., "Both Sm and DNA are Selecting Antigens in the Anti-Sm B Cell Response in Autoimmune MRL/lpr Mice," *J Immunol.*, 156:1296-1306 (1996).
Riechmann et al., "Reshaping Human Antibodies for Therapy," *Nature*, 332:323-327 (1988).
Rossi et al., "Development of New Multivalent-bispecific Agents for Pretargeting Tumor Localization and Therapy," *Clin. Cancer Res.*, 9:3886s-3896s (2003).
Roue et al. "Mitochondrial dysfunction in CD47-mediated caspase-independent cell death: ROS production in the absence of cytochrome c and AIF release," *Biochimie.*, 85:741-746 (2003).
Rozsnyay et al., "Phenylarsine oxide (PAO) blocks antigen receptor-induced calcium response and tyrosine phosphorylation of a distinct group of proteins," *Immunology Lett.*, 37(2-3):197-205 (1993).
Rudikoff et al., "Single amino acid substitution altering antigen-binding specificity," *Proceedings of the National Academy of Sciences*, 79:1979-1983 (1982).
Sackstein, "The lymphocyte homing receptors: gatekeepers of the multistep paradigm," *Current Opinion in Hematology*, 12:444-450 (2005).
Sato et al., "CD22 Is Both a Positive and Negative Regulator of B Lymphocyte Antigen Receptor Signal Transduction: Altered Signaling in CD22-Deficient Mice," *Immunity*, 5:551-562 (1996).
Sato et al., "Reshaping a Human Antibody to Inhibit the Interleukin 6-Dependent Tumor Cell Growth," *Cancer Research*, 53:851-856 (1993).
Scheurle et al., "Cancer Gene Discovery Using Digital Differential Display," *Cancer Res.*, 60:4037-4043 (2000).
Schickel, et al., "Gene for Integrin-Associated Protein (IAP, CD47): Physical Mapping, Genomic Structure, and Expression Studies in Skeletal Muscle," *Biochem. Cell. Biol.*, 80(2):169-176 (2002).
Schmidt et al., "A bivalent single-chain antibody-toxin specific for ErbB-2 and the EGF receptor," *Int. J. Cancer*, 65(4):538-546 (1996).
USPTO Final Office Action in U.S. Appl. No. 11/916,981, mailed Sep. 12, 2011, 10 pages.
USPTO Final Office Action in U.S. Appl. No. 11/910,117, mailed Sep. 9, 2011, 12 pages.
Fish & Richardson P.C., Amendment in Reply to Action dated Sep. 9, 2011 in U.S. Appl. No. 11/910,117, filed Mar. 9, 2012, 18 pages.
USPTO Final Office Action in U.S. Appl. No. 11/916,351, mailed Oct. 28, 2011, 10 pages.
USPTO Restriction Requirement in U.S. Appl. No. 12/307,042, mailed Dec. 6, 2011, 9 pages.
USPTO Notice of Allowance in U.S. Appl. No. 10/530,696, mailed Dec. 12, 2011, 8 pages.
Carrel et al., "Recognition of HLA-Al by murine monoclonal antibodies," *Tissue Antigens.*, 43:110-115 (1994).
USPTO Restriction Requirement in U.S. Appl. No. 13/497,545, dated Feb. 26, 2013, 8 pages.
Spada et al., "Reproducing the Natural Evolution of Protein Structural Features with the Selectively Infective Phage (SIP) Technology. The Kink in the First Strand of Antibody kappa Domains," *J. Mol. Biol.*, 283:395-407 (1998).

(56) References Cited

OTHER PUBLICATIONS

Wörn et al., "Different Equilibrium Stability Behavior of ScFv Fragments: Identification, Classification, and Improvement by Protein Engineering," *Biochemistry*, 38:8739-8750 (1999).

Fish & Richardson P.C., Amendment and Reply to Restriction Requirement dated Feb. 26, 2013 in U.S. Appl. No. 13/497,545, filed Jul. 26, 2013, 7 pages.

USPTO Office Action in U.S. Appl. No. 11/910,117, mailed Apr. 17, 2014, 10 pages.

Fish & Richardson P.C., Reply to Action dated Apr. 17, 2014 in U.S. Appl. No. 11/910,117, filed Sep. 16, 2014, 109 pages.

USPTO Interview Summary in U.S. Appl. No. 11/916,981, mailed Aug. 4, 2014, 3 pages.

Fish & Richardson P.C., Amendment in Reply to Final Office Action dated Feb. 28, 2014 in U.S. Appl. No. 11/916,981, filed Aug. 26, 2014, 7 pages.

Kashmiri et al., Generation, characterization, and in vivo studies of humanized anticarcinoma antibody CC49, *Hybridoma*, Oct. 1995;14(5):461-473.

McCall et al., "Isolation and characterization of an anti-CD16 single-chain Fv fragment and construction of an anti-HER2/neu/anti-CD16 bispecific scFv that triggers CD16-dependent tumor cytolysis," *Mol Immunol.*, May 1999;36:433-446.

Santos et al., "Generation and characterization of a single gene-encoded single-chain-tetravalent antitumor antibody," *Clin Cancer Res.*, Oct. 1999;5:3118s-3123s.

USPTO Final Office Action in U.S. Appl. No. 11/910,117, mailed Jan. 28, 2015, 20 pages.

\* cited by examiner

US 9,241,994 B2

PHARMACEUTICAL COMPOSITIONS CONTAINING SC(FV)2

CROSS-REFERENCE TO RELATED APPLICATIONS

This application is the National Stage of International Application No. PCT/JP2006/311600, filed on Jun. 9, 2006, which claims the benefit of Japanese Patent Application Serial No. 2005/171375, filed on Jun. 10, 2005, and International Application No. PCT/JP2006/306800, filed on Mar. 31, 2006. The contents of all of the foregoing applications are hereby incorporated by reference in their entireties.

TECHNICAL FIELD

The present invention relates to pharmaceutical compositions containing sc(Fv)2 and methods for producing such compositions. More specifically, the present invention relates to pharmaceutical compositions composed of an sc(Fv)2 molecule in which the isomerization reaction is suppressed, and methods for producing such compositions.

BACKGROUND ART sc(Fv)2 is a single chain antibody prepared by linking four variable regions, two light chain variable regions (VL) and two heavy chain variable regions (VH), using linkers and such (Hudson et al., J. Immunol. Methods 1999; 231:177-189).

For example, single chain antibodies having the sequence VH1-linker-VL2-linker-VH3-linker-VL4 or VL2-linker-VH1-linker-VL4-linker-VH3 are known in the art. Depending on the combination of Fvs (molecules in which VH and VL are noncovalently bound), the structure of sc(Fv)2 may exist as one of two types of conformational isomer: a first sc(Fv)2 in which VH1 and VL2, and VH3 and VL4 respectively form an Fv and a second sc(Fv)2 in which VH1 and VL4, and VH3 and VL2 respectively form an Fv.

However, to date, since studies on sc(Fv)2 had been mostly on bispecific sc(Fv)2, there are few if any reports on conformational isomers of sc(Fv)2.

Bispecific sc(Fv)2 is an sc(Fv)2 in which VH1 and VL4, and VH3 and VL2 (or VH1 and VL2, and VH3 and VL4) in the VH1-linker-VL2-linker-VH3-linker-VL4 sequence have variable regions derived from different monoclonal antibodies. In the case of bispecific sc(Fv)2, since VH1 and VL4, or VH3 and VL2 (or VH1 and VL2, or VH3 and VL4) are derived from the same monoclonal antibody, Fv formation is highly efficient and the occurrence of conformational isomers is thought to be to some extent suppressed. In fact, reports to date indicate the utilization of linker length (e.g., 15-5-15 or 15-15-15) in the production of bispecific sc(Fv)2 does not result in a difference in activity (Non-Patent Document 5). Therefore, for bispecific sc(Fv)2, oftentimes, details on conformational isomers are not mentioned. For example, Non-Patent Documents 3, 4, 8, and 9 indicate that correctly combined Fvs exist by confirming the bispecific binding activity; however, they do not provide any quantitative evaluation of the content ratio of the incorrect Fv combinations or the content ratio between the two. Non-Patent Document 6 confirms that monomer-dimer structural conversion resulting from changing the length of the linkers of bispecific sc(Fv)2 (modifying the length of the linkers at both ends or in the middle); however regarding the conformational isomers of sc(Fv)2, the discussion does not go beyond predictions of the molecular structural models. Accordingly, there is no description of the actual content ratio of conformational isomers in the sample or an identification of the structures.

Since conformational isomers of sc(Fv)2 have not been a focus of attention, the regulation of conformational isomers has also not been examined in detail. Non-Patent Document 10 predicts that by making the length of the linkers either 5-15-5 or 15-5-15, a single chain diabody or a bivalent scFv structure will be formed, respectively. This arises from the fact that when the length of a linker in scFv is 12 or less, adjacent VH and VL generally have difficulty in forming an Fv (that is, they difficultly form a monomer). However, it has been reported elsewhere (i.e., in Non-Patent Document 2) that monomers are formed with Fvs in which the linker length is 10 or 5, though in small amount. In fact, even Non-Patent Document 10 acknowledges that the sc(Fv)2 structures obtained using linker lengths of either 5-15-5 or 15-5-15 are not necessarily 100% single chain diabody or bivalent scFv.

As for conformational isomers, since reports made to date only provide predictions of structures arising from Fv combinations and linker lengths, quantitative analyses on the content ratio of conformational isomers and confirmations/demonstrations that the obtained structures are indeed the structures of interest or not have not been carried out. Thus, conformational isomers have not yet been sufficiently evaluated and regulated. Accordingly, in the context of sc(Fv)2 having any linker lengths, it is difficult to predict the content ratio of conformational isomers from Fv combinations and linker lengths. When sc(Fv)2-type molecules are composed of two sets of VH and VL, the existence of two conformational isomers is a problem that needs to be considered.

Regarding low-molecular-weight compounds, many methods for separating optical isomers and geometric isomers are known in the art; however, methods for separating protein isomers have not yet been reported. While numerous methods for separating proteins with one amino acid difference are reported in the literature, to date there have been no reports of methods for separating two conformational isomers possessing a completely identical primary amino acid sequence. Similarly, methods for separating and analyzing conformational isomers of sc(Fv)2, and for confirming the two types of conformational isomer of sc(Fv)2 are not found in the prior art to date.

Since methods for separating conformational isomers of sc(Fv)2 are not yet known in the art, there are accordingly no reports that focus on the differences in activity that arise between the two types of conformational isomers. In bispecific sc(Fv)2, a large difference in activity is easily predicted between correct Fv combinations and incorrect Fv combinations, depending on the conformational isomers. However, in monospecific sc(Fv)2, it is difficult to predict a difference in activity between conformational isomers that are similarly bivalent. In Non-Patent Document 10, the possibility that the activity of the two conformational isomers may differ is not considered; in fact, the activity (binding activity) was measured using a mixture of conformational isomers. This is due to the fact that it is difficult to separate and purify conformational isomers of sc(Fv)2. Accordingly, the conformational isomers could not be prepared in sufficiently high purity to permit a rigorous comparison of the activities.

For an sc(Fv)2 embodiment in which the linker lengths have been modified as well, it has to date been impossible to "identify", as opposed to making model predictions wherein each of the two conformational isomers are estimated from the linker lengths, or to quantitatively evaluate the content ratio of these conformational isomers. Therefore, quantitative examinations that elucidate the relationship between the sc(Fv)2 linker lengths and the content ratio of conformational isomers have not been carried out to date. Moreover, to date, there are no reports that substantially control the content ratio of conformational isomers by the linker lengths.

Since changing the linker length leads to an alteration in the distance between the two antigen binding sites of sc(Fv)2, the length of the linker(s) may influence the biological activity of the molecule (particularly agonistic activities such as those which dimerize receptors). Therefore, being able to arbitrarily adjust, depending on the type of antigen, the distance between two antigen binding sites by means of varied linker length is desirable. The linker length has been reported to significantly influence the stability (Non-Patent Documents 1 and 2), and in scFv, it is generally known that the shorter the linker, the lower the stability. It is considered to be similar in sc(Fv)2, and it has been reported that, by making the middle linker shorter, dimers are more easily formed (Non-Patent Document 6). To produce highly stable sc(Fv)2, it is desirable for the linker length to be arbitrarily adjustable. Therefore, when developing sc(Fv)2 as pharmaceuticals, being able to isolate the conformational isomer of interest with an arbitrary linker length is considered to be desirable. However, isolation of the two types of conformational isomer, the bivalent scFv and the single chain diabody, for an sc(Fv)2 having arbitrary linker lengths has not yet been reported.

It was previously reported that sc(Fv)2 of anti-human Mpl antibody show TPO-like agonistic activity; it was revealed that sc(Fv)2 has pharmaceutical utility (Non-Patent Document 12). To develop as pharmaceuticals sc(Fv)2 that include conformational isomers, it is necessary to separate and purify the conformational isomer of interest, and to produce a drug substance composed of only one of the conformational isomers; alternatively, when the drug substance is a mixture of conformational isomers, it is necessary to determine the properties of the two types of conformational isomer, and to carry out specification tests to quantitatively analyze the content ratio of each conformational isomer. However, to date, such methods for separating/purifying, quantitatively analyzing, and determining the structure of the conformational isomers of sc(Fv)2 are not known in the art.

Furthermore, while methods for regulating the content ratio of monomers/dimers/trimers/tetramers of scFv using the linker length have been reported in the literature, as noted above, since methods for quantitatively analyzing the conformational isomers of sc(Fv)2 have not been reported in the art, methods for regulating the content ratio of conformational isomers using the linker length are similarly not yet known.

[Non-Patent Document 1] Protein Engineering, 1993, 6(8), 989-995
[Non-Patent Document 2] Protein Engineering, 1994, 7(8), 1027-1033
[Non-Patent Document 3] Journal of Immunology, 1994, 152, 5368-5374
[Non-Patent Document 4] Journal of Immunology, 1995, 154, 4576-4582
[Non-Patent Document 5] PNAS, 1995, 92, 7021-7025
[Non-Patent Document 6] Journal of Molecular Biology, 1999, 293, 41-56
[Non-Patent Document 7] Protein Engineering, 2001, 14(10), 815-823
[Non-Patent Document 8] Journal of Molecular Biology, 2003, 330, 99-111
[Non-Patent Document 9] Protein Eng Des Sel. 2004 April; 17(4):357-66
[Non-Patent Document 10] Clinical Cancer Research, 2004, 10, 1274-1281
[Non-Patent Document 11] Int. J. Cancer, 1998, 77, 763-772
[Non-Patent Document 12] Blood, 2005, 105, 562-566

DISCLOSURE OF THE INVENTION

Problems to be Solved by the Invention

International Application PCT/JP06/306800 describes methods for separating and obtaining two types of conformational isomer found in sc(Fv)2 compositions, namely bivalent scFv and single chain diabodies. It further describes methods for identifying the structures of such separated conformational isomers and methods for quantitatively analyzing the two types of conformational isomer. Furthermore, methods for increasing the percentage of a specific conformational isomer in an sc(Fv)2 composition by adjusting the linker length are also described. Such methods enable the production of pharmaceutical compositions containing as an active ingredient a specific conformational isomer of sc(Fv)2. Such methods further enable the provision of pharmaceutical compositions having a higher than conventional activity. Furthermore, specification tests necessary for pharmaceutical development have enabled the provision as pharmaceutical compositions of sc(Fv)2 having a specified content ratio of conformational isomers having identified structures.

However, to develop as pharmaceuticals sc(Fv)2 that form two types of conformational isomer, the conformational isomer of interest must exist stably in the drug substance or formulation of pharmaceuticals. Generally, known pathways of protein degeneration include degeneration pathways that accompany physical association of protein molecules, such as formation of soluble multimers or production of precipitates/insoluble materials (Int. J. Pharm. 2005, 289, 1-30), and degeneration pathways caused by chemical modifications due to hydrolysis, a deamidation reaction, a methionine oxidation reaction, or such (Int. J. Pharm. 1999, 185, 129-188). When developing proteins as pharmaceuticals, it is necessary to provide formulations in which both of these degeneration pathways are minimized, and in which the biological activity of the protein(s) does not decrease during storage. Optimization of solution pH and optimization of the types and concentrations of buffer solutions/salts and stabilizers are examples of means for minimizing such degeneration pathways.

It was herein discovered that, in an sc(Fv)2 known to form two types of conformational isomer, there occurs a mutual structural conversion (isomerization) between the two isomers. More specifically, it was discovered that two conversion reactions take place, namely a first structural conversion reaction (isomerization reaction) in which a bivalent scFv type is converted to a single chain diabody type, and a second structural conversion reaction (isomerization reaction) in which a single chain diabody type is converted to a bivalent scFv type (FIG. 1). Monomer/dimer equilibrium reactions between two protein molecules have already been reported. For IgG molecules of antibodies, it was reported that monomers and dimers exist in a state of reversible equilibrium (Biochemistry, 1999, 38, 13960-13967). Regarding equilibrium reactions within a single molecule, it was reported that two types of CDR loop structures exist in a state of reversible equilibrium in a CDR region of an antibody IgG molecule (Science. 2003, 299(5611), 1362-7). This is a local isomerization reaction of the CDR site within the overall structure of the antibody, and, thus, these two isomers cannot be stably separated in a solution. It was further reported that the aspartic acid residue in the antibody IgG molecule isomerizes to an isoaspartic acid residue (Biochemistry, 1996, 35, 1897-1903). This is a chemical isomerization reaction of a single amino acid in the antibody, and thus constitutes an isomerization reaction associated with a change in the primary sequence of the protein. In contrast to such isomerization reactions, the mutual isomerization reaction of sc(Fv)2-type molecules described herein, characterized by an overall three-dimensional structural change of a single protein molecule, has not yet been reported. Thus, it is considered to be a reaction unique to sc(Fv)2, one not observed in conventional proteins. Suppression of this isomerization reaction is a primary objective in the formulation of sc(Fv)2.

Thus, when the activities of the bivalent scFv type and the single chain diabody type differ (for example, in humanized anti-human Mpl antibody hVB22B u2-wz4 sc(Fv)2 and mouse anti-human Mpl antibody mVB22B sc(Fv)2, the agonistic activity of the bivalent scFv type is significantly lower compared to the single chain diabody type: PCT/JP06/306800), isomerization reactions during storage of the formulation results in a change in activity. It is therefore revealed that in sv(Fv)2, in addition to the above-mentioned degradation pathways caused by associations and chemical modifications, there exists a degradation pathway caused by isomerization reactions, a process which has not been reported for conventional proteins. Even when the activities between the bivalent scFv type and the single chain diabody type are the same, progression of isomerization reactions during storage of the formulations results in a change in content ratio of the included conformational isomers before and after storage, a condition that is not preferable.

As discovered herein, the mutual isomerization reaction arising between conformational isomers of a sc(Fv)2-type molecule may take place in all sc(Fv)2-type molecules. Therefore, to develop sc(Fv)2-type molecules as pharmaceuticals, this isomerization reaction must be suppressed. However, to date, methods for suppressing such isomerization reactions have not been reported.

The present invention was achieved in view of the above circumstances. An objective of the present invention is to provide stabilized formulations and such that comprise sc(Fv)2 whose isomerization reaction has been suppressed.

Means for Solving the Problems

As a result of research dedicated to the solution of the above-mentioned problems, stabilizers/stabilization conditions for suppressing the isomerization reaction of sc(Fv)2 were herein discovered. It was further discovered that the above-mentioned isomerization reaction can be suppressed through the formation of freeze-dried formulations. Thus, by applying the discovered stabilizers/stabilization conditions or through the use of a freeze-dry formulation, to the present invention enables the suppression of the isomerization reactions of sc(Fv)2-type molecules, from the bivalent scFv type to the single chain diabody type and/or from the single chain diabody type to the bivalent scFv type, for both directions or for one direction.

Accordingly, the present invention provides:

[1] a pharmaceutical composition comprising an sc(Fv)2, to which at least one substance selected from the group consisting of salt, amino sugar, sugar alcohol, amino acid, and pH adjusting agent has been added;
[2] the pharmaceutical composition of [1], wherein the salt is at least one salt selected from the group consisting of sodium chloride and magnesium chloride;
[3] the pharmaceutical composition of [1], wherein the amino sugar is meglumine;
[4] the pharmaceutical composition of [1], wherein the sugar alcohol is mannitol;
[5] the pharmaceutical composition of [1], wherein the amino acid is lysine;
[6] the pharmaceutical composition of [1], wherein the pH adjusting agent is at least one pH adjusting agent selected from the group consisting of a sodium citrate buffer and histidine hydrochloride;
[7] a pharmaceutical composition comprising an sc(Fv)2, wherein the pH is 4.5 to 9.0;
[8] a pharmaceutical composition comprising an sc(Fv)2, wherein the pH is 6.0 to 9.0;
[9] a pharmaceutical composition comprising an sc(Fv)2, wherein the salt concentration is 50 mM to 1000 mM;
[10] the pharmaceutical composition of any one of [1] to [9], wherein the dosage form is a freeze-dried formulation;
[11] a pharmaceutical composition comprising an sc(Fv)2, wherein the dosage form is a freeze-dried formulation;
[12] the pharmaceutical composition of any one of [1] to [11], which comprises a single chain diabody-type sc(Fv)2 or a bivalent scFv-type sc(Fv)2 in high purity;
[13] a method for producing a pharmaceutical composition comprising an sc(Fv)2, wherein the method comprises the steps of:
   (i) preparing an sc(Fv)2 composition; and
   (ii) suppressing an isomerization reaction of the prepared sc(Fv)2 composition;
[14] a method for producing a pharmaceutical composition comprising sc(Fv)2, wherein the method comprises the steps of:
   (i) preparing an sc(Fv)2 composition; and
   (ii) adding at least one substance selected from the group consisting of salt, amino sugar, sugar alcohol, amino acid, and pH adjusting agent to the prepared sc(Fv)2 composition;
[15] the method of [14] wherein the salt is at least one salt selected from the group consisting of sodium chloride and magnesium chloride;
[16] the method of [14], wherein the amino sugar is meglumine;
[17] the method of [14], wherein the sugar alcohol is mannitol;
[18] the method of [14], wherein the amino acid is lysine;
[19] the method of [14], wherein the pH adjusting agent is at least one pH adjusting agent selected from the group consisting of a sodium citrate buffer and histidine hydrochloride;
[20] a method for producing a pharmaceutical composition comprising an sc(Fv)2, wherein the method comprises the steps of:
   (i) preparing an sc(Fv)2 composition; and
   (ii) adjusting the pH of the prepared sc(Fv)2 composition to pH 4.5 to 9.0;
[21] a method for producing a pharmaceutical composition comprising an sc(Fv)2, wherein the method comprises the steps of:
   (i) preparing an sc(Fv)2 composition; and
   (ii) adjusting the pH of the prepared sc(Fv)2 composition to pH6.0 to 9.0;
[22] a method for producing a pharmaceutical composition comprising an sc(Fv)2, wherein the method comprises the steps of:
   (i) preparing an sc(Fv)2 composition; and
   (ii) adjusting the salt concentration of the prepared sc(Fv)2 composition to 50 mM to 1000 mM;
[23] a method for producing a pharmaceutical composition comprising an sc(Fv)2, wherein the method comprises the steps of:
   (a) producing an sc(Fv)2 composition in which the content ratio of the single chain diabody type is higher than the content ratio of the bivalent scFv type by incubating the sc(Fv)2 composition at 15° C. to 50° C., and/or pH3.0 to 6.0, and/or salt concentration of 500 mM or less;

(b) obtaining the produced single chain diabody-type sc(Fv)2; and (c) stabilizing the single chain diabody-type sc(Fv)2 composition obtained in step (b);

[24] a method for producing a pharmaceutical composition comprising an sc(Fv)2, wherein the method comprises the steps of:

(a) producing an sc(Fv)2 composition in which the content ratio of the bivalent scFv type is higher than the content ratio of the single chain diabody type by incubating the sc(Fv)2 composition at 15° C. to 50° C., and/or pH3.0 to 6.0, and/or salt concentration of 500 mM or less;

(b) obtaining the produced bivalent scFv-type sc(Fv)2; and (c) stabilizing the bivalent scFv-type sc(Fv)2 composition obtained in step (b);

[25] a method for producing a pharmaceutical composition comprising an sc(Fv)2, wherein the method comprises the steps of:

(i) preparing an sc(Fv)2 composition; and (ii) freeze-drying the prepared sc(Fv)2 composition;

[26] a method for suppressing the isomerization of an active ingredient in a pharmaceutical composition, wherein the method comprises the step of adding at least one substance selected from the group consisting of salt, amino sugar, sugar alcohol, amino acid, and pH adjusting agent;

[27] the method of [26], wherein the salt is at least one salt selected from the group consisting of sodium chloride and magnesium chloride;

[28] the method of [26], wherein the amino sugar is meglumine;

[29] the method of [26], wherein the sugar alcohol is mannitol;

[30] the method of [26], wherein the amino acid is lysine;

[31] the method of [26], wherein the pH adjusting agent is at least one pH adjusting agent selected from the group consisting of a sodium citrate buffer and histidine hydrochloride;

[32] a method for suppressing the isomerization of an active ingredient in a pharmaceutical composition, wherein the method comprises the step of setting the pH to pH4.5 to 9.0;

[33] a method for suppressing the isomerization of an active ingredient in a pharmaceutical composition, wherein the method comprises the step of setting the pH to pH6.0 to 9.0;

[34] a method for suppressing the isomerization of an active ingredient in a pharmaceutical composition, wherein the method comprises the step of setting the salt concentration to 50 mM to 1000 mM;

[35] a method for suppressing the isomerization of an active ingredient in a pharmaceutical composition, wherein the method comprises the step of freeze-drying;

[36] the method of any one of [26] to [35], wherein the active ingredient in the pharmaceutical composition is an sc(Fv)2;

[37] a stabilizing agent used for suppressing the isomerization reaction of an sc(Fv)2, wherein the stabilizing agent comprises at least on substance selected from the group consisting of salt, amino sugar, sugar alcohol, amino acid, and pH adjusting agent;

[38] the stabilizing agent of [37], wherein the salt is at least one salt selected from the group consisting of sodium chloride and magnesium chloride;

[39] the stabilizing agent of [37], wherein the amino sugar is meglumine;

[40] the stabilizing agent of [37], wherein the sugar alcohol is mannitol;

[41] the stabilizing agent of [37], wherein the amino acid is lysine;

[42] the stabilizing agent of [37], wherein the pH adjusting agent is at least one pH adjusting agent selected from the group consisting of a sodium citrate buffer and histidine hydrochloride; and

[43] a method of screening for a substance that suppresses the isomerization reaction of an sc(Fv)2, wherein the method comprises the steps of:

(i) preparing an sc(Fv)2 composition;

(ii) contacting a test substance with the prepared sc(Fv)2 composition;

(iii) measuring the presence of suppression of an isomerization reaction of an sc(Fv)2 in the sc(Fv)2 composition contacted with the test substance; and (iv) selecting the substance that suppresses the isomerization reaction of the sc(Fv)2.

BEST MODE FOR CARRYING OUT THE INVENTION

Figure 1:
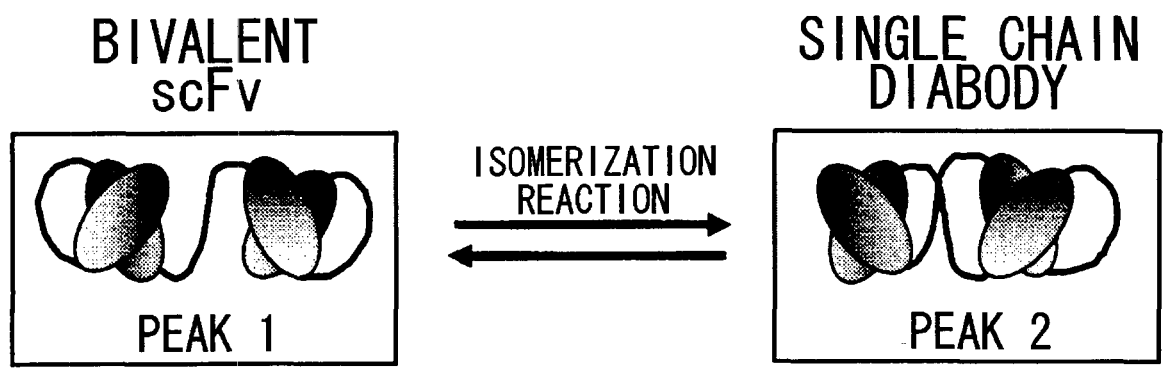
FIG. 1 is a schematic diagram depicting the isomerization reactions of sc(Fv)2.

In the course of analyzing the conformational isomers of sc(Fv)2, it was discovered that bivalent scFv and single chain diabodies, which are two types of conformational isomer, undergo mutual structural conversion (isomerization) (FIG. 1). Stabilizing agents that suppress this mutual isomerization reaction between the conformational isomers were subsequently discovered. The present invention is based on these discoveries.

The present invention provides pharmaceutical compositions containing sc(Fv)2, in which at least one substance selected from the group consisting of salt, amino sugar, sugar alcohol, amino acid, and pH adjusting agent has been added.

The pharmaceutical compositions of the present invention constitute stabilizing formulations which stably maintain the conformational isomer of interest and keep isomerization to other conformational isomers suppressed to a minimum level, and thus find substantial utility in the field of medicine.

In the present invention, sc(Fv)2 is a minibody (a low-molecular-weight antibody) in which four or more antibody variable regions are linked via linkers or such and formed into a single chain. Examples include an antibody having the following arrangement: [variable region 1]-(linker 1)-[variable region 2]-(linker 2)-[variable region 3]-(linker 3)-[variable region 4].

Ordinarily, sc(Fv)2 is an antibody in which four variable regions, two VLs and two VHs, are linked by linkers or such and made into a single chain (Hudson et al., J. Immunol. Methods 1999; 231:177-189). These two VHs and VLs may be derived from different monoclonal antibodies. Examples include bispecific sc(Fv)2 that recognize two types of antigens or two types of epitopes, such as those disclosed in Journal of Immunology, 1994, 152, 5368-5374.

sc(Fv)2 can be generated using methods well known to those skilled in the art, for example, by linking scFvs using linker. scFv comprise VH and VL of antibodies, and these regions exist on a single polypeptide chain (for a review on scFv, see Pluckthun "The Pharmacology of Monoclonal Antibodies" Vol. 113 (Rosenburg and Moore ed. (Springer Verlag, New York) pp. 269-315, 1994)).

Examples of sc(Fv)2 of the present invention include antibodies composed of two VHs and two VLs arranged in the order of VH, VL, VH, VL ([VH]-linker-[VL]-linker-[VH]-linker-[VL]) starting from the N-terminal side of the single chain polypeptide. However, the present invention is not limited to any one particular order and thus the arrangement of two VHs and two VLs may be as above-described or in any alternate order. Examples include the following arrangements:

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

sc(Fv)2 of the present invention may also include amino acid sequences other than the antibody variable regions and linkers.

Antibody variable regions used in the context of the present invention may correspond to the full length of the variable region or a partial sequence thereof, provided the antigen-binding activity is maintained. In addition, the amino acid sequences in the variable regions may be subjected to substitutions, deletions, additions, insertions, or such. For example, they may be chimerized or humanized to lower their antigenicity.

The sc(Fv)2 of the present invention may include another protein, such as the IgG Fc portion, fused to its N-terminus or C-terminus (Clinical Cancer Research, 2004, 10, 1274-1281). The protein to be fused can be appropriately selected by those skilled in the art. Furthermore, the sc(Fv)2 of the present invention may be conjugated with carrier polymers such as PEG or organic compounds such as anticancer agents. Carbohydrate chains may also be added by inserting glycosylation sequences.

As the linkers for linking the variable regions of antibodies, arbitrary peptide linkers that can be introduced by genetic engineering, synthetic linkers (for example, see Protein Engineering, 9(3), 299-305, 1996), or such can be used; however, in the context of the present invention, peptide linkers are preferred. The length of the peptide linkers is not particularly limited and can be suitably selected by those skilled in the art according to the intended purpose. However, the length is preferably 5 amino acids or more. While there is no particular upper limit, the length of the linker is ordinarily 30 amino acids or less, preferably 20 amino acids or less, particularly preferably 15 amino acids. When sc(Fv)2 is provided with three peptide linkers, the peptide linkers may all have the same length, or peptide linkers of different lengths may be used.

Examples of peptide linkers include the following:

```
Ser

Gly-Ser

Gly-Gly-Ser

Ser-Gly-Gly

Gly-Gly-Gly-Ser          (SEQ ID NO: 5)

Ser-Gly-Gly-Gly          (SEQ ID NO: 6)

Gly-Gly-Gly-Gly-Ser      (SEQ ID NO: 7)

Ser-Gly-Gly-Gly-Gly      (SEQ ID NO: 8)

Gly-Gly-Gly-Gly-Gly-Ser  (SEQ ID NO: 9)

Ser-Gly-Gly-Gly-Gly-Gly  (SEQ ID NO: 10)

Gly-Gly-Gly-Gly-Gly-Gly-Ser  (SEQ ID NO: 11)

Ser-Gly-Gly-Gly-Gly-Gly-Gly  (SEQ ID NO: 12)

(Gly-Gly-Gly-Gly-Ser (SEQ ID NO: 7))n (Ser-Gly-Gly-Gly-Gly (SEQ ID NO: 8))n
``` where n is an integer of 1 or larger. However, the length and sequence of the peptide linkers can be suitably selected by those skilled in the art according to the intended purpose.

Synthetic compound linkers (chemical crosslinking agents) include crosslinking agents routinely used to crosslink peptides, for example, N-hydroxy succinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(sulfosuccinimidoxycarbonyloxy)ethyl]sulfone (sulfo-BSOCOES). These crosslinking agents are commercially available.

Generally, three linkers are required to link four antibody variable regions together. However, the linkers utilized may be identical or different.

In the context of the present invention, "pharmaceutical compositions" refer to pharmaceutical compositions that contain sc(Fv)2, which are intended to be administered to humans for treating/preventing diseases, and such. To develop sc(Fv)2 comprising conformational isomers as pharmaceuticals, it is desirable to separate and purify the conformational isomer of interest to high purity and produce a drug substance comprising the separated and purified conformational isomer in high purity, or to increase the percentage of the conformational isomer of interest to produce a drug substance comprising the conformational isomer in sufficiently high purity. As methods for obtaining sc(Fv)2 comprising one of the conformational isomers in high purity, International Application PCT/JP06/306800 described methods for separating and obtaining two types of conformational isomer in an sc(Fv)2 composition, namely bivalent scFv and single chain diabodies; methods for identifying the structures of the two types of separated conformational isomer; and methods for quantitatively analyzing the two types of conformational isomer. Specifically, PCT/JP06/306800 describes a method for purifying one of the conformational isomers to high purity from a mixture of two types of conformational isomer through use of ion exchange chromatography and such. Whether one of the conformational isomers has been purified to high purity can be confirmed by ion exchange chromatography, isoelectric focusing, and limited proteolysis by proteases. Alternatively, as indicated in PCT/JP06/306800, the purity of one of the conformational isomers can be increased by incubating a mixture of two types of conformational isomer under specific buffer conditions and temperature. Furthermore, as indicated in PCT/JP06/306800, the purity of one of the conformational isomers can be increased by adjusting the length of the linkers in sc(Fv)2 or preparing VH/VLinterface-modified sc(Fv)2. Pharmaceutical compositions of the present invention containing one of the conformational isomers in high purity preferably include an sc(Fv)2 in which the isomerization reaction is suppressed.

As used herein, "isomerization reaction" refers to a structural conversion reaction within the sc(Fv)2 molecule, or more specifically: 1) a structural conversion reaction from a bivalent scFv type to a single chain diabody type; 2) a structural conversion reaction from a single chain diabody type to a bivalent scFv type; and 3) a structural interconversion reaction (mutual isomerization reaction) from a bivalent scFv type to a single chain diabody type, and from a single chain diabody type to a bivalent scFv type (FIG. 1).

In the context of the present invention, "suppression" not only encompasses "complete suppression" but also "incomplete suppression" of the isomerization reaction(s).

Suppression of the isomerization reaction(s) of sc(Fv)2 can be confirmed by methods known to those skilled in the art. For example, by analyzing the conformational isomer content ratio after storage of sc(Fv)2 under certain conditions for a set period of time using methods described in the Examples or methods described later, isomerization of the conformational isomers under those conditions can be evaluated. More particularly, the suppression of the isomerization reaction under the test conditions can be confirmed.

The pharmaceutical compositions of the present invention can be produced by mixing an sc(Fv)2 composition with at least one substance selected from the group consisting of salt, amino sugar, sugar alcohol, amino acid, and pH adjusting agent. For example, they can be produced by adding the substances to sc(Fv)2 compositions, or by adding sc(Fv)2 compositions to the substances.

The salt of the present invention is not particularly limited, and examples include sodium chloride, calcium chloride, calcium gluconate, magnesium chloride, and magnesium gluconate.

The amino sugar of the present invention includes, for example, meglumine, but it is not limited thereto (meglumine is also classified as a sugar alcohol).

In the present invention, the term "meglumine" refers to a compound also known by the name N-methylglucamine and the chemical formula 1-deoxy-1-methylamino-D-glucitol, and is represented by the following chemical formula:

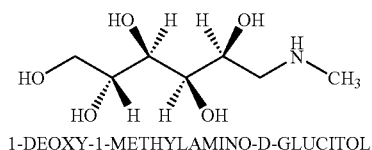

1-DEOXY-1-METHYLAMINO-D-GLUCITOL

In the present invention, the term "meglumine" includes meglumine derivatives, salts of meglumine, and such. Meglumine derivatives and salts of meglumine are for example, meglumine amidotrizoate, meglumine sodium amidotrizoate, meglumine gadopentetate, meglumine gadoterate, meglumine iotalamate, meglumine iotroxate, meglumine gadobenate, meglumine iodoxamate, meglumine flunixin, meglumine antimonate, and gastrografin (meglumine sulfate), but are not limited thereto. In addition, the above-mentioned meglumines whose hydroxyl groups, amino groups, or such have been chemically modified are also included in the meglumine of the present invention.

Sugar alcohols of the present invention include, for example, mannitol, sorbitol, xylitol, pentaerythritol, inositol, and meglumine, but are not limited thereto. Additional amino acids suitable for use in the context of the present invention include, for example, the following, but are not limited thereto: basic amino acids such as arginine, lysine, histidine, ornithine, and such, and amino acids are preferably used in the form of its inorganic salt (preferably in the form of hydrochloride salt or phosphate salt, thus as an amino acid phosphate).

When free amino acids are used, the pH can be adjusted to a preferred value by adding appropriate physiologically acceptable buffering substances, for example, inorganic acids, in particular hydrochloric acid, phosphoric acid, sulfuric acid, acetic acid, and formic acid, or salts thereof. In this case, the use of phosphate salt is particularly advantageous because quite stable freeze-dried products are obtained. Phosphate salt is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, and ornithine.

Examples of acidic amino acids include glutamic acid and aspartic acid, and salts thereof (preferably sodium salts). Neutral amino acids, for example, isoleucine, leucine, alanine, glycine, serine, threonine, valine, methionine, and cysteine, or aromatic amino acids, for example, phenylalanine, tyrosine, tryptophan, and N-acetyl tryptophan, can also be used.

pH adjusting agents of the present invention refer to buffer substances or buffer solutions for suitably adjusting the pH that had been altered by acids or alkali. pH adjusting agents of the present invention include for example, phosphoric acid, citric acid buffer (for example, sodium citrate buffer), histidine hydrochloride, acetic acid, malic acid, tartaric acid, succinic acid, fumaric acid, and such, other organic acids and such, or aqueous buffers known in the field of solution formulations, including tris buffer (for example, tris hydrochloride buffer), histidine buffer, imidazole buffer, carbonate buffer, lactic acid, potassium phosphate, sodium phosphate, gluconic acid, caprylic acid, deoxycholic acid, salicylic acid, or triethanolamine buffer, but are not limited thereto. The concentration of the buffer is generally 1 to 500 mM, preferably 5 to 100 mM, and more preferably 10 to 20 mM.

To suppress the isomerization of sc(Fv)2 in the pharmaceutical compositions of the present invention and to enable stable storage, the concentration of the salt in the pharmaceutical composition of the present invention preferably ranges from 50 mM to 1000 mM, more preferably in the range of 150 mM to 300 mM; however, the present invention is not limited thereto. The pH value is preferably in the range of 4.5 to 9.0, and more preferably in the range of 6.0 to 9.0, but is not limited thereto.

The final concentrations of amino sugars, sugar alcohols, and amino acids in the pharmaceutical compositions of the present invention are not particularly limited, but may, for example, range from 1 mM to 500 mM, 1 mM to 500 mM, and 1 mM to 500 mM, respectively.

The pharmaceutical compositions of the present invention may include pharmaceutically acceptable carriers in addition to the above-mentioned substances. Examples of pharmaceutically acceptable carriers include sterile water, physiological saline, stabilizers, excipients, antiseptics, detergents, chelating agents (for example, EDTA), and binding agents.

In the context of the present invention, suitable detergents include non-ionic detergents, illustrative examples of which include: sorbitan fatty acid esters, such as sorbitan monocaprylate, sorbitan monolaurate, and sorbitan monopalmitate; glycerin fatty acid esters, such as glycerin monocaprylate, glycerin monomyristate and glycerin monostearate; polyglycerin fatty acid esters, such as decaglyceryl monostearate, decaglyceryl distearate, and decaglyceryl monolinoleate; polyoxyethylene sorbitan fatty acid esters, such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters, such as polyoxyethylene glyceryl monostearate; polyethylene glycol fatty acid esters, such as polyethylene glycol distearate; polyoxyethylene alkyl ethers, such as polyoxyethylene lauryl ether; polyoxyethylene polyoxypropylene alkyl ethers, such as polyoxyethylene polyoxypropylene glycol, polyoxyethylene polyoxypropylene propyl ether, and polyoxyethylene polyoxypropylene cetyl ether; polyoxyethylene alkyl phenyl ethers, such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives, such as polyoxyethylene sorbit beeswax; polyoxyethylene lanolin derivatives, such as polyoxyethylene lanolin; and polyoxyethylene fatty acid amides and such with an HLB of 6 to 18, such as polyoxyethylene stearic acid amide.

Detergents also include anionic detergents, illustrative examples of which include: alkylsulfates having an alkyl group with 10 to 18 carbon atoms, such as sodium cetylsulfate, sodium laurylsulfate, and sodium oleylsulfate; polyoxyethylene alkyl ether sulfates in which the alkyl group has 10 to 18 carbon atoms and the average molar number of added ethylene oxide is 2 to 4, such as sodium polyoxyethylene lauryl sulfate; alkyl sulfosuccinate ester salts having an alkyl group with 8 to 18 carbon atoms, such as sodium lauryl sulfosuccinate ester; natural detergents, for example, lecithin; glycerophospholipids; sphingo-phospholipids such as sphingomyelin; and sucrose fatty acid esters in which the fatty acids have 12 to 18 carbon atoms.

One, two or more of these detergents can be combined and added to the pharmaceutical compositions of the present invention. Detergents that are preferably used in the pharmaceutical compositions of the present invention include polyoxyethylene sorbitan fatty acid esters, such as polysorbates 20, 40, 60, and 80. Polysorbates 20 and 80 are particularly preferred. Polyoxyethylene polyoxypropylene glycols, such as poloxamer (Pluronic F-68® and such), are also preferred.

The amount of detergent added varies with the type of detergent used. When polysorbate 20 or 80 is used, the amount generally ranges from 0.001 to 100 mg/ml, preferably in the range of 0.003 to 50 mg/ml, more preferably in the range of 0.005 to 2 mg/ml.

The pharmaceutical compositions of the present invention may also include other low-molecular-weight polypeptides; proteins such as serum albumin, gelatin, and immunoglobulin; and sugars and carbohydrates such as polysaccharides and monosaccharides.

In the present invention, suitable sugars and carbohydrates, such as polysaccharides and monosaccharides, include, for example, dextran, glucose, fructose, lactose, xylose, mannose, maltose, sucrose, trehalose, and raffinose.

When preparing aqueous solutions for injection, for example, isotonic solutions of glucose or such can be used. The aqueous solutions may be used in combination with appropriate solubilizing agents, such as alcohols (ethanol and such), polyalcohols (propylene glycol, PEG, and such), or non-ionic detergents (polysorbate 80 and HCO-50).

They may further include, if necessary, diluents, solubilizers, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having one to seven carbon atoms.

Moreover, the antioxidants suitable for use in the context of the present invention include, for example, erythorbic acid, dibutylhydroxy toluene, butylhydroxy anisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

If necessary, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science $16^{th}$ edition", Oslo Ed., 1980, and the like). Furthermore, methods for preparing agents as sustained-release agents are also known, and are: applicable to the present invention (Langer et al, J. Biomed. Mater. Res. 1981, 15: 167-277; Langer, Chem. Tech. 1982, 12: 98-105; U.S. Pat. No. 3,773,919; European Patent Application No. (EP) 58,481; Sidman et al., Biopolymers 1983, 22: 547-556; and EP 133,988).

The pharmaceutical compositions of the present invention may take the form (dosage form) of for example, an injection dosage form, freeze-dried dosage form, and solution dosage form; however, the present invention is not limited thereto.

Administration to patients can be performed either orally or parenterally, though parenteral administration is preferable, and for example, administration by injection is possible. Examples of suitable injections include systemic and local administrations by intravenous injection, intramuscular injection, intraperitoneal injection, subcutaneous injection, and such. Suitable methods of administration can be selected according to the age and symptoms of the patient. For example, the dose per administration can be selected within the range of 0.0001 mg to 1000 mg per 1 kg body weight. Alternatively, for example, the dose can be selected within the range of 0.001 to 100000 mg/body per patient. However, the present invention is not limited to these doses, administration methods, and such.

Moreover, pharmaceutical compositions containing an sc(Fv)2 in which the isomerization reaction is suppressed can be prepared by formulating sc(Fv)2 by freeze-drying or spray-drying. Accordingly, the present invention also provides the above-mentioned pharmaceutical compositions, in which the dosage form is a freeze-dried formulation or spray-dried formulation (hereinafter, referred to as a freeze-dried formulations).

Freeze-drying can be performed by methods known to those skilled in the art (Pharm. Biotechnol., 2002, 13, 109-33; Int. J. Pharm. 2000, 203(1-2), 1-60; Pharm. Res. 1997, 14(8), 969-75). For example, a suitable amount of a solution is dispensed into a container such as a vial used for freeze-drying, and the freeze drying is carried out in a freezer or a freeze-dryer, or by immersion in a cooling medium such as acetone/dry ice, liquid nitrogen, or such. Furthermore, freeze-drying can be carried out by the method described in the Examples. Preparation of Spray-Dried Formulations can be Carried Out by Methods Known to Those Skilled in the art (J. Pharm. Sci. 1998 November; 87(11):1406-11).

Freeze-dried formulations or spray-dried formulations of the present invention can be made into solution formulations before use. Therefore, the present invention also provides kits composed of the freeze-dried formulations or spray-dried formulations of the present invention in conjunction with pharmaceutically acceptable carriers. So long as the freeze-dried formulations or spray-dried formulations of the present invention can be formulated into solutions, the type of the pharmaceutically acceptable carrier, combinations thereof, or such are not particularly limited. However, by using at least one substance selected from the group consisting of salt, amino sugar, sugar alcohol, amino acid, and pH adjusting agent as the pharmaceutically acceptable carrier or as a part thereof, the sc(Fv)2 isomerization reaction in solution formulations can be suppressed.

In the present invention, sc(Fv)2 compositions refer to compositions composed of a single conformational isomer of sc(Fv)2, or compositions containing multiple conformational isomers of sc(Fv)2 (a mixture of conformational isomers).

sc(Fv)2 compositions can be generated by methods known to those skilled in the art. For example, sc(Fv)2 that form two or more types of conformational isomer can be produced by introducing into host cells vectors into which a DNA encoding sc(Fv)2 has been inserted, expressing the sc(Fv)2, and then collecting the expression products.

The vectors are not particularly limited, so long as the inserted DNA is maintained stably, and for example, when using *Escherichia coli* as the host, the vector for cloning is preferably the pBluescript vector (Stratagene) or such; however, a variety of commercially available vectors can be used. When using vectors with the aim of producing the sc(Fv)2 of the present invention, expression vectors are particularly useful. Expression vectors are not particularly limited so long as they are vectors that express sc(Fv)2 in test tubes, *E. coli*, cultured cells, or biological organisms, and for example, preferable vectors are: pBEST vector (Promega) for expression in test tubes; pET vector (Invitrogen) for expression in *E. coli*; pME18S-FL3 vector (GenBank Accession No. AB009864) for expression in cultured cells; and pME18S vector (Mol. Cell. Biol. 8:4±56-472 (1988)) for expression in biological organisms. Insertion of the DNAs of the present invention into vectors can be carried out by ordinary methods, such as ligase reactions using restriction enzyme sites (Current protocols in Molecular Biology edit. Ausubel et al. (1987) Publish. John Wiley & Sons, Section 11.4-11.11).

The above-mentioned host cells are not particularly limited, and various host cells are used depending on the objective. Cells for expressing sc(Fv)2 include for example, bacterial cells (such as *Streptococcus, Staphylococcus, E. coli, Streptomyces*, and *Bacillus subtilis*), fungal cells (such as yeast and *Aspergillus*), insect cells (such as *Drosophila* S2 and *Spodoptera* SF9), animal cells (such as CHO, COS, HeLa, C127, 3T3, BHK, HEK293, and Bowes melanoma cells), and plant cells. Introduction of vectors into host cells can be carried out by known methods such as calcium phosphate precipitation method, electroporation method (Current protocols in Molecular Biology edit. Ausubel et al. (1987) Publish. John Wiley & Sons, Section 9.1-9.9), lipofectamine method (GIBCO-BRL), and microinjection method.

When the sc(Fv)2 of the present invention are secreted into the culture medium, the sc(Fv)2 compositions can be collected by collecting the culture medium. When the sc(Fv)2 are produced within cells, those cells are first lysed, then the sc(Fv)2 compositions are collected.

The sc(Fv)2 compositions of the present invention may be in any state, so long as they are compositions containing one or more conformational isomers of sc(Fv)2. Examples include compositions in a crude state, such as a recombinant cell culture, or compositions in a purified state; however, the compositions are not limited thereto. Moreover, the ratio of the multiple conformational isomers that are present may be any ratio, though it is preferably one obtained (isolated) by a method described below.

In the present invention, "conformational isomers" refer to proteins whose amino acid sequences are the same but their three-dimensional structure (secondary structures or tertiary structures) are different. Ordinarily, at least one from among chemical, biological, or physical properties differs between conformational isomers.

Conformational isomers of sc(Fv)2 include, for example, the single chain diabody type and bivalent scFv type conformational isomer.

In the present invention, "single chain diabody type" refers to an sc(Fv)2 having a structure in which, in the case of an arrangement in the order of [variable region 1]-(linker 1)-[variable region 2]-(linker 2)-[variable region 3]-(linker 3)-[variable region 4], variable region 1 and variable region 4 are associated, and variable region 2 and variable region 3 are associated.

Furthermore, in the present invention, "bivalent scFv type" refers to an sc(Fv)2 having a structure in which variable region 1 and variable region 2 are associated, and variable region 3 and variable region 4 are associated.

Examples of the single chain diabody type and bivalent scFv type are sc(Fv)2 having the structures shown in FIG. 1. Whether a conformational isomer of sc(Fv)2 possesses the single chain diabody-type structure or the bivalent scFv-type structure can be confirmed by methods for identifying conformational isomers, which are described later. Identification can also be carried out by analyses using NMR, crystal structure analyses, and such.

sc(Fv)2 compositions used for the production of pharmaceutical compositions are preferably those in which the content ratio of a specific conformational isomer is higher than the content ratio of the other conformational isomer, and examples include: 1) specific conformational isomers obtained from sc(Fv)2 compositions; and 2) sc(Fv)2 compositions in which the content ratio of a specific conformational isomer is higher than the content ratio of the other conformational isomer.

The above-mentioned "specific conformational isomer" means a single chain diabody type or bivalent scFv type, and "the other conformational isomer" means a bivalent scFv type when the specific conformational isomer is of a single chain diabody type, or a single chain diabody type when the specific conformational isomer is of a bivalent scFv type.

In the present invention, methods for obtaining specific conformational isomers from sc(Fv)2 compositions can be performed by methods known to those skilled in the art. For example, conformational isomers in an sc(Fv)2 composition can be separated, and specific conformational isomers can be obtained from the separated conformational isomers. Thus, the present invention provides methods including the following steps (a) to (c), and pharmaceutical compositions produced by these methods:

(a) separating the conformational isomers in an sc(Fv)2 composition;

(b) obtaining a specific conformational isomer from the separated conformational isomers; and (c) mixing the specific conformational isomer obtained in step (b) with at least one substance selected from the group consisting of salt, amino sugar, sugar alcohol, amino acid, and pH adjusting agent.

The purity of the obtained (isolated) specific conformational isomer is preferably 80% or more, 90% or more, 95% or more, 100%, or close to 100%. Upper limit close to 100% depends on the purification techniques or analysis techniques of the skilled artisan; however, it is for example 99.999%, 99.99%, 99.9%, or 99%. Herein, "purity" means the percentage of a specific conformational isomer with respect to all of the obtained conformational isomers.

Separating and obtaining (purifying) conformational isomers in sc(Fv)2 compositions can be carried out for example by subjecting the sc(Fv)2 compositions to an ion exchange column or hydroxyapatite column, and obtaining or removing specific conformational isomers; however, the invention is not limited thereto, and can be carried out using methods known to those skilled in the art, such as various column chromatographies, filtration, ultrafiltration, salting out, solvent precipitation, solvent extraction, distillation, immunoprecipitation, SDS-polyacrylamide gel electrophoresis, isoelectric focusing, capillary isoelectric focusing, dialysis, and recrystallization.

Examples of chromatography include ion exchange chromatography, adsorption chromatography, isoelectric chromatography, gel filtration, reverse phase chromatography, hydrophobic chromatography, and affinity chromatography (Strategies for Protein Purification and Characterization: A Laboratory Course Manual. Ed Daniel R. Marshak et al., Cold Spring Harbor Laboratory Press, 1996). Chromatography can be carried out using liquid-phase chromatography such as HPLC or FPLC.

When using ion exchange chromatography, the type of ion exchange column to be used is not particularly limited, and cation exchange columns and anion exchange columns can both be used. The type of ion exchange column can be appropriately determined depending on the antibodies or conformational isomers of interest. For example, SP ion exchange column or Q ion exchange column can be used, but it is not limited thereto. Adsorption chromatography is, for example, hydroxyapatite chromatography, but is not limited thereto.

According to the present invention, purified products of specific conformational isomers can be obtained using these purification methods.

Furthermore, when there is a difference in activity between the conformational isomers in an sc(Fv)2 composition, the activities of the conformational isomers of sc(Fv)2 can be compared to determine the highly active conformational isomer in advance, then the highly active conformational isomer can be isolated and obtained from the conformational isomers in the sc(Fv)2 composition. Furthermore, before separating the conformational isomers in an sc(Fv)2 composition, the lengths of the linkers can be determined such that the ratio of the conformational isomers in the sc(Fv)2 composition becomes a preferable value, and an sc(Fv)2 composition having the determined linker lengths can be prepared, using a method described below. Furthermore, before separating the conformational isomers in an sc(Fv)2 composition, it is possible to prepare a number of sc(Fv)2 compositions of different linker lengths, analyze the ratio of conformational isomers by a method described below for analyzing the ratio of conformational isomers, select the sc(Fv)2 having linkers that give a preferable value for the ratio of the conformational isomers in the sc(Fv)2 composition, and prepare an sc(Fv)2 composition of the selected sc(Fv)2.

Therefore, the present invention provides methods described in any of the following (1) to (3), and pharmaceutical compositions produced by these methods:

(1) a method including the steps of:
(a) comparing the activities of the conformational isomers of an sc(Fv)2 to determine in advance the highly active conformational isomer;
(b) separating the conformational isomers in the sc(Fv)2 composition;
(c) obtaining the highly active conformational isomer determined in step (a); and
(d) mixing the highly active conformational isomer obtained in step (c) with at least one substance selected from the group consisting of salt, amino sugar, sugar alcohol, amino acid, and pH adjusting agent;

(2) a method including the steps of:
(a) determining linker lengths such that the ratio of the conformational isomers in an sc(Fv)2 composition is a preferable value;
(b) preparing an sc(Fv)2 composition in which the linker lengths are those determined in step (a);
(c) separating the conformational isomers in the prepared sc(Fv)2 composition;
(d) obtaining a specific conformational isomer from the separated conformational isomers; and
(e) mixing the specific conformational isomer obtained in step (d) with at least one substance selected from the group consisting of salt, amino sugar, sugar alcohol, amino acid, and pH adjusting agent; and (3) a method including the steps of:
(a) preparing a number of sc(Fv)2 compositions having different linker lengths;
(b) selecting an sc(Fv)2 having linkers that give rise to a preferred value for the ratio of the conformational isomers in the sc(Fv)2 compositions;
(c) preparing an sc(Fv)2 composition having linkers of the same lengths as the linkers of the sc(Fv)2 selected in step (b);
(d) separating the conformational isomers in the prepared sc(Fv)2 composition;
(e) obtaining a specific conformational isomer from the separated conformational isomers; and
(f) mixing the specific conformational isomer obtained in step (e) with at least one substance selected from the group consisting of salt, amino sugar, sugar alcohol, amino acid, and pH adjusting agent.

In the context of the present invention, the term "highly active conformational isomer" refers to a conformational isomer whose activity is high, more preferably the conformational isomer having the highest activity, when there is a difference in activity between the conformational isomers. For example, when there are two types of conformational isomers, the conformational isomer with the higher activity corresponds to the highly active conformational isomer of the present invention.

The highly active conformational isomer can be determined by methods well known to those skilled in the art; for example, the highly active conformational isomer can be determined by isolating each of the conformational isomers and measuring the activity of interest under the same conditions.

In the context of the present invention, the activity of interest may be any activity, such as binding activity, neutralizing activity, cytotoxicity, agonistic activity, antagonistic activity, or enzyme activity, and is not particularly limited; however, it is preferably an activity that brings about quantitative and/or qualitative changes or influences on a living organism, tissues, cells, proteins, DNA, RNA, or such, and is particularly preferably an agonistic activity.

An agonistic activity is an activity that induces some kind of change in physiological activity after the binding of an antibody to an antigen, such as a receptor, which leads to signal transduction and such in cells. Without limitation, examples of the physiological activity include proliferation activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity.

In the context of the present invention, the antigens are not particularly limited, and may be any type of antigen. Examples of suitable antigens include receptors, cancer antigens, MHC antigens, and differentiation antigens. Examples of receptors include receptors belonging to receptor families, such as the hematopoietic factor receptor family, cytokine receptor family, tyrosine kinase-type receptor family, serine/threonine kinase-type receptor family, TNF receptor family, G-protein coupled receptor family, GPI anchored-type receptor family, tyrosine phosphatase-type receptor family, adhesion factor family, and hormone receptor family. Such receptors as well as their characteristics are well studied and amply illustrated in the following references: Cooke B A., King R J B., van der Molen H J. ed., New Comprehensive Biochemistry Vol. 18B, "Hormones and their Actions Part II", pp. 1-46 (1988), Elsevier Science Publishers BV., New York, USA; Patthy L. (1990) Cell, 61: 13-14; Ulhrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; and Miyasaka M. ed, Cell Technology handbook series "adhesion factor handbook" (1994) (Shujunsha, Tokyo, Japan).

Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (HEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFNα/βR: Uze, G. et al. (1990) Cell 60, 225-234; and Novick, D. et al. (1994) Cell 77, 391-400).

Cancer antigens are antigens that are expressed as cells become malignant, and are often referred to as called tumor-specific antigens. Abnormal sugar chains that appear on cell surfaces or on protein molecules when cells become cancerous are also examples of cancer antigens, referred to as sugar chain cancer antigens. Examples of cancer antigens include CA19-9, CA15-3, and sialyl SSEA-1 (SLX).

MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD411, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Detection indicators used for measuring changes in activity can be used so long as quantitative and/or qualitative changes can be measured. For example, indicators for cell free assays, indicators for cell-based assays, indicators for tissue-based assays, and indicators for biological assays can be used.

Enzymatic reactions as well as quantitative and/or qualitative changes of proteins, DNAs, or RNAs can be used as indicators for cell free assays. For example, amino acid transfer reaction, sugar transfer reaction, dehydration reaction, dehydrogenation reaction, substrate cleaving-reaction, and such can be used for the enzymatic reactions. Protein phosphorylation, dephosphorylation, dimerization, multimerization, degradation, dissociation, and such, and DNA or RNA amplification, cleavage, and elongation can also be used. For example, phosphorylation of a protein existing downstream of a signal transduction pathway can be used as a detection indicator.

Changes in cell phenotype, for example, quantitative and/or qualitative changes in produced substances, changes in proliferation activity, changes in cell number, changes in morphology, and changes in properties can be used as indicators for cell-based assays. Secretory proteins, surface antigens, intracellular proteins, mRNAs, and such can be used for the produced substances. Formation of protrusions and/or change in the number of protrusions, change in flatness, change in the extent of elongation or in the horizontal to vertical ratio, change in cell size, change in internal structure, heteromorphy/homogeneity as a cell population, change in cell density, and such can be used for the change in morphology. Such changes in morphology can be confirmed through microscopic observations. Anchorage dependency, cytokine-dependent responsiveness, hormone dependency, drug resistance, cell motility, cell migration activity, pulsatility, change in intracellular substances, and such can be used for the change in properties. Cell motility includes cell infiltration activity and cell migration activity. Furthermore, for example, enzyme activity, mRNA levels, amount of intracellular signaling molecules (such as $Ca^{2+}$ and cAMP), intracellular protein levels, and such can be used to assess changes in intracellular substance. In the case of cell membrane receptors, changes in cell proliferation activity induced by receptor stimulation can be used as the indicator.

Functional changes in accordance with the tissues that are used can be used as the detection indicator for tissue-based assays. Changes in tissue weight, hematologic changes (such as change in the number of blood cells), changes in protein level, enzyme activity, or amount of electrolytes, or changes in the circulatory system (such as changes in blood pressure or heart rate) can be used as indicators for biological assays.

Methods for measuring these detection indicators are not particularly limited, and include measurements of absorbance, luminescence, coloring, fluorescence, radioactivity, fluorescence polarization, surface plasmon resonance signal, time-resolved fluorescence, mass, absorption spectrum, light scattering, fluorescence resonance energy transfer, and such. These measurement methods are well known to those skilled in the art, and can be suitably selected according to the purpose.

For example, absorption spectra can be measured with a conventional photometer, plate reader, or such; luminescence can be measured with a luminometer or such; and fluorescence can be measured with a fluorometer or such. The mass can be measured using a mass spectrometer. Radioactivity can be measured using measuring instruments such as a gamma counter according to the type of radiation; fluorescence polarization can be measured using BEACON (TaKaRa); surface plasmon resonance signals can be measured using BIACORE; time resolved fluorescence, fluorescence resonance energy transfer, and such can be measured using ARVO or such. Flow cytometers and such can also be used for the measurements. Regarding these measurement methods, two or more detection indicators may be measured using one measurement method. If simple, an even larger amount of detection indicators can be measured by performing two or more measurements simultaneously and/or sequentially. For example, fluorescence and fluorescence resonance energy transfer can be measured simultaneously on a fluorometer.

In the context of the present invention, measurement of agonistic activity can be performed by methods known to those skilled in the art. For example, as described in the Examples, determinations can be made by methods that measure the agonistic activity using cell proliferation as the indicator. More specifically, antibodies whose agonistic activity is to be measured are added to cells that show agonist-dependent proliferation and the cells are cultured. Then, a reagent, such as WST-8, which exhibits a chromogenic reaction at a particular wavelength depending on the number of live cells is added, the absorbance is measured, and agonistic activity can be measured using the obtained absorbance as the indicator.

Cells showing agonist-dependent proliferation can also be generated by methods known to those skilled in the art; for example, when the antigen is a receptor emitting a cell proliferation signal, cells expressing this receptor can be used. When the antigen is a receptor that does not emit any cell proliferation signal, a chimeric receptor containing the intracellular region of a receptor emitting a cell proliferation signal and the extracellular region of a receptor that does not emit any cell growth signal can be generated, and this chimeric receptor can be expressed in cells. Examples of receptors that emit a cell proliferation signal include G-CSF receptor, mpl, neu, GM-CSF receptor, EPO receptor, c-kit, and FLT-3. Examples of cells suitable for expressing such receptors include BaF3, NFS60, FDCP-1, FDCP-2, CTLL-2, DA-1, and KT-3.

Examples of sc(Fv)2 compositions in which the content ratio of a specific conformational isomer is higher than the content ratio of the other conformational isomer are sc(Fv)2 compositions in which the content ratio of the specific conformational isomer is 80% or more, preferably 90% or more, and particularly preferably 95% or more. More specifically, examples are sc(Fv)2 compositions in which the content ratio of the single chain diabody type is 80% or more, preferably 90% or more, and particularly preferably 95% or more, or sc(Fv)2 compositions in which the content ratio of the bivalent scFv type is 80% or more, preferably 90% or more, and particularly preferably 95% or more.

In the context of the present invention, the phrase "the content ratio of a specific conformational isomer is 80%" means that the percentage of the specific conformational isomer with respect to all conformational isomers contained in the sc(Fv)2 composition is 80%. For example, when two types of conformational isomers, the single chain diabody type and the bivalent scFv type, are present in an sc(Fv)2 composition, "the content ratio of the single chain diabody type is 80%" means that the ratio of the single chain diabody type to the bivalent scFv type is 80:20.

In the context of the present invention, the upper limit of a content ratio of 80% or more, 90% or more, or 95% or more is not particularly limited; however, 100% or close to 100% is preferable. An upper limit close to 100% depends on the purification technique or analysis technique used by those skilled in the art; however, it can be for example, 99.999%, 99.99%, 99.9%, or 99%. Content ratios of conformational isomers can be measured by separating the conformational isomers using, for example, ion exchange chromatography, isoelectric focusing, or capillary isoelectric focusing.

When using sc(Fv)2 compositions as pharmaceutical compositions, a higher activity is usually more preferable; therefore, an sc(Fv)2 composition in which the content ratio of the highly active conformational isomer is 80% or more is preferably included as an active ingredient. For example, since the agonistic activity of anti-Mpl antibody is higher in the single chain diabody type, when an sc(Fv)2 against Mpl is used as an agonist, the pharmaceutical compositions preferably contain as an active ingredient an sc(Fv)2 composition in which the content ratio of the single chain diabody type is 80% or more.

sc(Fv)2 compositions in which the content ratio of a specific conformational isomer is higher than the content ratio of the other conformational isomer can be produced, for example, by using the above-described methods for separating and obtaining a specific conformational isomer in an sc(Fv)2 composition, or by increasing the content ratio of a specific conformational isomer with regard to the content ratio of the other conformational isomer in an sc(Fv)2 composition.

For example, by increasing the percentage of the highly active conformational isomer in an sc(Fv)2 composition, sc(Fv)2 compositions having a high activity can be produced; in contrast, by lowering the percentage of the highly active conformational isomer in an sc(Fv)2 composition, sc(Fv)2 compositions having a suppressed activity can be produced.

When the activity of the single chain diabody type is higher than the bivalent scFv type, the activity of an sc(Fv)2 composition can be increased by increasing the content ratio of the single chain diabody type in the sc(Fv)2 composition; similarly, the activity of the sc(Fv)2 composition can be decreased by increasing the content ratio of the bivalent scFv type. Conversely, when the activity of the bivalent scFv type is higher than the single chain diabody type, the activity of an sc(Fv)2 composition can be increased by increasing the content ratio of the bivalent scFv type in the sc(Fv)2 composition and the activity of the sc(Fv)2 composition can be decreased by increasing the content ratio of the single chain diabody type. Which of the single chain diabody type or bivalent scFv type is highly active depends on the activity of interest; however, this can be easily measured by methods well known to those skilled in the art.

When using an sc(Fv)2 as a pharmaceutical composition, generally, a higher activity is often more preferable; therefore, the activity of a pharmaceutical composition can be increased by changing the percentage of a specific conformational isomer contained in an sc(Fv)2 composition.

Methods for increasing the content ratio of a specific conformational isomer with regard to the content ratio of the other conformational isomer in an sc(Fv)2 composition can be carried out by any method, and for example, the content ratio of the specific conformational isomer can be increased after obtaining the sc(Fv)2 composition, or DNAs encoding sc(Fv)2 can be designed such that the content ratio of the specific conformational isomer is increased.

Examples of methods for increasing the content ratio of a specific conformational isomer after obtaining an sc(Fv)2 composition include methods for isolating a conformational isomer of interest (or removing the conformational isomer that is not of interest) from the obtained sc(Fv)2 composition. The conformational isomer of interest can be isolated, as described above, by methods known to those skilled in the art for separating and obtaining proteins.

For example, by incubating sc(Fv)2 compositions in a heated state, the content ratio of a specific conformational isomer can also be increased. Furthermore, by incubating sc(Fv)2 compositions at a low pH and/or at low salt concentration, the content ratio of a specific conformational isomer can also be increased. More specifically, the present invention provides methods including the following steps (a) and (b), as well as pharmaceutical compositions produced by these methods:
(a) producing an sc(Fv)2 composition in which the content ratio of a specific conformational isomer is higher than the content ratio of the other conformational isomer by incubating the sc(Fv)2 composition in a heated state, or at low pH and/or low salt concentration; and
(b) mixing the sc(Fv)$_2$ composition produced in step (a) with at least one substance selected from the group consisting of salt, amino sugar, sugar alcohol, amino acid, and pH adjusting agent.

It was herein discovered that, when an sc(Fv)2 composition is a mixture of the bivalent scFv type and single chain diabody type and includes the bivalent scFv type in larger amount, by incubating the sc(Fv)2 composition at a given temperature and isomerizing the bivalent scFv type to the single chain diabody type, the content ratio of the single chain diabody type can be increased. By incubating an sc(Fv)2 composition at 15° C. to 50° C., preferably at 20° C. to 40° C., or particularly preferably at 25° C. to 35° C., the content ratio of the single chain diabody type can be increased. The incubated sc(Fv)2 composition retains the increased content ratio of the single chain diabody type, even when the temperature is returned to the original temperature afterward.

When an sc(Fv)2 composition is a mixture of the bivalent scFv type and single chain diabody type and includes the bivalent scFv type in larger amount, by incubating the sc(Fv)2 composition at pH3-6, or preferably pH 4.5, and isomerizing the bivalent scFv type to the single chain diabody type, the content ratio of the single chain diabody type can be increased. When incubating the sc(Fv)2 composition, the salt concentration depends on the pH; the salt concentration during incubation is preferably 0 mM to 500 mM, and more preferably 0 mM to 150 mM (FIG. 9A). sc(Fv)2 compositions in which the content ratio of the single chain diabody type has been increased by incubation can be subjected to methods described in PCT/JP06/306800 to purify the single chain diabody type to high purity. To suppress isomerization and stably store the highly pure single chain diabody-type sc(Fv)2 obtained by this method, the salt concentration is preferably in the range of 50 mM to 1000 mM, and more preferably in the range of 150 mM to 300 mM. The pH value is preferably in the range of 4.5 to 9.0, and more preferably in the range of 6.0 to 9.0.

Similarly, when an sc(Fv)2 composition is a mixture of the bivalent scFv type and single chain diabody type and includes the single chain diabody type in larger amount, by incubating the sc(Fv)2 composition at a given temperature and isomerizing the single chain diabody type to the bivalent scFv type, it was found that the content ratio of the bivalent scFv type can also be increased.

Hence, by returning the state of the presence of the conformational isomers in an sc(Fv)2 composition to a state of equilibrium, the amount of the conformational isomer which was included in lower amount (the minor component side) can be increased. Thereafter, pharmaceutical compositions of interest can be produced by obtaining one of the conformational isomers and stabilizing this conformational isomer.

Therefore, in one embodiment, the present invention provides methods including the following steps (a) to (c), as well as pharmaceutical compositions produced by these methods:
(a) preparing an sc(Fv)2 composition in which the content ratio of the single chain diabody type is higher than the content ratio of the bivalent scFv type, by incubating the sc(Fv)2 composition at 15'C' to 50° C., preferably 20° C. to 40° C., or particularly preferably 25° C. to 35° C., and/or pH3.0-6.0, and/or a salt concentration of 500 mM or less;
(b) obtaining (purifying) the produced single chain diabody-type sc(Fv)2; and
(c) stabilizing the single chain diabody-type sc(Fv)2 composition obtained in step (b).

Specific steps for stabilizing single chain diabody-type sc(Fv)2 compositions include: the step of adjusting the pH value to a range of 4.5 to 9.0, more preferably to a range of 6.0 to 9.0; the step of mixing at least one substance selected from the group consisting of salt, amino sugar, sugar alcohol, amino acid, and pH adjusting agent; and steps that combine these steps.

Moreover, stabilized bivalent scFv-type sc(Fv)2 compositions can similarly be produced.

Methods for designing DNAs encoding sc(Fv)2 such that the content ratio of a specific conformational isomer is increased include, for example, methods for designing DNAs such that the lengths of the linkers are appropriate, as described above.

Furthermore, by controlling the association of the sc(Fv)2 variable regions, the content ratio of a specific conformational isomer in an sc(Fv)2 composition can be increased. Specifically, DNA encoding sc(Fv)2 can be modified so that amino acid residues forming the interface of the sc(Fv)2 variable regions are modified.

In the context of the present invention, the term "association" indicates, for example, a state in which the variable regions of sc(Fv)2 interact.

In the context of the present invention, "controlling the association" refers to controlling so that a desired state of association is achieved, and more specifically, it refers to controlling so that undesirable associations are not form within the sc(Fv)2.

In the context of the present invention, "interface" generally indicates an association surface during association (interaction); 'amino acid residues forming the interface' generally refer to one or more amino acid residues contained in the sc(Fv)2 variable regions and which participate in the association, and more preferably, they are amino acid residues that come close during association and are involved in the interactions. Specifically, these interactions include cases in which amino acid residues that come close to each other during association form hydrogen bonds, electrostatic interactions, or salt brides, and such.

Specifically, in the present invention, the phrase "amino acid residues forming the interface" refers to amino acid residues included in variable regions of sc(Fv)2 variable regions that constitute an interface.

In the context of the present invention, "modification" of amino acid residues indicates a substitution of original amino acid residues (before modification) for other amino acid residues, deletion of original amino acid residues, or addition of new amino acid residues; however, it preferably refers to substitution of original amino acid residues with other amino acid residues.

In the above-described methods of the present invention, the phrase "modifying DNAs" refers to modifying DNAs in accordance with the amino acid residues that are introduced by the "modifications" of the present invention. More specifically, it refers to modifying DNAs encoding the original amino acid residues to DNAs encoding amino acid residues that are introduced through the modifications. Generally, it means performing gene manipulations or mutation treatments to original DNAs which would insert, delete, or substitute at least one nucleotide to obtain codons encoding the amino acid residues of interest. In other words, codons encoding the original amino acid residues are substituted with codons encoding amino acid residues that are introduced through the modifications. Such DNA modifications can be suitably carried out by those skilled in the art using known techniques such as site-specific mutagenesis or PCR mutagenesis.

In a preferred embodiment of the present invention, for example, amino acid mutations are introduced to an interface such that two or more amino acid residues forming the sc(Fv)2 variable region interface will have the same type of charge. It is considered that, due to a modification of two or more amino acid residues involved in association at the interface in a way that they will have the same type of charge, the association of these amino acid residues is inhibited by the repulsive force of their charges. Therefore, in the above-mentioned methods, the amino acid residues that are modified, in sc(Fv)2 variable regions forming an interface, are preferably two or more amino acid residues that approach each other during association.

Amino acid residues that come close during association can be found, for example, by analyzing the three-dimensional structure of sc(Fv)2 and examining the amino acid sequence of the variable regions forming the interface during association of the sc(Fv)2. Amino acid residues that approach each other at the interface are preferable targets for the "modification" in the methods of the present invention.

It is known that among amino acids, there are charged amino acids. Generally, lysine (K), arginine (R), and histidine (H) are known as positively charged amino acids (positive charge amino acids). Aspartic acid (D), glutamic acid (E), and such are known as negatively charged amino acids (negative charge amino acids). Therefore, preferably, the phrase "amino acids having the same type of charge" as used in the present invention refers to amino acids all having a positive charge, or amino acids all having a negative charge.

In the context of the present invention, the interface-forming amino acid residues are preferably modified to carry the same type of charge, and among the same type of amino acids, identical amino acids are further preferable. For example, the amino acid residues after modification may be lysine and arginine, but it is further preferable that they are two lysines or two arginines.

Furthermore, when a number of amino acid residues are introduced by the modification, a few uncharged amino acid residues may be included among these amino acid residues.

The number of amino acid residues subjected to modification in the methods of the present invention is not particularly limited; however, to avoid a decrease of the antigen binding activity, a small number of amino acid residues is preferably modified. The term "small number" mentioned above refers to, for example, a number of approximately 1 to 10, preferably a number of approximately 1 to 5, more preferably a number of approximately 1 to 3, and most preferably 1 or 2.

When an interface-forming amino acid residue (X) in the original sc(Fv)2 is already charged, or when it is forming hydrogen bonds, modifying an amino acid residue that comes close to and faces this amino acid residue during association in a way that it becomes the same amino acid residue (or an amino acid residue with the same type of charge) as the amino acid residue (X) is another preferred embodiment of the present invention. In this embodiment, it is only necessary to modify one of the amino acid residues forming the interface.

In a preferred embodiment of the present invention, amino acid residue mutations are introduced to the interface of sc(Fv)2 variable regions such that, through the modification of amino acid residues forming the interface, amino acid residues forming a hydrophobic core present at the interface become charged amino acid residues.

In general, the term "hydrophobic core" indicates a part that is formed when hydrophobic amino acid side chains assemble in the inside of the associated polypeptides. Examples of hydrophobic amino acids include alanine, isoleucine, leucine, methionine, phenylalanine, proline, tryptophan, and valine. Furthermore, amino acid residues other than hydrophobic amino acids (for example tyrosine) are sometimes involved in the formation of a hydrophobic core. This hydrophobic core, together with hydrophilic surfaces in which hydrophilic amino acid side chains are exposed to the outside, becomes a driving force for promoting the association of water-soluble polypeptides. When hydrophobic amino acids of two different domains are present on a molecular surface and are exposed to water molecules, the entropy will increase and the free energy will increase. Therefore, the two domains associate with each other to decrease the free energy and to become stable, and hydrophobic amino acids at the interface are buried in the inside of the molecule and form a hydrophobic core.

By modifying the amino acid residues that form the hydrophobic core to charged polar amino acids, one can inhibit the formation of a hydrophobic core during polypeptide association, and as a result, inhibit polypeptide association. A hydrophobic core is similarly formed by association of the variable regions in sc(Fv)2, which are polypeptides. Accordingly, by substituting amino acid residues in this hydrophobic core with charged amino acids, one can regulate the association of variable regions.

Those skilled in the art can readily determine the presence of a hydrophobic core, its site (region) of formation, and such by analyzing the amino acid sequence of a desired sc(Fv)2.

Moreover, the knobs-into-holes technique (Japanese Patent Kohyo Publication No. (JP-A) 2001-523971 (unexamined Japanese national phase publication corresponding to a non-Japanese international publication)) may be used on the amino acid residues forming the variable region interface to promote desirable associations. Knobs-into-holes is a method for introducing specific and complementary interactions at the interface of a first polypeptide and the interface of a second polypeptide, such that heteromultimer formation is promoted and homomultimer formation is suppressed (for example, a free thiol-containing residue is introduced at the interface of a first polypeptide and a corresponding free thiol-containing residue is introduced in the interface of a second polypeptide, such that a non-naturally occurring disulfide bond is formed between the first polypeptide and second polypeptide). Such methods can be used in the context of the present invention. Knobs-into-holes is a technique known to those skilled in the art, and can be appropriately introduced to sc(Fv)2 by those skilled in the art. Furthermore, the above-mentioned technique can be used in combination.

The variable region is usually composed of three CDR regions and four FR regions. In a preferred embodiment of the present invention, amino acid residues subjected to "modification" can be appropriately selected, for example, from among amino acid residues positioned in the CDR regions or FR regions. Generally, modification of amino acid residues in the CDR regions decreases the binding ability to antigens. Therefore, in the present invention, amino acid residues subjected to "modification" are not particularly limited, but are preferably appropriately selected from among amino acid residues located in the FR regions.

For desired sc(Fv)2 whose association is to be regulated by the methods of the present invention, those skilled in the art can appropriately determine the types of amino acid residues that approach each other at the FR interfaces upon association.

Specific examples of amino acid residues coming close to each other at the FR interfaces upon association include glutamine (Q) at position 39 on VH (FR2 region) and the facing (contacting) glutamine (Q) at position 38 on VL (FR2 region). Furthermore, favorable examples include leucine (L) at position 45 on VH (FR2) and the facing proline (P) at position 44 on VL (FR2). These positions are numbered according to the method of Kabat et al. (Kabat E A et al. 1991. Sequence of Proteins of Immunological Interest. NIH).

Since these amino acid residues are known to be highly conserved in humans and mice (J. Mol. Recognit. 2003; 16: 113-120), association of sc(Fv)2 variable regions can be regulated for sc(Fv)2 other than the sc(Fv)2 indicated in the Examples by modifying amino acid residues corresponding to the above-mentioned amino acid residues.

Examples of methods for increasing the content ratio of the single chain diabody type in sc(Fv)2 with an arrangement in the order of [variable region 1]-(linker 1)-[variable region 2]-(linker 2)-[variable region 3]-(linker 3)-[variable region 4] are described.

When the bivalent scFv type is produced in this sc(Fv)2, substitution mutations are introduced to the amino acid residues forming the interface of the variable regions, such that the association between variable region 1 and variable region 2 and the association between variable region 3 and variable region 4 are suppressed, while the association between variable region 1 and variable region 4 and the association between variable region 2 and variable region 3 are not suppressed (or are promoted).

When a conformational isomer having a structure in which variable region 1 and variable region 3 are associated and variable region 2 and variable region 4 are associated is produced in this sc(Fv)2, substitution mutations are introduced to the amino acid residues forming the interface of the variable regions, such that these associations are suppressed, while the association between variable region 1 and variable region 4 and the association between variable region 2 and variable region 3 are not suppressed (or are promoted).

When a conformational isomer having a structure in which variable region 1 and variable region 3 are associated is produced in this sc(Fv)2, substitution mutations are introduced to the amino acid residues forming the interface of the variable regions, such that this association is suppressed, while the association between variable region 1 and variable region 4 and the association between variable region 2 and variable region 3 are not suppressed (or are promoted).

When a conformational isomer having a structure in which variable region 2 and variable region 4 are associated is produced in this sc(Fv)2, substitution mutations are introduced to the amino acid residues forming the interface of the variable regions, such that this association is suppressed, while the association between variable region 1 and variable region 4 and the association between variable region 2 and variable region 3 are not suppressed (or are promoted).

Moreover, examples of methods for increasing the content ratio of the bivalent scFv type in sc(Fv)2 with an arrangement in the order of [variable region 1]-(linker 1)-[variable region 2]-(linker 2)-[variable region 3]-(linker 3)-[variable region 4] are described.

When the single chain diabody type is produced in this sc(Fv)2, substitution mutations are introduced to the amino acid residues forming the interface of the variable regions, such that the association between variable region 1 and variable region 4 and the association between variable region 2 and variable region 3 are suppressed, while the association between variable region 1 and variable region 2 and the association between variable region 3 and variable region 4 are not suppressed (or are promoted).

When a conformational isomer having a structure in which variable region 1 and variable region 3 are associated and variable region 2 and variable region 4 are associated is produced in this sc(Fv)2, substitution mutations are introduced to the amino acid residues forming the interface of the variable regions, such that these associations are suppressed, while the association between variable region 1 and variable region 2 and the association between variable region 3 and variable region 4 are not suppressed (or are promoted).

When a conformational isomer having a structure in which variable region 1 and variable region 3 are associated is produced in this sc(Fv)2, substitution mutations are introduced to the amino acid residues forming the interface of the variable regions, such that this association is suppressed, while the association between variable region 1 and variable region 2 and the association between variable region 3 and variable region 4 are not suppressed (or are promoted).

When a conformational isomer having a structure in which variable region 2 and variable region 4 are associated is produced in this sc(Fv)2, substitution mutations are introduced to the amino acid residues forming the interface of the variable regions, such that this association is suppressed, while the association between variable region 1 and variable region 2 and the association between variable region 3 and variable region 4 are not suppressed (or are promoted).

Without limitation, more detailed examples are described hereinafter.

For example, to decrease the percentage of the bivalent scFv type and increase the percentage of the single chain diabody type in an sc(Fv)2 with an arrangement in the order of [VH1]-linker-[VL2]-linker-[VH3]-linker-[VL4], the amino acid residues forming the interface of VH1 and VL2 are substituted with amino acid residues having the same type of charge, and the amino acid residues forming the interface of VH3 and VL4 are substituted with amino acid residues having the same type of charge and which are charges that do not repel (preferably charges having affinity to) the amino acid residues introduced in VH1 and VL2. Alternatively, for example, amino acid side chains forming the interface of VH1 and VL2 are substituted with larger side chains (knobs), and amino acid side chains forming the interface of VH3 and VL4 are substituted with smaller side chains (holes). By such substitutions, regulations are enabled such that the association of VH1 and VL2 and the association of VH3 and VL4 are suppressed, and the association of VH1 and VL4 and the association of VL2 and VH3 are not suppressed (or are promoted).

Moreover, to decrease the percentage of the single chain diabody type and increase the percentage of the bivalent scFv type in an sc(Fv)2 with an arrangement in the order of [VH1]-linker-[VL2]-linker-[VH3]-linker-[VL4], for example, amino acid residues forming the interface of VH1 and VL4 are substituted with amino acid residues having the same type of charge, and amino acid residues forming the interface of VH3 and VL2 are substituted with amino acid residues having the same type of charge and which are charges that do not repel (preferably charges having affinity to) the amino acid residues introduced in VH1 and VL4. Alternatively, for example, amino acid side chains forming the interface of VH1 and VL4 are substituted with larger side chains (knobs), and amino acid side chains forming the interface of VH3 and VL2 are substituted with smaller side chains (holes). By such substitutions, regulations are enabled such that the association of VH1 and VL4 and the association of VH3 and VL2 are suppressed. and the association of VH1 and VL2 and the association of VL3 and VH4 are not suppressed (or are promoted).

In the present invention, by substituting the following amino acid residues of (1) and (2) or of (3) and (4) to amino acid residues having the same type of charges, the content ratio of a specific conformational isomer in an (Fv)2 composition can be increased:
(1) an amino acid residue contained in the VH of an sc(Fv)2, which is an amino acid residue corresponding to position 39 in the amino acid sequence of the heavy chain;
(2) an amino acid residue contained in the VL of an sc(Fv)2, which is an amino acid residue corresponding to position 38 in the amino acid sequence of the light chain;
(3) an amino acid residue contained in the VH of an sc(Fv)2, which is an amino acid residue corresponding to position 45 in the amino acid sequence of the heavy chain; and
(4) an amino acid residue contained in the VL of an sc(Fv)2, which is an amino acid residue corresponding to position 44 in the amino acid sequence of the light chain.

Furthermore, in the present invention, by substituting either one of the following amino acid residues of (1) and (2) or either one of the amino acid residues of (3) and (4) to a charged amino acid residue, the content ratio of a specific conformational isomer in an sc(Fv)2 composition can be increased:
(1) an amino acid residue contained in the VH of an sc(Fv)2, which is an amino acid residue corresponding to position 39 in the amino acid sequence of the heavy chain;
(2) an amino acid residue contained in the VL of an sc(Fv)2, which is an amino acid residue corresponding to position 38 in the amino acid sequence of the light chain;
(3) an amino acid residue contained in the VH of an sc(Fv)2, which is an amino acid residue corresponding to position 45 in the amino acid sequence of the heavy chain; and
(4) an amino acid residue contained in the VL of an sc(Fv)2, which is an amino acid residue corresponding to position 44 in the amino acid sequence of the light chain.

The amino acid residues of (1) to (4) mentioned above are ordinarily (1) glutamine (Q), (2) glutamine (Q), (3) leucine (L), and (4) proline (P), respectively, in humans and mice; however, the present invention is not necessarily limited to such amino acid residues, and contemplates the inclusion of other amino acids corresponding to these amino acids. For example, in humans, the amino acid in the VL corresponding to position 38 in the amino acid sequence may be histidine (H). For any position, those skilled in the art can determine the type of amino acid residue corresponding to that position by referring to known references and such (for example, J. Mol. Recognit. 2003; 16:113-120).

The present invention provides any of the methods described in (1) to (4) below, and pharmaceutical compositions produced by these methods:
(1) a method including the following steps of:
  (a) producing an sc(Fv)2 composition in which the content ratio of a specific conformational isomer is higher than the content ratio of the other conformational isomer by substituting amino acid residues at an interface formed by the heavy chain variable region and light chain variable region of an sc(Fv)2 with charged amino acid residues; and
  (b) mixing the sc(Fv)2 composition produced in step (a) with at least one substance selected from the group consisting of salt, amino sugar, sugar alcohol, amino acid, and pH adjusting agent;
(2) a method including the following steps of:
  (a) preparing an sc(Fv)2 composition in which the content ratio of a specific conformational isomer is higher than the content ratio of the other conformational isomer by substituting the following amino acid residues of (i) and (ii) with amino acid residues having the same type of charge:
    (i) an amino acid residue contained in the heavy chain variable region of an sc(Fv)2 and corresponding to position 39 of the heavy chain variable region; and
    (ii) an amino acid residue contained in the light chain variable region of an sc(Fv)2 and corresponding to position 38 in the amino acid sequence of the light chain variable region; and
  (b) mixing the sc(Fv)2 composition produced in step (a) with at least one substance selected from the group consisting of salt, amino sugar, sugar alcohol, amino acid, and pH adjusting agent;
(3) a method including the following steps of:
  (a) preparing an sc(Fv)2 composition in which the content ratio of a specific conformational isomer is higher than the content ratio of the other conformational isomer by substituting the following amino acid residues of (i) and (ii) with amino acid residues having the same type of charge:
    (i) an amino acid residue contained in the heavy chain variable region of an sc(Fv)2 and corresponding to position 45 in the amino acid sequence of the heavy chain variable region; and
    (ii) an amino acid residue contained in the light chain variable region of an sc(Fv)2 and corresponding to position 44 in the amino acid sequence of the light chain variable region; and
  (b) mixing the sc(Fv)2 composition produced in step (a) with at least one substance selected from the group consisting of salt, amino sugar, sugar alcohol, amino acid, and pH adjusting agent; and
(4) a method including the following steps of:
  (a) producing an sc(Fv)2 composition in which the content ratio of a specific conformational isomer is higher than the content ratio of the other conformational isomer by substituting either one of the following amino acid residues of (i) and (ii) with a charged amino acid residue:
    (i) an amino acid residue contained in the heavy chain variable region of an sc(Fv)2 and corresponding to position 45 in the amino acid sequence of the heavy chain variable region; and (ii) an amino acid residue contained in the light chain variable region of an sc(Fv)2 and corresponding to position 44 in the amino acid sequence of the light chain variable region; and (b) mixing the sc(Fv)2 composition produced in step (a) with at least one substance selected from the group consisting of salt, amino sugar, sugar alcohol, amino acid, and pH adjusting agent.

It is also possible to increase the content ratio of a specific conformational isomer in an sc(Fv)2 composition by adjusting the length of the linkers at both ends and/or the linker in the middle of an sc(Fv)2. Hence, the present invention provides methods including the steps below, and pharmaceutical compositions produced by these methods:

(a) producing an sc(Fv)2 composition in which the content ratio of a specific conformational isomer is higher than the content ratio of the other conformational isomer by adjusting the length of the linkers of an sc(Fv)2; and (b) mixing the sc(Fv)2 composition prepared in step (a) with at least one substance selected from the group consisting of salt, amino sugar, sugar alcohol, amino acid, and pH adjusting agent.

In the present invention, when an sc(Fv)2 has an arrangement in the order of [variable region 1]-(linker 1)-[variable region 2]-(linker 2)-[variable region 3]-(linker 3)-[variable region 4], the 'linkers at both ends' are linker 1 and linker 3, and the 'linker in the middle' is linker 2.

Specifically, by making the linkers at both ends contain 0 to 12 amino acids and the linker in the middle contain 10 to 30 amino acids, the percentage of the single chain diabody type in an sc(Fv)2 composition can be increased, and by making the linkers at both ends contain 12 to 30 amino acids and the linker in the middle contain 0 to 10 amino acids, the percentage of the bivalent scFv type in an sc(Fv)2 composition can be increased.

Furthermore, by making the linkers at both ends contain 0 to 12 amino acids and the linker in the middle contain 0 to 10 amino acids, sc(Fv)2 compositions in which the content ratio of the single chain diabody type is 80% or more can be produced; and by making the linkers at both ends contain 12 to 30 amino acids and the linker in the middle contain 0 to 10 amino acids, sc(Fv)2 compositions in which the content ratio of the bivalent scFv type is 80% or more can be produced.

Therefore, the present invention provides the methods described in any of the following (1) to (3), and pharmaceutical compositions produced by these methods:

(1) a method including the steps of:
 (a) producing an sc(Fv)2 composition in which the content ratio of the single chain diabody type is higher than the content ratio of the bivalent scFv type by adjusting the sc(Fv)2 linkers at both ends to contain, 0 to 12 amino acids and the sc(Fv)2 linker in the middle to contain 10 to 30 amino acids; and
 (b) mixing the sc(Fv)2 composition produced in step (a) with at least one substance selected from the group consisting of salt, amino sugar, sugar alcohol, amino acid, and pH adjusting agent;

(2) a method including the steps of:
 (a) producing an sc(Fv)2 composition in which the content ratio of the single chain diabody type is higher than the content ratio of the bivalent scFv type by adjusting the sc(Fv)2 linkers at both ends to contain 0 to 12 amino acids and the sc(Fv)2 linker in the middle to contain 0 to 10 amino acids; and (b) mixing the sc(Fv)2 composition produced in step (a) with at least one substance selected from the group consisting of salt, amino sugar, sugar alcohol, amino acid, and pH adjusting agent; and (3) a method including the steps of:
 (a) producing an sc(Fv)2 composition in which the content ratio of the bivalent scFv type is higher than the content ratio of the single chain diabody type by adjusting the sc(Fv)2 linkers at both ends to contain 12 to 30 amino acids and the sc(Fv)2 linker in the middle to contain 0 to 10 amino acids; and
 (b) mixing the sc(Fv)2 composition produced in step (a) with at least one substance selected from the group consisting of salt, amino sugar, sugar alcohol, amino acid, and pH adjusting agent.

Whether a certain sc(Fv)2 composition is an sc(Fv)2 composition in which the content ratio of a specific conformational isomer is higher than the content ratio of the other conformational isomer can be determined by methods known to those skilled in the art, such as analyses using NMR and crystal structure analyses. Furthermore, it can also be confirmed by methods for determining the structures of conformational isomers in an sc(Fv)2 composition, which include the step of cleaving linker regions of sc(Fv)2.

In the context of the present invention, the term "linker regions" refers to regions containing a linker and linker-proximal regions. A "linker-proximal region" refers to a region containing 20 amino acids, starting from the amino acid adjacent to the linker to the 20th amino acid toward the variable region side. Therefore, the linker region is a region in which a region containing 20 amino acids have been added to both sides of a linker.

Methods for determining the structure of conformational isomers in an sc(Fv)2 composition, which include the step of cleaving the linker regions of sc(Fv)2, are simpler than methods for analyzing the single chain diabody type and bivalent scFv type by chromatography and such. Chromatography enables the separation of conformational isomers; however, it does not enable the determination of the structures of the separated sc(Fv)2. Using these methods, one can determine the structures of the conformational isomers separated by chromatography and such.

Since three dimensional structures differ between the single chain diabody type and bivalent scFv type, when any one linker region from among the three linker regions is cleaved by an enzyme or such, the products after cleavage will be different for the single chain diabody type and the bivalent scFv type.

Figure 13:
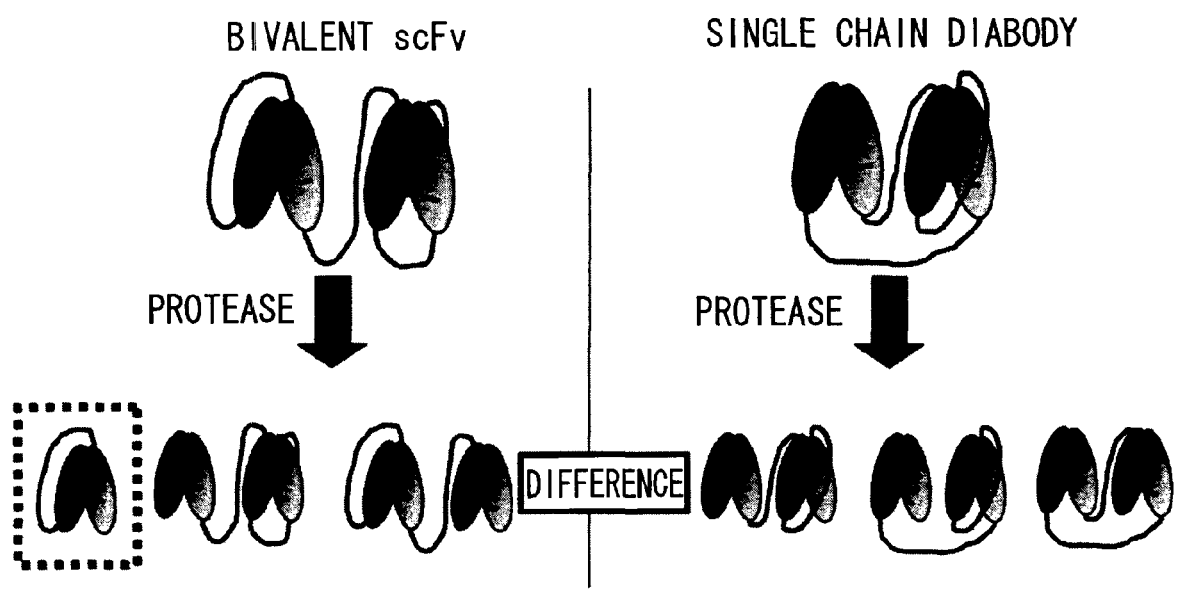
FIG. 13 depicts the difference in degradation patterns after limited subtilisin degradation, which is caused by differences in the conformations of the bivalent scFv and the single chain antibody. In the case of the bivalent scFv structure, the low molecular weight fragment framed in a dotted line is formed.

Specifically, in the case of an sc(Fv)2 having an arrangement in the order of [variable region 1]-(linker 1)-[variable region 2]-(linker 2)-[variable region 3]-(linker 3)-[variable region 4], in the bivalent scFv type, cleavage at the linker 1 or 3 region will not lead to separation into two scFv since the four variable regions are bound by covalent bonds or noncovalent bonds; however, cleavage at the linker 2 region will lead to separation into two scFv, an scFv composed of the variable regions 1 and 2 and an scFv composed the variable regions 3 and 4. In the single chain diabody type, even if the linker region is cleaved at any of linker 1, 2, or 3, since the four variable regions are bound by covalent bonds or noncovalent bonds, they will not separate into two scFv (FIG. 13).

Therefore, when any one of the three linker regions is cleaved in the bivalent scFv type, two types of products, a product composed of four variable regions and a product composed of two variable regions, are produced; however, when any one of the three linker regions is cleaved in the single chain diabody type, only products composed of four variable regions are produced.

As described above, by cleaving one of the linker regions of sc(Fv) using an enzyme or such and comparing the products after cleavage, it is possible to examine whether the sc(Fv)2 are of a single chain diabody type or a bivalent scFv type.

Methods for determining the structures of conformational isomers in an sc(Fv)2 composition, which include the step of cleaving the linker regions of sc(Fv)2, are for example methods including the steps of: (a) cleaving a linker region of an sc(Fv) in an sc(Fv)2 composition; and (b) measuring the molecular weight or structure of products after cleavage.

Since the linker regions of sc(Fv)2 generally do not form higher order structures, they are known to be readily degraded by proteases and such (Hoedemaeker et al., J. Biol. Chem. 1997; 272:29784-29789). Methods for cleaving linkers are not particularly limited; however, cleavage by enzymes is preferable, and cleavage by proteases is particularly preferable. The proteases to be used are not particularly limited, and both exopeptidases and endopeptidases may be used; however, since the objective is to cleave linkers, endopeptidases are preferable. The endopeptidases may be of any kind such as serine proteases, thiol peptidases, acidic proteases, and metalloproteases; those skilled in the art can make a suitable selection according to the type and amino acid sequence of the linkers. Examples of serine proteases include trypsin which specifically hydrolyzes the C-terminal side of Arg and Lys residues, and subtilisin which non-specifically hydrolyzes proteins and peptides. Examples of thiol proteases include pyroglutamate aminopeptidase, which specifically hydrolyzes pGlu residues at the N-terminus of proteins and peptides, and papain, which non-specifically hydrolyzes proteins and peptides.

The number of cleaved linkers is not limited, but is preferably one. The conditions for cleaving one linker can be determined by methods known to those skilled in the art.

Further, the molecular weight or structure of products after cleavage is preferably measured while maintaining the non-covalent bonds between the variable regions, and for example, native page or gel filtration can be used.

The present invention provides methods for suppressing the isomerization of sc(Fv)2, which include the step of adding at least one substance selected from the group consisting of salt, amino sugar, sugar alcohol, amino acid, and pH adjusting agent to the sc(Fv)2. Since specific conformational isomers of sc(Fv)2 can be stabilized by the methods of the present invention, the methods of the present invention can be used for analyzing specific conformational isomers of sc(Fv)2, and such.

Moreover, in pharmaceutical compositions containing sc(Fv)2, the substances of the present invention are useful for making specific conformational isomers exist stably, and for maintaining the content ratio of the multiple conformational isomers present constant during storage; thus, they can be used as stabilizers when storing pharmaceutical drug substances or formulations. Hence, the present invention also provides methods for suppressing the isomerization of active ingredients in a pharmaceutical composition, which include the step of adding at least one substance selected from the group consisting of salt, amino sugar, sugar alcohol, amino acid, and pH adjusting agent. Isomerization of sc(Fv)2 can also be suppressed by freeze-drying the sc(Fv)2.

Furthermore, the present invention provides stabilizing agents to be used for suppressing the isomerization reactions of sc(Fv)2, which include at least one substance selected from the group consisting of salt, amino sugar, sugar alcohol, amino acid, and pH adjusting agent, as well as methods for using the stabilizing agents. It also provides uses of salts, amino sugars, amino acids, or pH adjusting agents in the production of the stabilizing agents of the present invention, and uses of salts, amino sugars, amino acids, or pH adjusting agents for suppressing the isomerization reactions of sc(Fv)2. Therefore, the present invention provides novel uses of salts, amino sugars, amino acids, and pH adjusting agents. The stabilizing agents of the present invention can be prepared by methods known to those skilled in the art. The manufacturers and suppliers of the substances comprised in the stabilizing agents of the present invention are known to those skilled in the art.

Further, the present invention provides methods of screening for substances that suppress the isomerization reactions of sc(Fv)2. The screened substances can be used as stabilizing agents used for suppressing the isomerization reactions of sc(Fv)2.

In these methods, first, test substances are contacted with prepared sc(Fv)2 compositions. In the context of methods of the present invention, the "test substances" are not particularly limited; examples include single compounds such as known pharmaceutically acceptable carriers, naturally-derived compounds, organic compounds, inorganic compounds, proteins, and peptides, as well as compound libraries, expression products of gene libraries, cell extracts, cell culture supernatants, fermented products of microorganisms, marine organism extracts, plant extracts, prokaryotic cell extracts, eukaryotic unicellular extracts, and animal cell extracts. In the context of the present invention, "contact" may be carried out by adding test substances to sc(Fv)2 compositions or by adding sc(Fv)2 compositions to test substances.

Next, in these methods, whether the isomerization reactions of sc(Fv)2 are suppressed or not is measured, and substances that suppress the isomerization reactions of sc(Fv)2 are selected. As described above, suppression of the isomerization reactions of sc(Fv)2 can be measured by methods known to those skilled in the art.

All prior art references cited herein are incorporated by reference into this description.

EXAMPLES

Herein below, the present invention will be specifically described with reference to Examples, but it is not to be construed as being limited thereto.

Example 1

Investigation into Stabilizing Agents for the Isomerization Reactions of Humanized Anti-Human Mpl Antibody hVB22B Sc(Fv)2

As shown in FIG. 1, sc(Fv)2 undergo mutual structural conversion (isomerization) between two types of conformational isomer. To suppress the mutual isomerization reactions of sc(Fv)2, the two types of conformational isomer of hVB22B u2-wz4 sc(Fv)2 purified to high purity, which are peak 1 (91.4% peak 1) and peak 2 (99.6% peak 2), were used and stabilizing agents that suppress the isomerization reaction of each of the conformational isomers (peak 1 which is the bivalent scFv type or peak 2 which is the single chain diabody type) were investigated.

Figure 2:
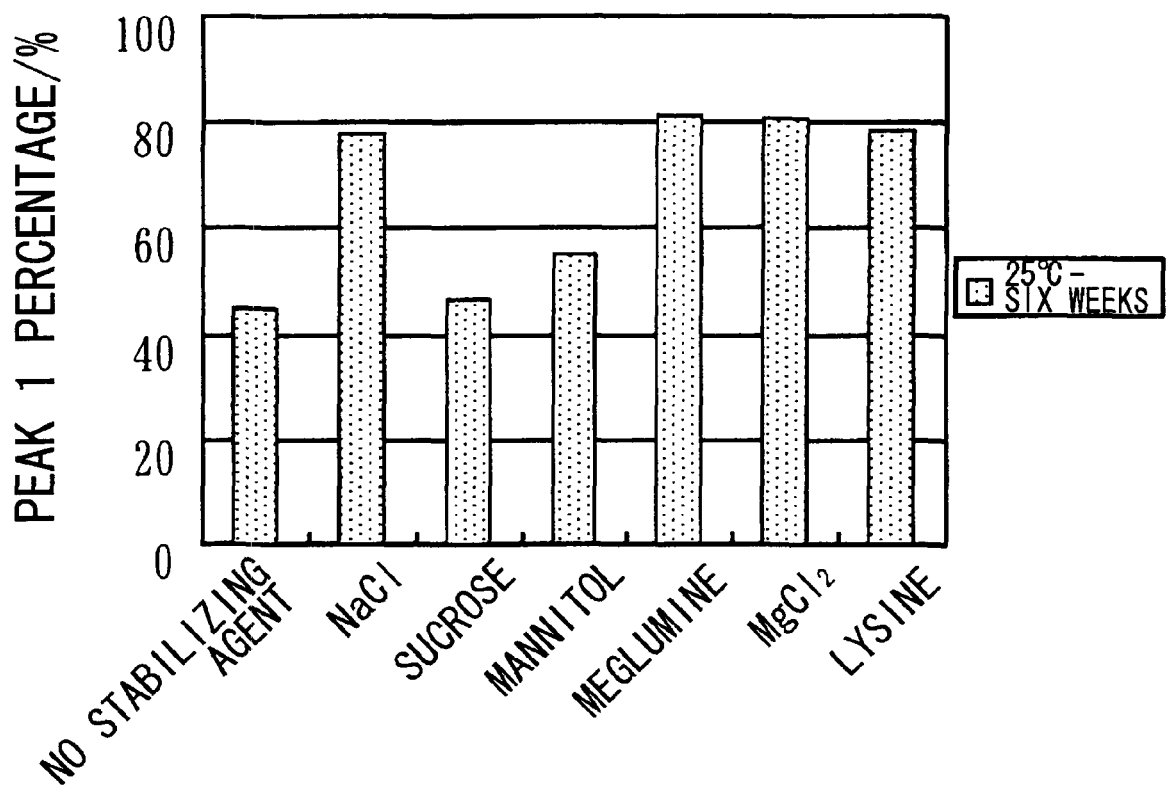
FIG. 2 depicts the percentages of peak 1 remaining after 25° C.-six weeks, starting from 91.4% peak 1.

Specifically, the content ratio of each conformational isomer after reaction under the following conditions was measured using cation exchange chromatography:

<Stability Test Conditions>
20 mM sodium citrate, pH6.5+the following additives
Additives: none, 10% sucrose, 10% mannitol, 10% meglumine, 50 mM magnesium chloride, 100 mM lysine hydrochloride
hVB22B u2-wz4 sc(Fv)2 peak 1: 62 μg/mL
hVB22B u2-wz4 sc(Fv)2 peak 2: 62 μg/mL
25° C.-six weeks After reaction under the above-described conditions, the content ratio of each conformational isomer after 25° C.-six weeks was measured using cation exchange chromatography. The elution conditions for the cation exchange chromatography are as follows:
<Elution Conditions>
Column: Bioassist S (TOSOH)
Mobile phase A: 20 mM sodium phosphate, pH7.0
Mobile phase B: 20 mM sodium phosphate, 500 mM KCl, pH7.0
Flow rate: 0.8 ml/min
Detection: 220 nm The percentage of peak 1 after 25° C.-six weeks when started from 91.4% peak 1 is shown in FIG. 2. The peak 1 percentage was calculated from: peak 1 peak area/(peak 1+peak 2 peak area)*100.

In the absence of a stabilizing agent (none), the percentage of peak 1 after 25° C.-six weeks decreased to about 45%, and half or more isomerized to peak 2. In contrast, under conditions in which NaCl, meglumine, $MgCl_2$, or lysine was added, the isomerization reaction was considerably suppressed, and the percentage of peak 1 after 25° C.-six weeks was about 80%. When mannitol was added, only a slight isomerization-suppressing effect was observed, and almost no stabilizing effect was observed with sucrose.

Figure 3:
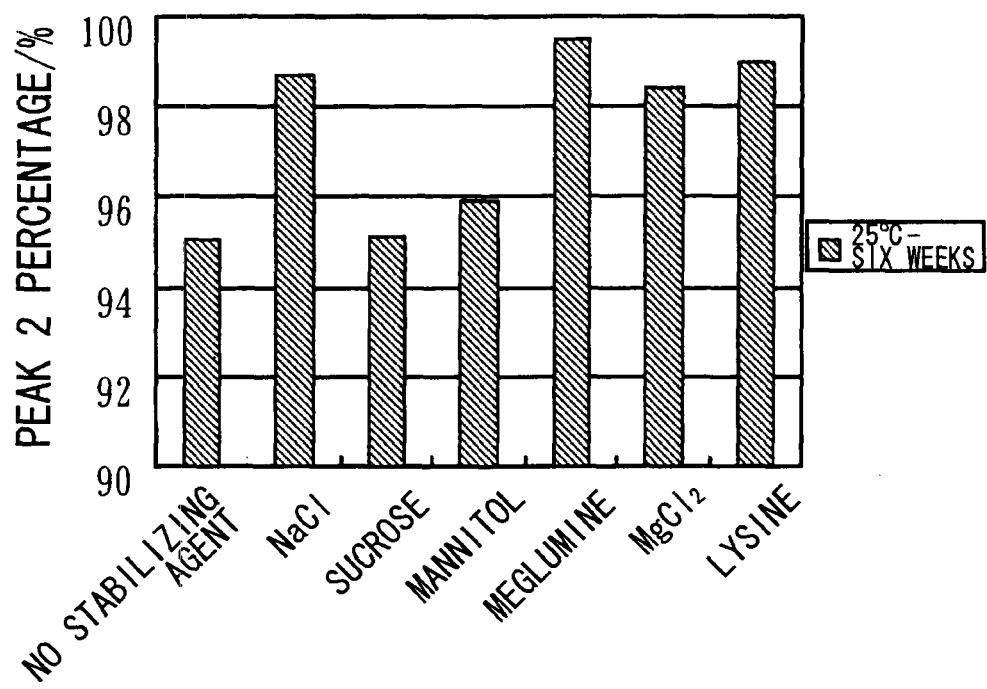
FIG. 3 depicts the percentages of peak 2 remaining after 25° C.-six weeks, starting from 99.6% peak 2.

The percentage of peak 2 after 25° C.-six weeks when started from 99.6% peak 2 is shown in FIG. 3. The peak 2 percentage was calculated from: peak 2 peak area/(peak 1+peak 2 peak area)*100.

In the absence of a stabilizing agent (none), the percentage of peak 2 after 25° C.-six weeks decreased to about 95%, and 5% or so isomerized to peak 1. In contrast, under conditions in which NaCl, meglumine, $MgCl_2$, or lysine was added, the isomerization reaction was considerably suppressed, and the percentage of peak 2 after 25° C.-six weeks was 98% or more. In particular, the isomerization-suppressing effect was highest when meglumine was added. When mannitol was added, only a slight isomerization-suppressing effect was observed, and almost no stabilizing effect was observed with sucrose.

From the above, stabilizing agents which suppress the mutual isomerization reactions between the conformational isomers of hVB22B sc(Fv)2 were found. Since NaCl, meglumine, $MgCl_2$, and lysine showed a significant effect as stabilizing agents, it was revealed that isomerization reactions could be suppressed by adding salts such as NaCl, amino sugars such as meglumine, divalent salts such as $MgCl_2$, or amino acids such as lysine.

Example 2 pH Dependence and NaCl Concentration Dependence of the Isomerization Reactions of hVB22B sc(Fv)2

Next, using the two types of conformational isomer of hVB22B u2-wz4 sc(Fv)2 purified to high purity, i.e. peak 1 (91.4% peak 1) and peak 2 (99.6% peak 2), the pH and NaCl concentrations at which the isomerization reaction of each of the conformational isomers (peak 1 or peak 2) could be suppressed were investigated.

Figure 4:
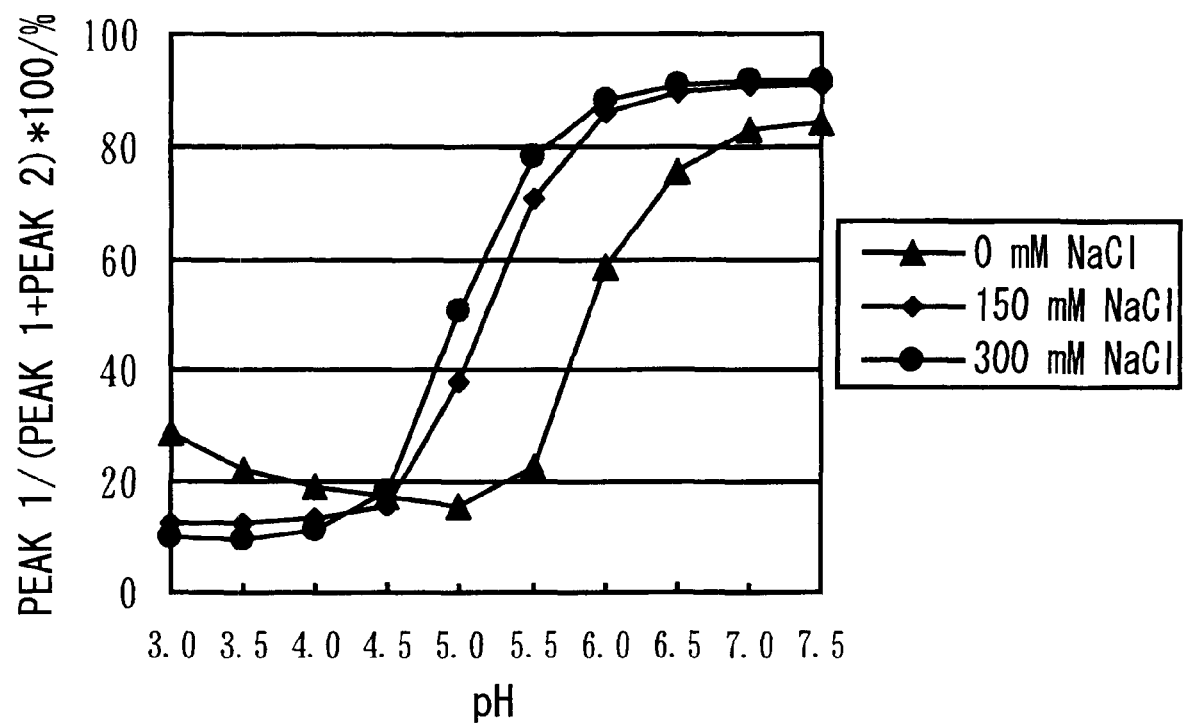
FIG. 4 depicts the percentages of peak 1 remaining after 25° C.-five days, starting from 91.4% peak 1.
Figure 5:
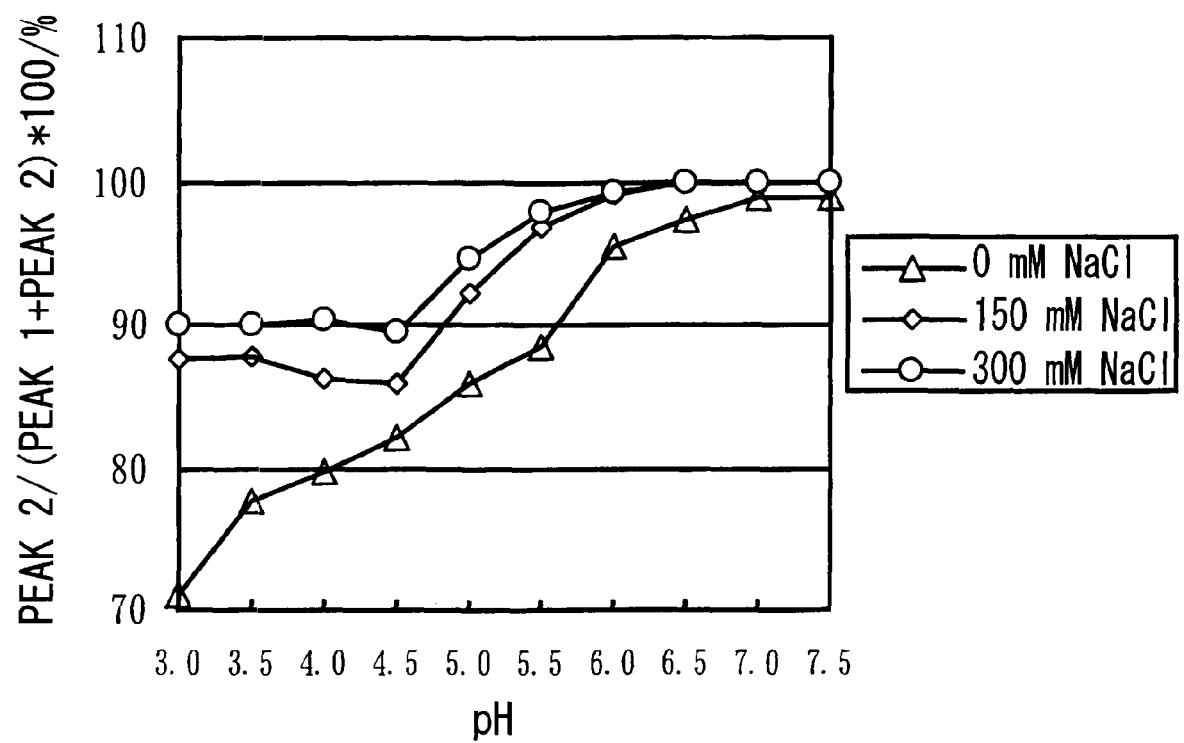
FIG. 5 depicts the percentages of peak 2 remaining after 25° C.-five days, starting from 99.6% peak 2.

Specifically, the content ratio of each conformational isomer after reaction under the following conditions was measured using cation exchange chromatography:
<Stability Test Conditions>
20 mM sodium citrate,
0/150/300 mM NaCl,
pH3.0/3.5/4.0/4.5/5.0/5.5/6.0/6.5/7.0/7.5
hVB22B u2-wz4 sc(Fv)2 peak 1: 0.2 mg/mL
hVB22B u2-wz4 sc(Fv)2 peak 2: 0.2 mg/mL
25° C.-five days After reaction under the above-described conditions, the content ratio of each conformational isomer after 25° C.-five days was determined using cation exchange chromatography. The elution conditions for the cation exchange chromatography are as follows:
<Elution Conditions>
Column: Bioassist S (TOSOH)
Mobile phase A: 20 mM sodium phosphate, pH7.0
Mobile phase B: 20 mM sodium phosphate, 500 mM KCl, pH7.0
Flow rate: 0.8 ml/min
Detection: 220 nm The percentage of peak 1 after 25° C.-five days when started from 91.4% peak 1 is shown in FIG. 4. The percentage of peak 2 after 25° C.-five days when started from 99.6% peak 2 is shown in FIG. 5. The methods for calculating the peak 1 percentage and peak 2 percentage are the same as in Example 1.

According to the above, the isomerization reaction from peak 1 to peak 2 and the isomerization reaction from peak 2 to peak 1 both showed a large pH dependence and NaCl concentration dependence. It was revealed that isomerization is promoted the lower the pH and the lower the NaCl concentration. Since it is known that ordinary IgGs are stable at around pH5.5 to 6.0 and that salt concentrations do not have a large effect on aggregation (Pharm. Res. 1994, 11(5), 764-771), the isomerization reactions of sc(Fv)2 showed a completely different profile compared to the IgG aggregations.

So far, there have been no reports on such isomerization reactions of proteins. Accordingly, the present study shows for the first time that isomerization reactions in hVB22B sc(Fv)2 can be suppressed by pH or NaCl concentration.

Example 3

Buffer/pH Dependence and NaCl Concentration Dependence of the Isomerization Reaction of the Single Chain Diabody-Type hVB22B Sc(Fv)2

Using peak 2 (99.6% peak 2), which is a conformational isomer of hVB22B u2-wz4 sc(Fv)2 purified to high purity, the pH and NaCl concentrations at which the isomerization reaction from peak 2, which is single chain diabody, to peak 1, which is bivalent scFv, could be suppressed were investigated using two types of buffer solutions. Detailed investigations were carried out particularly on the NaCl concentrations.

Figure 6:
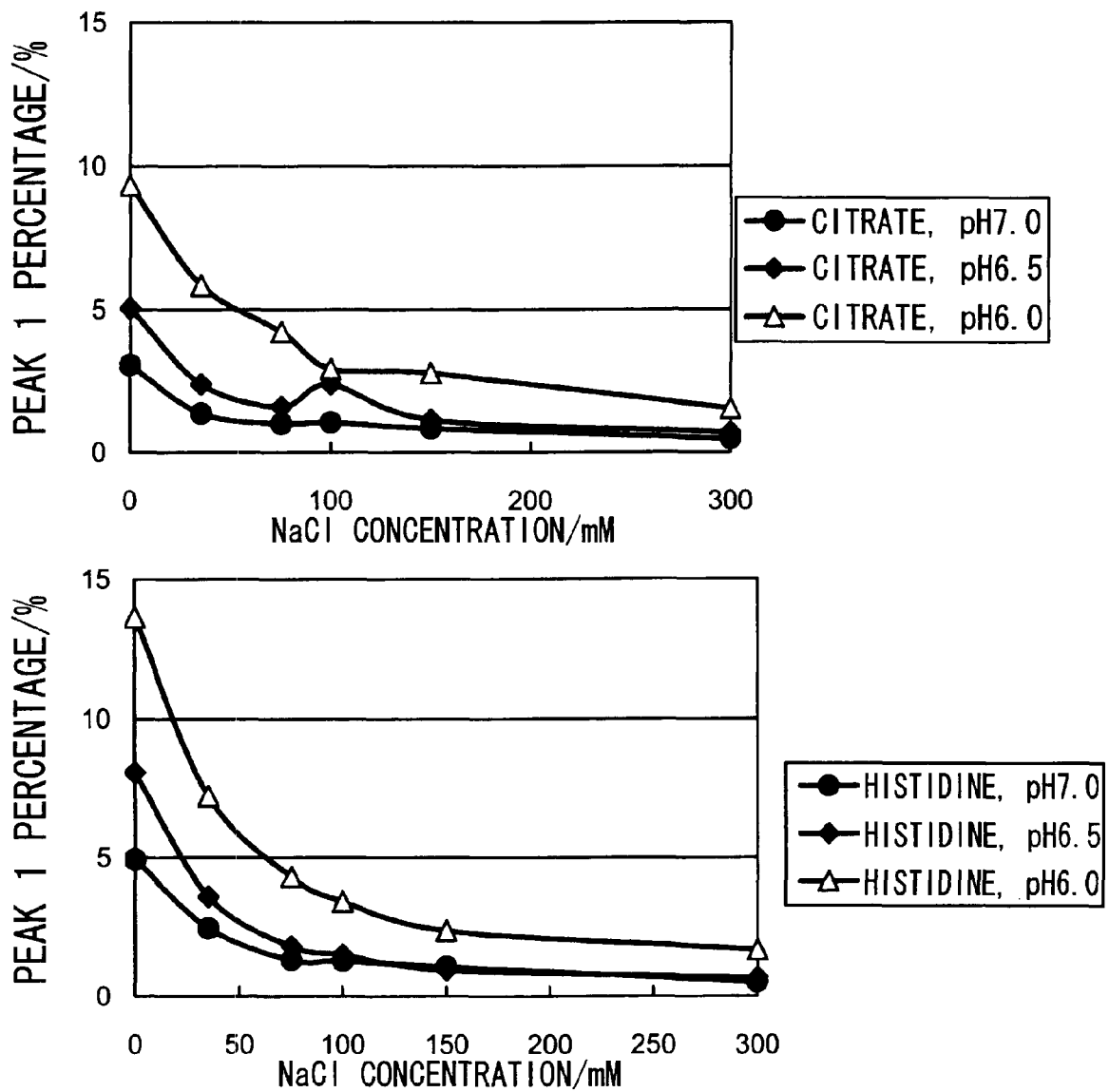
FIG. 6 depicts the percentages of peak 1 remaining after 25° C.-20 days when peak 2 was subjected to each of the conditions.

Specifically, the content ratio of each conformational isomer after reaction under the following conditions was measured using cation exchange chromatography:
<Stability Test Conditions>
Buffer: 20 mM sodium citrate/20 mM histidine HCl
NaCl: 0 mM/35 ml/75 mM/0 mM/150 mM/300 mM
pH: 6.0/6.5/7.0
25° C.-20 days After reaction under the above-described conditions, the content ratio of each conformational isomer after 25° C.-20 days was measured using cation exchange chromatography. The elution conditions for the cation exchange chromatography are as follows:
<Elution Conditions>
Column: Bioassist S (TOSOH)
Mobile phase A: 20 mM sodium phosphate, pH7.0
Mobile phase B: 20 mM sodium phosphate, 500 mM KCl, pH7.0
Flow rate: 0.8 ml/min
Detection: 220 nm The percentage of peak 1 after 25° C.-20 days for 99.6% peak 2 is shown in FIG. 6. The method for calculating the peak 1 percentage is the same as in Example 1.

According to the above, the isomerization reaction from peak 2 to peak 1 showed both a large pH dependence and NaCl concentration dependence. Regarding the pH, a trend similar to that in Example 2 was observed. As a result of a more detailed investigation on NaCl concentrations, the isomerization reactions were found to be suppressed as the NaCl concentration increases, and in particular, the suppressive effect was found to become significant at NaCl concentrations of approximately 50 mM or more. This trend was confirmed at all pHs and with all types of buffer solutions. Therefore, it was revealed isomerization reactions could be suppressed by adding NaCl to sc(Fv)2 formulations.

Example 4 pH Dependence and NaCl Concentration Dependence of the Isomerization Reaction of the Bivalent scFv-Type Mouse Anti-Human Mpl Antibody mVB22B sc(Fv)2

Using bivalent scFv among the two types of conformational isomer of mVB22B sc(Fv)2 purified to high purity, the pH and NaCl concentrations at which the isomerization reaction from peak 1, which is bivalent scFv, to peak 2, which is single chain diabody, could be suppressed were investigated.

Figure 7:
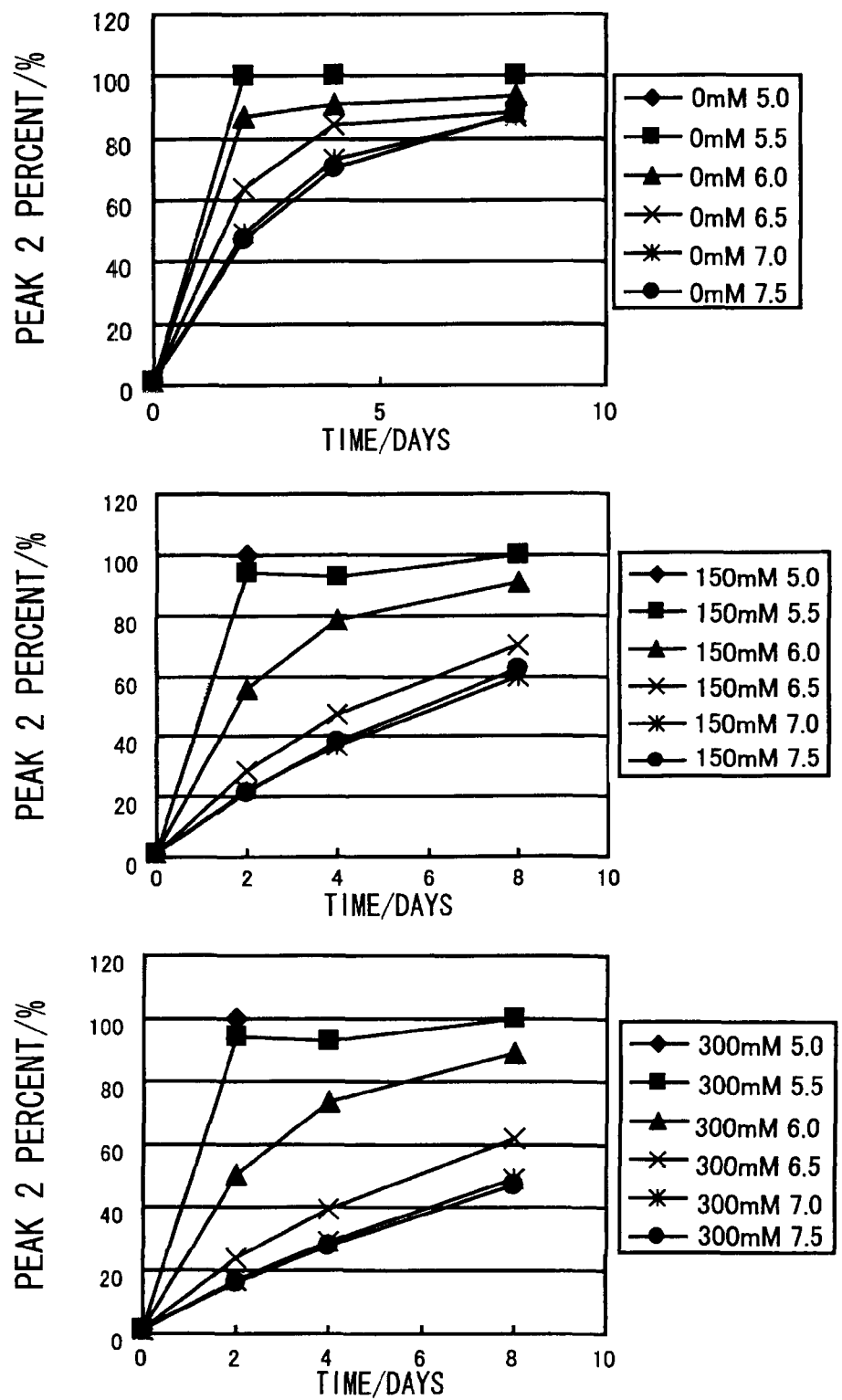
FIG. 7 depicts the percentages of peak 2 remaining after 25° C.-five days under each solution condition, when started from approximately 99% peak 1.

Specifically, the content ratio of each conformational isomer after reaction under the following conditions was measured using anion exchange chromatography:
<Stability Test Conditions>
20 mM sodium citrate,
0/150/300 mM NaCl,
pH: 5.0/5.5/6.0/6.5/7.0/7.5
mVB22B sc(Fv)2 peak 1: 0.1 mg/mL
40° C.-two, four, eight days After reaction under the above-described conditions, the initial content ratio of each conformational isomer and those after 40° C.-two, four, eight days were measured using anion exchange chromatography. The elution conditions for the anion exchange chromatography are as follows:
<Elution Conditions>
Column: MONO Q (Amersham bioscience)
Mobile phase A: 50 mM Tris-HCl, pH8.0
Mobile phase B: 50 mM Tris-HCl, 500 mM NaCl, pH8.0
Flow rate: 1.0 ml/min
Detection: 220 nm The percentages, for each of the solution conditions, of peak 2 produced by isomerization after 40° C.-two, four, eight-day stabilization tests performed on peak 1 are shown in FIG. 7. The method for calculating the peak 2 percentage is the same as in Example 1.

According to the above, the isomerization reaction from peak 1 to peak 2 showed large pH dependence and NaCl concentration dependence. It was revealed that isomerization is promoted the lower the pH and the lower the NaCl concentration. Since it is known that ordinary IgGs are stable at around pH5.5 to 6.0 and that salt concentrations do not to have a large effect on aggregation (Pharm. Res. 1994, 11(5), 764-771), the isomerization reaction of sc(Fv)2 showed a completely different profile compared to IgG aggregations.

To date, there have been no reports on such isomerization reactions of proteins. Accordingly, the present study shows for the first time that isomerization reactions in mVB22B sc(Fv)2 can be suppressed by pH or NaCl concentration.

Example 5

Stabilization of Isomerization Reaction Through Freeze-Dried Formulation

The effectiveness of freeze-dried formulation as a method for suppressing the isomerization reactions was investigated. Examination on whether the isomerization reactions could be suppressed through freeze-dried formulation of a mixture of the two types of conformational isomer of mVB22B sc(Fv)2 was attempted.
<Conditions for Preparing Freeze-Dried Formulations and Solution Formulations>
20 mM sodium citrate, 150 mM NaCl, 5% sucrose,
~% polysorbate 80, pH7.0
VB22B sc(Fv)2: 0.2, 1.0, 5.0 mg/mL
Scale: 500 μL Freeze-dried formulations and solution formulations were prepared under the above-described conditions. For freeze-dried formulations, samples were loaded into a freeze-drier (KYOWAC Triomaster IIA-04, Kyowa Shinku) that had been pre-frozen to −50° C., and then left to stand for one hour. The sample temperature was confirmed to be −40° C. or less and after pulling a vacuum to 0.1 Torr or less, primary drying at −20° C. and secondary drying at 30° C. were carried out.

Figure 8:
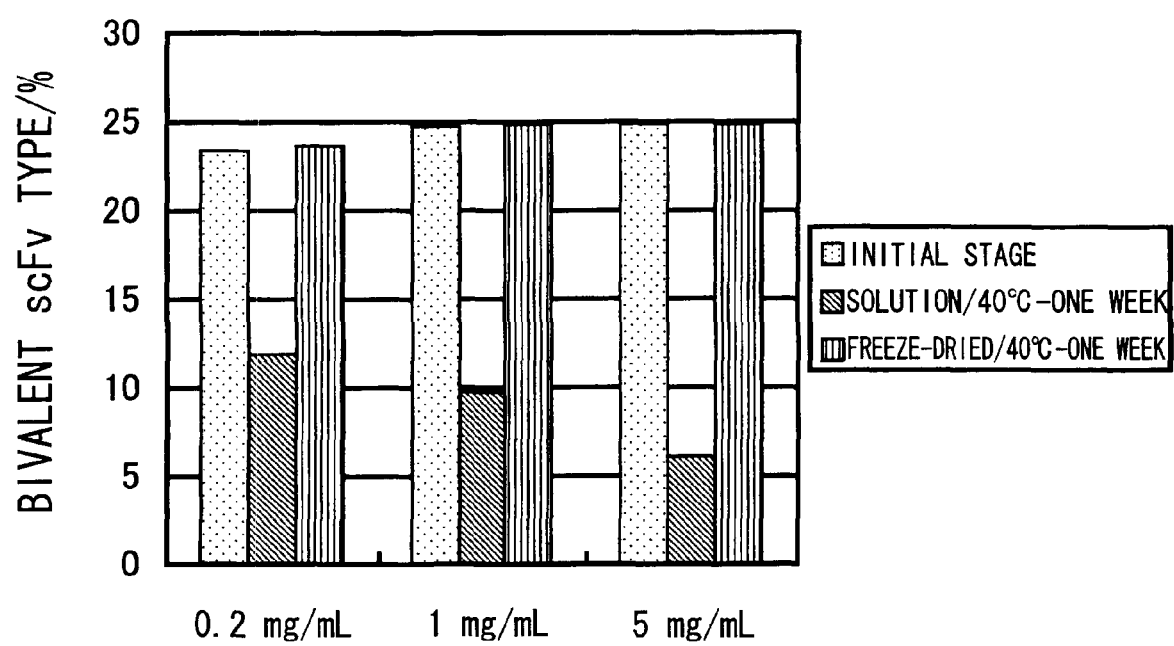
FIG. 8 depicts the percentages of bivalent scFv, initially and after 40° C.-one week.

The content ratio of conformational isomers, initially and after 40° C.-one week under the above-described conditions, were measured using anion exchange chromatography (the method for calculating the peak 2 percentage is the same as in Example 1). The elution conditions for the anion exchange chromatography are as follows:
<Elution Conditions>
Column: MONO Q (Amersham bioscience)
Mobile phase A: 50 mM Tris-HCl, pH8.0
Mobile phase B: 50 mM Tris-HCl, 500 mM NaCl, pH8.0
Flow rate: 1.0 ml/min
Detection: 220 nm The percentages of bivalent scFv, initially and after 40° C.-one week, are shown in FIG. 8.

Under solution conditions, bivalent scFv isomerized to single chain diabody as indicated in Example 4, but in contrast, isomerization was suppressed under freeze-dried conditions. It was thus discovered that isomerization reactions are suppressed through freeze-dried formulation of sc(Fv)2. Preparation of freeze-dried formulations has been reported so far in relation to association, which is a reaction between two molecules, and deamidation reaction in which water molecules are involved. However, to date, there have been no reports on such isomerization reactions of proteins. Accordingly, the present study represents the first discovery that isomerization reactions can be suppressed through freeze-dried formulation.

So far, there have been no reports on such isomerization reactions of proteins, and by the present study, it was discovered for the first time that isomerization reactions in sc(Fv)2 can be suppressed through freeze-dried formulation.

Example 6

Methods for Obtaining Bivalent scFv or Single Chain Diabody in High Yield

Using peak 1 (91.4% peak 1), a conformational isomer of hVB22B u2-wz4 sc(Fv)2 purified to high purity, whether isomerization reaction from peak 1 to peak 2 could be promoted was examined. hVB22B sc(Fv)2 is secreted from expressing cells as a mixture of peak 1 and peak 2; however, if peak 1 can be isomerized to peak 2 in the production process, the yield of peak 2 can be increased. Therefore, isomerization of peak 1 to peak 2 was examined at the pHs and NaCl concentrations shown below.

Figure 9A:
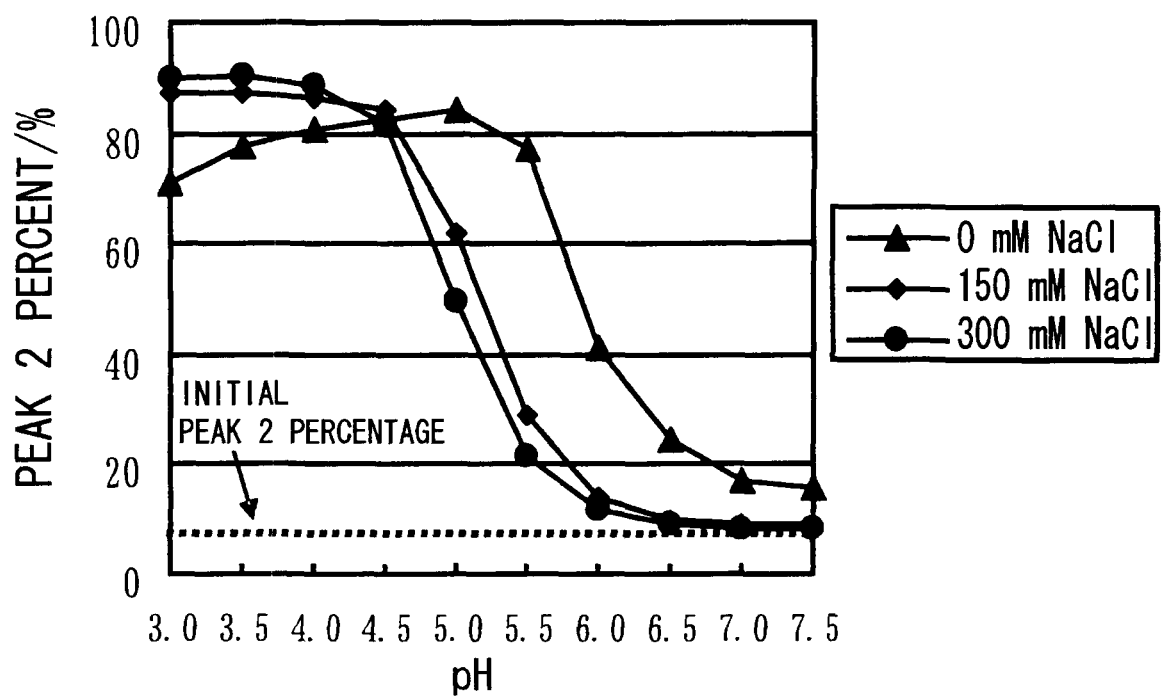
FIG. 9A depicts the isomerization to peak 2 as a result of incubating peak 1 at 25° C. under each condition.

Specifically, the content ratio of conformational isomers after reaction under the following conditions was measured using cation exchange chromatography:
<Conditions for Peak 1 to Peak 2 Isomerization Tests>
20 mM sodium citrate
0 mM/150 mM/300 mM NaCl
pH3.0/3.5/4.0/4.5/5.0/5.5/6.0/6.5/7.0/7.5
25° C.-five days After reaction under the above-described conditions, the content ratio of each conformational isomer after 25° C.-five days was measured using cation exchange chromatography. The elution conditions for the cation exchange chromatography are as shown below. The method for calculating the peak 1 percentage is the same as in Example 1.
<Elution Conditions>
Column: Bioassist S (TOSOH)
Mobile phase A: 20 mM sodium phosphate, pH7.0
Mobile phase B: 20 mM sodium phosphate, 500 mM KCl, pH7.0
Flow rate: 0.8 ml/min
Detection: 220 nm As a result of measuring the ratio of peak 1 and peak 2 by the cation exchange chromatography method indicated in Example 1, the peak area of peak 1 decreased and instead, the peak area of peak 2 increased as shown in FIG. 9A. It was thus discovered that peak 1, which is the bivalent scFv, undergoes structural conversion to peak 2, which is the single chain diabody, in hVB22B u2-wz4 sc(Fv)2 as well. It was found that the lower the pH and the lower the salt concentration, the faster the rate of this isomerization. By using the present method of isomerizing peak 1 to peak 2 and isomerizing peak 1 to peak 2 from a mixture of peak 1 and peak 2 produced by cells, peak 2 which is the single chain diabody can be obtained in high yield.

Example 7 pH Dependence of the Isomerization Reactions of Humanized Anti-Human IL-6 Receptor Antibody sc(Fv)2

Figure 9B:
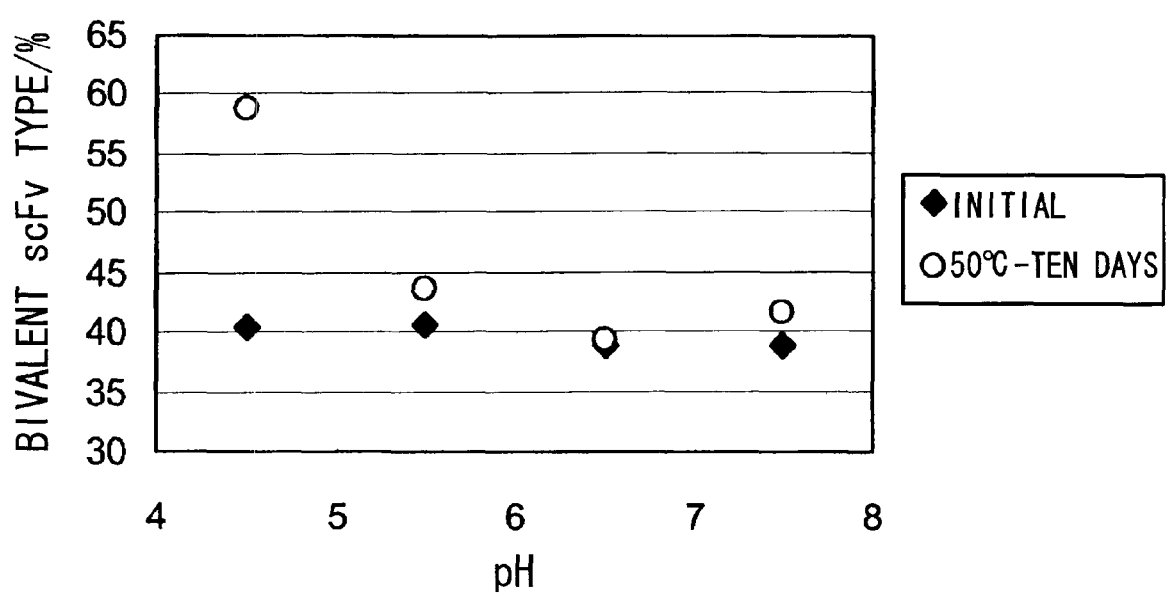
FIG. 9B depicts the content ratio of the bivalent scFv type of the humanized anti-human IL-6 receptor antibody sc(Fv)2, initially and after 50° C.-ten days. It shows that the isomerization reaction can be suppressed at pH 5.5 or higher.

The pH at which the isomerization reactions of humanized anti-human IL-6 receptor antibody sc(Fv)2 obtained by the method described in Reference Example 7 could be suppressed was investigated.
<Stability Test Conditions>
20 mM sodium citrate, 150 mM NaCl, pH 4.5/5.5/6.5/7.5
humanized anti-human IL-6 receptor antibody sc(Fv)2: 0.1 mg/mL
50° C.-ten days After reaction under the above-described conditions, the content ratio of each conformational isomer after 50° C.-ten days was measured using gel filtration chromatography. As indicated in Reference Example 7, the bivalent scFv type is eluted earlier than the single chain diabody type in gel filtration chromatography, and this was used to measure the content ratio of the two isomers. The elution conditions for the gel filtration chromatography are as follows.
<Elution Conditions>
Column: TSKgel Super SW2000 (TOSOH)
Mobile phase: 50 mM sodium phosphate, 300 mM KCl, pH7.0
Flow rate: 0.2 ml/min The content ratio of each conformational isomer (content ratio of the bivalent scFv type) initially and after 50° C.-ten days are shown in FIG. 9B. In humanized anti-human IL-6 receptor antibody sc(Fv)2, isomerization reaction from the single chain diabody type to the bivalent scFv type structure progressed at 50° C.-ten days and pH4.5, and the content ratio of the bivalent scFv type increased. While isomerization reaction from the bivalent scFv type to the single chain diabody type progressed in hVB22B sc(Fv)2, isomerization reaction from the single chain diabody type to the bivalent scFv type structure progressed in humanized anti-human IL-6 receptor antibody sc(Fv)2. As indicated in FIG. 9B, since the isomerization reaction of humanized anti-human IL-6 receptor antibody sc(Fv)2 is suppressed at pH5.5 or higher, it was revealed that the isomerization reaction of humanized anti-human IL-6 receptor antibody sc(Fv)2 can be suppressed by pH.

Reference Example 1

Separation, Structure Determination, and Activity Assessment of the Conformational Isomers of VB22B sc(Fv)2

1-1. Production of Mouse Anti-Human Mpl Antibody mVB22B Sc(Fv)2

Mouse anti-human Mpl antibody mVB22B sc(Fv)2 (hereinafter, referred to as VB22B sc(Fv)2) was produced as indicated in Blood, 2005, 105, 562-566. Specifically, the antibody variable region cDNA of anti-human Mpl antibody-producing mouse hybridoma VB22B was cloned, and a DNA carrying a nucleotide sequence (SEQ ID NO: 3) composed of a VH-linker sequence-VL-linker sequence-VH-linker sequence-VL-Flag tag sequence was produced using a nucleotide sequence encoding a linker sequence (GlyGlyGlyGlySer)×3 (SEQ ID NO: 1) and a nucleotide sequence encoding a FLAG sequence (AspTyrLysAspAspAspAspLys) (SEQ ID NO: 2). This DNA fragment was cloned into a pCXND3 expression vector to construct a VB22B sc(Fv)2 expression vector, and stable expression cell lines were prepared by gene introduction into CHO-DG44 cells. Specifically, a mixture of the expression vector (25 μg) and 0.75 mL of CHO-DG44 cells suspended in PBS (1×10$^7$ cells/mL) was cooled on ice for ten minutes, and after transferring to a cuvette, the mixture was pulsed at 1.5 kV and a capacitance of 25 μFD using a Gene Pulser II (BioRad). After a recovery period of 10 minutes at room temperature, the cells subjected to electroporation treatment were added to CHO-S-SFMII medium (Invitrogen) containing 500 μg/mL Geneticin (Invitrogen) for selection, and a VB22B sc(Fv)2-producing CHO cell line was established.

Next, the culture supernatant from this cell line was loaded onto a Macro-Prep Ceramic Hydroxyapatite Type I (Bio-Rad) column equilibrated with 20 mM phosphate buffer solution (pH6.8), and eluted stepwise with 250 mM phosphate buffer (pH6.8). The eluted fraction was concentrated using an ultrafilter membrane, then by performing gel filtration chromatography using a HiLoad 26/60 Superdex 200 pg column, a fraction in which the molecular weights correspond to approximately 70 kD to 40 kD was collected. This fraction was adsorbed onto an Anti-Flag M2 Affinity Gel (SIGMA-ALDRICH) column equilibrated with 50 mM Tris-HCl (pH7.4), 150 mM NaCl, 0.05% Tween 20, and eluted with 100 mM Glycine-HCl (pH 3.5). The eluted fraction was immediately neutralized with 1 M Tris-HCl (pH8.0), and gel filtration chromatography was performed using a HiLoad 26/60 Superdex 200 pg (Amersham-Bioscience) column. The buffer used for the gel filtration chromatography was 20 mM acetic acid (pH6.0), 150 mM NaCl, and 0.01% Tween 80.

1-2. Separation of the Conformational Isomers of VB22B sc(Fv)2

Figure 10:
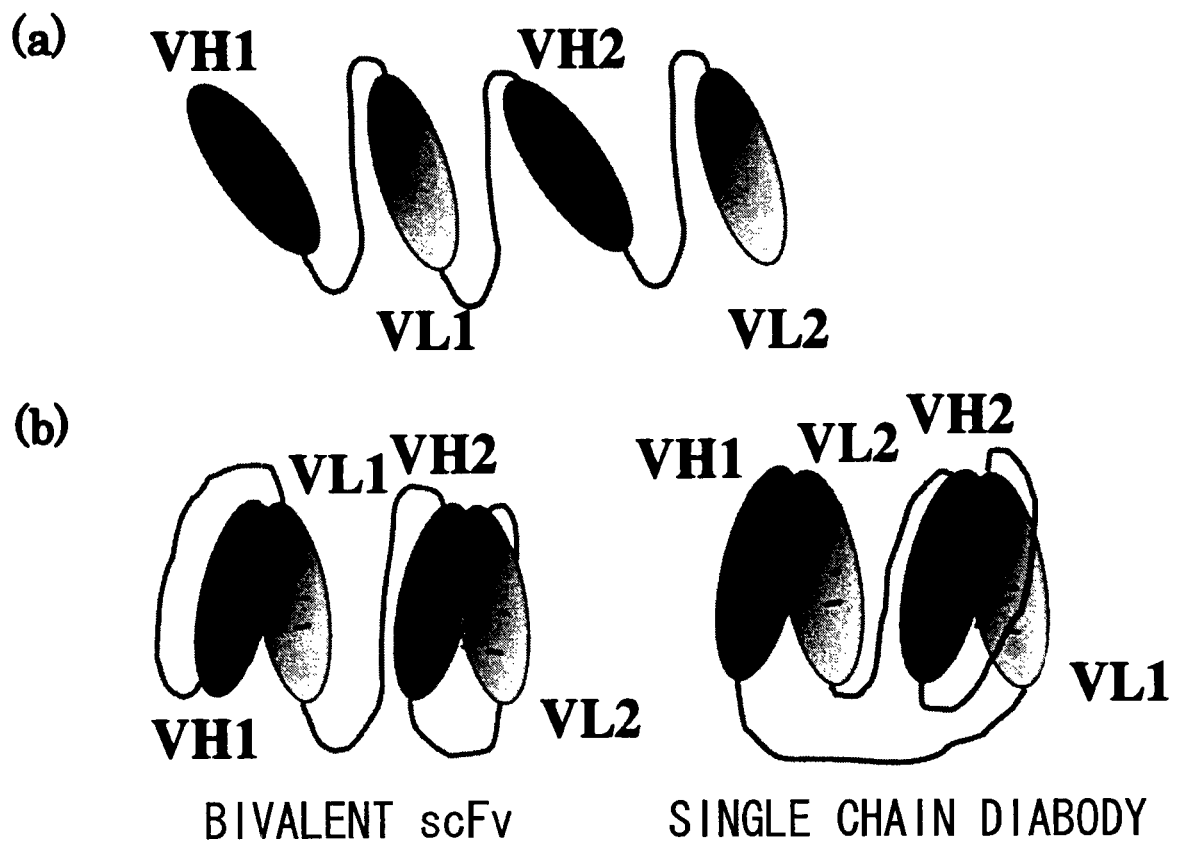
FIG. 10(a) depicts the VH1-linker-VL1-linker-VH2-linker-VL2 conformation of VB22B sc(Fv)2.
FIG. 10(b) depicts the two types of conformational isomers of the VH1-linker-VL1-linker-VH2-linker-VL2 conformation. The bivalent scFv conformation in which VH1/VL1 and VH2/VL2 are each associated (left) and the single chain diabody conformation in which VH1/VL2 and VH2/VL1 are each associated (right) are shown.

Since VB22B sc(Fv)2 is an sc(Fv)2 composed of a VH1-linker-VL2-linker-VH3-linker-VL4 sequence, depending on the combination of Fvs (molecules in which VH and VL are noncovalently bound), two types of conformational isomer structures are believed to exist: the bivalent scFv type in which VH1 and VL2, and VH3 and VL4 respectively form Fvs; and the single chain diabody type in which VH1 and VL4, and VH2 and VL3 respectively form Fvs (FIG. 10). As a result of investigating the separation of the conformational isomers of VB22B sc(Fv)2, each of the conformational isomers of VB22B sc(Fv)2 were successfully separated using anion exchange chromatography MONO Q (Amersham Bioscience) under the following elution conditions:

<Elution Conditions>
Mobile phase A: 20 mM Tris-HCl, pH8.0
Mobile phase B: 20 mM Tris-HCl, 500 mM NaCl, pH8.0
Flow rate: 1.0 ml/min
Gradient: 0% B to 35% B (30 min)

Figure 11:
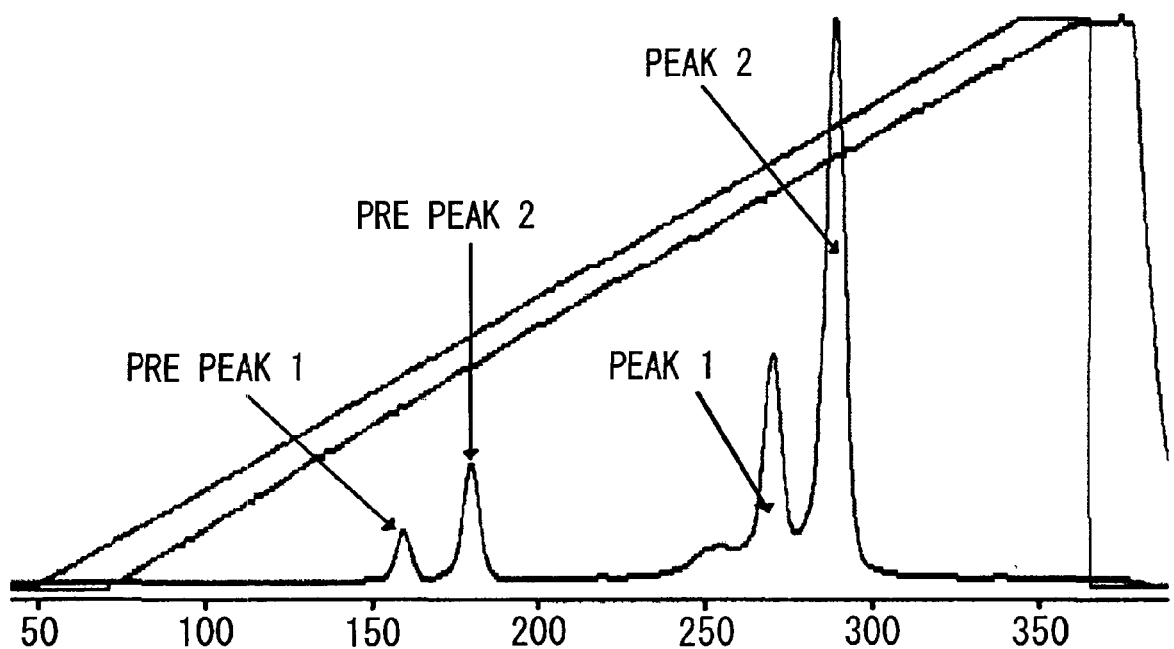
FIG. 11 depicts the results of anion exchange chromatography separation of peak 1 and peak 2.

Under the above-described conditions, VB22B sc(Fv)2 was separated into four peaks. A chromatogram such as that shown in FIG. 11 was obtained, and starting from the peak with the shortest retention time, the peaks were named 'pre peak 1', 'pre peak 2', 'peak 1', and 'peak 2', respectively.

A multivalent ion spectrum (+) of peak 1 and peak 2 obtained by injecting a sample solution by infusion to a Q-TOF-type mass spectrometer (Q T of Ultima, Micro Mass) was deconvoluted using an attached software (MassLynx), and as a result, the respective molecular weights were 54115 Da for peak 1 and 54112 Da for peak 2; therefore, peak 1 and peak 2 were found to have the same molecular weight.

Since VB22B sc(Fv)2 is not glycosylated, and since peak 1 and peak 2 have the same amino acid primary sequence and possess three dimensional structures that differ from each other and that can be separated by ion exchange chromatography, peak 1 and peak 2 were suggested to be conformational isomers. The presence of conformational isomers had been suggested in public literatures; however, separation of the conformational isomers is enabled for first time by the present investigation.

1-3. Determination of the Structures of the Conformational Isomers of VB22B sc(Fv)2

Since VB22B sc(Fv)2 is an sc(Fv)2 composed of a VH1-linker-VL2-linker-VH3-linker-VL4 sequence, depending on the combination of Fv (a molecule in which VH and VL are noncovalently bound), it is predicted that two types of conformational isomers exist: the bivalent scFv type, in which VH1 and VL2, and VH3 and VL4 respectively form Fvs, and the single chain diabody type, in which VH1 and VL4, and VH2 and VL3 respectively form Fvs. Accordingly, peak 1 and peak 2 are considered to be these conformational isomers.

Figure 12:
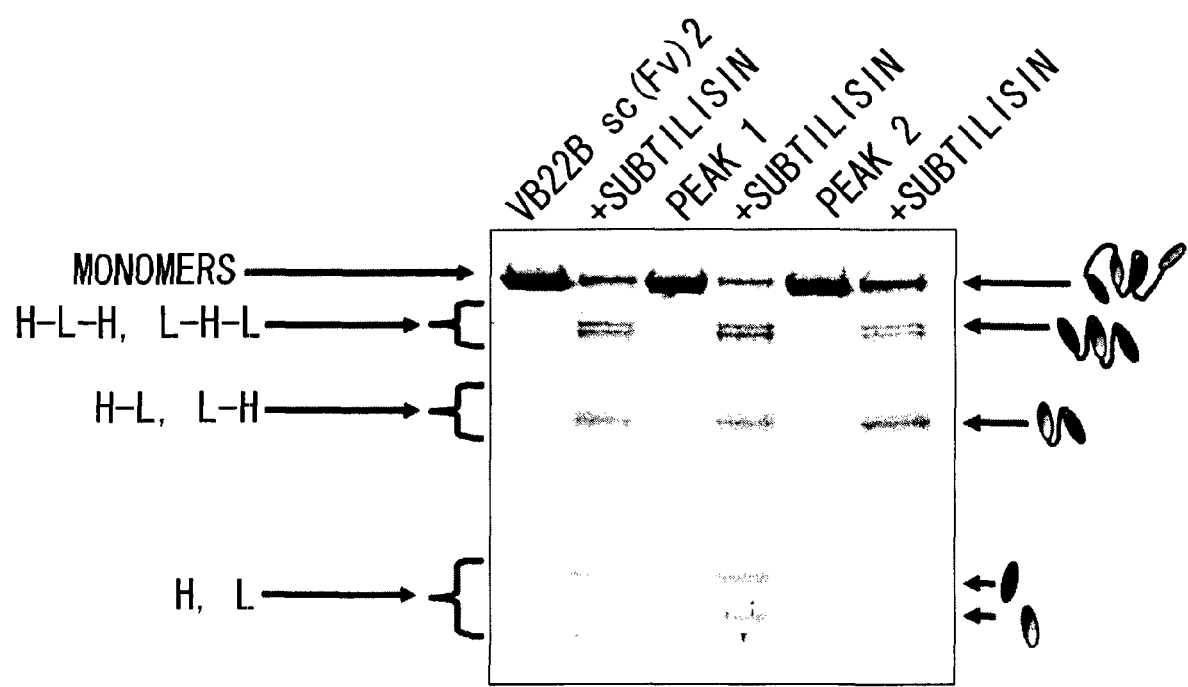
FIG. 12 depicts the results of a reducing SDS-PAGE assay on peak 1, peak 2, and VB22B sc(Fv)2, before and after subtilisin treatment. The putative conformations for the obtained bands are shown on the right.

Through the present investigation, the limited protease degradation method was found as an analysis method for identifying the two types of conformational isomer. It is considered that linker regions of sc(Fv)2 have relatively free structures and that their resistance to proteases is low; thus, using subtilisin A which is a type of protease, peak 1, peak 2, and VB22B bulk (peak 1:peak 2 is approximately 1:3) were reacted under the following conditions:

<Reaction Conditions>
20 mM sodium citrate, 150 mM NaCl, pH7.5
VB22B sc(Fv)2 peak 1 or peak 2: 0.14 mg/mL
Subtilisin A: 1 µg/mL
37° C., 30 min After the above-described reaction, a 12% Tris-Glycine SDS gel was used to perform a reducing SDS-PAGE. As a result, VB22B bulk (before separation of the conformational isomers), peak 1, and peak 2 all showed similar band patterns (FIG. 12). Since bands specific to each of the fragments considered to be formed by cleavage at the three linker regions of VB22B sc(Fv)2 were obtained, it was revealed that, by using the above-described reaction conditions, partial and limited degradations of the linker regions of VB22B sc(Fv)2 are possible.

Figure 14:
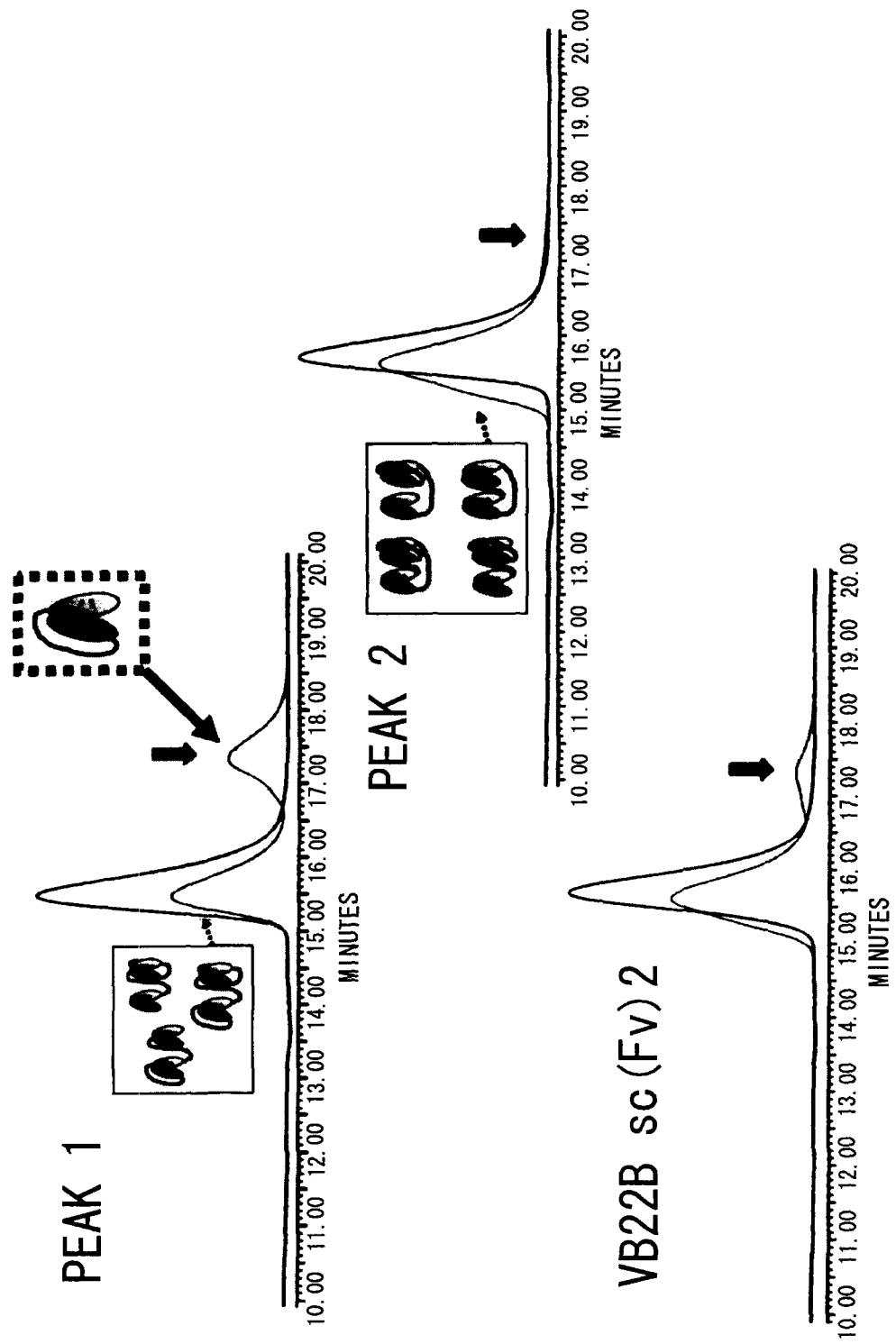
FIG. 14 depicts the results of gel filtration chromatography after limited degradation of peak 1, peak 2, and VB22B sc(Fv)2 by subtilisin.

Regarding the two types of conformational isomer, when cleavage takes place at one of the three linker regions, in the non-denatured state, due to noncovalent bonds between VH and VL, a change in the apparent molecular weight cannot be seen in the single chain diabody-type structures even if cleavage occurs in any one of the three linkers; however, in the bivalent scFv type, when the linker in the middle is cleaved, molecular species having half the molecular weight is produced, as shown in FIG. 13. Given this, VB22B bulk, peak 1, and peak 2, in which the linkers have been partially cleaved under the above-described reaction conditions, were subjected to gel filtration chromatographic analysis using TSK Super2000 (TOSOH). As a result, as shown in FIG. 14, while a low molecular weight peak was not observed at all for peak 2, a low molecular weight (approximately half the molecular weight) peak was confirmed for peak 1. For VB22B bulk, which is a mixture of peak 1 and peak 2, a low molecular weight peak was observed at an amount corresponding to the content ratio of peak 1. Therefore, peak 1 was identified as the bivalent scFv type, and peak 2 was identified as the single chain diabody type.

A series of techniques enabled separation of the conformational isomers contained in VB22B sc(Fv)2 and identification of their structures. Public literatures had estimated the structure of the conformational isomers through model predictions; however, the present investigation discovered methods for identifying the structures of the separated conformational isomers. Furthermore, from the ion exchange chromatography peak areas, the present invention enables the quantitative evaluation of the content ratio of the conformational isomer having either the bivalent scFv structure or the single chain diabody structure contained in VB22B sc(Fv)2.

1-4. Assessment of Biological Activities of the Conformational Isomers of VB22B sc(Fv)2

Anti-human Mpl antibody VB22B sc(Fv)2 has been reported in the literature (Blood 2005; 105:562-566) to show a TPO-like agonistic activity. Therefore, TPO-like agonistic activities of the separated conformational isomers were assessed using BaF3-human Mpl or BaF3-monkey Mpl which show TPO-dependent growth.

Both cells were washed twice with RPMI1640 containing 1% Fetal Bovine Serum (Invitrogen), then suspended at $4 \times 10^5$ cells/ml in RPMI 1640 containing 10% Fetal Bovine Serum, and this was aliquoted into 96-well plates at 60

μl/well. A 40-μL aliquot of rhTPO (R&D) or conformational isomer samples prepared at various concentrations was added into each well, and these were incubated at 37° C. under 5% $CO_2$ for 24 hours. WST-8 reagent (Cell Count Reagent SF, Nacalai Tesque) was added at 10 μL/well, and the absorbance at 450 nm (655 nm for the control) was measured using Benchmark Plus immediately after. Absorbance at 450 nm (655 nm for the control) was again measured after two hours of incubation. Since the WST-8 reagent gives a chromogenic reaction at 450 nm in accordance with the viable cell number, TPO-like agonistic activities were evaluated using the change in the absorbance during the two hours as an indicator.

Figure 15:
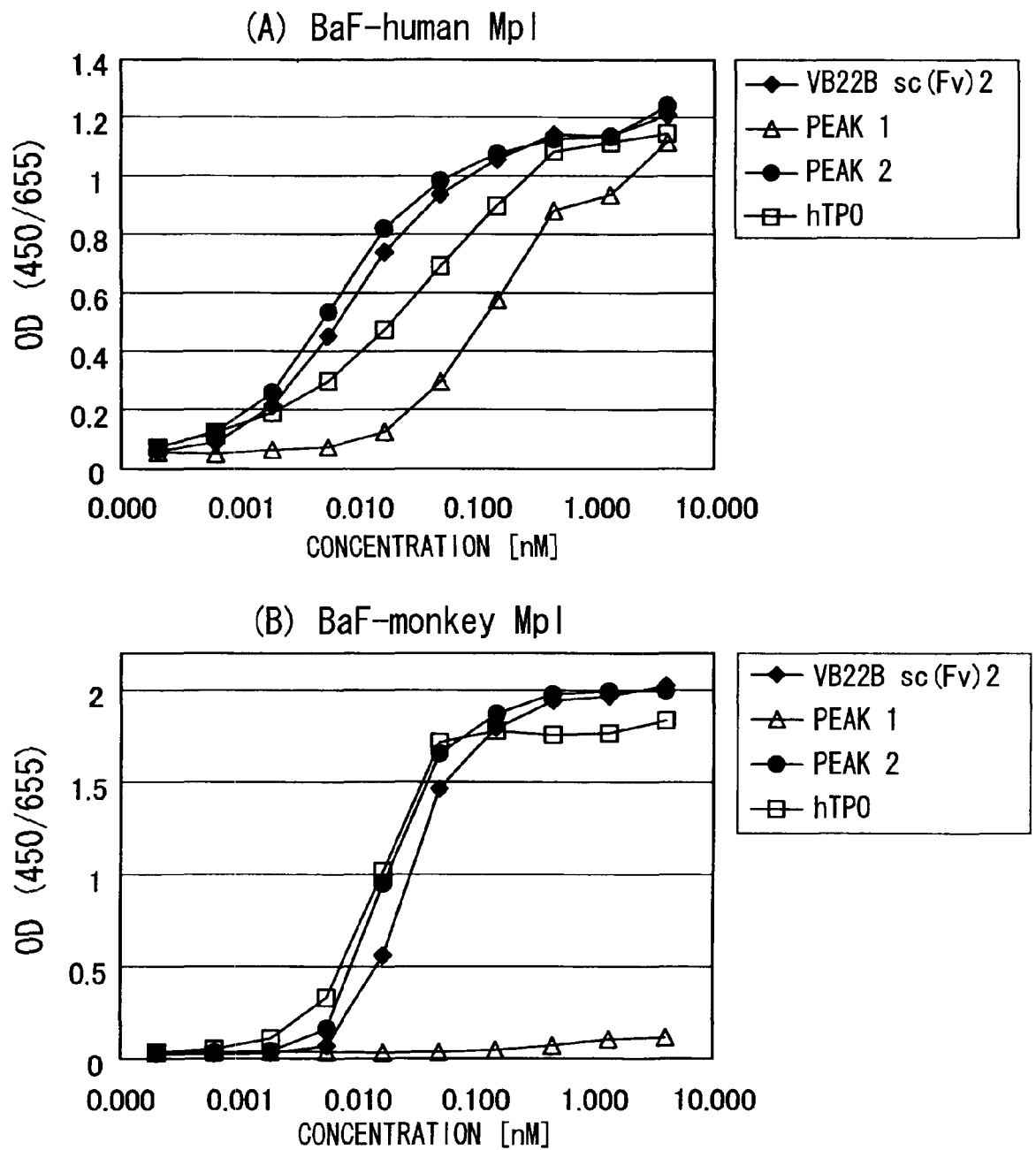
FIGS. 15A and 15B depict the results of assays evaluating the TPO-like agonistic activity of the conformational isomers of VB22B sc(Fv)2 in BaF3-human Mpl cells (FIG. 15A) and in BaF3-monkey Mpl cells (FIG. 15B).

The result of assessing TPO-like agonistic activities in BaF3-human Mpl and BaF3-monkey Mpl using the purified conformational isomers of VB22B sc(Fv)2 are shown in FIG. 15. When the agonistic activities of the conformational isomers of peak 1 and peak 2 were compared, peak 2 was found to show a significantly higher activity. This suggested that in order for anti-Mpl antibody sc(Fv)2 to exhibit TPO-like agonistic activity, it must have a single chain diabody structure.

Reference Example 2

Separation, Structure Determination, and Activity Assessment of the Conformational Isomers of hVB22B u2-wz4 sc(Fv)2

2-1. Production of Humanized Anti-Human Mpl Antibody hVB22B u2-wz4 sc(Fv)2

A humanized antibody in which complementarity determining regions (hereinafter, CDRs) have been transplanted into the framework regions (hereinafter, FRs) of the variable regions of VB22B sc(Fv)2 prepared in Reference Example 1 was prepared. Specifically, using a nucleotide sequence encoding a nucleotide sequence encoding a linker sequence (GlyGlyGlyGlySer)×3 (SEQ ID NO: 1), synthetic oligo-DNAs of 50 bases or so were designed so that approximately 20 bases or so will hybridize, such that they will form a gene having a nucleotide sequence (SEQ ID NO: 4) composed of VH-linker sequence-VL-linker sequence-VH-linker sequence-VL. These synthetic oligo-DNAs were assembled by PCR and a gene encoding each of the variable regions was produced. To express the obtained gene in animal cells, the construction of expression vectors and the production of stably expressing CHO-DG44 cell lines were carried out similarly as in the method of Reference Example 1-1, and culture supernatants were collected. Since humanized antibody hVB22B u2-wz4 sc(Fv)2 does not have an added Flag tag, purification from the culture supernatant was carried out using an MG10-GST fusion protein, in which MG10 (Gln 213 to Ala 231 of the human Mpl amino acid sequence) is an epitope recognized by VB22B sc(Fv)2. Purification of the MG10-GST fusion proteins was carried out using Glutathione Sepharose 4B (Amersham Biosciences) according to the manufacturer's protocol. Furthermore, the purified MG10-GST fusion proteins were immobilized onto HiTrap NHS-activated HP (Amersham Biosciences) following the manufacturer's protocol to prepare an affinity column. The culture supernatant of humanized antibody hVB22B u2-wz4 sc(Fv)2-expressing CHO cells was passed through the MG10-GST fusion protein-immobilized column, humanized antibody hVB22B u2-wz4 sc(Fv)2 were adsorbed, then eluted with 100 mM Glycine-HCl (pH3.5), 0.01% Tween 80. The eluted fractions were immediately neutralized with 1 M Tris-HCl (pH7.4), and gel filtration chromatography was performed using HiLoad 16/60 Superdex 200 pg (Amersham-Biosciences). The buffer used for the gel filtration chromatography was 20 mM citric acid buffer (pH7.5), 300 mM NaCl, 0.01% Tween 80.

2-2. Separation and Purification of the Conformational Isomers of hVB22B u2-wz4 sc(Fv)2

Since hVB22B u2-wz4 sc(Fv)2 is an sc(Fv)2 composed of a VH1-linker-VL2-linker-VH3-linker-VL4 sequence, depending on the combination of Fvs (molecules in which VH and VL are noncovalently bound), just as in VB22B sc(Fv)2, it is considered that structurally, two types of conformational isomers exist: the bivalent scFv type in which VH1 and VL2, and VH3 and VL4 respectively form Fvs; and the single chain diabody type in which VH1 and VL4, and VH2 and VL3 respectively form Fvs (FIG. 10).

The results of investigation into the separation of the conformational isomers of hVB22B u2-wz4 sc(Fv)2 suggested that each type of hVB22B u2-wz4 sc(Fv)2 components can be separated using cation exchange chromatography BioAssist S (TOSOH) under the following elution conditions:

Mobile phase A: 20 mM sodium phosphate, pH7.5
Mobile phase B: 20 mM sodium phosphate, 500 mM NaCl, pH7.5
Flow rate: 0.8 mL/min
Gradient: 0% B to 35% B (30 minutes)

Figure 16:
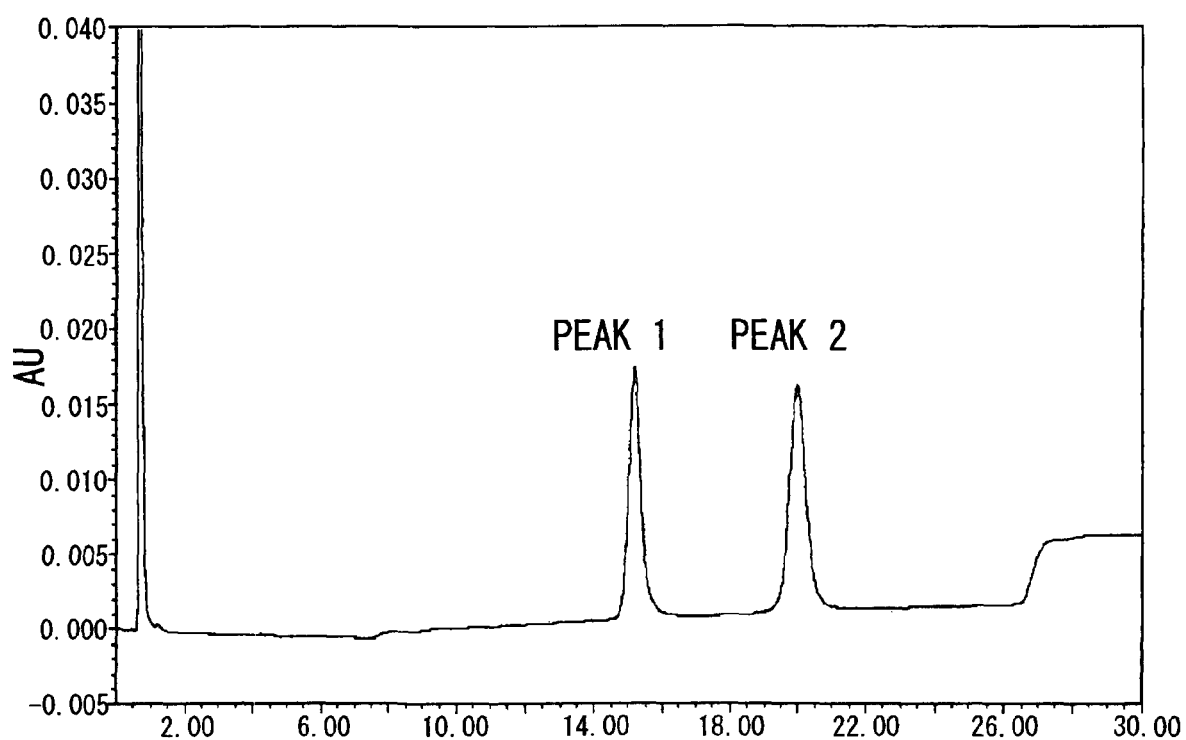
FIG. 16 depicts the results of cation exchange chromatography separation of peak 1 and peak 2.

Under the above-described conditions, hVB22B u2-wz4 sc(Fv)2 were separated into two peaks. A chromatogram such as that shown in FIG. 16 was obtained, and starting from the peak with the shortest retention time, the peaks were named peak 1 and peak 2, respectively.

The molecular weights of peak 1 and peak 2 were measured using a Q-TOF-type mass spectrometer (Q T of Ultima, Micro Mass). Sample solutions were injected to Q-TOF by infusion, and the obtained multivalent ion spectra (+) were deconvoluted using an attached software (MassLynx), and as a result, the molecular weight obtained for peak 1 was 53768 Da and that for peak 2 was 53769 Da. Therefore, peak 1 and peak 2 were found to have the same molecular weight.

Figure 17:
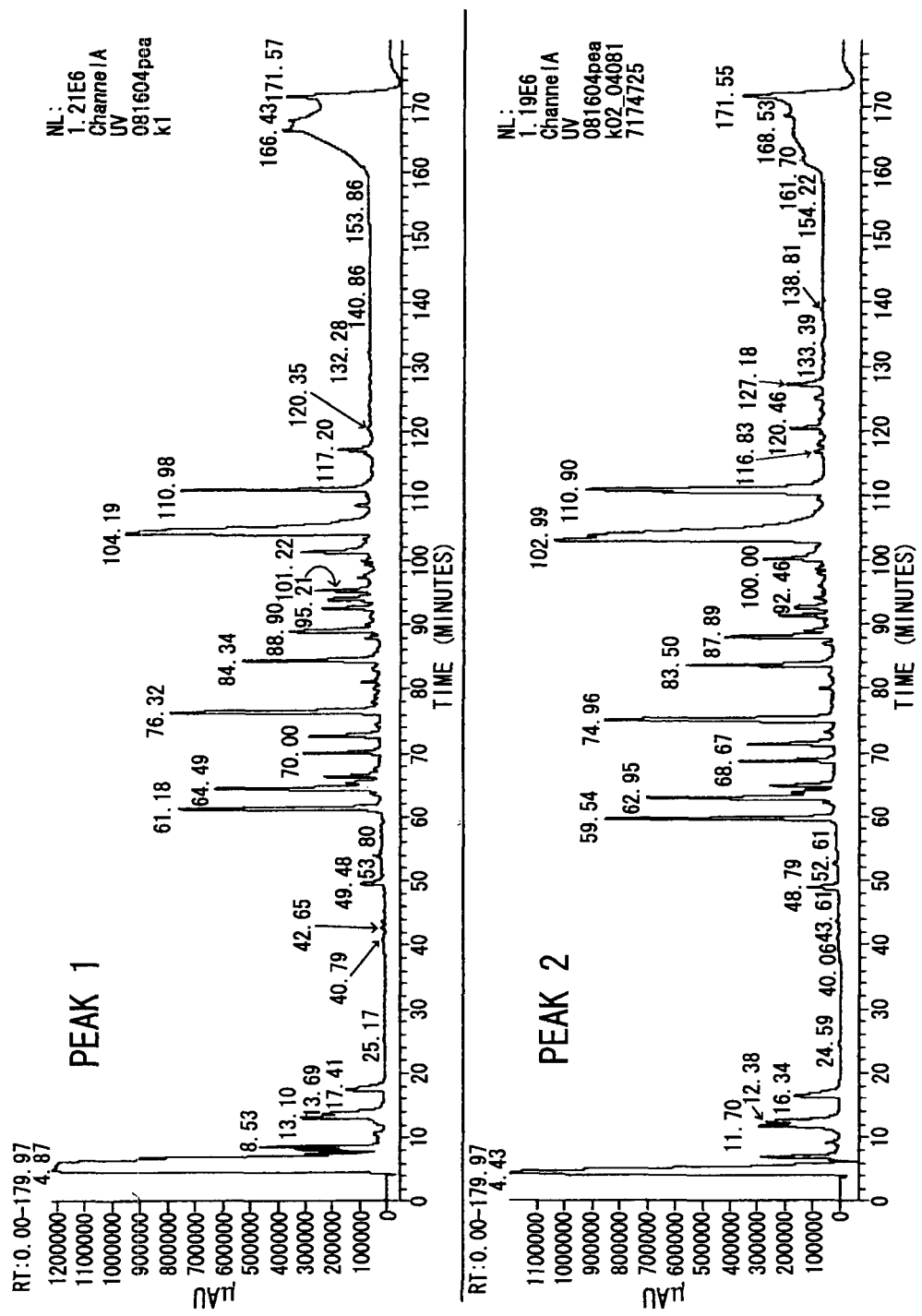
FIG. 17 depicts the peptide mapping of peak 1 and peak 2 separated by cation exchange chromatography.

Peptide mapping was performed on peak 1 and peak 2. After reductive denaturation and carboxymethylation, trypsin was used for digestion into peptide fragments, and peptide maps were obtained by reverse phase chromatography (YMC-Pack-ODS). When the peptide maps of peak 1 and peak 2 were compared, the mapping patterns of peak 1 and peak 2 were the same, as shown in FIG. 17; therefore, the amino acid primary structure was found to be the same.

Since hVB22B u2-wz4 sc(Fv)2 is not glycosylated, and since peak 1 and peak 2 have the same molecular weight according to TOF-MASS measurements, and the mapping patterns of peak 1 and peak 2 are the same, peak 1 and peak 2 were found to be conformational isomers having mutually different three dimensional structures.

Since hVB22B u2-wz4 sc(Fv)2 is an sc(Fv)2 composed of a VH1-linker-VL2-linker-VH3-linker-VL4 sequence, depending on the combination of Fvs (molecules in which VH and VL are noncovalently bound), structurally, two types of conformational isomer exist (FIG. 10): the bivalent scFv type in which VH1 and VL2, and VH3 and VL4 respectively form Fvs; and the single chain diabody type in which VH1 and VL4, and VH2 and VL3 respectively form Fvs. It is considered that peak 1 and peak 2 each have either one of the bivalent scFv type or single chain diabody type structure.

Figure 18:
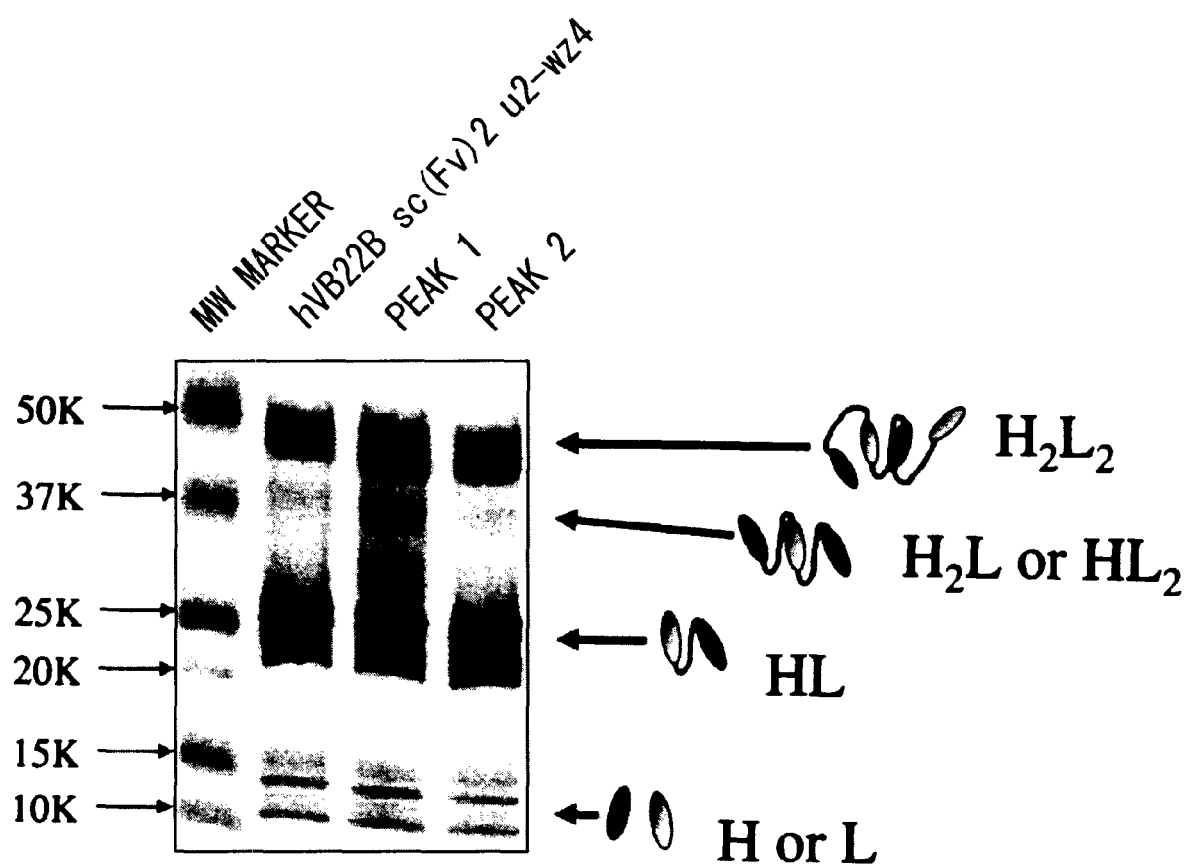
FIG. 18 depicts the results of a reducing SDS-PAGE assay on peak 1, peak 2, and hVB22B u2-wz4 sc(Fv)2 after subtilisin treatment. The conformations for the obtained bands are shown on the right.

The limited protease degradation method was discovered as an analysis method for identifying the two types of conformational isomer. Since the sc(Fv)2 linker regions have relatively free structures, it is considered that their resistance to proteases is low; thus, using subtilisin A which is a type of protease, peak 1, peak 2, and hVB22B u2-wz4 sc(Fv)2 (peak 1:peak 2 is approximately 1:4) were reacted under the following conditions:
20 mM sodium citrate, 150 mM NaCl, pH7.5
hVB22B u2-wz4 sc(Fv)2 peak 1 or peak 2: 0.15 mg/mL
Subtilisin A: 10 μg/mL
37° C., 30 min After the reaction, a 12.5% Phastgel Homogeneous was used to perform a reducing SDS-PAGE. As a result, hVB22B u2-wz4 sc(Fv)2 bulk, peak 1, and peak 2 all showed similar band patterns as shown in FIG. 18. Since bands specific to each of the fragments considered to be formed by cleavage at the three linker regions of hVB22B u2-wz4 sc(Fv)2 were obtained, it was revealed that, by using the above-described reaction conditions, partial and limited degradations of the linker regions of hVB22B u2-wz4 sc(Fv)2 are possible.

Figure 19:
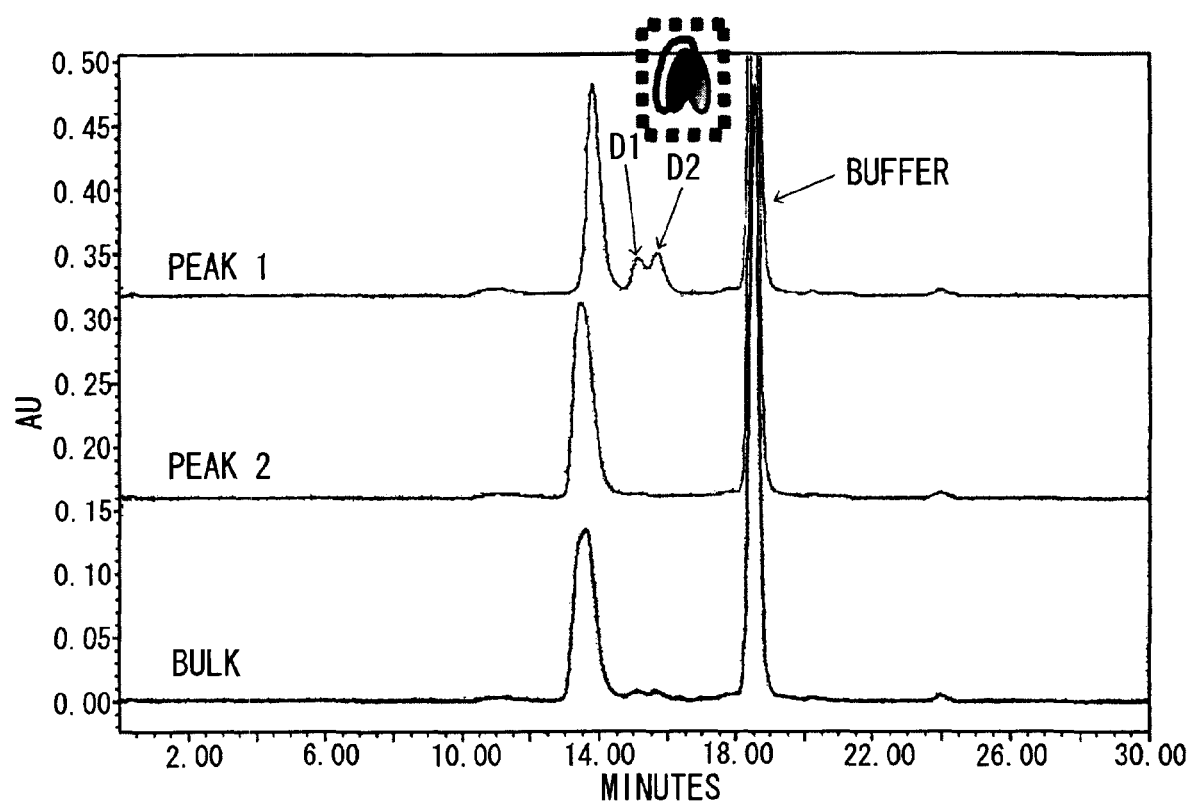
FIG. 19 depicts the results of gel filtration chromatography after limited degradation of peak 1, peak 2, and hVB22B u2-wz4 sc(Fv)2 by subtilisin. The elution positions of the low-molecular-weight peaks are indicated by arrows.

Regarding bivalent scFv-type and single chain diabody-type structures, when cleavage takes place at one of the three linkers, in the non-denatured state, due to noncovalent bonds between VH and VL, a change in the apparent molecular weight cannot be seen in the single chain diabody-type structures even if cleavage occurs in any one of the three linkers; however, in the bivalent scFv type, when the linker in the middle is cleaved, molecular species having half the molecular weight is produced, as shown in FIG. 13. Given this, hVB22B u2-wz4 sc(Fv)2 bulk, peak 1, and peak 2, in which the linkers have been partially cleaved under the above-described reaction conditions, were subjected to gel filtration chromatographic analysis using TSK SuperSW2000 (TOSOH). As a result, as shown in FIG. 19, while a low molecular weight peak was not observed at all for peak 2, a low molecular weight (approximately half the molecular weight) peak was confirmed for peak 1. For hVB22B sc(Fv)2 u2-wz4 bulk, which is a mixture of peak 1 and peak 2, a low molecular weight peak was observed at an amount corresponding to the content ratio of peak 1. From this result, peak 1 was identified as the bivalent scFv type and peak 2 was identified as the single chain diabody type.

2-3. Assessment of the Binding Activities of the Conformational Isomers of hVB22B u2-wz4 sc(Fv)2

Assessment of the binding activities of peak 1 and peak 2 separated from hVB22B u2-wz4 sc(Fv)2 and of hVB22B u2-wz4 sc(Fv)2 was performed as follows. Biacore 3000 (Biacore) was equipped with Sensor Chip CM5 (Biacore), and MG10 (fusion protein of Gln 213 to Ala 231 of human Mpl and GST) indicated in 2-1 was immobilized by the amine coupling method. HBS-EP Buffer (Biacore) was used as the running buffer for the measurements, and the flow rate was 20 μL/min. Humanized VB22B u2-wz4 sc(Fv)2 bulk, peak 1, and peak 2 were prepared at six concentrations ranging from about 5 nM to approximately 150 nM using HBS-EP buffer. These samples were added for two minutes to the aforementioned MG10-immobilized cells to obtain bound regions, then dissociated regions were measured for two minutes. VB22B sc(Fv)2 bound to MG10-GST fusion proteins were removed by adding 20 mM HCl for one minute, and the immobilized cells were regenerated. From the obtained sensorgram, BIAevaluation ver.3.1 software (Biacore) was used and Bivalent analyte model was applied to calculate the binding rate constants (ka) and the dissociation rate constants (kd). As a result, as shown in Table 1, the dissociation constants (KD) of hVB22B u2-wz4 sc(Fv)2 bulk, peak 1, and peak 2 were $1.02 \times 10^{-8}$ M, $1.24 \times 10^{-8}$ M, and $9.92 \times 10^{-9}$ M respectively, and the two conformational isomers were found to have a nearly equivalent binding activity.

TABLE 1

|  | ka(1/Ms) [×10$^5$] | kd(1/s) [×10$^{-3}$] | KD (nM) | |
|---|---|---|---|---|
| VB22B peak1 | 5.86 ± 0.06 | 7.27 ± 0.25 | 12.4 ± 0.05 | n = 3 |
| VB22B peak2 | 5.71 ± 0.17 | 5.66 ± 0.24 | 9.92 ± 0.53 | n = 3 |
| VB22B bulk | 6.08 ± 0.30 | 6.17 ± 0.23 | 10.2 ± 0.8 | n = 3 |

2-4. Assessment of the Agonistic Activities of the Conformational Isomers of hVB22B u2-wz4 sc(Fv)2

Figure 20:
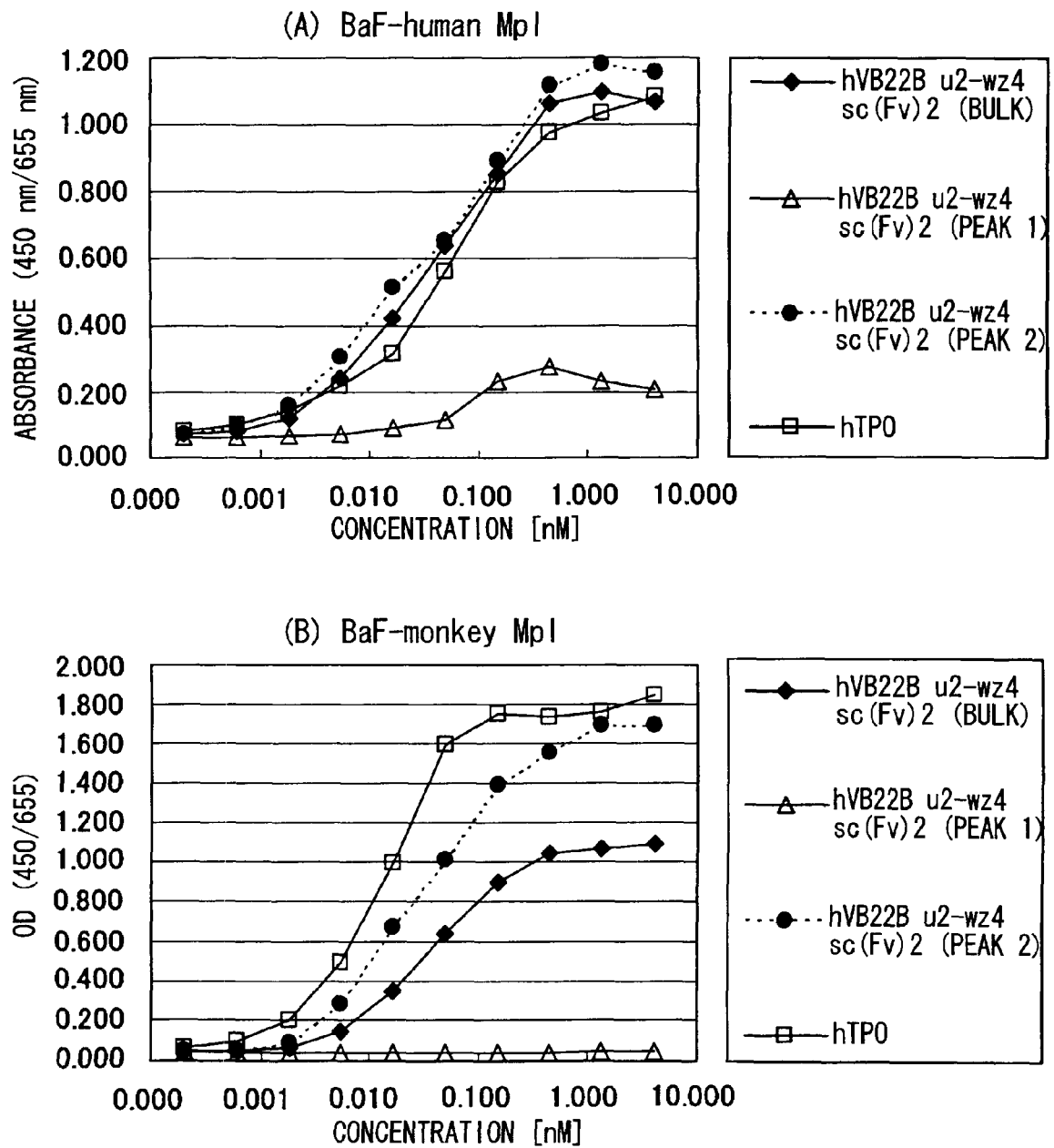
FIGS. 20A and 20B depict the results of assays evaluating the TPO-like agonistic activity of the conformational isomers of hVB22B u2-wz4 sc(Fv)2 in BaF3-human Mpl cells (FIG. 20A) and in BaF3-monkey Mpl cells (FIG. 20B).

Agonistic activities of peak 1, peak 2, and hVB22B u2-wz4 sc(Fv)2 were assessed. As shown in FIG. 20, agonistic activities differed significantly between conformational isomers, and while peak 2 having a single chain diabody structure showed very high agonistic activity, the activity of peak 1 having a bivalent scFv structure was extremely low. While the two conformational isomers had nearly the same binding activity, their agonistic activities were remarkably different. Separation and identification of the conformational isomers had not been performed in public literature; accordingly, the present investigation represents a first discovery that biological activities are different between the two types of conformational isomer.

In the present Reference Example, it became possible to separate the conformational isomers contained in hVB22B u2-wz4 sc(Fv)2 and identify their structures. Furthermore, from the chromatographic peak areas, it became possible to quantitatively analyze the content ratio of conformational isomers having the bivalent scFv structure and single chain diabody structure contained in hVB22B u2-wz4 sc(Fv)2. In hVB22B u2-wz4 sc(Fv)2, the bivalent scFv structure and single chain diabody structure were found to have remarkably different agonistic activities, and to develop hVB22B u2-wz4 sc(Fv)2 containing these conformational isomers with remarkably different activities as pharmaceuticals, it is absolutely necessary to determine the characteristics of the two types of conformational isomer and perform specification tests to quantitatively analyze the content ratio of each conformational isomer.

Reference Example 3

Analysis of the Content Ratio of Conformational Isomers of Linker-Modified VB22B sc(Fv)2 and Regulation of Conformational Isomer Ratio Since VB22B sc(Fv)2 are sc(Fv)2 composed of a VH1-linker-VL2-linker-VH3-linker-VL4 sequence, depending on the combination of Fvs (molecules in which VH and VL are noncovalently bound), it is considered that structurally, two types of conformational isomer exist: the bivalent scFv type in which VH1 and VL2, and VH3 and VL4 respectively form Fvs; and the single chain diabody type in which VH1 and VL4, and VH2 and VL3 respectively form Fvs.

Figure 21:
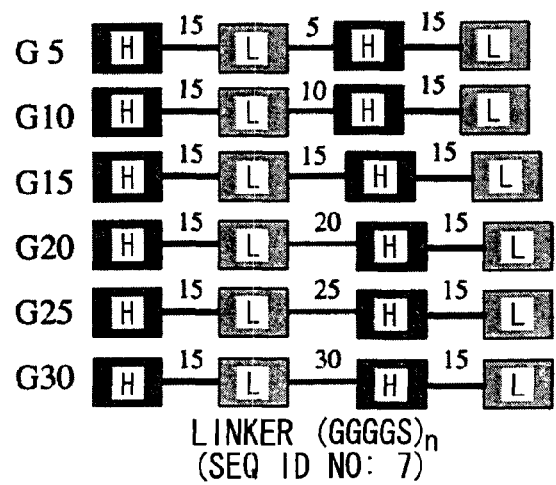
FIG. 21 depicts the constructs of each of the linker variants. The length of the linker in the middle is xx in Gxx; the length of the linkers at both ends is xx in Lxx; and in each of these constructs, (GGGGS (SEQ ID NO: 7))n sequences are used as the linkers. Pxx are constructs in which (GGPGS (SEQ ID NO: 13))n sequences are used as linkers and the length of the linker in the middle is xx.
Figure 21:
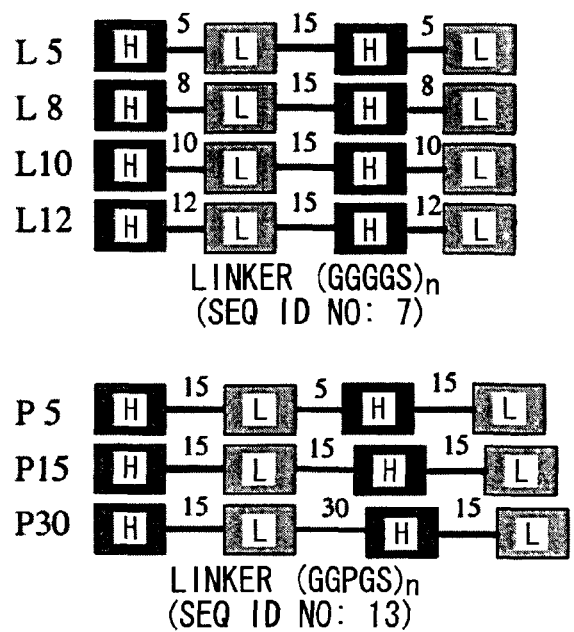

The linker in the middle was referred to as the 'middle linker', and the linkers at both ends were referred to as the 'edge linkers'. Various VB22B sc(Fv)2 having middle linkers and edge linkers of different lengths, such as those shown in FIG. 21, were produced and the content ratios of their conformational isomers were quantitatively analyzed under the following conditions:
Column: MONO Q (Amersham Bioscience)
Mobile phase A: 20 mM Tris-HCl, pH8.0
Mobile phase B: 20 mM Tris-HCl, 500 mM NaCl, pH8.0
Flow rate: 1.0 ml/min
Gradient: 0% B to 35% B (30 min)

Figure 22:
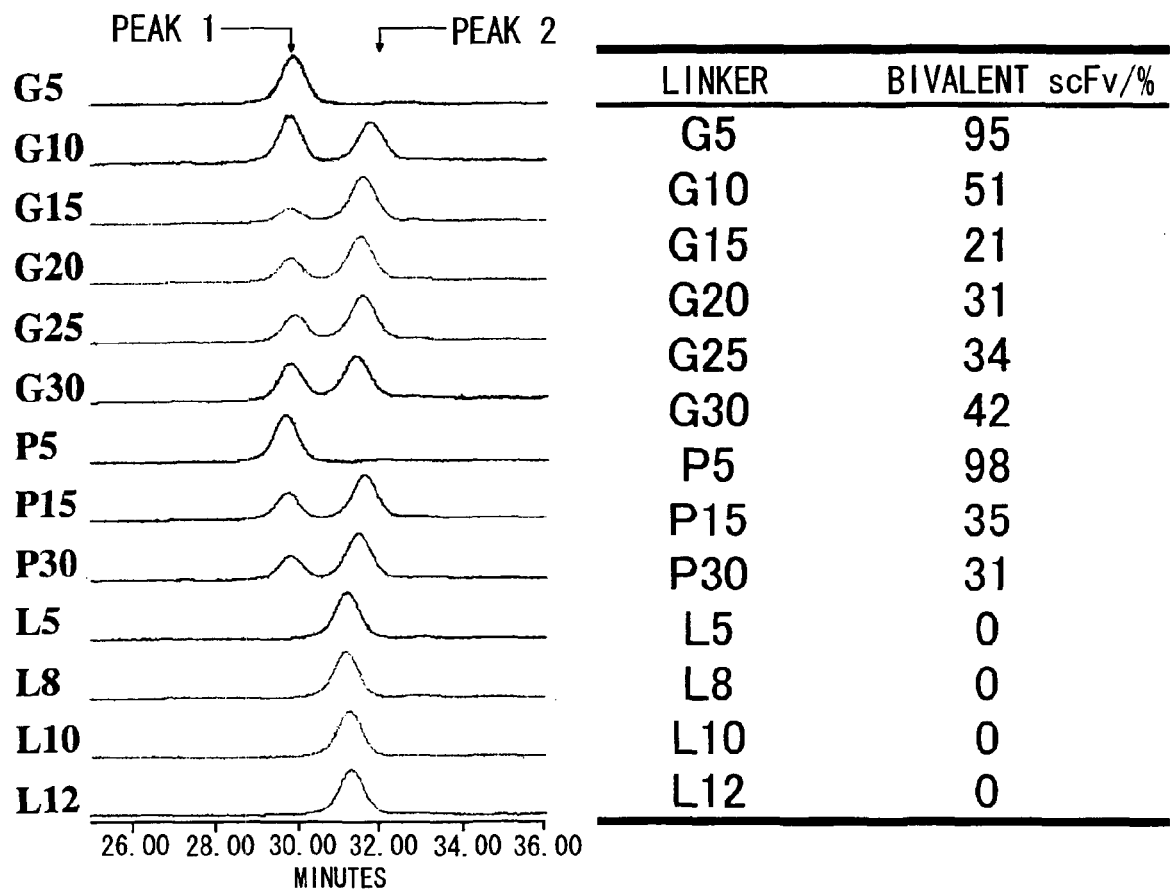
FIG. 22 depicts the results of anion exchange chromatographic analyses of each of the linker variants and the content ratio of the obtained conformational isomers indicated as a percentage of the bivalent scFv-type structure.

As a result, as shown in FIG. 22, for any linker length, it was possible to separate two conformational isomers by the analysis method indicated in Reference Example 2, and to measure the content ratio of the conformational isomers. Regulation of the ratio of bivalent scFv type and single chain diabody type by the linker length was found to be possible, and by using the present analysis method, it became possible to design suitable linker lengths that enable to obtain the conformational isomer ratios of interest.

Since methods for determining the structures of the two conformational isomers and quantitative analysis methods had not been found in public literature, such quantitative assessment of the linker lengths and content ratios of conformational isomers had not previously been possible. It had been reported in Protein Engineering, 1993, 6(8), 989-995, Protein Engineering, 1994, 7(8), 1027-1033, and such that generally, when the linker length is 12 or less, adjacent VH and VL, difficulty form Fvs; however, the present investigation revealed that single chain diabody-type structures in which adjacent VH and VL form Fvs exist in G5 and G10, though in small amount. Thus, the possibility that two structures (that is, conformational isomers) exist with any linker was considered. Therefore, to develop sc(Fv)2-type molecules as pharmaceuticals, it may be necessary to quantitatively analyze the content ratio of each conformational isomer for any linker; hence, the present separation and analysis methods that allow quantitative analyses of the content ratio as well as separation and production of conformational isomers are extremely useful when developing sc(Fv)2-type pharmaceutical molecules.

Reference Example 4

Large Scale Purification of Conformational Isomers by Cation Exchange Chromatography (SOURCE 15S)

Purification was carried out from the culture supernatant of hVB22B u2-wz4 sc(Fv)2-expressing CHO cells used in Reference Example 2-1. The culture supernatant was diluted three times with purified water and then the pH was adjusted to 6.0 using 1 M acetic acid. Thereafter, the diluted supernatant was subjected to an SP Sepharose Fast Flow column (Amersham Biosciences) equilibrated with 20 mM sodium acetate buffer at pH6.0. After washing the column with the same buffer, polypeptides adsorbed onto the column were eluted with a linear concentration gradient of 0 M to 0.5 M NaCl in the same buffer (first step). The obtained fractions were analyzed by reducing SDS-PAGE using a 12% TrisGlycine SDS gel, and the fractions containing hVB22B u2-wz4 were collected.

Figure 23:
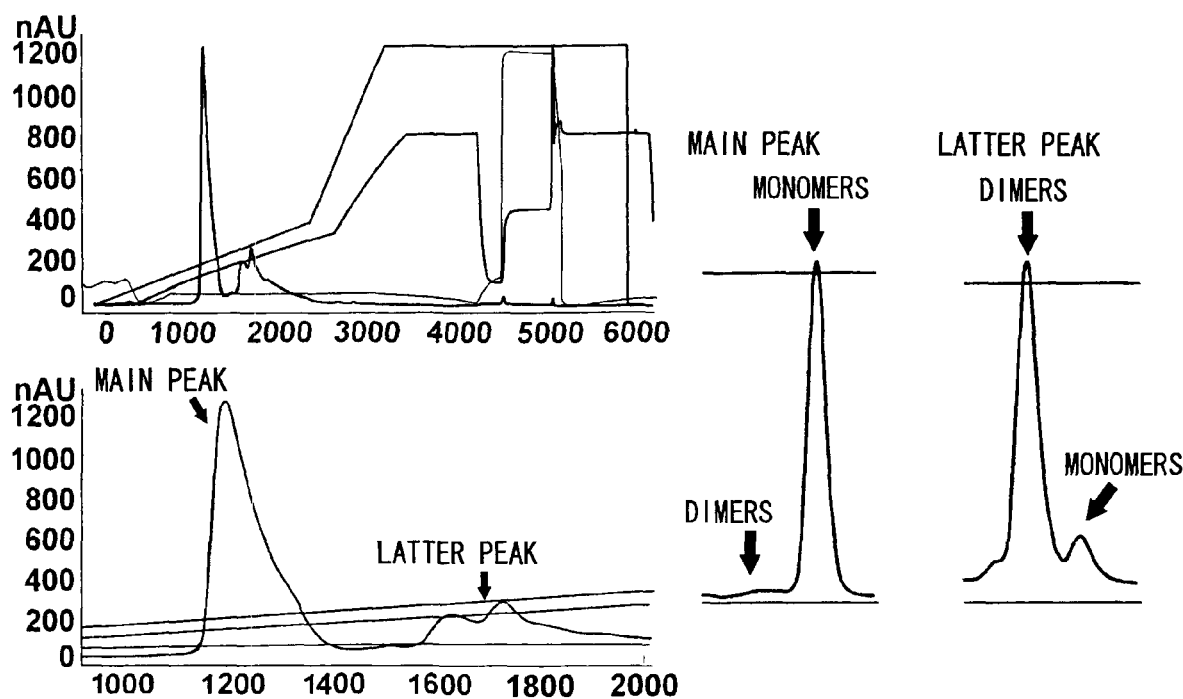
FIG. 23 depicts the chromatograms of a hydroxyapatite column and the results of gel filtration chromatographic analyses of the purified fractions.

The hVB22B u2-wz4 sc(Fv)2 fraction of the first step was applied to a hydroxyapatite column, type I, 20 µm (BIO-RAD) equilibrated with 10 mM phosphate buffer at pH6.8. After washing the column with the same buffer, the concentration of the phosphate buffer at pH 6.8 was raised linearly to 160 mM and the polypeptides adsorbed onto the column were eluted (FIG. 23). A small peak was eluted after the main peak; however, the results of SDS-PAGE analyses confirmed that these were both hVB22B u2-wz4 sc(Fv)2. As indicated in FIG. 23, right panel, analytical gel filtration using a Superdex 200 PC 3.2/30 column (Amersham Biosciences) showed that the main peak was mainly hVB22B u2-wz4 sc(Fv)2 monomers, and the latter peak was a fraction of hVB22B u2-wz4 sc(Fv)2 dimers or larger aggregates. This revealed that the hVB22B u2-wz4 sc(Fv)2 monomer fraction can be separated by this step.

Figure 24:
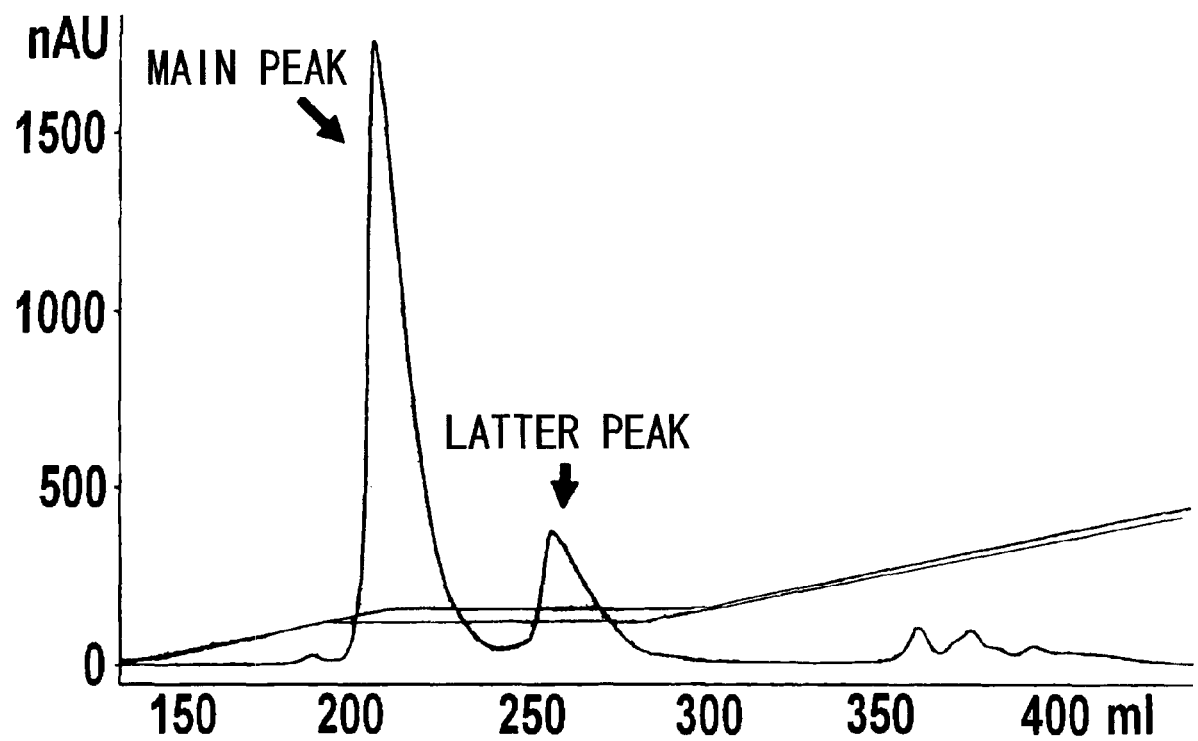
FIG. 24 depicts the results of SOURCE 15S column chromatogram analyses.
Figure 25:
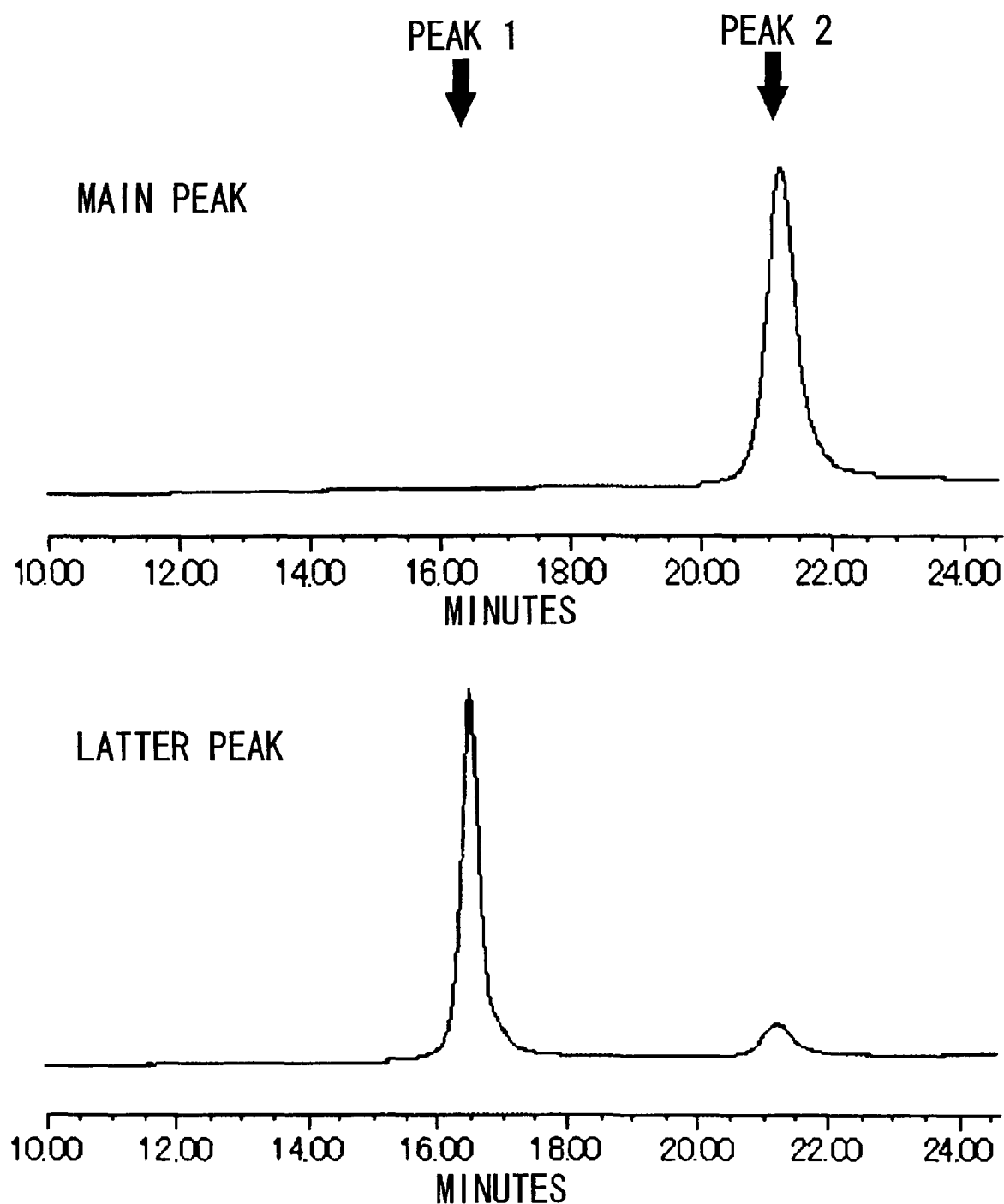
FIG. 25 depicts the results of cation exchange chromatographic analyses.

The monomer fraction of hVB22B u2-wz4 sc(Fv)2 obtained in the second step was diluted five times with purified water and subjected to a SOURCE 15S column (Amersham Biosciences) equilibrated with 20 mM sodium phosphate buffer at pH 7.0. After washing the column with the same buffer, a linear concentration gradient of 0 mM to 36 mM NaCl in the same buffer was applied. Then, to separate and elute the two peaks at a maximum, the NaCl concentration was once fixed at 36 mM. As shown in FIG. 24, after the two hVB22B u2-wz4 sc(Fv)2 peaks were eluted, the NaCl concentration was raised again and the polypeptides that were even more strongly adsorbed onto the column were eluted, and the column was washed. By analyzing the two peaks using the BioAssist S column indicated in 2-2, it was revealed that the main peak eluted earlier is peak 2 and the peak eluted later is peak 1 (FIG. 25).

Figure 26:
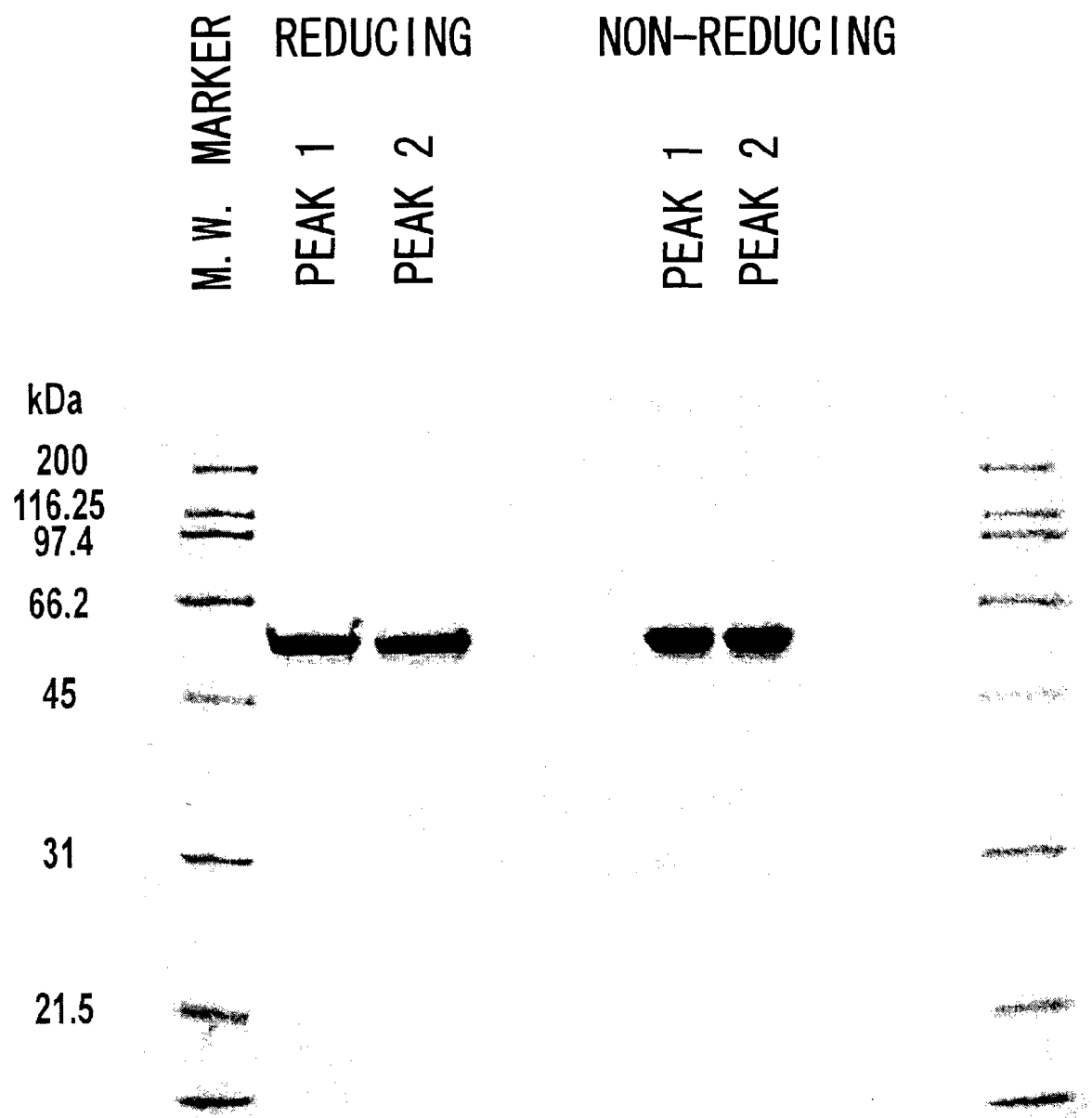
FIG. 26 depicts the results of SDS-PAGE analyses of large-scale-purified hVB22B u2-wz4 sc(Fv)2 peak 1 and hVB22B u2-wz4 sc(Fv)2 peak 2.
Figure 27:
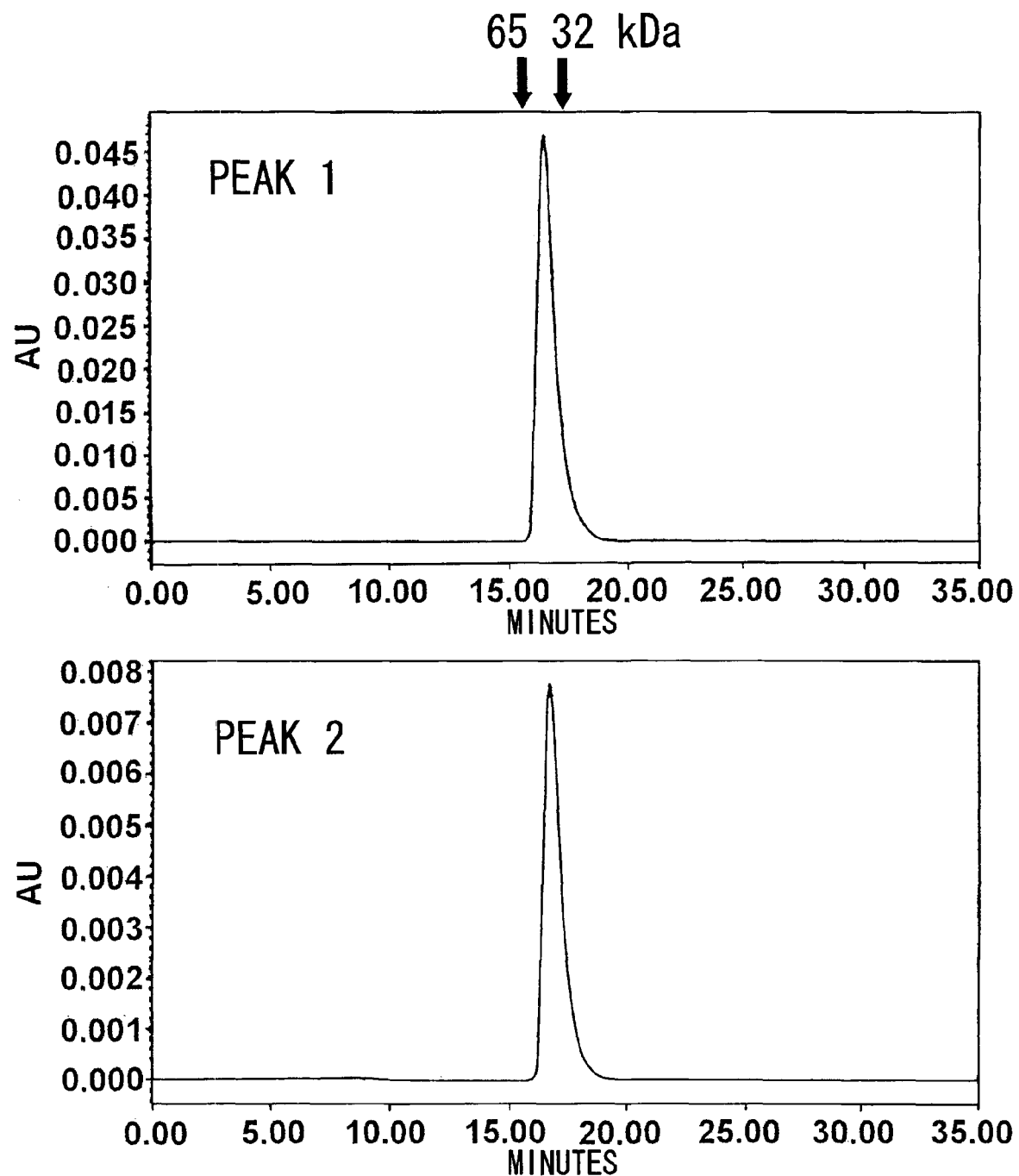
FIG. 27 depicts the results of gel filtration analyses of large-scale-purified hVB22B u2-wz4 sc(Fv)2 peak 1 and hVB22B u2-wz4 sc(Fv)2 peak 2.

The purified peak 1 and peak 2 of hVB22B u2-wz4 sc(Fv)2 were both observed as a single band at a molecular weight position of approximately 55 kDa when SDS-PAGE analyses were performed under both reducing and non-reducing conditions using the aforementioned SDS gels (FIG. 26). Furthermore, peak 1 and peak 2 of hVB22B u2-wz4 sc(Fv)2 both showed single peaks with an apparent molecular weight of approximately 50 kDa in gel filtration chromatographic analyses using the TSK Super2000 column indicated in 1-3 (FIG. 27).

From the above, a method for purifying only monomers of the conformational isomer of interest of hVB22B u2-wz4 sc(Fv)2 without using gel filtration chromatography, which is not suitable for large scale purification, was successfully developed.

Reference Example 5

Preparation of VH/VL Interface-Modified sc(Fv)2, and Analysis and Identification of its Conformational Isomers 5-1. Production of VH/VL Interface-Modified sc(Fv)2.

Gln on position 39 of VH (position 39 in the amino acid sequence of SEQ ID NO: 289 of WO 2005/56604) and Gln on position 38 of VL (position 43 in the amino acid sequence of SEQ ID NO: 291 of WO2005/56604), which are amino acids forming the VH/VL interface of hVB22B u2-wz4 sc(Fv)2 (hereinafter, u2-wz4) produced in Reference Example 2, were modified as follows:

u2-wz4 is linked in the order of [VH1]-linker-[VL2]-linker-[VH3]-linker-[VL4] with an amino acid linker sequence (GlyGlyGlyGlySer)$_{x3}$ (SEQ ID NO: 1), and is transcribed and translated from the nucleotide sequence of SEQ ID NO: 4.

First, the hVB22B u2-wz4 (v1) sc(Fv)2 gene (hereinafter v1; the nucleotide sequence is SEQ II) NO: 14, and the amino acid sequence is SEQ ID NO: 15), in which Gln on position 39 of VH1 (genetic coclon: CAG) was modified to Glu (genetic codon: GAG), Gln on position 38 of VL2 (genetic codon: CAG) was modified to Glu (genetic codon: GAG), Gln on position 39 of VH3 (genetic codon: CAG) was modified to Lys (genetic codon: AAG), and Gln on position 38 of VL4 (genetic codon: CAG) was modified to Lys (genetic codon: AAG), was produced.

Furthermore, the hVB22B u2-wz4 (v3) sc(Fv)2 gene (hereinafter v3; the nucleotide sequence is SEQ ID NO: 16, and the amino acid sequence is SEQ ID NO: 17), in which Gln on position 39 of VH1 (genetic codon: CAG) was modified to Glu (genetic codon: GAG), Gln on position 38 of VL2 (genetic codon: CAG) was modified to Lys (genetic codon:

AAG), Gln on position 39 of VH3 (genetic codon: CAG) was modified to Lys (genetic codon: AAG), and Gln on position 38 of VL4 (genetic codon: CAG) was modified to Glu (genetic codon: GAG), was produced. Gene modification involved introducing point mutations using QuikChange Site-Directed Mutagenesis Kit (STRATAGENE) by following the manufacturer's protocol.

After confirming the nucleotide sequences of each of the genes, the DNA fragments were cloned into the expression vector pCXND3 to construct expression vectors, and stable expression cell lines were generated by introducing the genes into CHO-DG44 cells. Specifically, a mixture of the expression vector (20 μg) and 0.75 mL of CHO-DG44 cells suspended in PBS ($1 \times 10^7$ cells/mL) was cooled on ice for ten minutes and transferred to a cuvette, then a pulse was applied at 1.5 kV and a capacitance of 25 μFD using Gene Pulser Xcell (BioRad). After a recovery period of ten minutes at room temperature, cells subjected to electroporation treatment were added into CHO-S-SFMII medium (Invitrogen) containing 500 μg/mL Geneticin (Invitrogen) and selected. Thus, v1-producing CHO cell line and v3-producing CHO cell line were established.

Figure 28:
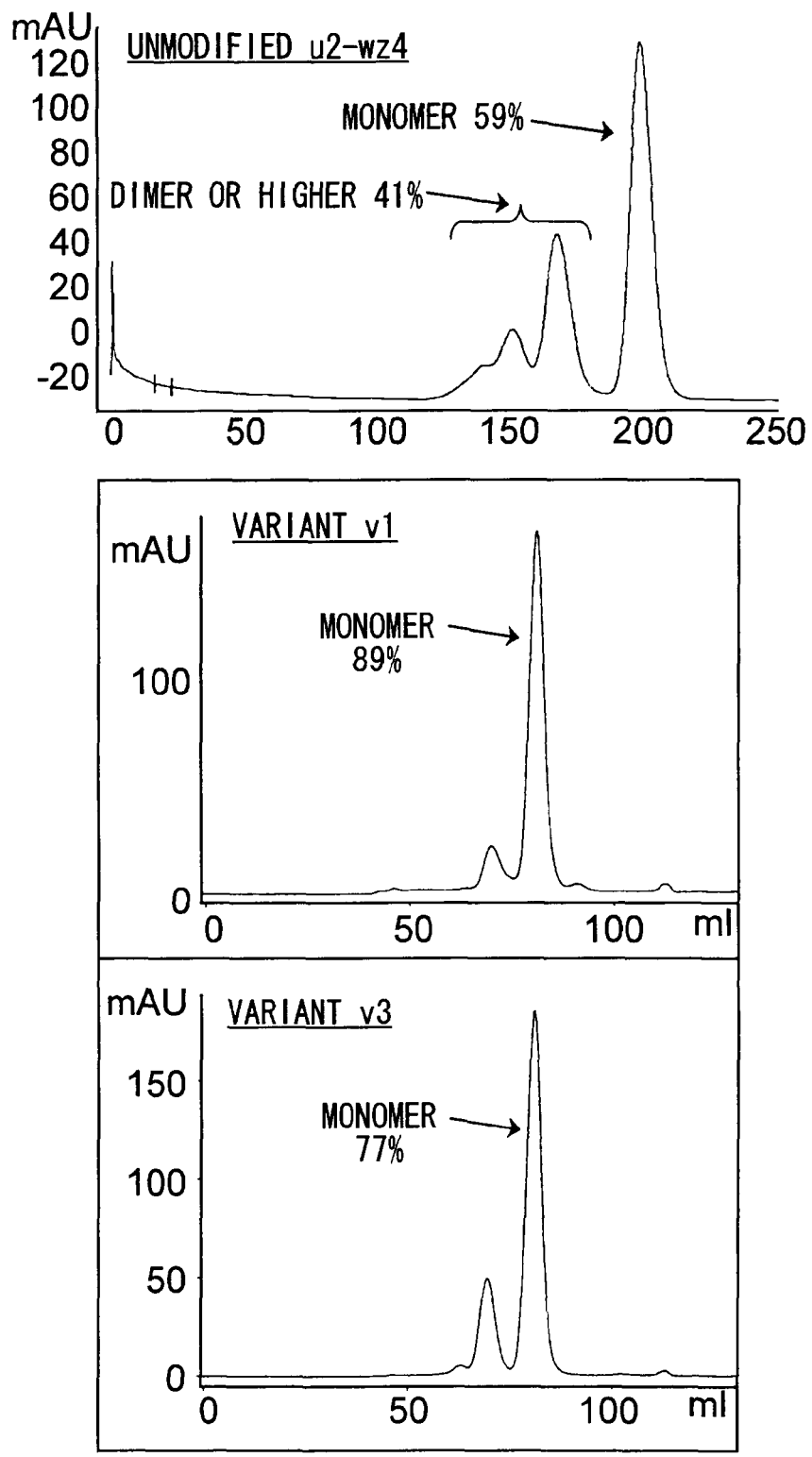
FIG. 28 depicts the results of gel filtration chromatography of u2-wz4, variant v1, and variant v3.

Since the VH/VL interface-modified sc(Fv)2 do not have an added Flag tag, purification from the culture supernatant was carried out using an MG10-GST fusion protein; MG10 (Gln213 to Ala231 of the amino acid sequence of human Mpl) is an epitope recognized by VB22Bsc(Fv)2. The MG10-GST fusion protein was purified using Glutathione Sepharose 4B (Amersham Biosciences) according to the manufacturer's protocol. Further, the purified MG10-GST fusion protein was immobilized onto HiTrap NHS-activated HP (Amersham Biosciences) according to the manufacturer's protocol to prepare an affinity column. The culture supernatant of v1-expressing CHO cell line or v3-expressing CHO cell line was applied to the MG10-GST fusion protein-immobilized column to adsorb v1 or v3, which were then eluted using 100 mM Glycine-HCl (pH 3.5), 0.01% Tween 80. The eluted fractions were immediately neutralized with 1 M Tris-HCl (pH7.4), and the monomeric molecules were purified by gel filtration chromatography using HiLoad 16/60 Superdex 200 pg (Amersham Biosciences). 20 mM citrate buffer (pH7.5) with 300 mM NaCl and 0.01% Tween 80 was used as the buffer for the gel filtration chromatography. The results of gel filtration chromatography shown in FIG. 28 revealed that dimers and larger aggregates in the culture supernatant decreased for variants v1 and v3, and the proportion of monomers increased from 59% for u2-wz4 before modification to 89% for v1 and 770%, for v3. It is speculated that modification of amino acids at the VH/VL interface inhibited unfavorable associations through charge repulsion and promoted favorable association in variants v1 and v3. Accordingly, efficient expression of monomeric molecules was successfully accomplished by this association regulation.

5-2. Analysis and Identification of the Conformational Isomers of VH/VL Interface-Modified sc(Fv)2

The content ratio of conformational isomers of the obtained VH/VL interface-modified v1 and v3 and the unmodified u2-wz4 were analyzed by cation exchange chromatography and isoelectric focusing. Structure identification by the limited protease degradation method was also carried out.

Cation exchange chromatography was performed as described below:
 Column: TSK-gel Bioassist S, 4.6 mm ϕ×50 mm (TOSOH)
 Flow rate: 0.8 mL/min
 Detection wavelength: 220 nm Elution conditions:
 Eluent A: 20 mmol/L Phosphate buffer (pH7.0)
 Eluent B: 20 mmol/L Phosphate buffer/500 mmol/L NaCl (pH7.0)

| Gradient: | |
| --- | --- |
| Time (min) | B % |
| 0 | 0 |
| 5 | 0 |
| 25 | 30 |
| 25.1 | 100 |
| 35 | 100 |
| 35.1 | 0 |

Isoelectric focusing was performed as follows. PhastGel Dry IEF gels (Amersham Biosciences) were swollen for 30 minutes or more in the gel swelling solution shown below. Samples were applied to the pre-swollen gels, and electrophoresis was performed using the PhastSystem under the electrophoresis conditions shown below. Following electrophoresis, they were soaked for 30 minutes in a 20% TCA solution, washed three times or more for five minutes each with MilliQ water, and Coomasie stained or silver stained depending on the protein concentration of the samples. In Coomasie staining, 0.02% CBB containing 0.1% $CuSO_4$ (w/v) was used as the staining solution, and 30% methanol containing 10% acetic acid was used for destaining. In silver staining, the Silver stain kit, Protein (Amersham Biosciences) was used, and staining was performed by a standard protocol attached to the kit.

| <Gel swelling solution> | |
| --- | --- |
| Pharmalyte 8.5-10 | 80 μL |
| Biolyte 7-9 | 10 μL |
| Biolyte 3-9 | 10 μL |
| 20% Glycerol | 2.0 mL |

| <Electrophoresis program> | | | | | |
| --- | --- | --- | --- | --- | --- |
| SAMPLE APPLICATION DOWN AT step 2 | | | | | 0 Vh |
| SAMPLE APPLICATION UP AT step 3 | | | | | 0 Vh |
| Step 1 | 2000 V | 2.5 mA | 3.5 W | 15° C. | 75 Vh |
| Step 2 | 200 V | 2.5 mA | 3.5 W | 15° C. | 15 Vh |
| Step 3 | 2000 V | 2.5 mA | 3.5 W | 15° C. | 410 Vh |

Figure 29:
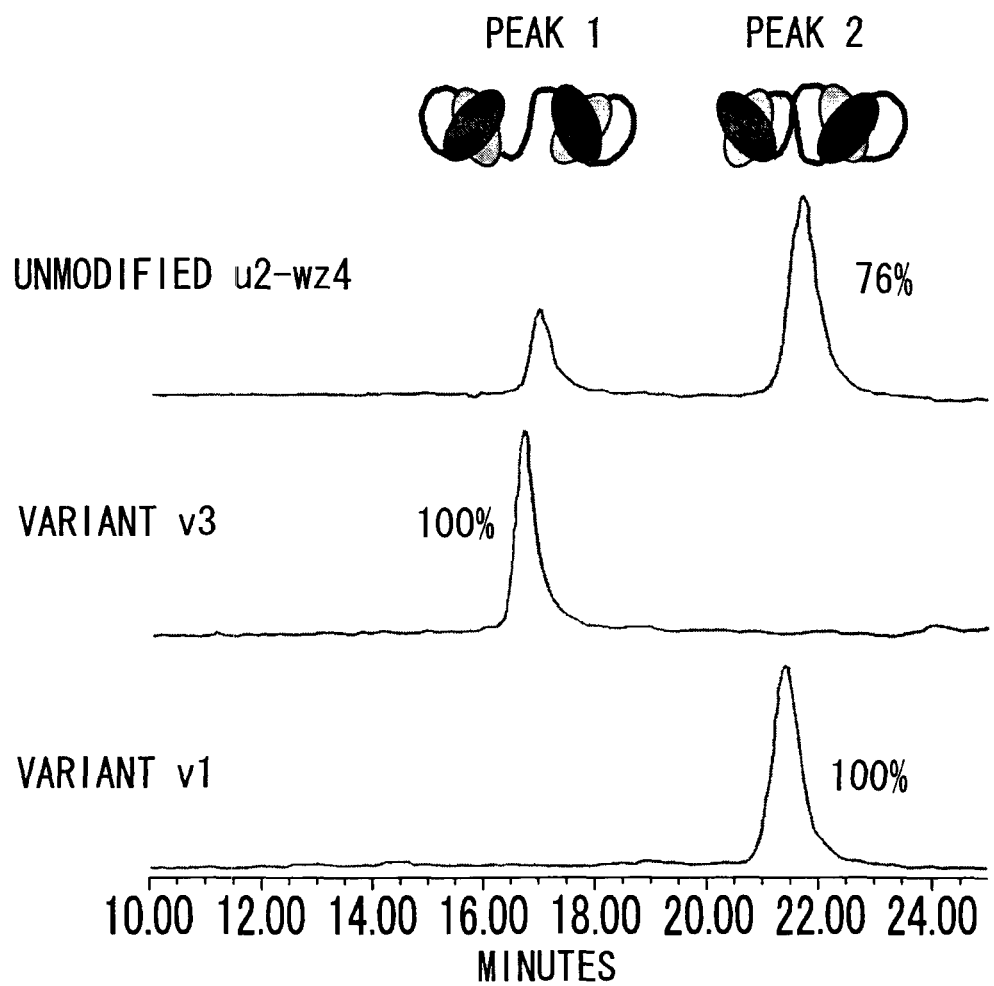
FIG. 29 depicts the results of cation exchange chromatographic analyses of u2-wz4, variant v1, and variant v3.
Figure 30:
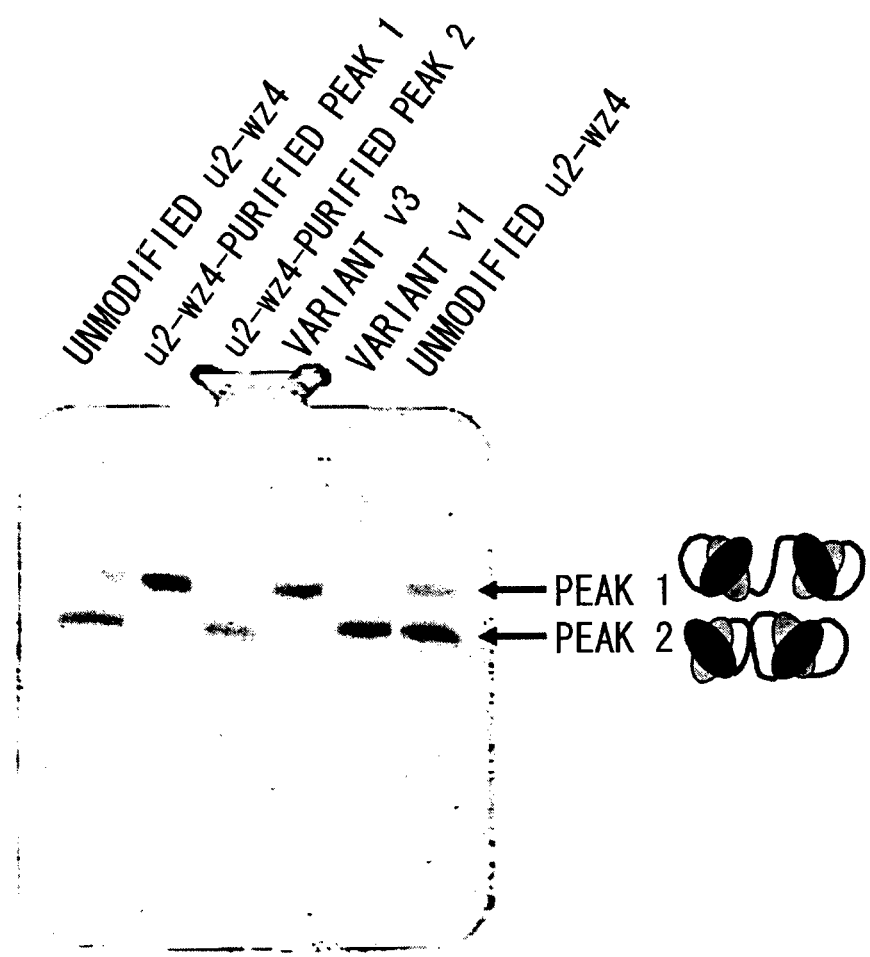
FIG. 30 depicts the results of isoelectric focusing of u2-wz4, u2-wz4-purified peak 1, u2-wz4-purified peak 2, variant v1, and variant v3.
Figure 31:
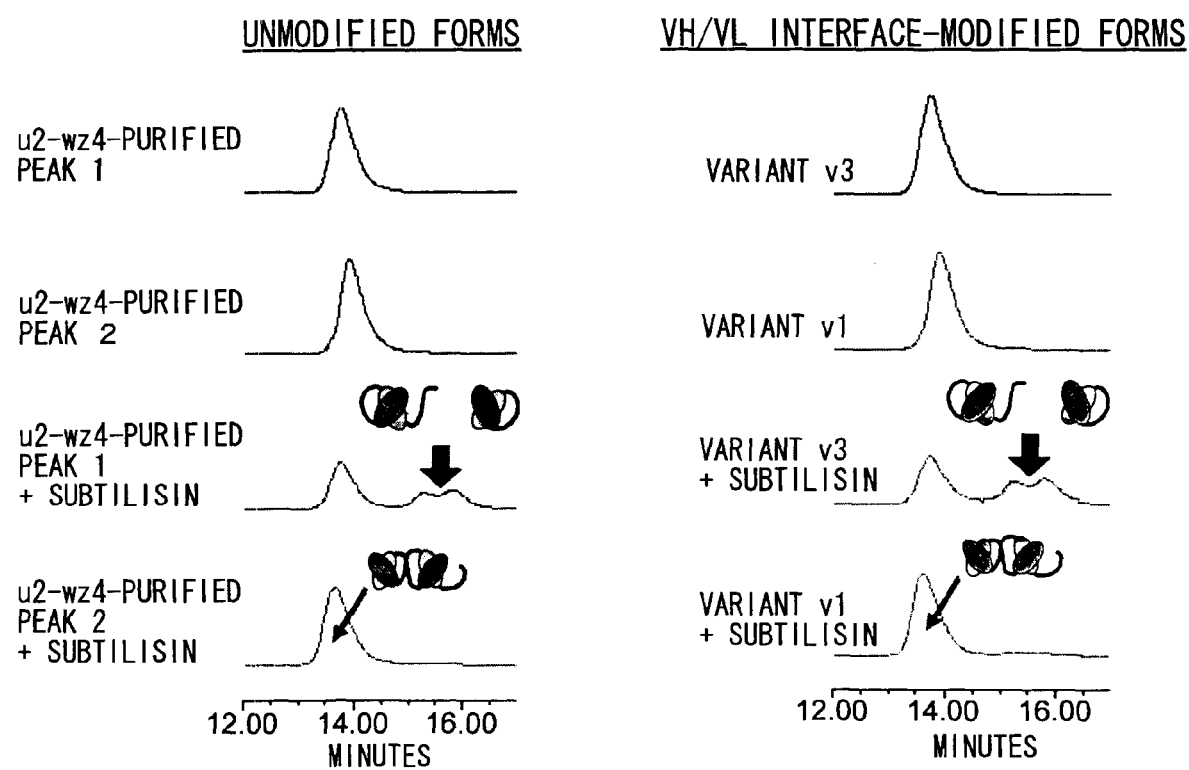
FIG. 31 depicts the results of gel filtration chromatographic analyses of u2-wz4-purified peak 1, u2-wz4-purified peak 2, variant v1, and variant v3 after limited protease degradation.

Structure identification by the limited protease degradation method was performed under the conditions shown below. Under the following conditions, u2-wz4-purified peak 1, u2-wz4-purified peak 2, variant v1, and variant v3 were reacted using subtilisin A:
 20 mM sodium citrate, 150 mM NaCl, pH7.5
 hVB22B u2-wz4 sc(Fv)2 peak 1 or peak 2: 0.15 mg/mL
 Subtilisin A: 10 g/mL
 37° C., 30 min The obtained reaction solutions were analyzed by gel filtration chromatography under the following conditions:
 Column: TSKgel Super 2000 sw (TOSOH)
 Eluent: 50 mM sodium phosphate, 300 mM KCl, pH7.0
 Flow rate: 0.2 ml/min
 Detection: 220 nm From the results of analyses of conformational isomers by cation exchange chromatography and isoelectric focusing indicated in FIGS. 29 and 30, it was found that u2-wz4 is expressed as a mixture of both conformational isomers, with 24% being the bivalent scFv type and 76% being the single chain diabody type, whereas variant v1 is expressed as 100% single chain diabody-type conformational isomer, and variant v3 is expressed as 100% bivalent scFv-type conformational isomer. Furthermore, as shown in FIG. 31, a low-molecular weight peak is observed for variant v3 similarly to u2-wz4-purified peak 1 and a low molecular weight peak is not observed for variant v1 similarly to u2-wz4-purified peak 2 in the results of limited protease degradation also; therefore, this indicated that variant v1 is expressed as a single chain diabody-type conformational isomer, and variant v3 is expressed as a bivalent scFv-type conformational isomer.

Reference Example 6

Activity and Stability Assessments of VH/VL Interface-Modified sc(Fv)2

6-1. Assessment of the Biological Activity of VH/VL Interface-Modified sc(Fv)2

Figure 32:
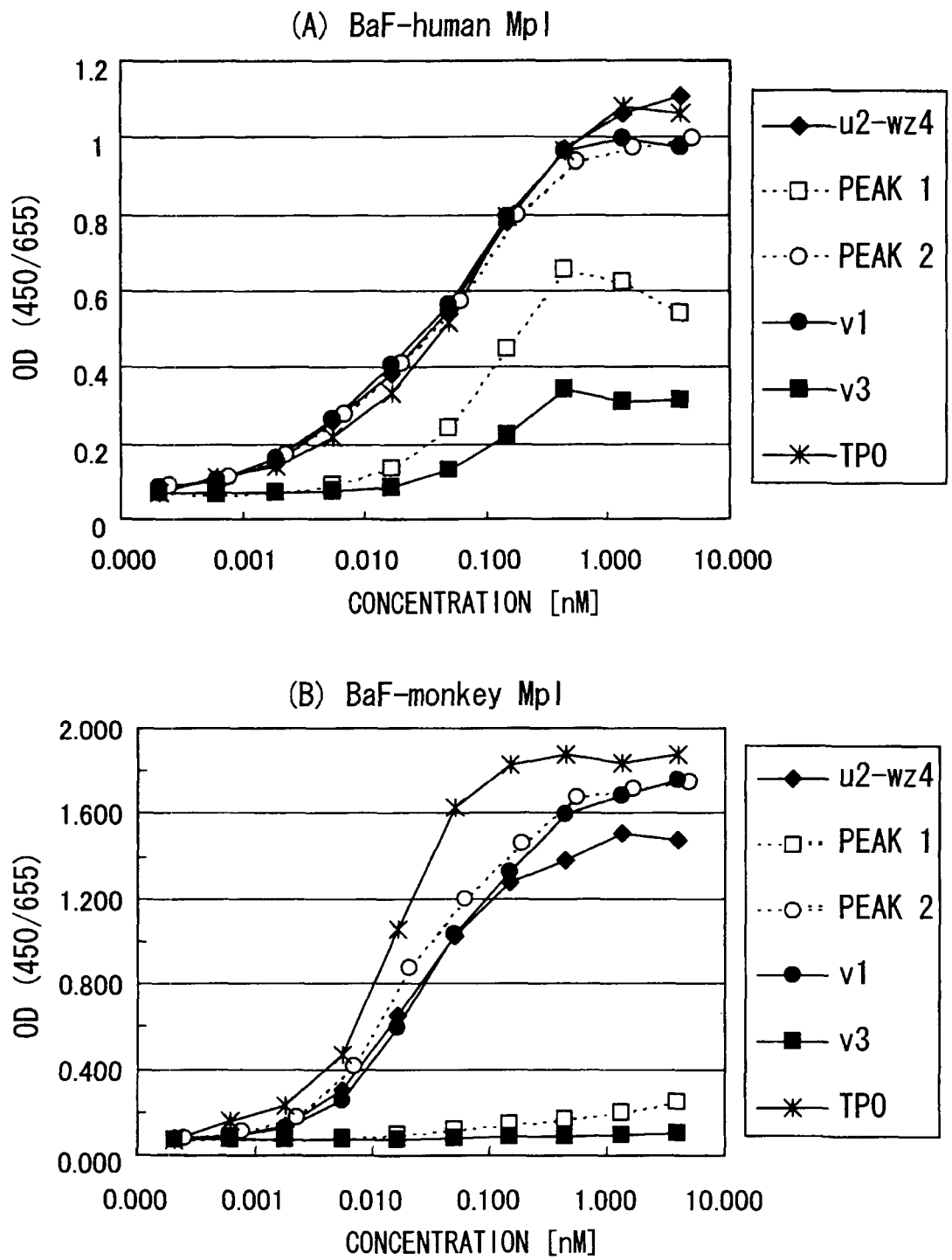
FIGS. 32A and 32B depict the results of assays evaluating the TPO-like agonistic activity of u2-wz4-purified peak 1, u2-wz4-purified peak 2, variant v1, and variant v3 in BaF3-human Mpl cells (FIG. 20A) and in BaF3-monkey Mpl cells (FIG. 20B).

Assessment of agonistic activity of VH/VL interface-modified v1 and v3 was carried out according to the method set forth in Reference Example 1. The agonistic activity differs significantly between conformational isomers, and, as shown in FIG. 20, while peak 2 having a single chain diabody structure shows very high agonistic activity, the activity of peak 1 having a bivalent scFv structure significantly decreases. As shown in FIG. 32, variant v1 showed an activity equivalent to that of peak 2, and variant v3 showed nearly the same activity as peak 1. Accordingly, from the biological activity also, it was also confirmed that variant v1 forms a single chain diabody structure and variant v3 forms a bivalent scFv structure.

6-2. Assessment of the Stability of VH/VL Interface-Modified sc(Fv)2

Figure 33:
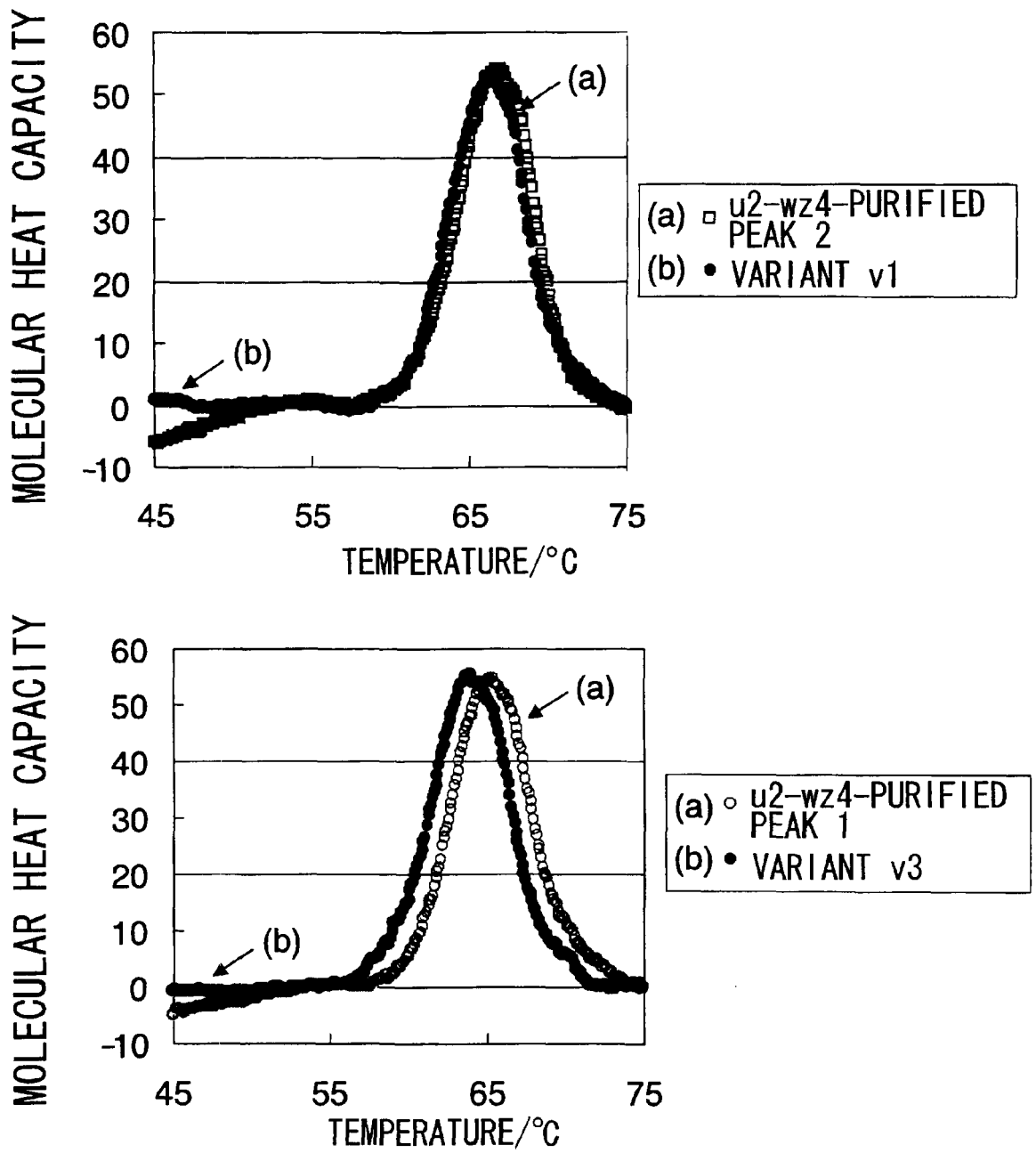
FIG. 33 depicts the results of DSC analysis of u2-wz4-purified peak 1, u2-wz4-purified peak 2, variant v1, and variant v3.

To assess the stability of u2-wz4-purified peak 1, u2-wz4-purified peak 2, variant v1, and variant v3, the denaturation midpoint temperature (Tm value) was measured using differential scanning; calorimetry under the following conditions:
 DSC: N-DSCII (Applied Thermodynamics)
 Solution conditions: 20 mM sodium citrate, 300 mM NaCl, pH7.0
 Protein concentration: 0.1 mg/mL
 Scanning speed: 1° C./minute
The results of each DSC measurement are shown in FIG. 33. The Tm values for u2-wz4-purified peak 2 and variant v1 were nearly the same as the unmodified form, and their stabilities were found to be the same. Between u2-wz4-purified peak 1 and variant v3, variant v3 showed a slightly lower stability. As for interface regulation performed by methods using the knobs-into-hole technique, it has been reported that, for example in the heterologous association of IgG CH3 domains, the Tm value for the unmodified CH3 domain was 80.4° C., whereas the Tm value for the modified CH3 domain was 69.4° C.; thus the Tm value significantly decreased and the stability decreased (Acta Pharmacologica Sinica, 2005, 26, 649-658). In contrast, in the present invention, it was confirmed that aggregation can be regulated without decreasing stability.

Next, stability was evaluated by thermal acceleration tests under the following conditions for u2-wz4-purified peak 1 and u2-wz4-purified peak 2 as well as for the VH/VL interface-modified variants v1 and v3.
 <Thermal Acceleration Conditions>
 Solution conditions: 20 mM sodium citrate, pH 6.0
 Protein concentration: 0.25 mg/mL
 Acceleration conditions: 40° C.-6 days, 12 days The thermal acceleration samples were analyzed by gel filtration chromatography and cation exchange chromatography under the following conditions.

Figure 34:
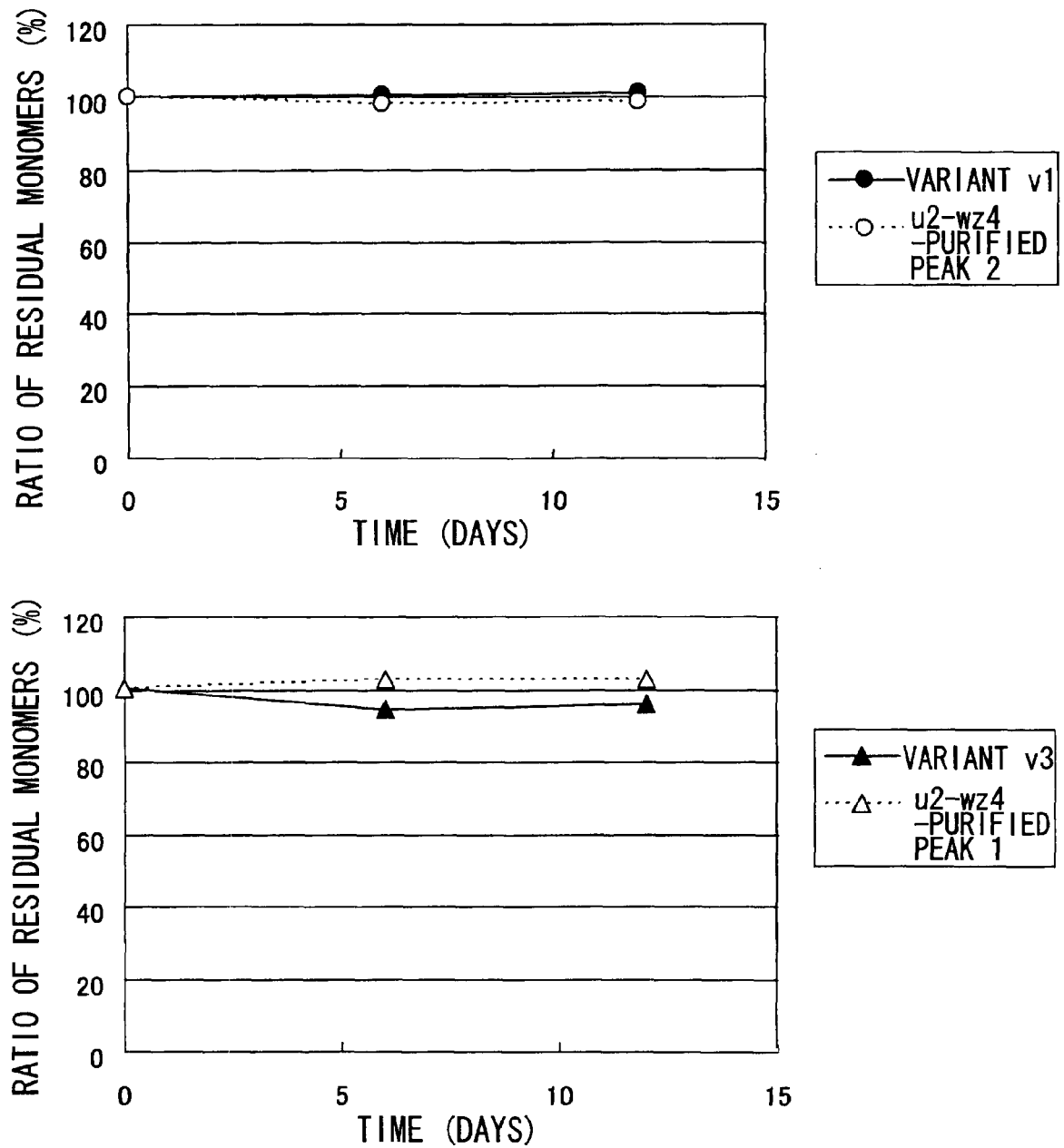
FIG. 34 depicts the results of gel filtration chromatographic analyses in thermal acceleration tests of u2-wz4-purified peak 1, u2-wz4-purified peak 2, variant v1, and variant v3.

As shown in FIG. 34, the results of gel filtration chromatography analysis confirmed that the rate of residual monomers is nearly the same for u2-wz4-purified peak 2 and variant v1, and the stability against aggregation was nearly the same. The rate of residual monomers was also nearly the same for u2-wz4-purified peak 1 and variant v3, and the stability against aggregation was nearly the same for both conformational isomers.

Figure 35:
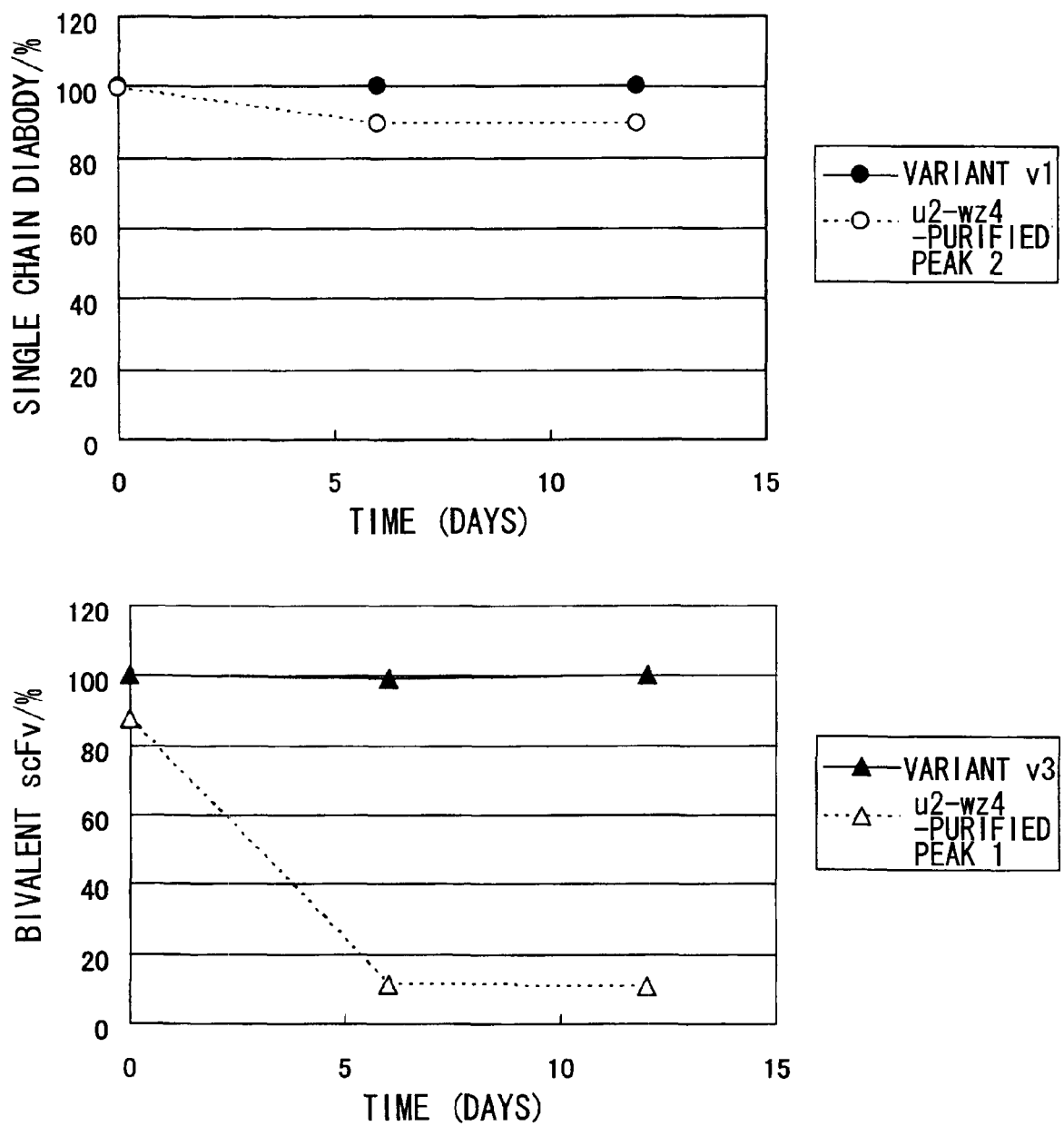
FIG. 35 depicts the results of cation exchange chromatographic analyses in thermal acceleration tests of u2-wz4-purified peak 1, u2-wz4-purified peak 2, variant v1, and variant v3.

As shown in FIG. 35, according to the cation exchange chromatography results, the unmodified form purified peak 1 isomerized to peak 2 through isomerization reaction, and the unmodified form purified peak 2 isomerized to peak 1 through isomerization reaction, whereas the VH/VL interface variants v1 and v3 did not undergo an isomerization reaction even after thermal acceleration. By applying modifications to the VH/VL interface, only one of the two types of conformational isomers can be expressed at 100%; it was additionally found that each of the obtained conformational isomers can be stored stably without undergoing an isomerization reaction.

The present Reference Example demonstrates that, by applying VH/VL interface modifications to v1 and v3, one can restrict expression to only one of the two types of conformational isomers, expressed at 100%. A known method for VH/VL-interface regulation for obtaining a single chain antibody having the conformation of interest is a method which regulates the conformations of bispecific diabodies using the knobs-into-holes technique (Protein Sci. 1997 April; 6(4): 781-8, Remodeling domain interfaces to enhance heterodimer formation, Zhu Z, Presta L G, Zapata G, Carter P). This method has been reported to increase the percentage of formation of the heterodimeric conformation of interest from 72% to 92%, by modifying amino acids at a total of four sites per VH/VL interface. In contrast, the present invention succeeded in obtaining the conformation of interest at a percentage of 100% without lowering the thermal and the conformational isomer stabilities by modifying amino acids at four positions (two positions around the VH/VL interface region).

Reference Example 7

Separation and Structure Determination of Conformational Isomers of Humanized Anti-Human IL-6 Receptor Antibody sc(Fv)2

6-1. Production of Humanized Anti-Human IL-6 Receptor Antibody sc(Fv)2

Using the VH and VL of the humanized anti-human IL-6 receptor antibody reported by Sato K. et al. (Cancer Research 1993; 53:851-856), an sc(Fv)2 gene (amino acid sequence: SEQ ID NO: 18; nucleotide sequence: SEQ ID NO: 19) in which linkages were made to constitute VH-linker sequence-VL-linker sequence-VH-linker sequence-VL was produced using a gene encoding the linker sequence (GlyGlyGlyGlySer)×3 (SEQ ID NO: 1). The obtained gene was inserted into the expression vector pMCDN to allow for expression in animal cells. The course of construction of the present vector pMCDN is described below. A vector into which the enhancer and promoter of mouse cytomegalovirus (mCMV) and the late polyadenylation site of simian virus-40 (SV40) have been inserted into the pUC19 vector, referred to as pMC, was selected. Next, DHFR-ΔE-rVH-PM1-f (see WO92/19759) was digested on the restriction enzyme sites EcoRI and SmaI to separate the antibody H-chain gene and vector, the vector side only was collected, and the EcoRI-NotI-BamHI adaptor (TaKaRa) was cloned therein. This vector is referred to as pCHOI. An expression vector referred to as pMCDN was produced by inserting the DHFR gene expression site of pCHOI and the Neomycin resistance gene expression site of the restriction enzyme of pCXN (Niwa et al., Gene 1991; 108:193-200) into the pMC vector. After linearizing the constructed humanized anti-human IL-6 receptor antibody sc(Fv)2 expression vector with restriction enzymes, gene introduction into CHO-DG44 cells was carried out to establish antibody-expressing cell lines.

Stable expression cell lines were produced as follows: Genes were introduced into cells by the electroporation method using Gene Pulser Xcell (Bio-Rad). Mixtures of each antibody expression vector and 0.75 mL of CHO cells suspended in PBS ($1\times10^7$ cells/mL) were cooled on ice for 10 minutes, and, after transferring to a cuvette, were pulsed at 1.5 kV and a capacitance of 25 µFD. After a recovery period of 10 minutes at room temperature, the cells subjected to electroporation treatment were suspended in 40 mL of CHO-S-SFMII medium (Invitrogen) containing HT supplement (Invitrogen) at 1× concentration. 10 to 50-fold diluted solutions were prepared in the same medium and aliquoted into 96-well culture plates at 100 µL/well. After culturing in a $CO_2$ incubator (5% $CO_2$) for 24 hours, Geneticin (Invitrogen) was added at 0.5 mg/mL, and this was cultured for two weeks. Colonies of transformed cells showing drug resistance were cultured and expanded sequentially, an established high-producing cell line was used for large-scale culturing, and the culture supernatant was obtained.

By using the binding of the L chain of humanized anti-human IL-6 receptor antibody to Protein L, the culture supernatant of humanized anti-human IL-6 receptor antibody sc(Fv)2-expressing CHO cells was passed through a column packed with Protein L (Actigen), humanized anti-human IL-6 receptor antibody sc(Fv)2 were adsorbed thereto and eluted with 100 mM Glycine-HCl (pH2.7). The eluted fractions were immediately neutralized with 1 M Tris-HCl (pH8.5), and gel filtration chromatography was performed using HiLoad 26/60 Superdex 200 pg (Amersham-Biosciences). The buffer used for the gel filtration chromatography was Dulbecco PBS.

6-2. Separation and Purification of the Conformational Isomers of Humanized Anti-Human IL-6 Receptor Antibody sc(Fv)2

Since humanized anti-human IL-6 receptor antibody sc(Fv)2 is an sc(Fv)2 composed of a $VH_1$-linker-$VL_2$-linker-$VH_3$-linker-VL4 sequence, combinations of Fvs (molecules in which VH and VL are noncovalently bound) result from a structural perspective into two types of conformational isomers, similarly to VB22B of Reference Example 1 and hVB22B of Reference Example 2—namely, the bivalent scFv type in which $VH_1$ and $VL_2$, and $VH_3$ and $VL_4$ respectively form Fvs, and the single chain diabody type in which $VH_1$ and $VL_4$, and $VH_2$ and $VL_3$ respectively form Fvs (FIG. 10). After investigating the separation of the conformational isomers of humanized anti-human IL-6 receptor antibody sc(Fv)2, the conformational isomers of humanized anti-human IL-6 receptor antibody sc(Fv)2 were successfully separated using a cation exchange chromatography column BioAssist S (TOSOH) under the following elution conditions:
<Elution Conditions>
Mobile phase: 20 mM Tris-HCl pH8.5, 75 mM NaCl
Flow rate: 0.8 mL/min
Gradient: isocratic (no gradient)

Figure 36:
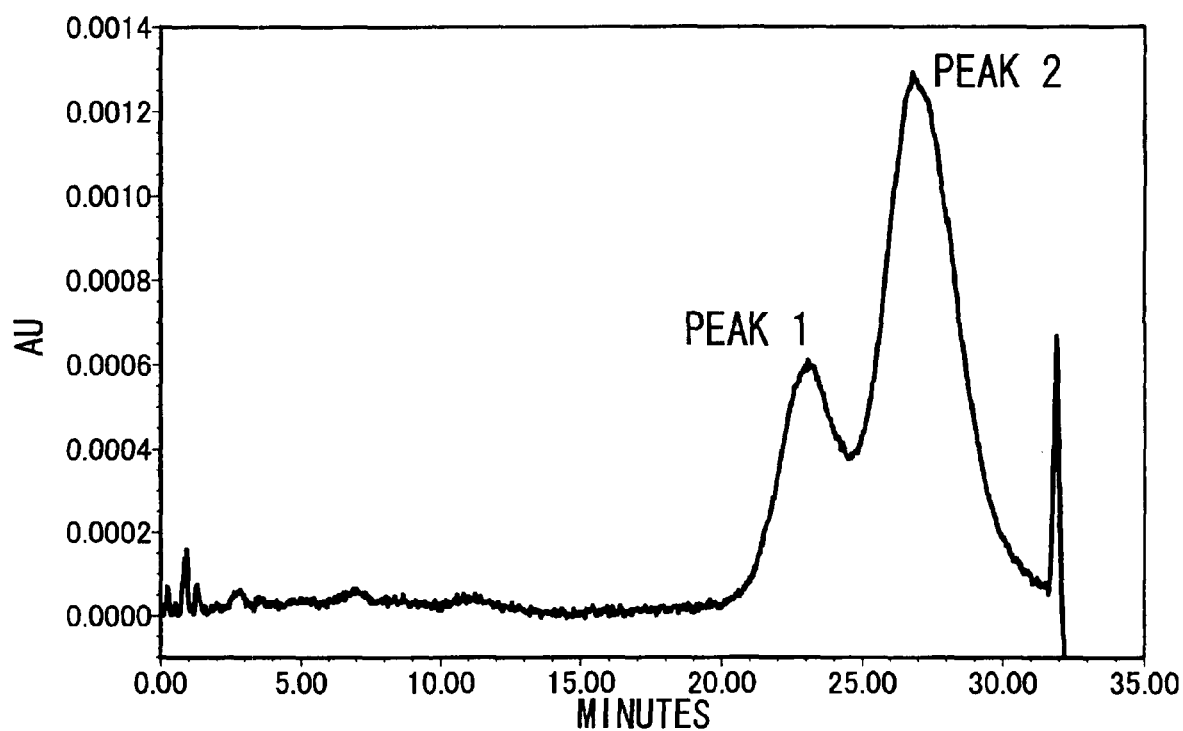
FIG. 36 depicts the results of cation exchange chromatography separation of peak 1 and peak 2 of humanized anti-human IL-6 receptor antibody sc(Fv)2.
Figure 37:
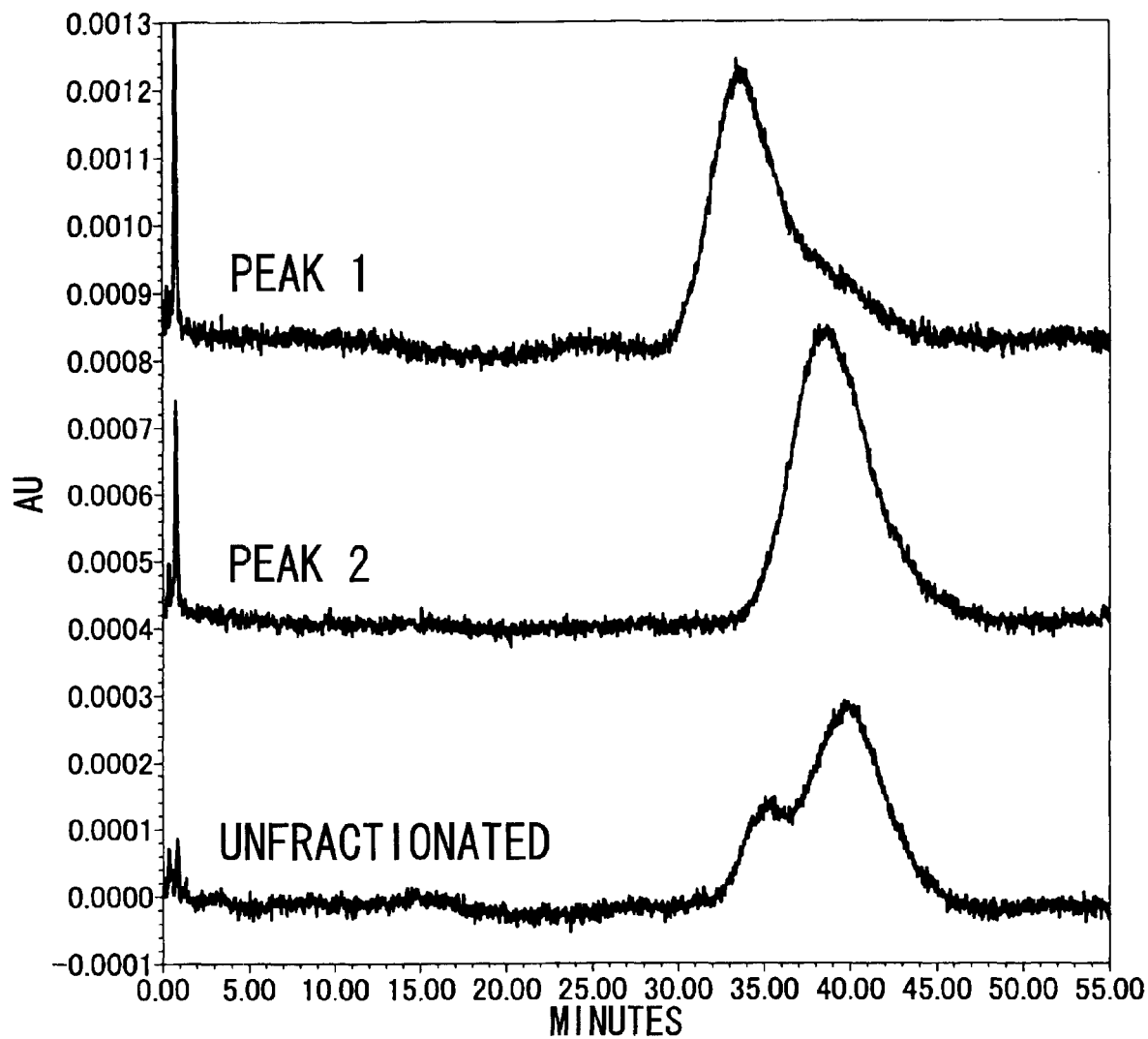
FIG. 37 depicts the results of cation exchange chromatographic analyses of peak 1 and peak 2 of humanized anti-human IL-6 receptor antibody sc(Fv)2.

Under the above-described conditions, humanized anti-human IL-6 receptor antibody sc(Fv)2 was separated into two peaks. A chromatogram, such as that shown in FIG. 36, was obtained, and the peak with shorter retention time was named peak 1 and the peak with longer retention time was named peak 2. Peak 1 and peak 2 were purified by the same method. The results of cation exchange chromatographic analyses on the purified peak 1 and peak 2 are shown in FIG. 37.

6-3. Identification of the Conformational Isomers of Humanized Anti-Human IL-6 Receptor Antibody sc(Fv)2

Figure 38:
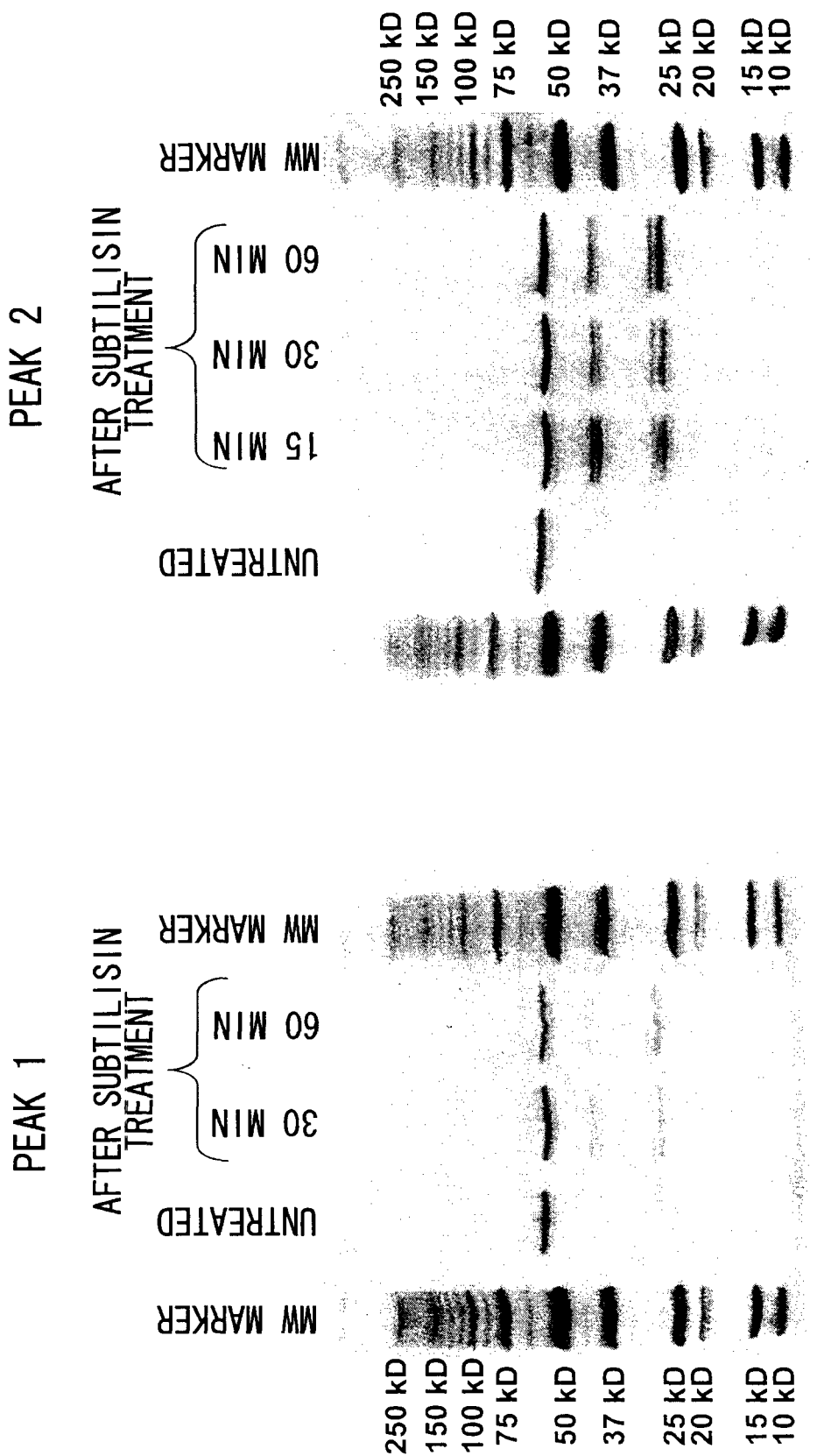
FIG. 38 depicts the results of a reducing SDS-PAGE assay on peak 1 and peak 2 of humanized anti-human IL-6 receptor antibody sc(Fv)2 after subtilisin treatment. The putative conformations of the obtained bands are shown on the right.
Figure 39:
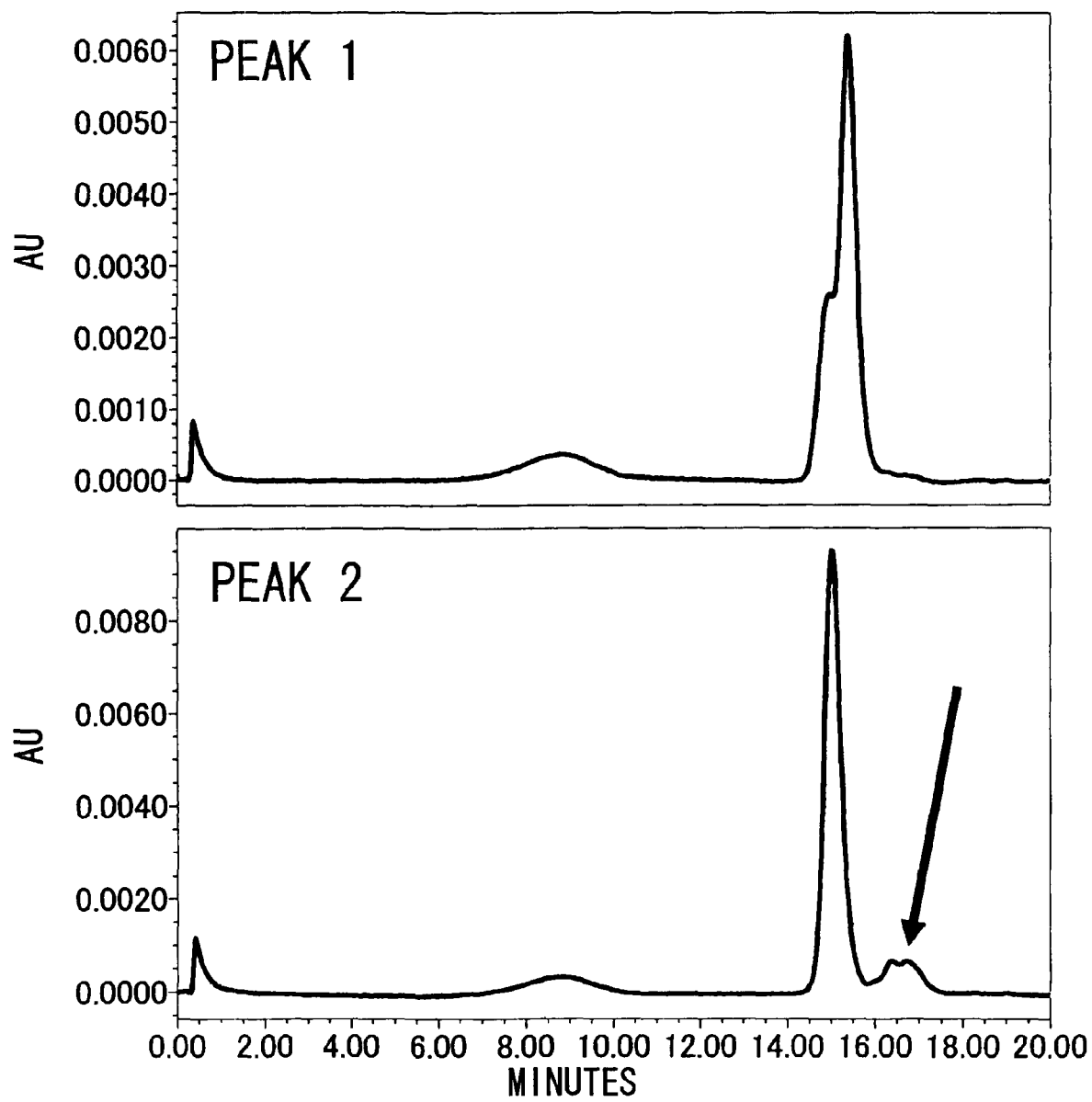
FIG. 39 depicts the results of gel filtration chromatography of peak 1 and peak 2 of humanized anti-human IL-6 receptor antibody sc(Fv)2 after limited degradation by subtilisin. The elution position for the low-molecular-weight peaks is indicated by an arrow.

Since the collected peak 1 and peak 2 of humanized anti-human IL-6 receptor antibody sc(Fv)2 were considered to be conformational isomers, the limited protease degradation method performed in Reference Examples 1, 2, and 3 was used as the method for identifying the two types of conformational isomers. Peak 1 and peak 2 of humanized anti-human IL-6 receptor antibody sc(Fv)2 were reacted under the following conditions:
PBS (pH7.4)
Humanized anti-human IL-6 receptor antibody sc(Fv)2 peak 1 or peak 2: 0.05 mg/mL
Subtilisin A: 0.5 µg/mL
37° C., 60 min After the above reaction, a 12.5% Phastgel Homogeneous was used to perform a reducing SDS-PAGE. As a result, peak 1 and peak 2 both showed similar band patterns as shown in FIG. 38. Peak 1 and peak 2 in which the linkers were partially cleaved under the above-described conditions were subjected to gel filtration chromatographic analysis using TSK Super SW 2000 (TOSOH) under the following conditions:
Mobile phase: 50 mM sodium phosphate, 300 mM KCl, pH7.0
Flow rate: 0.2 mL/min As a result, as shown in FIG. 39, while a low molecular weight peak was hardly observed for peak 1, a low molecular weight (approximately half the molecular weight) peak was observed for peak 2. From these results, peak 1 was identified as the single chain diabody type, and peak 2 was identified as the bivalent scFv type. Since, according to FIG. 36, the content of peak 2 is higher than peak 1 in humanized anti-human IL-6 receptor antibody sc(Fv)2, the bivalent scFv type was found to be the main component, and the single chain diabody type the minor component, in humanized anti-human IL-6 receptor antibody sc(Fv)2. Since the single chain diabody type was the major component in VB22B sc(Fv)2 in Reference Example 1 and in hVB22B u2-wz4 sc(Fv)2 in Reference Example 2, differences in the sc(Fv)2 variable region sequences were found to cause significant changes in the conformational isomer content ratio. Since the conformational isomer content ratio changes significantly depending on the sc(Fv)2 variable region sequences, separation and structural identification of the conformational isomers are considered important for developing sc(Fv)2 as pharmaceuticals.

Reference Example 8

Evaluation of the Activity of the Conformational Isomers of Humanized Anti-Human IL-6 Receptor Antibody sc(Fv)2

7-1. Establishment of Human gp130-Expressing BaF3 Cell Lines and Human gp130/Human IL-6 Receptor-Coexpressing BaF3 Cell Lines To obtain cell lines showing IL-6-dependent growth, a BaF3 cell line that expresses human gp130 was established as indicated below.

Full length human gp130 cDNA (Hibi et al., Cell 1990; 63:1149-1157 (GenBank#NM_002184)) was amplified by PCR, the DHFR gene expression site of pCHOI (Hirata et al., FEBS Letter 1994; 356:244-248) was removed, and cloning into the expression vector pCOS2Zeo having an inserted Zeocin resistance gene expression site was carried out to construct pCOS2Zeo/gp130.

10 μg of pCOS2Zeo/gp130 was mixed with BaF cells suspended in PBS ($0.8 \times 10^7$ cells), and this was pulsed at 0.33 kV and a capacitance of 950 μFD using a Gene Pulser (Bio-Rad). BaF3 cells subjected to gene introduction by electroporation treatment were cultured for one day in RPMI1640 medium (Invitrogen) containing 0.2 ng/mL of mouse interleukin-3 (Peprotech) and 10% Fetal Bovine Serum (hereinafter FBS; HyClone), and selected by adding RPMI1640 medium containing 100 ng/mL of human interleukin-6 (R&D), 100 ng/mL of human interleukin-6 soluble receptor (R&D systems), and 10% FBS to establish human gp130-expressing BaF3 cell lines (hereinafter, BaF3/gp130).

7-2. Assessment of the Human IL-6 Neutralizing Activity of the Conformational Isomers of Humanized Anti-Human IL-6 Receptor Antibody sc(Fv)2

IL-6 neutralizing activity was assessed as indicated below using BaF3/gp130 showing IL-6-dependent growth. A purified conformational isomer of humanized anti-human IL-6 receptor antibody sc(Fv)2 was diluted in RPMI1640 containing 10% FBS to produce a 10 μg/mL solution. Using this solution, a total of six series of diluted solutions whose common dilution ratio is 3 were prepared, and these were dispensed at 50 μL per well in 96-well plates (FALCON). Next, BaF3/gp130 was washed three times with RPMI1640 medium containing 10% FBS (HyClone), then suspended to have $5 \times 10^4$ cells/mL in RPMI1640 medium containing 60 ng/mL of human interleukin-6 (R&D systems), 60 ng/mL of soluble human IL-6 receptor (prepared in-house), and 10% FBS, and 50 μL of this was mixed into each of the wells into which the antibody samples had been dispensed. Human soluble IL-6 receptor was prepared by the following method: the receptor was prepared by introduction of a gene encoding amino acid 1 to 344 of the human soluble IL-6 receptor (Yamasaki et al., Science 1988; 241:825-828 (GenBank #X12830)) into CHO cells, followed by purification from the culture supernatant.

After culturing for 72 hours under conditions of 37° C. and 5% $CO_2$, WST-8 reagent (Cell Counting Kit-8; Dojindo Laboratories) diluted two-fold with PBS was added at 20 μL/well, and the absorbance at 450 nm (reference wavelength of 620 nm) was measured immediately thereafter using SUN-RISE CLASSIC (TECAN). After two hours of culturing, the absorbance at 450 nm (reference wavelength of 620 nm) was measured again, and IL-6 neutralization activities were assessed using the changes in absorbance in the two hours as an indicator.

Figure 40:
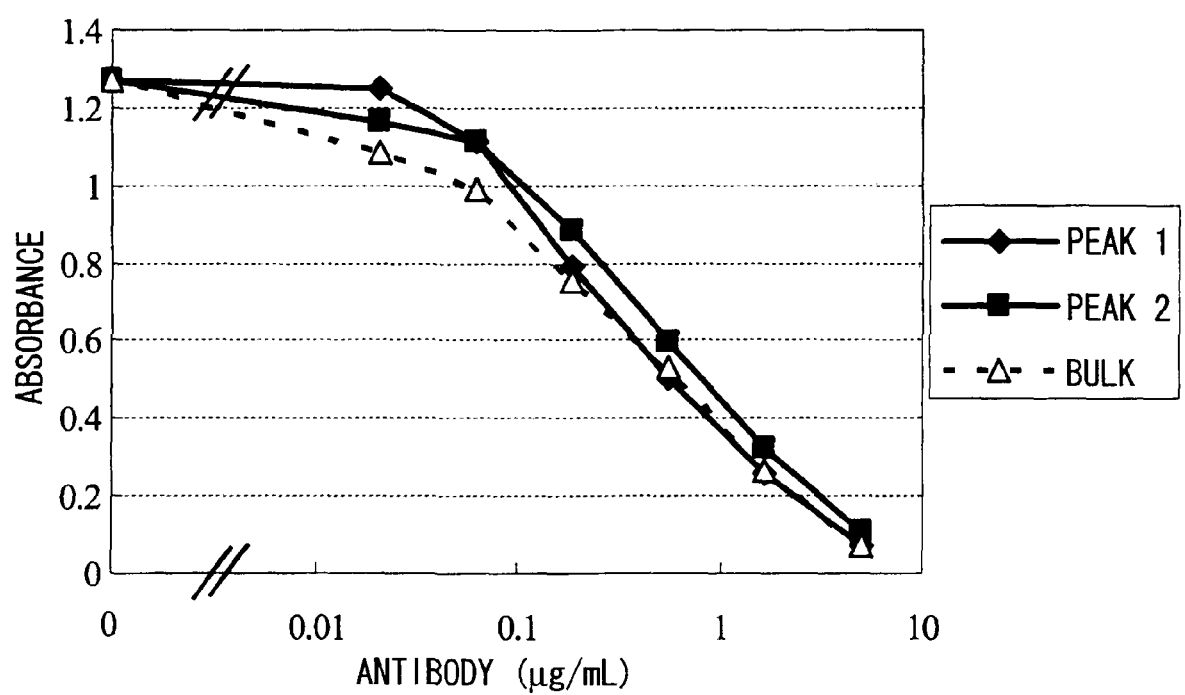
FIG. 40 depicts the result of an assay assessing the IL-6 neutralizing activity of peak 1 and peak 2 of humanized anti-human IL-6 receptor antibody sc(Fv)2 in BaF3/gp130.

Results shown in FIG. 40 confirm that the conformational isomers of humanized anti-human IL-6 receptor antibody sc(Fv)2 (peak 1 and peak 2) had the same neutralizing activity as the purified product before fractionation (bulk). Although significant differences in activity were observed between the two conformational isomers in VB22B sc(Fv)2 of Reference Example 1 and in hVB22B sc(Fv)2 of Reference Example 2, a difference in neutralizing activity was not observed for the humanized anti-human IL-6 receptor antibody sc(Fv)2 of the present Reference Example. Therefore, the difference in activity between the two conformational isomers of sc(Fv)2 may differ depending on the type of the targeted antigen or the amino acid sequence of the sc(Fv)2 molecule, and to develop sc(Fv)2 molecules as pharmaceuticals, separation and structural identification of the conformational isomers and regulation of the conformational isomers may be important. Furthermore, as indicated in Reference Example 6, each of the conformational isomers may undergo isomerization reaction during storage, and separation and structural identification of the conformational isomers and regulation of the conformational isomers may also be important from the standpoint of quality specification of sc(Fv)2 formulations.

Reference Example 9

Methods for Obtaining the Single Chain Diabody of VB22B sc(Fv)2 in High Yield

Figure 41:
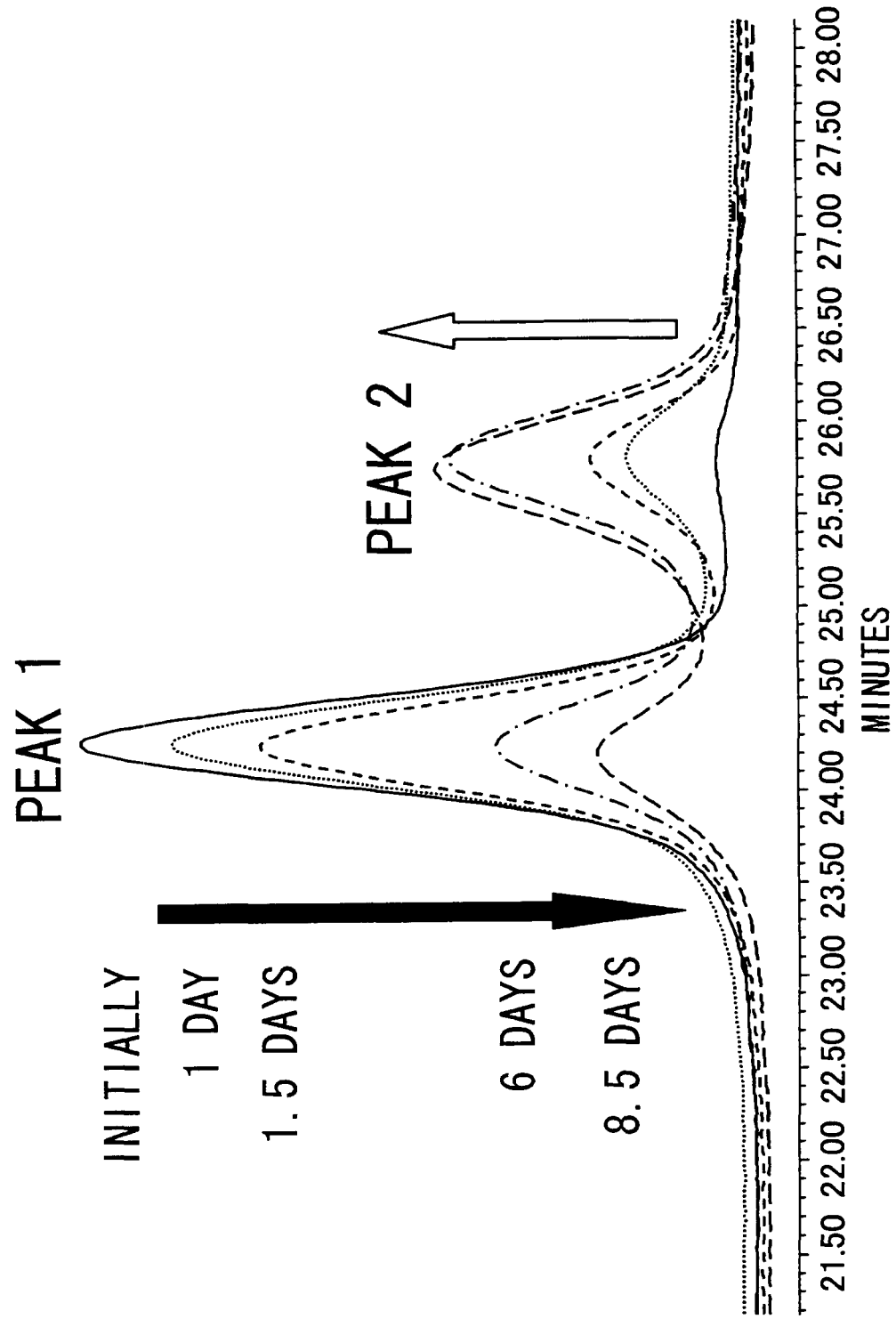
FIG. 41 depicts an anion exchange chromatographic analysis of samples prepared by incubating peak 1 of VB22B sc(Fv)2 in 20 mM sodium acetate, 150 mM NaCl, pH6.0, and at 40° C., and shows that peak 2 increases with time.
Figure 42:
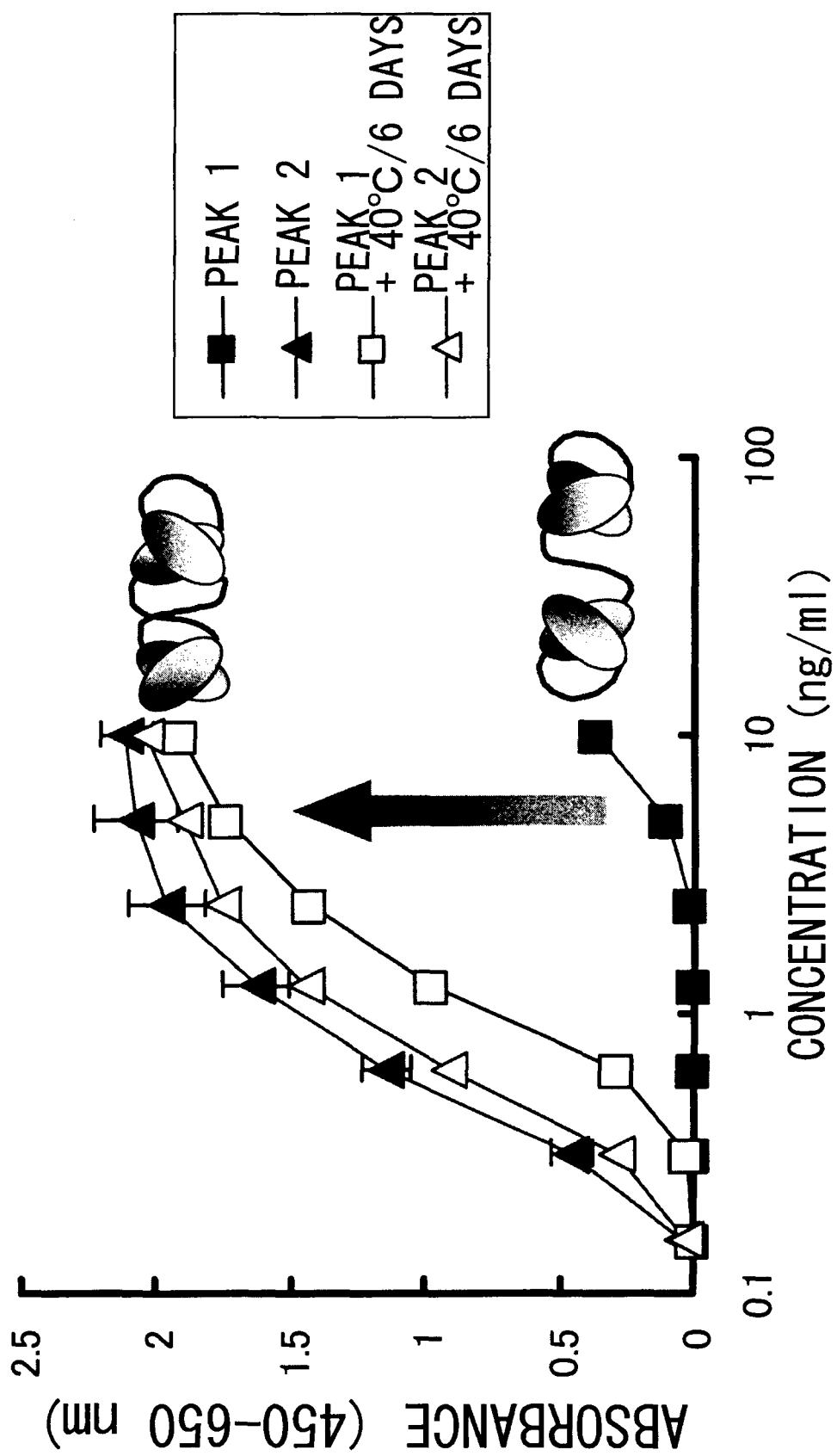
FIG. 42 depicts the results of an assay assessing the agonistic activities of peak 1 and peak 2 of VB22B sc(Fv)2 and of samples incubated at 40° C. for six days, and confirms that activity increases when peak 1 isomerizes to peak 2.

Single chain diabody (peak 2) and bivalent scFv (peak 1) purified from VB22B sc(Fv)2 were individually incubated at 40° C. under conditions of 20 mM sodium acetate, 150 mM NaCl, and pH6.0. As a result of measuring the ratio of peak 1 to peak 2 by the anion exchange chromatography method described in Reference Example 1, as shown in FIG. 41, the peak area of peak 1 decreased, and instead the peak area of peak 2 increased. Consequently, when a sample of peak 1 incubated for six days under the same conditions was subjected to evaluation of agonistic activity by the method indicated in Reference Example 1, the agonistic activity increased significantly as compared to the sample before incubation as shown in FIG. 42. As indicated in Reference Example 1, since the activity of peak 1, which corresponds to a bivalent scFV, is remarkably low as compared to peak 2, which corresponds to single chain diabody, peak 1 was found to undergo a structural conversion (isomerization of conformational isomers) to peak 2 which is highly active single chain diabody by incubation at 40° C. in 20 mM sodium acetate and 150 mM NaCl at pH6.0. This confirms that by exposing a mixture of bivalent scFv and single chain diabody to suitable conditions, peak 1, which is bivalent scFv, can be converted to peak 2, which is single chain diabody, and the content ratio of peak 2 can be increased. By using the present method of isomerizing peak 1 to peak 2 to isomerize peak 1 to peak 2 in a mixture of peak 1 and peak 2 produced by cells, peak 2, which is single chain diabody, can be obtained in high yield.

Reference Example 10

Figure 43:
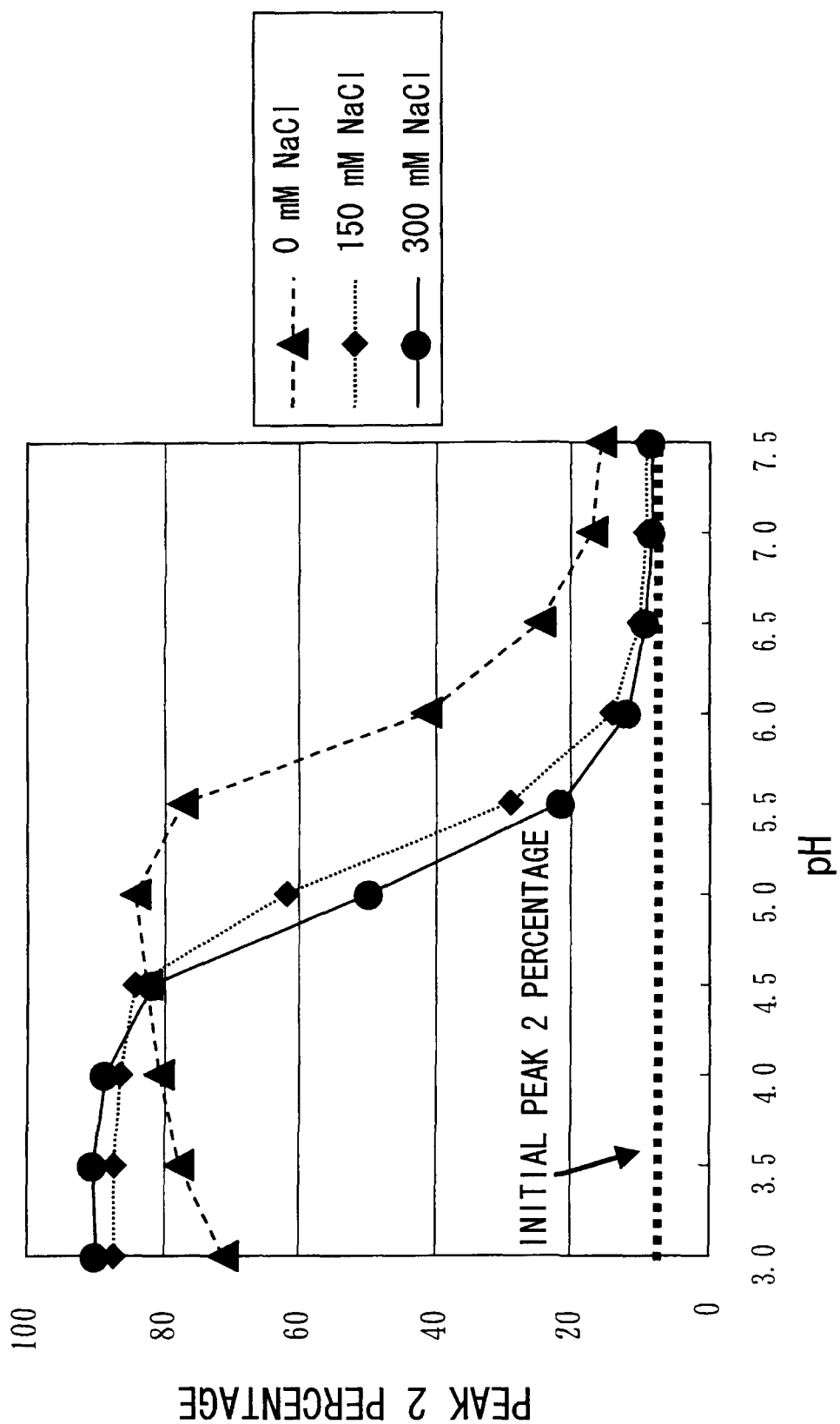
FIG. 43 depicts the isomerization to peak 2 resulting from incubation of peak 1 of hVB22B u2-wz4 sc(Fv)2 at 25° C. for ten days under each of the conditions.

Methods for Obtaining the Single Chain Diabody-Type hVB22B sc(Fv)2 in High Yield Bivalent scFv (peak 1) purified from hVB22B u2-wz4 sc(Fv)2 in Reference Example 4 was incubated for ten days at 25° C. under a total of 30 conditions: 20 mM sodium citrate, 0 mM/150 mM/300 mM NaCl, and pH3.0/3.5/4.0/4.5/5.0/5.5/6.0/6.5/7.0/7.5. The ratio of peak 1 to peak 2 was measured by the cation exchange chromatography method indicated in Reference Example 1. Results demonstrate that the content ratio of peak 2 increased as compared to that before incubation (see FIG. 43). This finding demonstrates that peak 1, which is bivalent scFv, undergoes structural conversion to peak 2, which is single chain diabody, in hVB22B u2-wz4 sc(Fv)2 as well. It was further discovered that the lower the pH and the lower the salt concentration, the faster the rate of isomerization. By using the present method of isomerizing peak 1 to peak 2 to isomerize peak 1 to peak 2 in a mixture of peak 1 and peak 2 produced by cells, peak 2, which is single chain diabody, can be obtained in high yield.

INDUSTRIAL APPLICABILITY

By applying the stabilizing agents/stabilizing conditions or freeze-dried formulation of the present invention, the isomerization reactions of sc(Fv)2 can be suppressed. More specifically, the present invention enables the suppression of the mutual isomerization reactions between two types of conformational isomers in an sc(Fv)2 composition so that one of the conformational isomers can exist stably. It further enables the suppression of the isomerization reaction of a specific conformational isomer obtained from an sc(Fv)2 composition so that the isomer can exist stably.

To develop sc(Fv)2 as a pharmaceutical, one of the conformational isomers, whichever is the substance of interest, must be made to exist stably, and isomerization to the other conformational isomer during storage of the formulation must be kept to a minimum. Alternatively, the content ratio of conformational isomers in formulations must be controlled to be within a specified content ratio of conformational isomers. By applying the stabilizing agents/stabilizing conditions or freeze-dried formulation of the present invention to sc(Fv)2 formulations, the present invention enables the provision of stable formulations having an assured specified content ratio of conformational isomers.

The invention claimed is:

1. A method for suppressing the isomerization of a specific conformational isomer of sc(Fv)2 in a pharmaceutical composition comprising sc(Fv)2, the sc(Fv)2 having four variable regions connected by three peptide linkers arranged in order V1, linker, V2, linker, V3, linker, and V4, wherein each linker comprises 15 amino acids, and wherein the method comprises:
   (a) providing the pharmaceutical composition, wherein the content ratio of the specific conformational isomer is 80% or more in the composition;
   (b) adding a pH adjusting agent to the composition, thereby adjusting the pH of the composition to a pH in the range of 6.0 to 9.0; and
   (c) adjusting the salt concentration of the composition to a concentration of about 300 mM, thereby producing a pharmaceutical composition in which isomerization of sc(Fv)2 is suppressed.

2. The method of claim 1, wherein the salt is selected from the group consisting of sodium chloride and magnesium chloride.

3. The method of claim 1, wherein the pH adjusting agent is selected from the group consisting of a sodium citrate buffer and histidine hydrochloride.

4. The method of claim 1, further comprising freeze-drying the pharmaceutical composition produced in (c).

5. A method for producing a pharmaceutical sc(Fv)2 composition comprising a specific conformational isomer of sc(Fv)2, the specific conformational isomer of sc(Fv)2 being either a bivalent scFv-type sc(Fv)2 or a single chain diabody type sc(Fv)2, wherein the content ratio of the specific conformational isomer is 80% or more in the pharmaceutical sc(Fv)2 composition, wherein the method comprises:
   (a) providing a first composition comprising both bivalent scFv-type sc(Fv)2 and single chain diabody type sc(Fv)2 conformational isomers of an sc(Fv)2, wherein both conformational isomers of the sc(Fv)2 have four variable regions connected by three peptide linkers arranged in order V1, linker, V2, linker, V3, linker, and V4, wherein each linker comprises 15 amino acids, and wherein, in the bivalent scFv-type sc(Fv)2, V1 is associated with V2, and V3 is associated with V4, and, in the single chain diabody type sc(Fv)2, V1 is associated with V4, and V2 is associated with V3, and wherein the content ratio of the specific conformational isomer of sc(Fv)2 in the first composition is 20% or less;
   (b) incubating the first composition at a pH in the range of 3.0 to 6.0 and at a salt concentration of 500 mM or less, for two or more days, to produce a second composition in which the content ratio of the specific conformational isomer of sc(Fv)2 is increased compared to the content ratio of the specific conformational isomer of sc(Fv)2 in the first composition;
   (c) isolating the specific conformational isomer of sc(Fv)2 from the second composition, thereby forming a third composition comprising the isolated specific conformational isomer at a content ratio of 80% or more;
   (d) stabilizing the specific conformational isomer of sc(Fv)2 in the third composition; and
   (e) formulating the stabilized specific conformational isomer of sc(Fv)2 as a pharmaceutical composition.

6. The method of claim 5, wherein, in step (b), the salt concentration is 150 mM or less.

7. The method of claim 5, wherein step (d) comprises adjusting the pH and salt concentration of the third composition to a pH in the range of 6.0 to 9.0 and a salt concentration in the range of 50 mM to 1000 mM.

8. The method of claim 7, wherein, in step (d), the salt concentration is adjusted to 150 mM to 300 mM.

9. The method of claim 5, wherein the specific conformational isomer is a single chain diabody-type sc(Fv)2.

10. The method of claim 5, wherein the specific conformational isomer is a bivalent scFv-type sc(Fv)2.

11. The method of claim 5, wherein the method further comprises:
    (f) freeze-drying the composition of (e).

* * * * *

SEQUENCE LISTING

```
<160> NUMBER OF SEQ ID NOS: 19

<210> SEQ ID NO 1
<211> LENGTH: 15
<212> TYPE: PRT
<213> ORGANISM: Artificial
<220> FEATURE:
<223> OTHER INFORMATION: An artificially synthesized linker sequence

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 8
<212> TYPE: PRT
<213> ORGANISM: Artificial
<220> FEATURE:
<223> OTHER INFORMATION: An artificially synthesized flag sequence

<400> SEQUENCE: 2

Asp Tyr Lys Asp Asp Asp Asp Lys
1               5

<210> SEQ ID NO 3
<211> LENGTH: 1572
<212> TYPE: DNA
<213> ORGANISM: Mus musculus

<400> SEQUENCE: 3
atggaatggc ctttgatctt tctcttcctc ctgtcaggaa ctgcaggtgt ccactcccag      60
gttcagctgc agcagtctgg acctgagctg gtgaagcctg gggcctcagt gaagatttcc     120
tgcaaggctt ctggctatgc attcactaac tcctggatga actgggtgaa gcagaggcct     180
ggaaagggtc ttgagtggat tggacggatt tatcctggag atggagaaac tatctacaat     240
gggaaattca gggtcaaggc cacactgact gcagacaaat cctccagcac agcctacatg     300
gatatcagca gcctgacatc tgaggactct gcggtctact tctgtgcaag aggctatgat     360
gattactcgt ttgcttactg gggccaaggg actctggtca ctgtctctgc aggtggtggt     420
ggttcgggtg gtggtggttc gggtggtggc ggatcggata ttgtgatgac tcaggctgca     480
ccctctatac ctgtcactcc tggagagtca gtatccatct cctgtaggtc tagtaagagt     540
ctcctgcata gtaatggcaa cacttacttg tattggttcc tgcagaggcc aggccagtct     600
cctcaactcc tgatatatcg gatgtccaac cttgcctcag gagtcccaga taggttcagt     660
ggcagtgggt caggaactgc tttcacactg agaatcagta gtgtggaggc tgaggatgtg     720
ggtgtttatt actgtatgca acatatagaa tatccttta cgttcggatc ggggaccaag     780
ctggaaataa aggaggtgg tggatcgggt ggtggtggtt cggaggcgg tggatcgcag     840 gttcagctgc agcagtctgg acctgagctg gtgaagcctg gggcctcagt gaagatttcc     900
```

```
tgcaaggctt ctggctatgc attcactaac tcctggatga actgggtgaa gcagaggcct    960
ggaaagggtc ttgagtggat tggacggatt tatcctggag atggagaaac tatctacaat   1020
gggaaattca gggtcaaggc cacactgact gcagacaaat cctccagcac agcctacatg   1080
gatatcagca gcctgacatc tgaggactct gcggtctact tctgtgcaag aggctatgat   1140
gattactcgt ttgcttactg gggccaaggg actctggtca ctgtctctgc aggtggtggt   1200
ggttcgggtg gtggtggttc gggtggtggc ggatcggata ttgtgatgac tcaggctgca   1260
ccctctatac ctgtcactcc tggagagtca gtatccatct cctgtaggtc tagtaagagt   1320
ctcctgcata gtaatggcaa cacttacttg tattggttcc tgcagaggcc aggccagtct   1380
cctcaactcc tgatatatcg gatgtccaac cttgcctcag gagtcccaga taggttcagt   1440
ggcagtgggt caggaactgc tttcacactg agaatcagta gagtggaggc tgaggatgtg   1500
ggtgtttatt actgtatgca acatatagaa tatccttttta cgttcggatc ggggaccaag   1560
ctggaaataa aa                                                        1572
```

<210> SEQ ID NO 4
<211> LENGTH: 1572
<212> TYPE: DNA
<213> ORGANISM: Mus musculus

<400> SEQUENCE: 4

```
atggactgga cctggaggtt cctctttgtg gtggcagcag ctacaggtgt ccagtcccag     60
gtgcagctgg tgcagtctgg acctgaggtg aagaagcctg ggcctcagt gaaggtctcc    120
tgcaaggctt ctggatacac cttcaccaac tcctggatga actgggtgag gcagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480
ctctccctgc ccgtcacccc tggagagccg gcctccatct cctgcaggtc tagtaagagt    540
ctcctgcata gtaatggcaa cacttacttg tattggttcc tgcagaagcc agggcagtct    600
ccacagctcc tgatctatcg gatgtccaac cttgcctcag ggtccctga caggttcagt    660
ggcagtggat caggcacaga ttttacactg aaaatcagca gagtggaggc tgaggatgtt    720
ggggtttatt actgcatgca acatatagaa tatccttttta cgttcggcca agggaccaaa    780
ctggaaatca aggaggtgg tggatcgggt ggtggtggtt cgggaggcgg tggatcgcag    840
gtgcagctgg tgcagtctgg acctgaggtg aagaagcctg ggcctcagt gaaggtctcc    900
tgcaaggctt ctggatacac cttcaccaac tcctggatga actgggtgag gcagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
caactgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctcca   1260
ctctccctgc ccgtcacccc tggagagccg gcctccatct cctgcaggtc tagtaagagt   1320
ctcctgcata gtaatggcaa cacttacttg tattggttcc tgcagaagcc agggcagtct   1380
ccacagctcc tgatctatcg gatgtccaac cttgcctcag ggtccctga caggttcagt   1440
```

```
ggcagtggat caggcacaga ttttacactg aaaatcagca gagtggaggc tgaggatgtt   1500
ggggtttatt actgcatgca acatatagaa tatccttta cgttcggcca agggaccaaa   1560
ctggaaatca aa                                                       1572
```

<210> SEQ ID NO 5
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 5

Gly Gly Gly Ser
1

<210> SEQ ID NO 6
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 6

Ser Gly Gly Gly
1

<210> SEQ ID NO 7
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 7

Gly Gly Gly Gly Ser
1               5

<210> SEQ ID NO 8
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 8

Ser Gly Gly Gly Gly
1               5

<210> SEQ ID NO 9
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 9

Gly Gly Gly Gly Gly Ser
1               5

<210> SEQ ID NO 10
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 10

Ser Gly Gly Gly Gly Gly
1               5

<210> SEQ ID NO 11
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 11

Gly Gly Gly Gly Gly Gly Ser
1               5

<210> SEQ ID NO 12
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 12

Ser Gly Gly Gly Gly Gly Gly
1               5

<210> SEQ ID NO 13
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 13

Gly Gly Pro Gly Ser
1               5

<210> SEQ ID NO 14
<211> LENGTH: 1572
<212> TYPE: DNA
<213> ORGANISM: Mus musculus

<400> SEQUENCE: 14

```
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120 tgcaaggctt ctggatacac cttcaccaac tcctggatga actgggtgag ggagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480
ctctccctgc ccgtcacccc tggagagccg gcctccatct cctgcaggtc tagtaagagt    540
ctcctgcata gtaatggcaa cacttacttg tattggttcc tggagaagcc agggcagtct    600
ccacagctcc tgatctatcg gatgtccaac cttgcctcag ggtccctga caggttcagt    660 ggcagtggat caggcacaga tttttacactg aaaatcagca gagtggaggc tgaggatgtt    720
ggggtttatt actgcatgca acatatagaa tatccttttta cgttcggcca agggaccaaa    780
```

```
ctggaaatca aaggaggtgg tggatcgggt ggtggtggtt cgggaggcgg tggatcgcag      840
gtgcagctgg tgcagtctgg acctgaggtg aagaagcctg ggcctcagt gaaggtctcc       900 tgcaaggctt ctggatacac cttcaccaac tcctggatga actgggtgag gaagaggcct      960
ggaaagggtc ttgagtggat tggacggatt tatcctggag atggagaaac tatctacaat     1020
gggaaattca gggtcagagt cacgattacc gcggacgaat ccacgagcac agcctacatg     1080
caactgagca gcctgagatc tgaggacacg gccgtgtatt actgtgcgag aggctatgat     1140
gattactcgt ttgcttactg gggccaggga accacggtca ccgtctcttc aggtggtggt     1200
ggatccggag gtggtggatc gggtggtgga ggatcggata ttgtgatgac tcagtctcca     1260
ctctccctgc ccgtcacccc tggagagccg gcctccatct cctgcaggtc tagtaagagt     1320
ctcctgcata gtaatggcaa cacttacttg tattggttcc tgaagaagcc agggcagtct     1380
ccacagctcc tgatctatcg gatgtccaac cttgcctcag gggtcctga caggttcagt      1440 ggcagtggat caggcacaga ttttacactg aaaatcagca gagtggaggc tgaggatgtt     1500
ggggtttatt actgcatgca acatatagaa tatccttta cgttcggcca agggaccaaa      1560
ctggaaatca aa                                                         1572
```

<210> SEQ ID NO 15
<211> LENGTH: 524
<212> TYPE: PRT
<213> ORGANISM: Mus musculus

<400> SEQUENCE: 15

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Ser Gly Gly
    130                 135                 140

Gly Gly Ser Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Leu Glu Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Asp Phe Thr Leu Lys Ile Ser Arg Val Glu Ala Glu Asp Val
```

```
            225                 230                 235                 240
Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Ser Gly Gly Gly
            260                 265                 270

Gly Ser Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Lys Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Gln Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Phe Leu Lys Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Asp Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520

<210> SEQ ID NO 16
<211> LENGTH: 1572
<212> TYPE: DNA
<213> ORGANISM: Mus musculus

<400> SEQUENCE: 16
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120 tgcaaggctt ctggatacac cttcaccaac tcctggatga actgggtgag ggagaggcct     180
ggaaagggtc ttgagtggat tggacggatt tatcctggag atggagaaac tatctacaat     240
gggaaattca gggtcagagt cacgattacc gcggacgaat ccacgagcac agcctacatg     300
caactgagca gcctgagatc tgaggacacg gccgtgtatt actgtgcgag aggctatgat     360
gattactcgt ttgcttactg gggccaggga accacggtca ccgtctcttc aggtggtggt     420
ggatccggag gtggtggatc gggtggtgga ggatcggata ttgtgatgac tcagtctcca     480
```

```
ctctccctgc ccgtcacccc tggagagccg gcctccatct cctgcaggtc tagtaagagt      540
ctcctgcata gtaatggcaa cacttacttg tattggttcc tgaagaagcc agggcagtct      600
ccacagctcc tgatctatcg gatgtccaac cttgcctcag ggtccctga caggttcagt       660
ggcagtggat caggcacaga ttttacactg aaaatcagca gagtggaggc tgaggatgtt      720
ggggtttatt actgcatgca acatatagaa tatccttta cgttcggcca agggaccaaa       780
ctggaaatca aggaggtgg tggatcgggt ggtggtggtt cggaggcgg tggatcgcag        840
gtgcagctgg tgcagtctgg acctgaggtg aagaagcctg ggcctcagt gaaggtctcc       900
tgcaaggctt ctggatacac cttcaccaac tcctggatga actgggtgag gagaggcct      960
ggaaagggtc ttgagtggat tggacggatt tatcctggag atggagaaac tatctacaat      1020
gggaaattca gggtcagagt cacgattacc gcggacgaat ccacgagcac agcctacatg      1080
caactgagca gcctgagatc tgaggacacg gccgtgtatt actgtgcgag aggctatgat      1140
gattactcgt ttgcttactg gggccaggga accacggtca ccgtctcttc aggtggtggt      1200
ggatccggag gtggtggatc gggtggtgga ggatcggata ttgtgatgac tcagtctcca      1260
ctctccctgc ccgtcacccc tggagagccg gcctccatct cctgcaggtc tagtaagagt      1320
ctcctgcata gtaatggcaa cacttacttg tattggttcc tgaagaagcc agggcagtct      1380
ccacagctcc tgatctatcg gatgtccaac cttgcctcag ggtccctga caggttcagt       1440
ggcagtggat caggcacaga ttttacactg aaaatcagca gagtggaggc tgaggatgtt      1500
ggggtttatt actgcatgca acatatagaa tatccttta cgttcggcca agggaccaaa       1560
ctggaaatca aa                                                          1572
```

<210> SEQ ID NO 17
<211> LENGTH: 524
<212> TYPE: PRT
<213> ORGANISM: Mus musculus

<400> SEQUENCE: 17

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Ser Gly Gly
    130                 135                 140

Gly Gly Ser Gly Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175
```

-continued

```
Ser Ser Lys Ser Leu Leu His Ser Asn Gly Asn Thr Tyr Leu Tyr Trp
            180                 185                 190

Phe Leu Lys Lys Pro Gly Gln Ser Pro Gln Leu Leu Ile Tyr Arg Met
            195                 200                 205

Ser Asn Leu Ala Ser Gly Val Pro Asp Arg Phe Ser Gly Ser Gly Ser
210                 215                 220

Gly Thr Asp Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
            260                 265                 270

Gly Ser Gly Gly Gly Gly Ser Gln Val Gln Leu Val Gln Ser Gly Pro
            275                 280                 285

Glu Val Lys Lys Pro Gly Ala Ser Val Lys Val Ser Cys Lys Ala Ser
            290                 295                 300

Gly Tyr Thr Phe Thr Asn Ser Trp Met Asn Trp Val Arg Lys Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Gln Leu Ser Ser Leu Arg Ser Glu
            355                 360                 365

Asp Thr Ala Val Tyr Tyr Cys Ala Arg Gly Tyr Asp Asp Tyr Ser Phe
            370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
            435                 440                 445

Tyr Leu Tyr Trp Phe Leu Glu Lys Pro Gly Gln Ser Pro Gln Leu Leu
450                 455                 460

Ile Tyr Arg Met Ser Asn Leu Ala Ser Gly Val Pro Asp Arg Phe Ser
465                 470                 475                 480

Gly Ser Gly Ser Gly Thr Asp Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
            515                 520

<210> SEQ ID NO 18
<211> LENGTH: 516
<212> TYPE: PRT
<213> ORGANISM: Artificial
<220> FEATURE:
<223> OTHER INFORMATION: An artificially synthesized scFv sequence

<400> SEQUENCE: 18

Met Gly Trp Ser Cys Ile Ile Leu Phe Leu Val Ala Thr Ala Thr Gly
1               5                   10                  15
```

```
Val His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Tyr Ser Ile
            35                  40                  45

Thr Ser Asp His Ala Trp Ser Trp Val Arg Gln Pro Pro Gly Arg Gly
50                  55                  60

Leu Glu Trp Ile Gly Tyr Ile Ser Tyr Ser Gly Ile Thr Thr Tyr Asn
65                  70                  75                  80

Pro Ser Leu Lys Ser Arg Val Thr Met Leu Arg Asp Thr Ser Lys Asn
            85                  90                  95

Gln Phe Ser Leu Arg Leu Ser Ser Val Thr Ala Ala Asp Thr Ala Val
            100                 105                 110

Tyr Tyr Cys Ala Arg Ser Leu Ala Arg Thr Thr Ala Met Asp Tyr Trp
            115                 120                 125

Gly Gln Gly Ser Leu Val Thr Val Ser Ser Gly Gly Gly Gly Ser Gly
            130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Ile Ser Ser Tyr Leu Asn Trp Tyr Gln Gln Lys
            180                 185                 190

Pro Gly Lys Ala Pro Lys Leu Leu Ile Tyr Tyr Thr Ser Arg Leu His
            195                 200                 205

Ser Gly Val Pro Ser Arg Phe Ser Gly Ser Gly Ser Gly Thr Asp Phe
            210                 215                 220

Thr Phe Thr Ile Ser Ser Leu Gln Pro Glu Asp Ile Ala Thr Tyr Tyr
225                 230                 235                 240

Cys Gln Gln Gly Asn Thr Leu Pro Tyr Thr Phe Gly Gln Gly Thr Lys
                245                 250                 255

Val Glu Ile Lys Gly Gly Gly Gly Ser Gly Gly Gly Gly Ser Gly Gly
            260                 265                 270

Gly Gly Ser Gln Val Gln Leu Gln Glu Ser Gly Pro Gly Leu Val Arg
            275                 280                 285

Pro Ser Gln Thr Leu Ser Leu Thr Cys Thr Val Ser Gly Tyr Ser Ile
            290                 295                 300

Thr Ser Asp His Ala Trp Ser Trp Val Arg Gln Pro Pro Gly Arg Gly
305                 310                 315                 320

Leu Glu Trp Ile Gly Tyr Ile Ser Tyr Ser Gly Ile Thr Thr Tyr Asn
                325                 330                 335

Pro Ser Leu Lys Ser Arg Val Thr Met Leu Arg Asp Thr Ser Lys Asn
            340                 345                 350

Gln Phe Ser Leu Arg Leu Ser Ser Val Thr Ala Ala Asp Thr Ala Val
            355                 360                 365

Tyr Tyr Cys Ala Arg Ser Leu Ala Arg Thr Thr Ala Met Asp Tyr Trp
            370                 375                 380

Gly Gln Gly Ser Leu Val Thr Val Ser Ser Gly Gly Gly Gly Ser Gly
385                 390                 395                 400

Gly Gly Gly Ser Gly Gly Gly Gly Ser Asp Ile Gln Met Thr Gln Ser
                405                 410                 415

Pro Ser Ser Leu Ser Ala Ser Val Gly Asp Arg Val Thr Ile Thr Cys
            420                 425                 430
```

```
Arg Ala Ser Gln Asp Ile Ser Ser Tyr Leu Asn Trp Tyr Gln Gln Lys
            435                 440                 445

Pro Gly Lys Ala Pro Lys Leu Leu Ile Tyr Tyr Thr Ser Arg Leu His
        450                 455                 460

Ser Gly Val Pro Ser Arg Phe Ser Gly Ser Gly Ser Gly Thr Asp Phe
465                 470                 475                 480

Thr Phe Thr Ile Ser Ser Leu Gln Pro Glu Asp Ile Ala Thr Tyr Tyr
                    485                 490                 495

Cys Gln Gln Gly Asn Thr Leu Pro Tyr Thr Phe Gly Gln Gly Thr Lys
                500                 505                 510

Val Glu Ile Lys
        515

<210> SEQ ID NO 19
<211> LENGTH: 1548
<212> TYPE: DNA
<213> ORGANISM: Artificial
<220> FEATURE:
<223> OTHER INFORMATION: An artificially synthesized scFv sequence

<400> SEQUENCE: 19
atgggatgga gctgtatcat cctcttcttg gtagcaacag ctacaggtgt ccactcccag      60
gtccaactgc aggagagcgg tccaggtctt gtgagaccta gccagaccct gagcctgacc    120
tgcaccgtgt ctggctactc aattaccagc gatcatgcct ggagctgggt tcgccagcca    180
cctggacgag tcttgagtg gattggatac attagttata gtggaatcac aacctataat    240
ccatctctca aatccagagt gacaatgctg agagacacca gcaagaacca gttcagcctg    300
agactcagca gcgtgacagc cgccgacacc gcggtttatt attgtgcaag atccctagct    360
cggactacgc tatggactac tggggtcaa ggcagcctcg tcacagtctc ctccggaggt    420
ggtggtagtg gaggtggtgg tagtggaggt ggtggtagtg acatccagat gacccagagc    480
ccaagcagcc tgagcgccag cgtgggcgac agagtgacca tcacctgtag agccagccag    540
gacatcagca gttacctgaa ttggtaccag cagaagccag gaaaggctcc aaagctgctg    600
atctactaca cctccagact gcactctggt gtgccaagca gattcagcgg tagcggtagc    660
ggtaccgact caccttcac catcagcagc ctccagccag gacatcgc tacctactac    720 tgccaacagg gtaacacgct tccatacacg ttcggccaag gaccaaggt ggaaatcaaa    780 ggtggtggtg gttctggcgg cggcggctcc ggtggtggtg gatctcaggt ccaactgcag    840
gagagcggtc caggtcttgt gagacctagc cagaccctga cctgacctg caccgtgtct    900 ggctactcaa ttaccagcga tcatgcctgg agctgggttc gccagccacc tggacgaggt    960
cttgagtgga ttggatacat tagttatagt ggaatcacaa cctataatcc atctctcaaa   1020
tccagagtga caatgctgag agacaccagc aagaaccagt tcagcctgag actcagcagc   1080
gtgacagccg ccgacaccgc ggtttattat tgtgcaagat ccctagctcg gactacggct   1140
atggactact ggggtcaagg cagcctcgtc acagtctcct caggaggagg aggatctgga   1200
ggaggaggat ctggaggagg aggatccgac atccagatga cccagagccc aagcagcctg   1260
agcgccagcg tgggcgacag agtgaccatc acctgtagag ccagccagga catcagcagt   1320
tacctgaatt ggtaccagca gaagccagga aaggctccaa agctgctgat ctactacacc   1380
tccagactgc actctggtgt gccaagcaga ttcagcggta gcggtagcgg taccgacttc   1440
```

```
accttcacca tcagcagcct ccagccagag gacatcgcta cctactactg ccaacagggt    1500
aacacgcttc catacacgtt cggccaaggg accaaggtgg aaatcaaa                 1548
```